US011291732B1

(12) United States Patent
Jang et al.

(10) Patent No.: US 11,291,732 B1
(45) Date of Patent: Apr. 5, 2022

(54) COMPOUNDS FOR DEGRADING α-SYNUCLEIN AGGREGATES AND USES THEREOF

(71) Applicant: Aprinoia Therapeutics Limited, Wanchai (CN)

(72) Inventors: Ming-Kuei Jang, Taipei (TW); Paul Tempest, Taipei (TW); Yih-Shyan Lin, Kaohsiung (TW)

(73) Assignee: APRINOIA THERAPEUTICS LIMITED, Wanchai (HK)

( * ) Notice: Subject to any disclaimer, the term of this patent is extended or adjusted under 35 U.S.C. 154(b) by 0 days.

(21) Appl. No.: 17/320,913

(22) Filed: May 14, 2021

Related U.S. Application Data

(63) Continuation-in-part of application No. PCT/US2020/060459, filed on Nov. 13, 2020.

(60) Provisional application No. 62/935,017, filed on Nov. 13, 2019.

(51) Int. Cl.
| | |
|---|---|
| *A61K 47/55* | (2017.01) |
| *A61P 25/28* | (2006.01) |
| *A61K 31/506* | (2006.01) |
| *A61K 31/427* | (2006.01) |
| *A61K 31/4439* | (2006.01) |
| *A61K 31/437* | (2006.01) |
| *A61K 31/454* | (2006.01) |

(52) U.S. Cl.
CPC ............ *A61K 47/55* (2017.08); *A61K 31/427* (2013.01); *A61K 31/437* (2013.01); *A61K 31/4439* (2013.01); *A61K 31/454* (2013.01); *A61K 31/506* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 3,833,863 | A | 9/1974 | Webster et al. |
| 5,130,228 | A | 7/1992 | Wade et al. |
| 5,264,329 | A | 11/1993 | Wade et al. |
| 7,060,697 | B2 | 6/2006 | Marsilje et al. |
| 7,910,579 | B2 | 3/2011 | Kudo et al. |
| 9,750,816 | B2 | 9/2017 | Bradner et al. |
| 9,770,512 | B2 | 9/2017 | Bradner et al. |
| 9,821,068 | B2 | 11/2017 | Bradner et al. |
| 10,125,114 | B2 | 11/2018 | Bradner et al. |
| 10,308,871 | B2 | 6/2019 | Yano |
| 10,464,925 | B2 | 11/2019 | Bradner et al. |
| 10,604,516 | B2 | 3/2020 | Higuchi et al. |
| 10,669,253 | B2 | 6/2020 | Bradner et al. |
| 10,730,870 | B2 | 8/2020 | Crew et al. |
| 10,772,962 | B2 | 9/2020 | Qian et al. |
| 10,849,980 | B2 | 12/2020 | Bradner et al. |
| 2006/0018825 | A1 | 1/2006 | Kudo et al. |
| 2009/0028787 | A1 | 1/2009 | Gravenfors et al. |
| 2009/0257949 | A1 | 10/2009 | Hefti et al. |
| 2011/0130305 | A1 | 6/2011 | Patton et al. |
| 2017/0233655 | A1 | 8/2017 | Saito |
| 2017/0362507 | A1 | 12/2017 | Okabe |
| 2018/0125821 | A1 | 5/2018 | Crew et al. |
| 2020/0085793 | A1 | 3/2020 | Crew et al. |

FOREIGN PATENT DOCUMENTS

| | | |
|---|---|---|
| AU | 2017204357 A1 | 8/2017 |
| CN | 1791592 A | 6/2006 |
| CN | 1867552 A | 11/2006 |
| CN | 102639135 A | 8/2012 |
| CN | 107207459 A | 9/2017 |
| EP | 1 655 287 A1 | 5/2006 |
| EP | 2 397 139 A1 | 12/2011 |
| JP | S4874796 A | 10/1973 |
| JP | S55-053333 A | 4/1980 |
| JP | S61-275836 A | 12/1986 |
| JP | H03-144569 A | 6/1991 |
| JP | 2007-106755 A | 4/2007 |
| JP | 2009-519239 A | 5/2009 |
| JP | 2011-512354 A | 4/2011 |
| JP | 2011-516866 A | 5/2011 |
| JP | 2012-102106 A | 5/2012 |
| WO | WO-2005/016888 A1 | 2/2005 |
| WO | WO-2008/078424 A1 | 7/2008 |
| WO | WO-2010/011964 A2 | 1/2010 |
| WO | WO-2010/024769 A1 | 3/2010 |
| WO | WO-2010/087315 A1 | 8/2010 |
| WO | WO-2011/045415 A2 | 4/2011 |
| WO | WO-2011/065980 A2 | 6/2011 |
| WO | WO-2015/188368 A1 | 12/2015 |
| WO | WO-2016/105518 A1 | 6/2016 |
| WO | WO-2016/149668 A1 | 9/2016 |
| WO | WO-2017/007612 A1 | 1/2017 |
| WO | WO-2017/030814 A1 | 2/2017 |
| WO | WO-2018/102067 A2 | 6/2018 |

(Continued)

OTHER PUBLICATIONS

Braymer, Joseph J., et al., "Recent Development of Bifunctional Small Molecules to Study Metal-Amyloid-β Species in Alzheimer's Disease," International Journal of Alzheimer's Disease, vol. 2011, Article ID 623051, (2011), doi: 10.4061/2011/623051, 9 pages.
International Search Report dated Feb. 9, 2021 issued in International Application No. PCT/US2020/060459, 3 pages.
Written Opinion of the International Searching Authority dated Feb. 9, 2021 issued in International Application No. PCT/US2020/060459, 4 pages.
Cary, Brian P., et al., "Targeting Metal-Aβ Aggregates with Bifunctional Radioligand [11 C]L2-b and a Flourine-18 Analogue [18 F]FL2-b," ACS Medicinal Chemistry Letters, vol. 6, Nov. 9, 2014, pp. 112-116.

(Continued)

*Primary Examiner* — Heidi Reese
(74) *Attorney, Agent, or Firm* — Foley & Lardner LLP

(57) ABSTRACT

The present disclosure provides compounds, compositions and methods useful for the treatment of neurodegenerative diseases, in particular synucleinopathies.

18 Claims, 3 Drawing Sheets

Specification includes a Sequence Listing.

(56) References Cited

FOREIGN PATENT DOCUMENTS

| WO | WO-2018/119448 A1 | 6/2018 |
|---|---|---|
| WO | WO-2019/014429 A1 | 1/2019 |
| WO | WO-2019/214681 A1 | 11/2019 |
| WO | WO-2020/041331 A1 | 2/2020 |
| WO | WO-2021/011913 A1 | 1/2021 |

OTHER PUBLICATIONS

Ehrenberg, Benjamin, et al., "Surface potential on purple membranes and its sidedness studied by a resonance Raman dye probe", Biophysical Journal, 1984, vol. 45, pp. 663-670.
Final Office Action on U.S. Appl. No. 16/798,226 dated Feb. 16, 2021.
Final Office Action on U.S. Appl. No. 16/798,226 dated Sep. 7, 2021.
International Preliminary Report on Patentability dated Sep. 18, 2020 issued in International Application No. PCT/CN2019/086201, 72 pages.
International Search Report dated Aug. 12, 2019 issued in International Application No. PCT/CN2019/0826201, 7 pages.
International Search Report for PCT/JP2012/083286, dated Mar. 5, 2013, 3 pgs.
Maruyama, Masahiro, et al., "Imaging of Tau Pathology in a Tauopathy Mouse Model and in Alzheimer Patients Compared to Normal Controls," Neuron, (2013), 79(6), pp. 1094-1108, doi:10.1016/j.neuron.2013.07.037.
Non-Final Office Action on U.S. Appl. No. 16/798,226 dated Oct. 26, 2020.
Non-Final Office Action on U.S. Appl. No. 17/320,882 dated Oct. 7, 2021.
Notice of Allowance on U.S. Appl. No. 14/346,914 dated Nov. 1, 2019.
Notice of grant for patent dated Jul. 30, 2019 issued in Australian Application No. 2017204357, 1 page.
Ono, Maiko, et al., "Distinct binding of PET ligands PBB3 and AV-1451 to tau fibril strains in neurodegenerative tauopathies," Brain, (2017), 140(3), pp. 764-780, doi:10.1093/brain/aww339.
SantaCruz, K., et al., "Tau Suppression in a Neurodegenerative Mouse Model Improves Memory Function," Science, (2005), 309(5733), pp. 476-481.
Tomita, Yutaka, et al., "Long-term in vivo investigation of mouse cerebral microcirculation by fluorescence confocal microscopy in the area of focal ischemia," Journal of Cerebral Blood Flow & Metabolism, (2005), vol. 25, pp. 858-867, doi: 10.1038/sj.jcbfm.9600077.
Written Opinion of the International Searching Authority dated Aug. 12, 2019 issued in International Application No. PCT/CN2019/086201, 4 pages.
Yoshiyama, et al., Synapse Loss and Microglial Activation Precede Tangles in a P301S Tauopathy Mouse Model, Neuron, Feb. 1, 2007, vol. 53, pp. 337-351.

COMPOUNDS FOR DEGRADING α-SYNUCLEIN AGGREGATES AND USES THEREOF

CROSS-REFERENCE TO RELATED APPLICATIONS

This application is a continuation-in-part of International Patent Application No. PCT/US2020/060459, filed Nov. 13, 2020, which claims priority to U.S. Provisional Application No. 62/935,017, filed Nov. 13, 2019, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 23, 2021, is named 127353-0108_SL.txt and is 16,958 bytes in size.

BACKGROUND

Neurodegenerative diseases affect an estimated 50 million Americans each year, exacting an incalculable personal toll and an annual economic cost of hundreds of billions of dollars in medical expenses and lost productivity. Synucleinopathies are neurodegenerative diseases characterized by the abnormal accumulation of α-synuclein (α-Syn) aggregates in neurons and glial cells.

α-Synuclein is a 140 amino acid protein preferentially expressed in neurons at pre-synaptic terminals where it is thought to play a role in regulating synaptic transmission (Bendor et al., Neuron 2013; 79:1044-66). α-Synuclein can form pathological aggregates in neurons known as Lewy bodies, which are characteristic of both Parkinson's Disease (PD) and dementia with Lewy bodies (DLB). The pathological aggregates consist of aggregated, insoluble accumulations of misfolded α-synuclein proteins in neurons, nerve fibers or glial cells and are a characteristic feature of synucleinopathies. Synucleinopathies include Parkinson's disease (PD), dementia with Lewy bodies (DLB), and multiple system atrophy (MSA), the Lewy body variant of Alzheimer's disease (LBVAD), combined Parkinson's disease (PD) and Alzheimer's disease (AD), and neurodegeneration with brain iron accumulation type-1 (NBIA-1). In PD and DLB, α-Syn aggregates are in the neuronal cytoplasm and axonal processes into Lewy bodies and Lewy neurites, respectively, whereas α-Syn inclusions in oligodendroglia are the recognized neuropathologic hallmarks of MSA.

There is currently a lack of therapeutics that target synucleinopathies from the perspective of α-synuclein aggregation. Strategies aimed at reducing α-synuclein aggregation possess therapeutic potential in the treatment of patients with synucleinopathies.

SUMMARY

The present disclosure stems from the recognition that a bispecific conjugate compound that includes an E3 ubiquitin ligase binding moiety that is based on an imide drug (e.g., lenalidomide, thalidomide, VHL ligand) and also includes a binder of α-synuclein may induce proteasome degradation of α-synuclein aggregates. The disclosure therefore provides compounds, compositions, and methods for the treatment of various neurodegenerative diseases associated with α-synuclein aggregates based on this discovery. The bispecific conjugate compounds described herein degrade the α-synuclein aggregates by removing α-synuclein aggregates or reducing the degree of α-synuclein aggregation to low levels in a cellular model and/or animal model, thereby possessing therapeutic potential in the treatment of patients with synucleinopathies including but not limited to Parkinson's disease (PD), dementia with Lewy bodies (DLB), or multiple system atrophy (MSA).

The present disclosure also provides methods to remove α-synuclein aggregation or reduce Lewy bodies or α-synuclein aggregate in a patient having Lewy body disease or risk of Lewy body disease, and methods to reduce dementia with Lewy bodies (DLB) or multiple system atrophy (MSA) or other synucleinopathies.

One aspect of the present disclosure is a compound of Formula A,

EBM-L-SBM          (Formula A)

wherein
EBM is an E3 ubiquitin ligase binding moiety;
L is a linker covalently attached to EBM and SBM; and
SBM is an α-synuclein protein binding moiety of the formula:

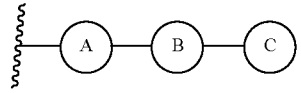

or a pharmaceutical acceptable salt, an enantiomer, a non-enantiomer, a tautomer, a racemate, a solvate, a metabolic precursor, a prodrug thereof,
wherein

is covalently linked to L; and
(i)

is a substituted or unsubstituted bicyclic fused aromatic ring containing at least 1 ring heteroatom selected from O, S, and N;

B is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
 (ii)

Ⓐ is a substituted or unsubstituted monocyclic aromatic ring containing 0 to 2 ring heteroatoms selected from O, S, and N;

Ⓑ is a substituted or unsubstituted monocyclic aromatic ring containing 0 to 2 ring heteroatoms selected from O, S, and N; and

5

Ⓒ is a substituted or unsubstituted bicyclic fused aromatic ring containing at least 1 ring heteroatom selected from O, S, and N.

Another aspect of the disclosure is a compound of any one of the Formula (I)-(VI):

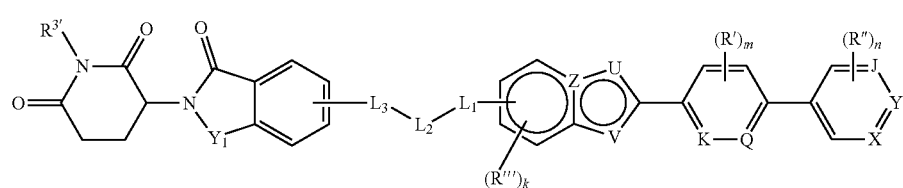

I

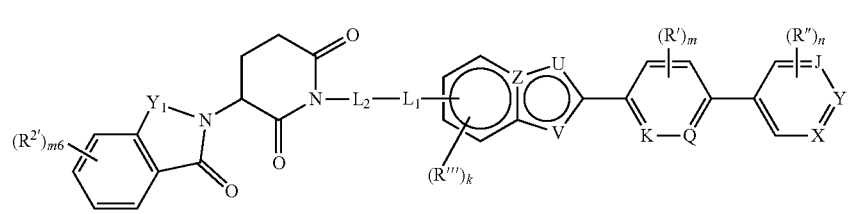

II

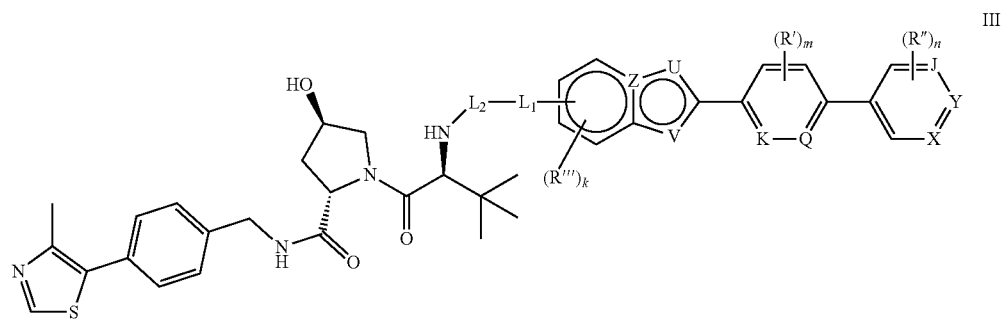

III

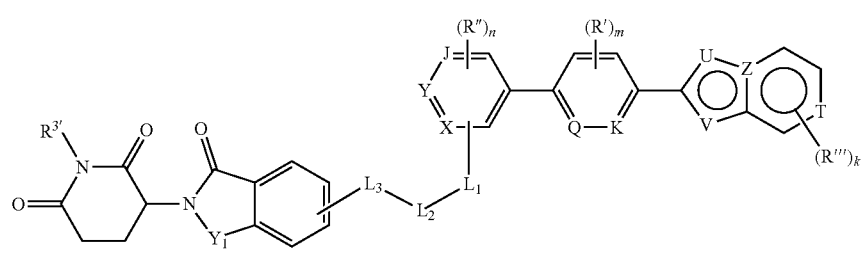

IV

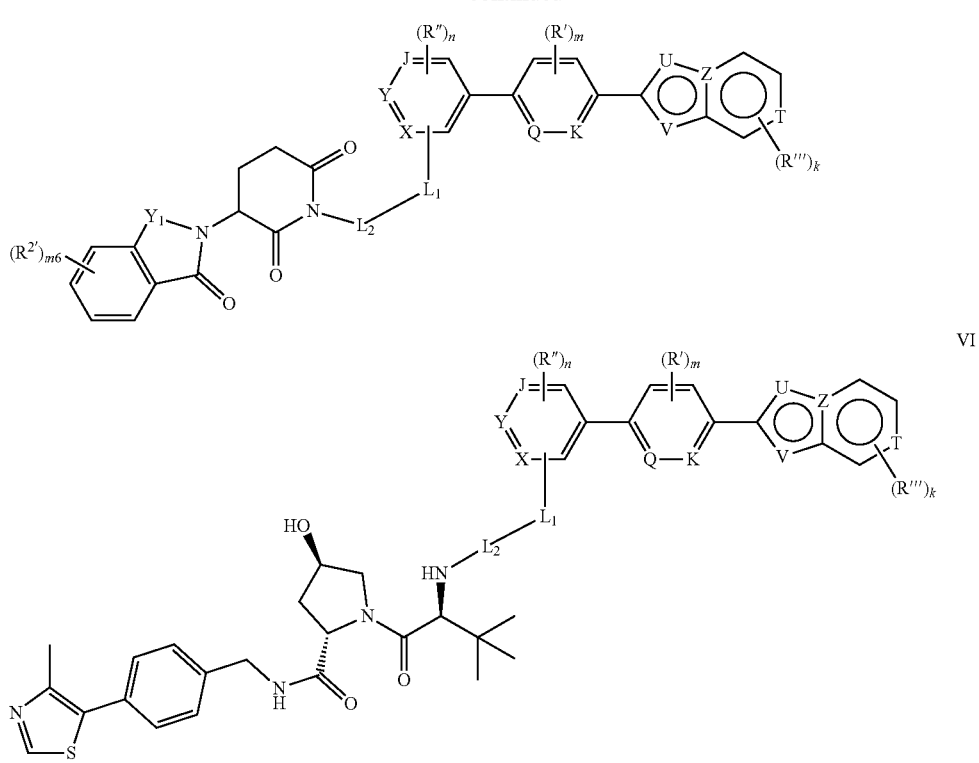

or pharmaceutically acceptable salts, solvates, hydrates, polymorphs, co-crystals, tautomers, stereoisomers, isotopically labeled derivatives, or prodrugs thereof, wherein $L_1$, $L_2$, $L_3$, X, Y, J, Q, K, T, U, V, Z, $Y_1$, R', R'', R''', $R^{2'}$, $R^{3'}$, n, m, k and m6 are as defined herein.

Another aspect of the present disclosure is a composition comprising a compound of the disclosure, and a pharmaceutically acceptable excipient.

Another aspect of the present disclosure is a method of treating, lessening the severity of, delaying the progression of, reducing the risk of developing, and/or delaying the onset of a disease characterized by the presence of Lewy bodies or pathological aggregates of α-synuclein, the method comprising administering to a subject in need thereof an effective amount of a compound or a composition of the present disclosure.

Another aspect of the present disclosure is a method for synthesizing the compounds of the disclosure.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 2A: DMSO (0.1%); FIG. 2B: compound 132168 (3 μM); FIG. 2C: compound 166362 (3 μM); and FIG. 2D: compound 170357 (10 μM).

DETAILED DESCRIPTION OF THE DISCLOSURE

Figure 1:
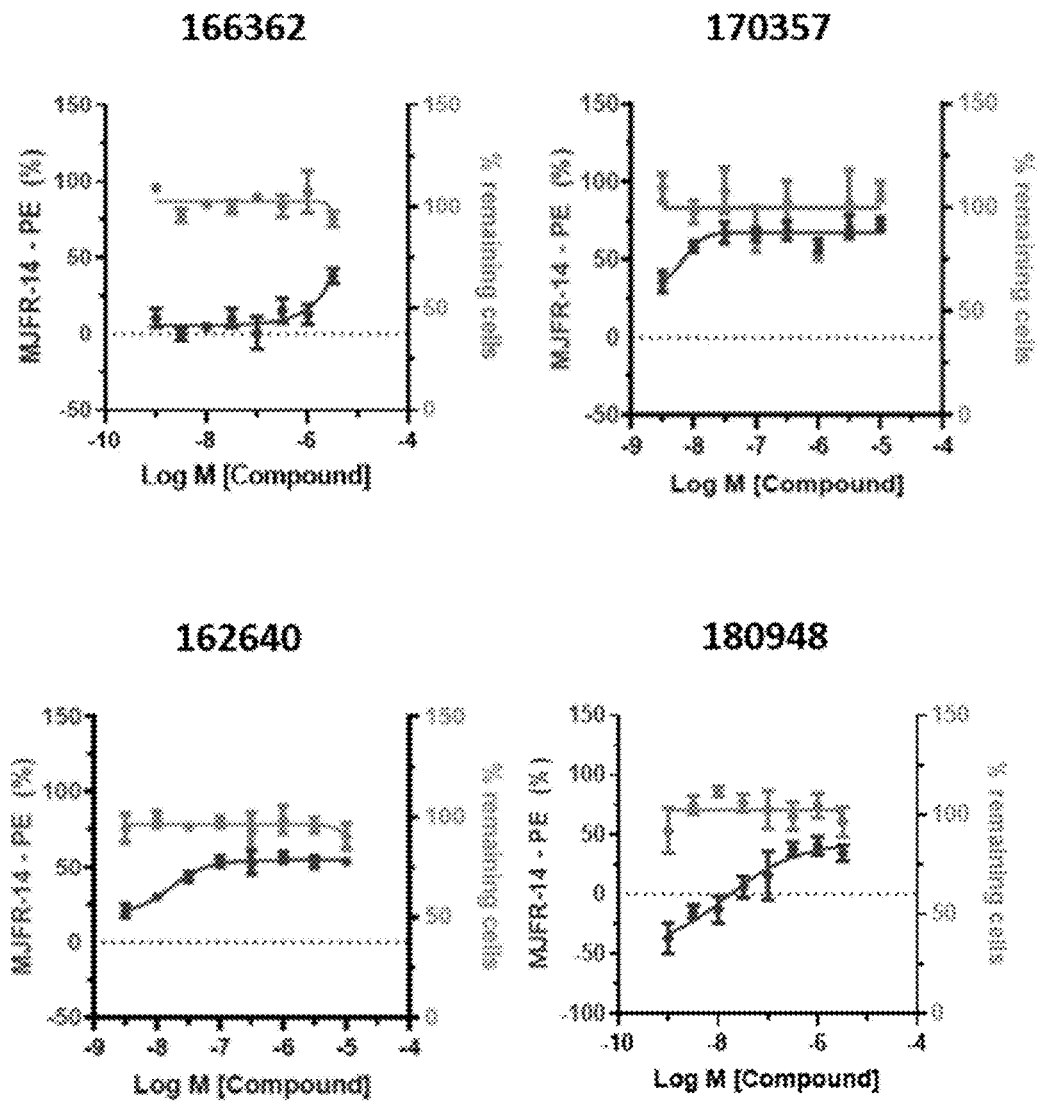
FIG. 1 shows the high content-based quantifications of aggregated α-synuclein species in combination with determination of nuclei count (% remaining cells) in differentiated ReNcell VM cells. Results showed that 24 hour treatment with test compounds 166362, 170357, 162640 and 180948, respectively, induced a concentration-dependent inhibition of MJFR14 immunoreactivity, indicative of decreased α-synuclein aggregation.
Figure 2A:
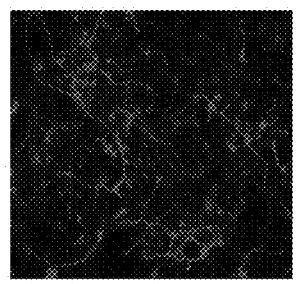
FIGS. 2A-D show the immunocytochemical images of cells treated with vehicle (0.1% DMSO) and test compounds 132168, 166362, and 170357, and immunostained with MJFR14, illustrating the reduction in α-synuclein expression following treatment with compounds 132168 and 166362.
Figure 2B:
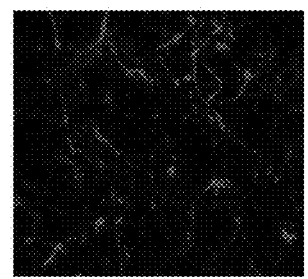
Figure 2C:
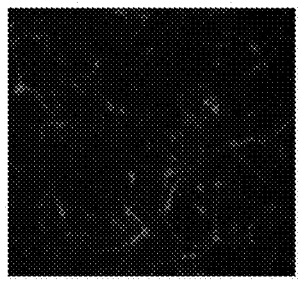
Figure 2D:
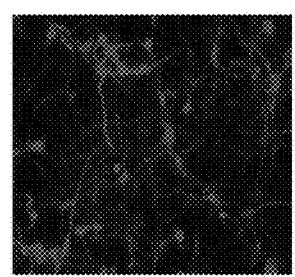

The present disclosure provides compounds, compositions, and methods useful for removing α-synuclein aggregates or reducing the degree of α-synuclein aggregation to low levels, thereby possessing therapeutic potential in the treatment of patients with synucleinopathies.

Provided herein are bispecific conjugate compounds that can simultaneously bind a target protein (i.e., aggregated α-synuclein) and an E3 ubiquitin ligase. The bispecific conjugate compounds exhibit desirable functional properties including binding preferentially to α-synuclein aggregates, and allowing α-synuclein to be placed in proximity to the E3 ubiquitin ligase, thereby facilitating the selective ubiquitination and eventual proteasome-mediated degradation of α-synuclein aggregates.

Methods described herein include the administration of a compound or a composition of the present disclosure to a subject to treat, alleviate or prevent a neurodegenerative disease or disorder characterized by the presence of Lewy bodies or pathological aggregates of α-synuclein.

Compounds

One aspect of the present disclosure is a compound of Formula A,

EBM-L-SBM (Formula A)

wherein
EBM is an E3 ubiquitin ligase binding moiety;
L is a linker covalently attached to EBM and SBM; and
SBM is an α-synuclein protein binding moiety of the formula:

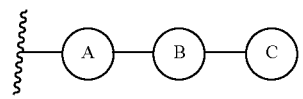

or a pharmaceutical acceptable salt, an enantiomer, a non-enantiomer, a tautomer, a racemate, a solvate, a metabolic precursor, a prodrug thereof,
wherein

is covalently linked to L; and
(i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
(ii)

is a substituted or unsubstituted monocyclic aromatic ring containing 0 to 2 ring heteroatoms selected from O, S, and N;

is a substituted or unsubstituted monocyclic aromatic ring containing 0 to 2 ring heteroatoms selected from O, S, and N; and

C is a substituted or unsubstituted bicyclic fused aromatic ring containing at least 1 ring heteroatom selected from O, S, and N.

In some embodiments, the substituted or unsubstituted bicyclic fused aromatic ring is a substituted or unsubstituted bicyclic 5-6 system. Non-limiting examples include

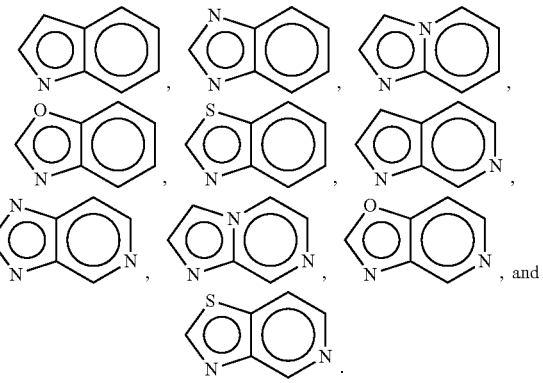

In some embodiments, SBM is of Formula B or Formula C

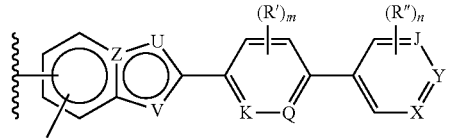
(Formula B)

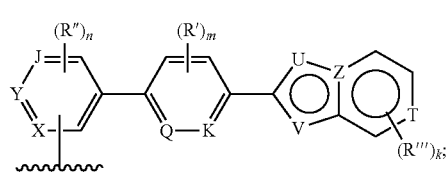
(Formula C)

wherein
Z is C or N; U is O, S or CH; V is N or NH;
K is CH or N; Q is CH or N; where K and Q are not N at the same time;
each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3;

each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;

each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;

J is $CR^6$ or N; X is $CR^6$ or N; Y is $CR^6$ or N; where at least one of J, X and Y is N, but J and Y are not N at the same time, X and Y are not N at the same time;

$R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo; and in Formula B, V is N, where Z and U are not heteroatoms at the same time; and in Formula C, V is N or NH; T is CH or N; where up to two of U, Z, V and T contain heteroatoms.

In some embodiments, EBM is

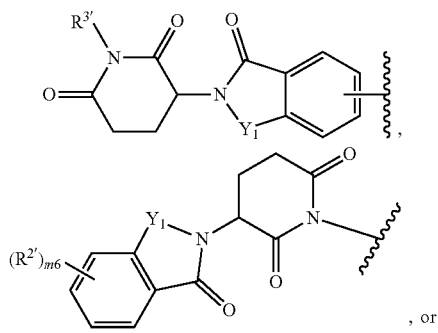

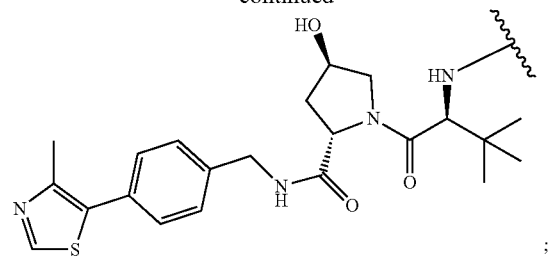

;

wherein $R^{3'}$ is H or $C_{1-6}$ alkyl;

each occurrence of $R^{2'}$ is independently selected from the group consisting of H, OH, $C_{1-6}$ alkyl, $C_{1-6}$ alkoxy, $C_{1-6}$ alkylamino and $NH_2$;

m6 is 0, 1, 2, 3 or 4; and $Y_1$ is $CH_2$ or

.

, or

In some embodiments, the compound is of any one of the Formula (I)-(VI):

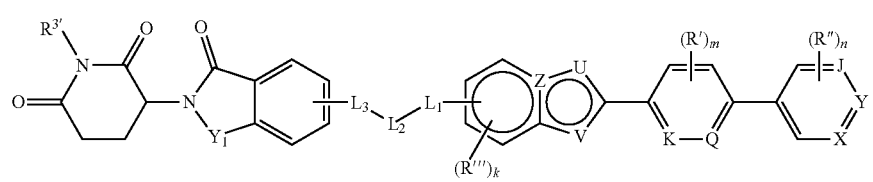

I

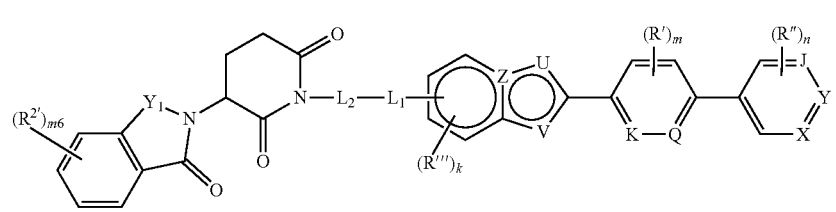

II

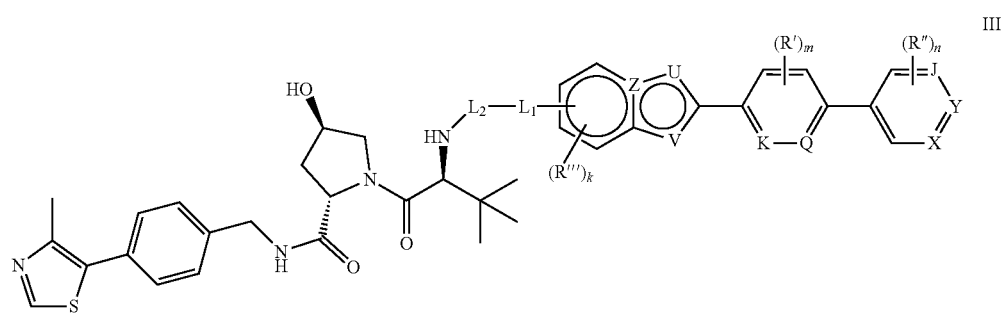

III

-continued

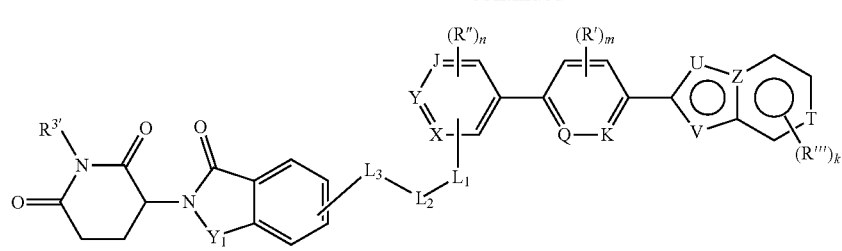
IV

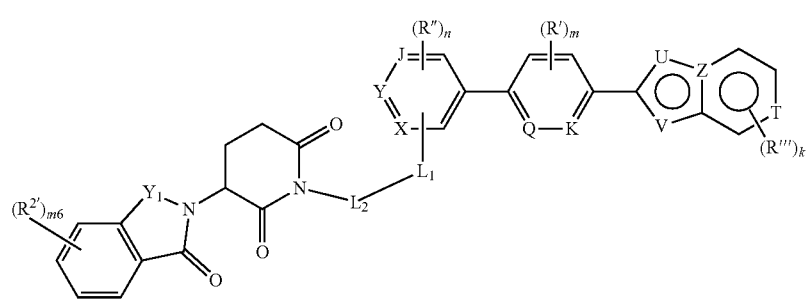
V

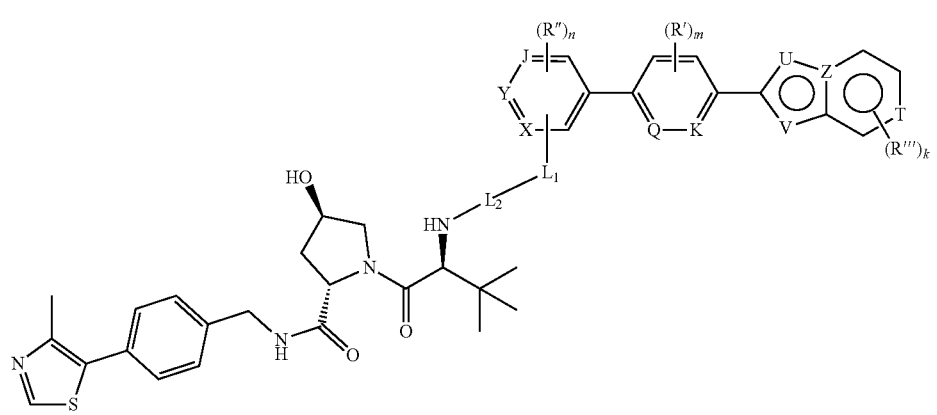
VI wherein, in Formula I, $R^{3'}$ is H or $C_{1-6}$ alkyl; $Y_1$ is $CH_2$ or

;

$L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N, where Z and U are not heteroatoms at the same time; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula II, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

;

$L_1$ is a bond, —C(=O)—, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N, where Z and U are not heteroatoms at the same time; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo; in Formula III, $L_1$ is a bond, —C(=O)—, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N, where Z and U are not heteroatoms at the same time; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula IV, $R^{3'}$ is H or $C_{1-6}$ alkyl; $Y_1$ is $CH_2$ or

$L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N or NH; T is CH or N; where up to two of U, Z, V and T contain heteroatoms; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino, and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo; in Formula V, each occurrence of R" is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

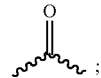

$L_1$ is a bond, —C(=O)—, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N or NH; T is CH or N; where up to two of U, Z, V and T contain heteroatoms; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo. Optionally, one or more chain atoms of the substituted or unsubstituted $C_{1-50}$ hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl (e.g., substituted or unsubstituted methyl or ethyl), or a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl or p-toluenesulfonamide (Ts)).

In certain embodiments, the compound is of the structure of Formula I.

In certain embodiments, the compound is of the structure of Formula II.

In certain embodiments, the compound is of the structure of Formula III.

In certain embodiments, the compound is of the structure of Formula IV.

In certain embodiments, the compound is of the structure of Formula V.

In certain embodiments, the compound is of the structure of Formula VI.

In certain embodiments, the moiety

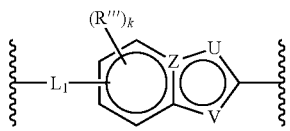

in Formula (I), (II) and (III) is

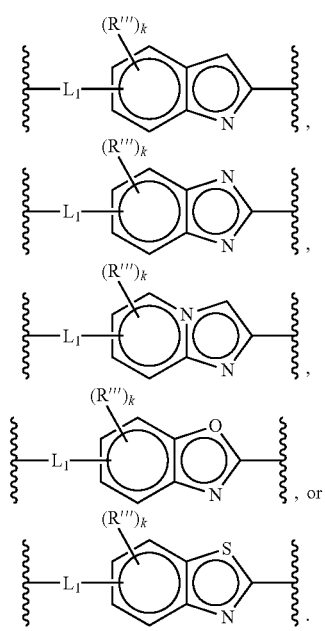

In certain embodiments, the moiety

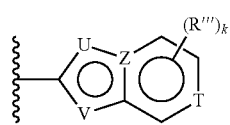

in Formula (IV), (V) and (VI) is

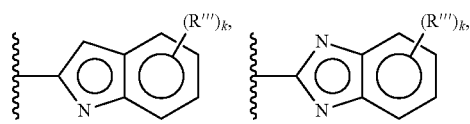

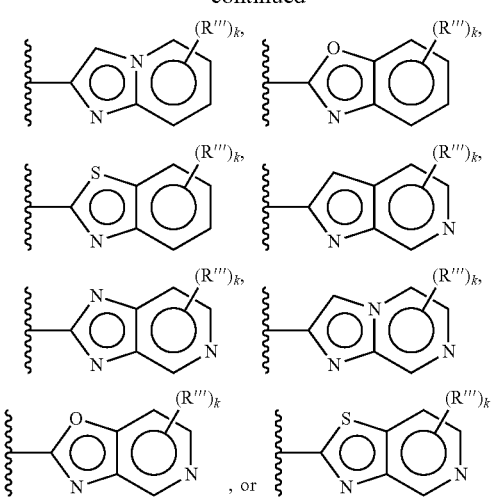

In certain embodiments, the moiety

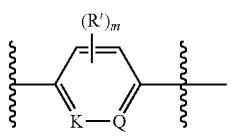

in Formulae (I)-(VI) is

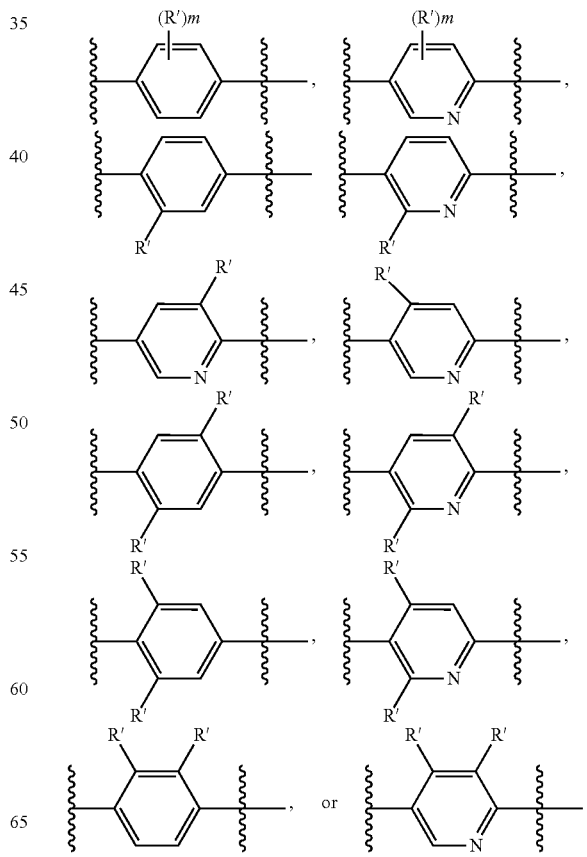

-continued

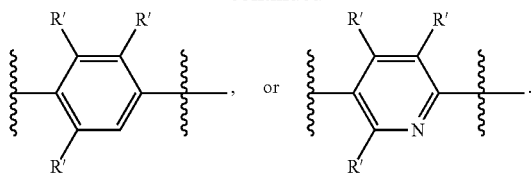

In certain embodiments, the moiety

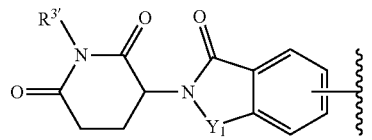

in Formula (I) and (IV) is

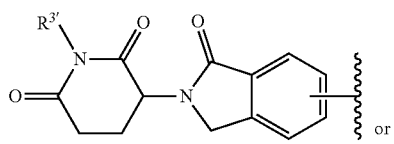

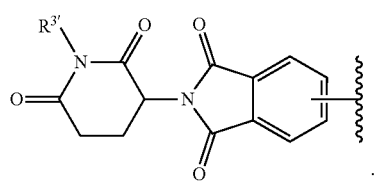

In certain embodiments, the moiety

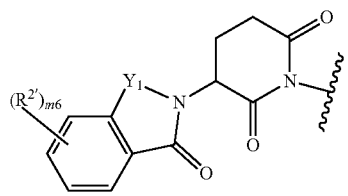

in Formula (II) and (V) is

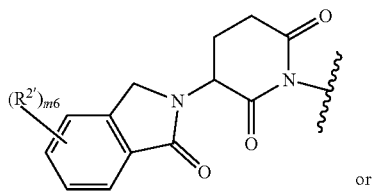

or

-continued

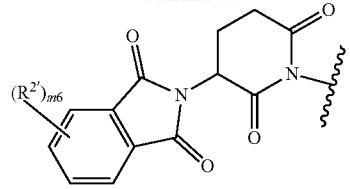

In one embodiment of the disclosure, L1 is a bond.
In one embodiment of the disclosure, L1 is —C(=O)—, —NH—, —O—, or —S—.
In one embodiment of the disclosure, L3 is a bond.
In one embodiment of the disclosure, L3 is —NH—, —O—, or —S—.
In one embodiment of the disclosure, L2 is a substituted or unsubstituted $C_{1-30}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is an unsubstituted $C_{1-30}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is a substituted or unsubstituted $C_{1-24}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is an unsubstituted $C_{1-24}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is a substituted or unsubstituted $C_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein Rai is independently hydrogen, substituted or unsubstituted $C_{1-6}$ alkyl or a nitrogen protecting group.

In certain embodiments, L2 is an unsubstituted $C_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, at least one chain atom of the hydrocarbon chain of L2 is independently replaced with —O—.

In certain embodiments, the chain of L2 comprises up to 50 consecutive covalently bonded atoms in length, excluding hydrogen atoms and substituents.

In certain embodiments, L2 comprises up to, for example 46, 45, 40, 35, 32, 30, 25, 23, 20, 15, 14, 12, 11, 10, 9, 8, 7, 6, 5, 3 consecutive covalently bonded atoms in length, excluding hydrogen atoms and substituents.

In certain embodiments, any of the atoms in L2 can be substituted. In certain embodiments, none of the atoms in the linker L2 are substituted. In certain embodiments, none of the carbon atoms in the linker are substituted.

In certain embodiments, L2 is a linker that contains an asymmetric carbon/stereocenter, i.e., an sp3 hybridized carbon atom bearing 4 different groups attached thereto. In certain embodiments, the compound comprising such an L2 group is enantiomerically enriched or substantially enantiomerically enriched. In certain embodiments, the compound comprising such an L2 group is enantiomerically pure. In certain embodiments, the compound comprising such an L2 group is racemic.

In certain embodiments, L2 comprises substituted or unsubstituted carbocyclylene, substituted or unsubstituted heterocyclylene, substituted or unsubstituted arylene, substituted or unsubstituted heteroarylene, or substituted or unsubstituted heteroalkylene, or combinations thereof. In certain embodiments, L2 is substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, L2 is a linker selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof.

Reference to L2 being a combination of at least two instances of the divalent moieties described herein refers to a linker consisting of at least one instance of a first divalent moiety and at least one instance of a second divalent moiety, wherein the first and second divalent moieties are the same or different and are within the scope of the divalent moieties described herein, and the instances of the first and second divalent moieties are consecutive covalently attached to each other. For example, when L2 is a combination of alkylene and heteroalkylene linkers, -alkylene-heteroalkylene-, -alkylene-(heteroalkylene)$_2$-, and -heteroalkylene-alkylene-heteroalkylene- are all within the scope of L2, wherein each instance of alkylene in any one of the linkers may be the same or different, and each instance of heteroalkylene in any one of the linkers may be the same or different.

In certain embodiments, L2 comprises at least one instance of substituted or unsubstituted alkylene, e.g., substituted or unsubstituted $C_{1-6}$ alkylene, substituted or unsubstituted $C_{1-2}$ alkylene, substituted or unsubstituted $C_{1-3}$ alkylene, substituted or unsubstituted $C_{3-4}$ alkylene, substituted or unsubstituted $C_{4-5}$ alkylene, substituted or unsubstituted $C_{5-6}$alkylene, substituted or unsubstituted $C_{3-6}$alkylene, or substituted or unsubstituted $C_{4-6}$alkylene. Exemplary alkylene groups include unsubstituted alkylene groups such as methylene (—CH$_2$—), ethylene (—(CH$_2$)$_2$—), n-propylene (—(CH$_2$)$_3$—), n-butylene (—(CH$_2$)$_4$—), n-pentylene (—(CH$_2$)$_5$—), and n-hexylene (—(CH$_2$)$_6$—).

In certain embodiments, L2 comprises at least one instance of substituted or unsubstituted alkenylene, e.g., substituted or unsubstituted $C_{2-6}$ alkenylene, substituted or unsubstituted $C_{1-3}$ alkenylene, substituted or unsubstituted $C_{3-4}$ alkenylene, substituted or unsubstituted $C_{4-5}$ alkenylene or substituted or unsubstituted $C_{5-6}$ alkenylene.

In certain embodiments, L2 comprises at least one instance of substituted or unsubstituted alkynylene, e.g., substituted or unsubstituted $C_{2-6}$ alkynylene, substituted or unsubstituted $C_{2-3}$ alkynylene, substituted or unsubstituted $C_{3-4}$ alkynylene, substituted or unsubstituted $C_{4-5}$ alkynylene or substituted or unsubstituted $C_{5-6}$ alkynylene.

In certain embodiments, L2 comprises at least one instance of substituted or unsubstituted heteroalkylene, e.g., substituted or unsubstituted heteroC$_{1-6}$alkylene, substituted or unsubstituted heteroC$_{1-2}$alkylene, substituted or unsubstituted heteroC$_{2-3}$alkylene, substituted or unsubstituted heteroC$_{3-4}$alkylene, substituted or unsubstituted heteroC$_{4-5}$alkylene or substituted or unsubstituted heteroC$_{5-6}$alkylene. Exemplary heteroalkylene groups include unsubstituted heteroalkylene groups, such as —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$O—, —O(CH$_2$)$_5$—, —(CH$_2$)$_5$O—, —O(CH$_2$)$_6$—, and —O(CH$_2$)$_6$O—, and amide groups (e.g., —NH—C(=O)— and —C(=O)NH—).

In certain embodiments, L2 comprises at least one instance of substituted or unsubstituted heteroalkenylene, e.g., substituted or unsubstituted heteroC$_{2-4}$alkenylene, substituted or unsubstituted heteroC$_{1-3}$alkenylene, substituted or unsubstituted heteroC$_{3-4}$ alkenylene, substituted or unsubstituted heteroC$_{4-5}$alkenylene, or substituted or unsubstituted heteroC$_{5-6}$alkenylene.

In certain embodiments, L2 comprises at least one instance of substituted or unsubstituted heteroalkynylene, e.g., substituted or unsubstituted heteroC$_{2-6}$alkynylene, substituted or unsubstituted heteroC$_{2-3}$alkynylene, substituted or unsubstituted heteroC$_{3-4}$ alkynylene, substituted or unsubstituted heteroC$_{4-5}$alkynylene, or substituted or unsubstituted heteroC$_{5-6}$alkynylene.

In certain embodiments, L2 comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$carbocyclylene, or substituted or unsubstituted $C_{5-6}$ carbocyclylene.

In certain embodiments, L2 comprises at least one instance of substituted or unsubstituted heterocyclylene, e.g., substituted or unsubstituted 3-6 membered heterocyclylene, substituted or unsubstituted 3-4 membered heterocyclylene, substituted or unsubstituted 4-5 membered heterocyclylene, or substituted or unsubstituted 5-6 membered heterocyclylene. In certain embodiments, at least one chain atom of the hydrocarbon chain of L2 is independently replaced with a 5-8 membered heterocyclyl group with 1-4 ring heteroatoms selected from the group consisting of nitrogen, oxygen, and sulfur. In certain embodiments, at least one chain atom of the hydrocarbon chain of L2 is independently replaced with a 6-membered heterocyclyl group with 1-3 ring heteroatoms selected from the group consisting of nitrogen and oxygen. In certain embodiments, at least one chain atom of the hydrocarbon chain of L2 is independently replaced with piperidine, piperazine or morpholine.

In certain embodiments, L2 comprises at least one instance of substituted or unsubstituted arylene, e.g., substituted or unsubstituted phenylene. In certain embodiments, at least one chain atom of the hydrocarbon chain of L2 is independently replaced with an optionally substituted phenyl group.

In certain embodiments, L2 comprises at least one instance of substituted or unsubstituted heteroarylene, e.g., substituted or unsubstituted 5- to 6-membered heteroarylene.

In certain embodiments, L2 is an unsubstituted hydrocarbon chain, optionally wherein one or more chain atoms of the hydrocarbon chain are independently replaced with —NR$^{a1}$— and each instance of R$^{a1}$ is independently hydrogen, substituted or unsubstituted C$_{1-6}$ alkyl or a nitrogen protecting group, or optionally two instances of R$^{a1}$ are taken together with their intervening atoms to form a substituted or unsubstituted heterocyclic or substituted or unsubstituted heteroaryl ring. In certain embodiments, at least one instance of R$^{a1}$ is hydrogen. In certain embodiments, at least one instance of R$^a$ is substituted or unsubstituted C$_{1-6}$ alkyl (e.g., substituted or unsubstituted methyl or ethyl). In certain embodiments, at least one instance of R$^{a1}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl or p-toluenesulfonamide (Ts)).

In certain embodiments, L2 is an optionally substituted C$_{1-45}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl or a nitrogen protecting group. In certain embodiments, L2 is an unsubstituted C$_{1-45}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl or a nitrogen protecting group. In certain embodiments, L2 is an optionally substituted C$_{1-24}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl or a nitrogen protecting group. In certain embodiments, L2 is an unsubstituted C$_{1-24}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl or a nitrogen protecting group. In certain embodiments, L2 is an optionally substituted C$_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl, or a nitrogen protecting group. In certain embodiments, L2 is an unsubstituted C$_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl, or a nitrogen protecting group. In certain embodiments, L2 is an optionally substituted C$_{1-30}$ hydrocarbon chain, wherein one or more chain atoms of the hydrocarbon chain are independently replaced with —O— or —NR$^{a1}$—. In certain embodiments, L2 is an unsubstituted C$_{1-30}$ hydrocarbon chain, wherein one or more chain atoms of the hydrocarbon chain are independently replaced with —O— or —NR$^{a1}$—. In certain embodiments, L2 is an unsubstituted C$_{1-30}$ hydrocarbon chain, wherein at least one chain atom of the hydrocarbon chain is independently replaced with —O—. In certain embodiments, L2 is an unsubstituted C$_{1-26}$ hydrocarbon chain, wherein one or more chain atoms of the hydrocarbon chain are independently replaced with —C(=O)—, —O— or —NR$^{a1}$—. In certain embodiments, L2 is an unsubstituted C$_{1-20}$ hydrocarbon chain, wherein one or more chain atoms of the hydrocarbon chain are independently replaced with —O—. In certain embodiments, L2 is an unsubstituted C$_{5-26}$ hydrocarbon chain, wherein one or more chain atoms of the hydrocarbon chain are independently replaced with —C(=O)—, —O— or —NR$^{a1}$—. In certain embodiments, L2 is an unsubstituted C$_{5-26}$ hydrocarbon chain, wherein one or more chain atoms of the hydrocarbon chain are independently replaced with —O—. In certain embodiments, L2 is an unsubstituted C$_{5-20}$ hydrocarbon chain, wherein one or more chain atoms of the hydrocarbon chain are independently replaced with —C(=O)—, —O— or —NR$^{a1}$—. In certain embodiments, L2 is an unsubstituted C$_{5-20}$ hydrocarbon chain, wherein one or more chain atoms of the hydrocarbon chain are independently replaced with —O—, or —NR$^{a1}$—. In certain embodiments, L2 is an unsubstituted C$_{5-15}$ hydrocarbon chain, wherein one or more chain atoms of the hydrocarbon chain are independently replaced with —C(=O)—, —O— or —NR$^{a1}$—. In certain embodiments, L2 is an unsubstituted C$_{15-20}$ hydrocarbon chain, wherein one or more chain atoms of the hydrocarbon chain are independently replaced with —C(=O)—, —O— or —NR$^{a1}$—. In certain embodiments, L2 is an unsubstituted C$_{20-25}$ hydrocarbon chain, wherein one or more chain atoms of the hydrocarbon chain are independently replaced with —C(=O)—, —O— or —NR$^{a1}$—. In certain embodiments, L2 is a substituted or unsubstituted C$_{1-45}$ hydrocarbon chain. In certain embodiments, L2 is a substituted or unsubstituted C$_{5-40}$ hydrocarbon chain. In certain embodiments, one or more chain atoms of the hydrocarbon chain of L2 are independently replaced with —C(=O)—, —O—, —S—, —NR$^{a1}$—, —N= or =N—. In certain embodiments, one or more chain atoms of the hydrocarbon chain of L2 are independently replaced with —C(=O)—, —O— or —NR$^{a1}$—, wherein R$^{a1}$ is independently hydrogen, substituted or unsubstituted C$_{1-6}$ alkyl or a nitrogen protecting group. In certain embodiments, L2 is an unsubstituted C$_{1-26}$ hydrocarbon chain, wherein at least one chain atom of the hydrocarbon chain is independently replaced with —O—. The cyclic moiety herein refers to a cycloalkylene or a heterocycloalkylene, such as

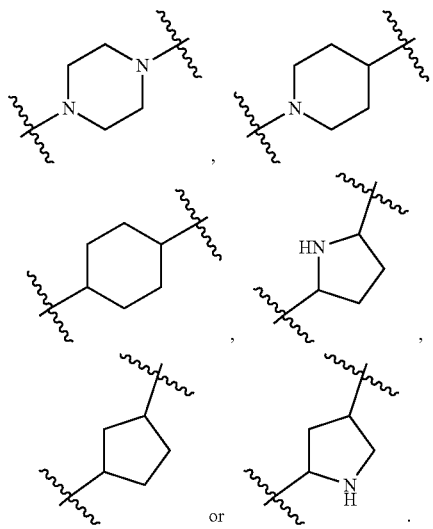

In certain embodiments, L2 is an all-carbon, substituted or unsubstituted C$_{1-45}$ hydrocarbon chain. In certain embodiments, L2 is an all-carbon, substituted or unsubstituted C$_{1-30}$ hydrocarbon chain. In certain embodiments, L2 is an all-carbon, substituted or unsubstituted C<sub>1-26</sub> hydrocarbon chain. In certain embodiments, L2 is an all-carbon, substituted or unsubstituted $C_{1-24}$ hydrocarbon chain. In certain embodiments, L2 is an all-carbon, substituted or unsubstituted $C_{1-20}$ hydrocarbon chain. In certain embodiments, L2 is an all-carbon, substituted or unsubstituted $C_{1-20}$ hydrocarbon chain.

In certain embodiments, L2 is

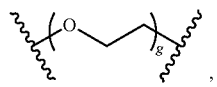

wherein g is 1, 2, 3, 4, 5, or 6. In certain embodiments, g is 1. In certain embodiments, g is 2. In certain embodiments, g is 3. In certain embodiments, g is 4. In certain embodiments, g is 5. In certain embodiments, g is 6.

In certain embodiments, L2 comprises at least one instance selected from the group consisting of substituted or unsubstituted methylene, ethylene, n-propylene, n-butylene, n-pentylene, n-hexylene, —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$O—, —O(CH$_2$)$_5$—, —(CH$_2$)$_5$O—, —O(CH$_2$)$_6$—, —O(CH$_2$)$_6$O—, —C(=O)O—, —O—C(=O)—, —NH—C(=O)— and —C(=O)NH—.

In certain embodiments, L2 comprises at least one instance selected from the group consisting of substituted or unsubstituted methylene, ethylene, n-propylene, n-butylene, n-pentylene, n-hexylene, —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$O—, —O(CH$_2$)$_5$—, —(CH$_2$)$_5$O—, —O(CH$_2$)$_6$—, —O(CH$_2$)$_6$O—, —NH—C(=O)— and —C(=O)NH—.

In certain embodiments, L2 includes the moiety —NHC(=O)—.

In certain embodiments, L2 includes the moiety —NH—.

Examples of L2 of the disclosure include, but are not limited to:

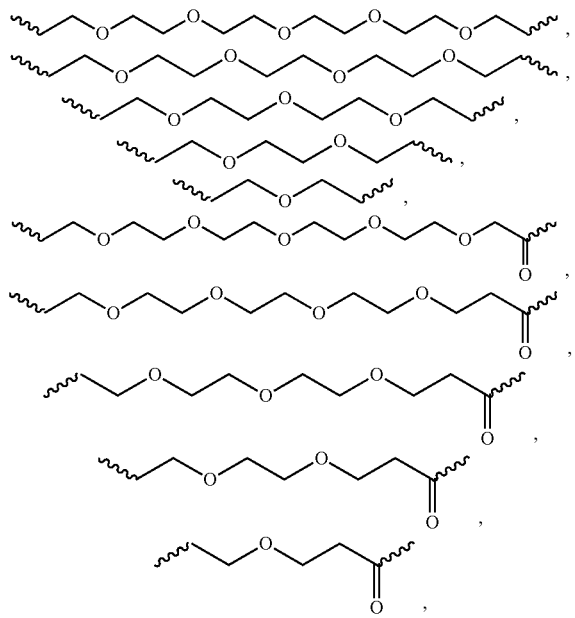

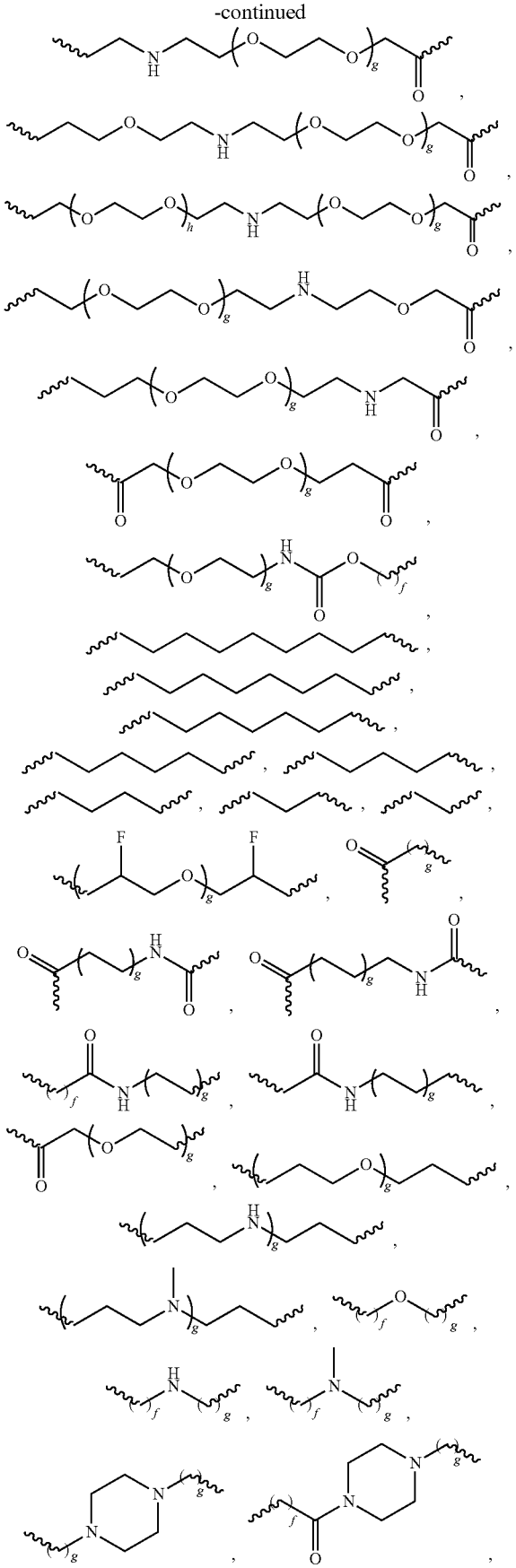

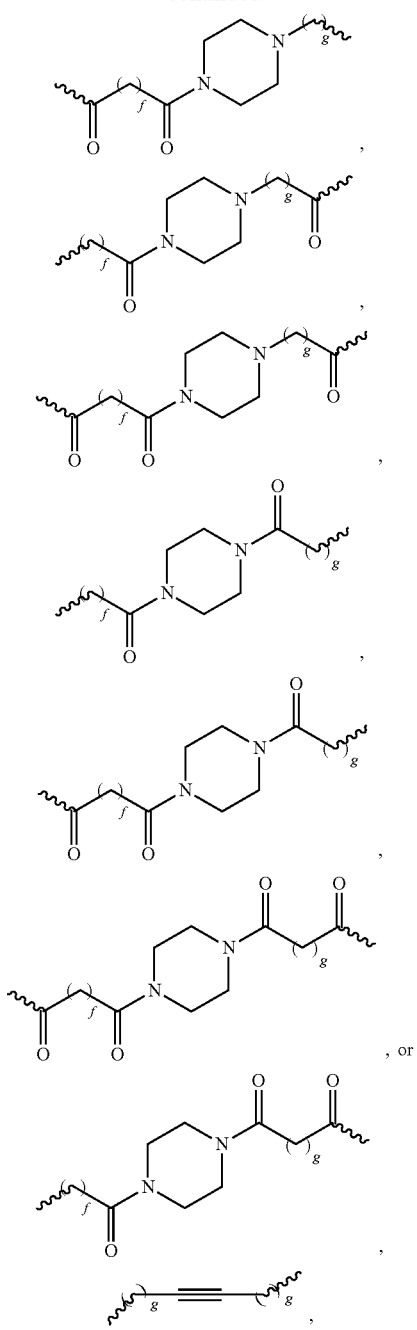
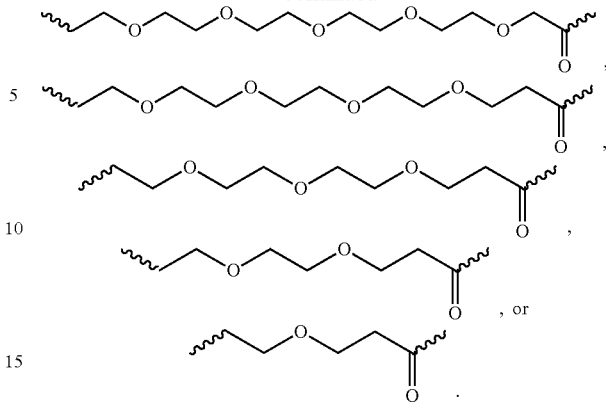
In certain embodiments, L2 is of the formula:
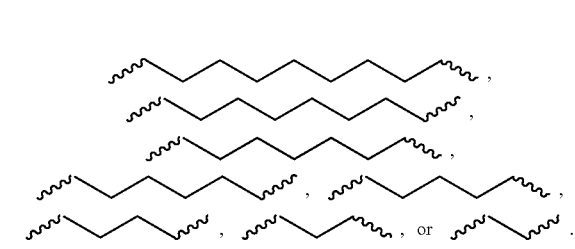
In certain embodiments, L2 is of the formula:
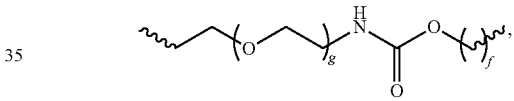
wherein each g is independently 1, 2, 3, 4, 5, or 6; f is 1, 2, 3, 4, 5, or 6, and h is 1, 2, 3, 4, 5, or 6.
In certain embodiments, L2 is of the formula:
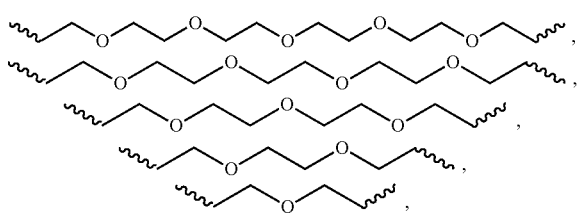
wherein g is 1, 2, 3, 4 or 5; h is 0, 1, 2, 3, 4 or 5; and f is 1, 2, 3, 4, 5, 6, 7 or 8.
In certain embodiments, L2 is of the formula:
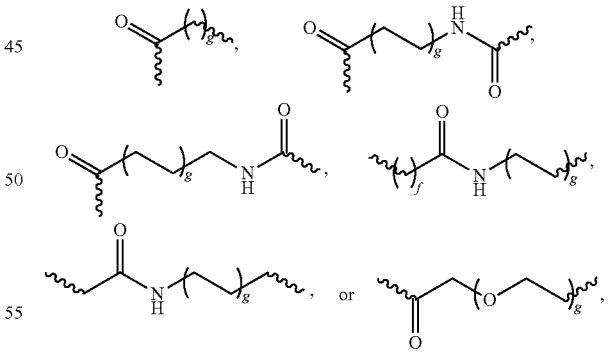
wherein g is 1, 2, 3, 4, 5, 6, 7 or 8; and f is 1, 2, 3, 4, 5, 6, 7 or 8.
In certain embodiments, L2 is of the formula:
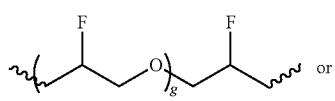

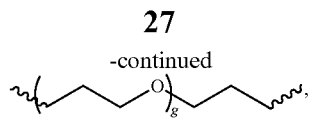
wherein g is 1, 2, 3, 4, 5, 6, 7 or 8.
In certain embodiments, L2 is of the formula:
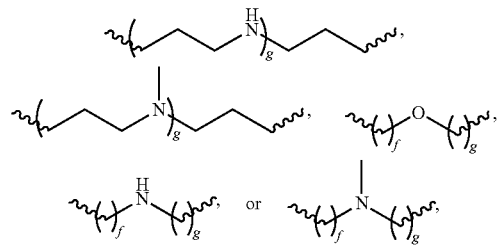
wherein g is 1, 2, 3, 4, 5, 6, 7 or 8; and f is 1, 2, 3, 4, 5, 6, 7 or 8.
In certain embodiments, L2 is of the formula:
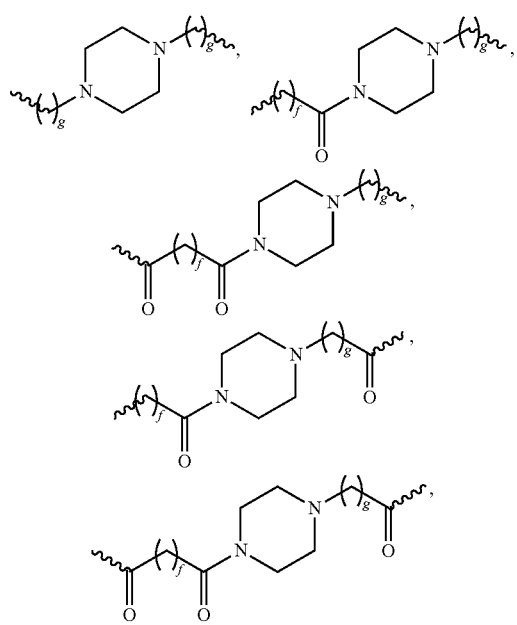
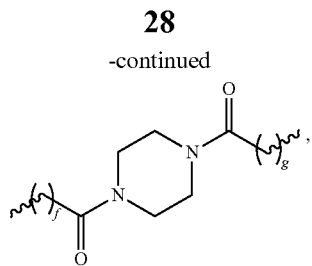
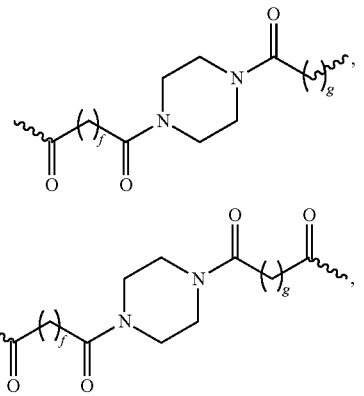
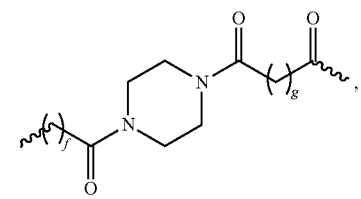
wherein g is 1, 2, 3, 4, 5, 6, 7 or 8; and f is 1, 2, 3, 4, 5, 6, 7 or 8.
In certain embodiments, L2 is of the formula:
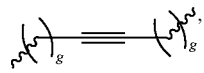
wherein g is 1, 2, 3, 4, 5, 6, 7 or 8.
In certain embodiments, the compound of the disclosure is of any one of the structure as follows,
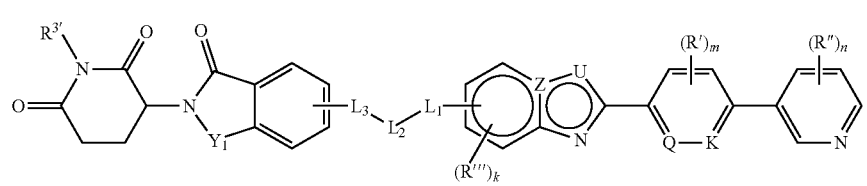
I-1
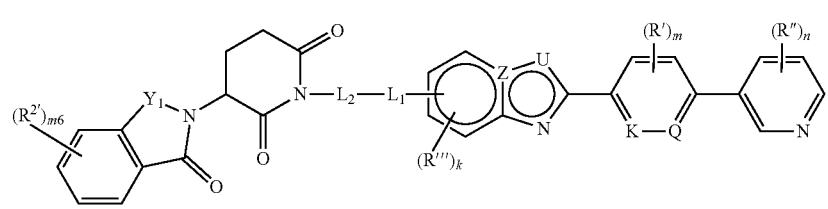
II-1

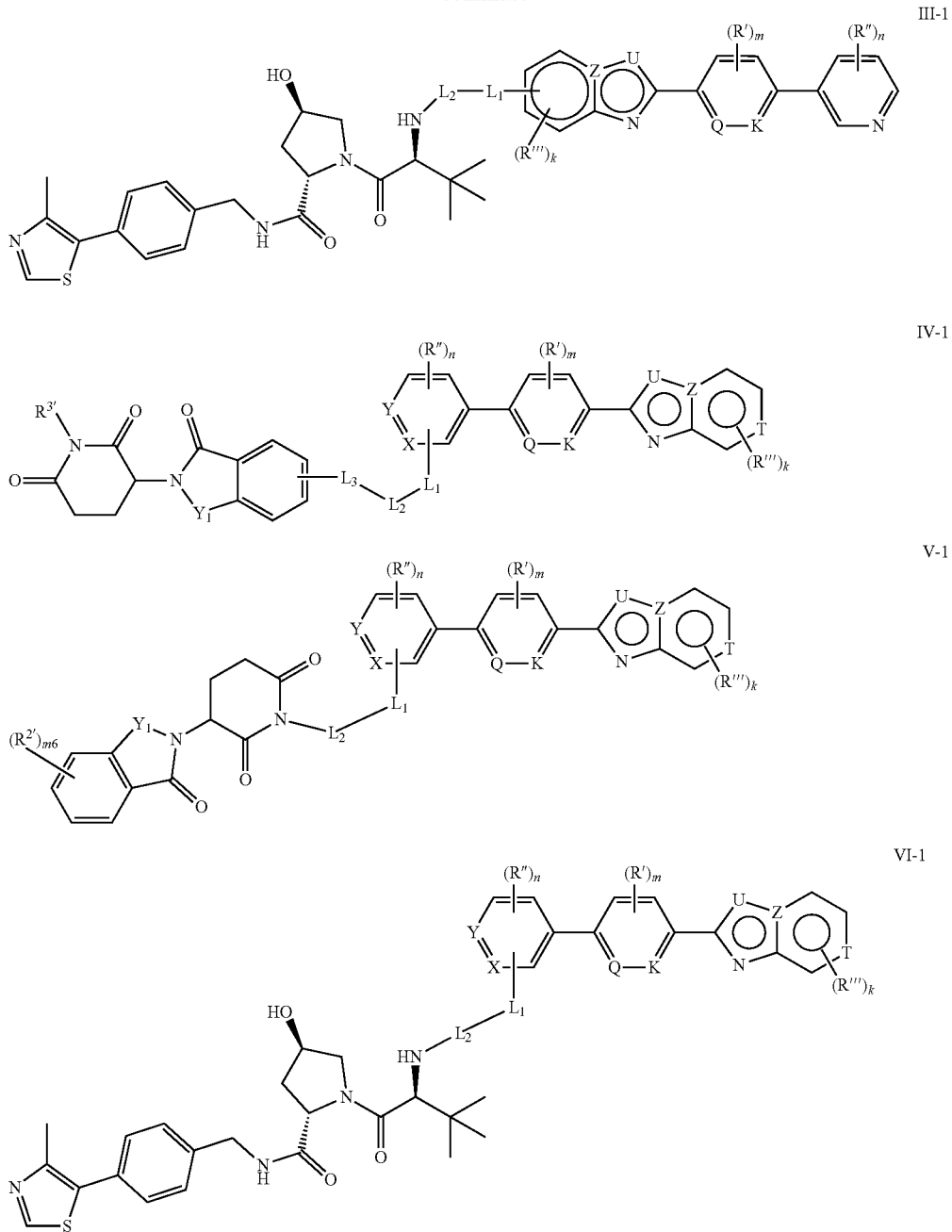

wherein, in Formula I-1, $R^{3'}$ is H or $C_{1-6}$ alkyl; $Y_1$ is $CH_2$ or

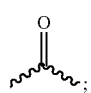;

$L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; where Z and U are not heteroatoms at the same time; Q is CH or N; K is CH or N; where Q and K are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; in Formula II-1, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

$L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; where Z and U are not heteroatoms at the same time; Q is CH or N; K is CH or N; where Q and K are not N at the same time; each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, NH$_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2;

in Formula III-1, $L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; where Z and U are not heteroatoms at the same time; Q is CH or N; K is CH or N; where Q and K are not N at the same time; each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, NH$_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2;

in Formula IV-1, $R^{3'}$ is H or $C_{1-6}$ alkyl; $Y_1$ is CH$_2$ or

$L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; T is CH or N; where only one of U, Z and T is heteroatom; Q is CH or N; K is CH or N; where Q and K are not N at the same time; each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, NH$_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; X is CR$^6$ or N; Y is CR$^6$ or N; where one of X and Y is N, while the other is CR$^6$; R$^6$ is independently selected from the group consisting of H, NH$_2$, $C_{1-6}$ alkyl and $C_{1-6}$ alkoxy, wherein NH$_2$, $C_{1-6}$ alkyl or $C_{1-6}$ alkoxy is optionally substituted by 1 to 3 of $C_{1-3}$ alkyl, $C_{3-6}$ cycloalkyl and/or halo; in Formula V-1, each occurrence of R'' is independently selected from the group consisting of H, OH, $C_{1-6}$ alkyl, $C_{1-6}$ alkoxy, $C_{1-6}$ alkylamino and NH$_2$; m6 is 0, 1, 2, 3 or 4; $Y_1$ is CH$_2$ or

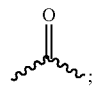

$L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; T is CH or N; where only one of U, Z and T is heteroatom; Q is CH or N; K is CH or N; where Q and K are not N at the same time; each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3; each occurrence of R'' is independently selected from the group consisting of H, NH$_2$, $C_{1-6}$ alkyl and $C_{1-6}$ alkoxy, wherein NH$_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula VI-1, $L_1$ is a bond, —C(=O)—, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; T is CH or N; where only one of U, Z and T is heteroatom; Q is CH or N; K is CH or N; where Q and K are not N at the same time; each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; X is $CR^6$ or N; Y is $CR^6$ or N; where one of X and Y is N, while the other is $CR^6$; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo.

In certain embodiments, the compound of Formula I-1 is of the following Formula 1, 5, 6, 8, 10 or 13,

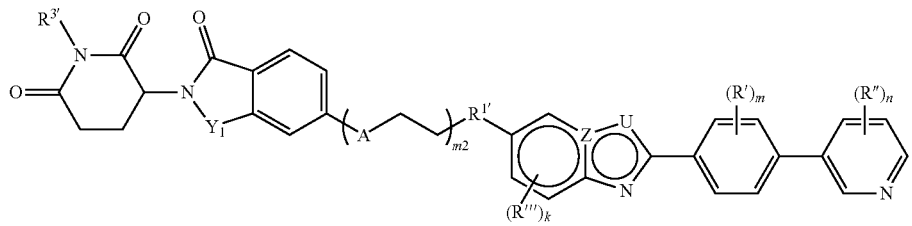

Formula 1

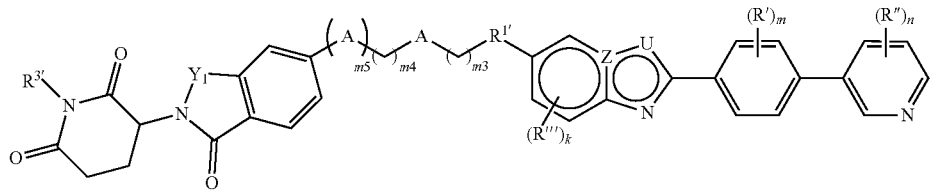

Formula 5

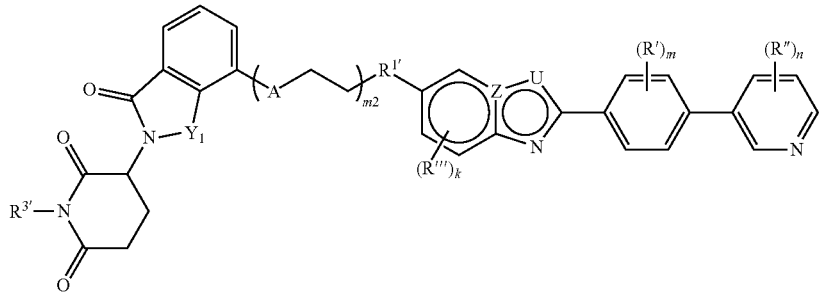

Formula 6

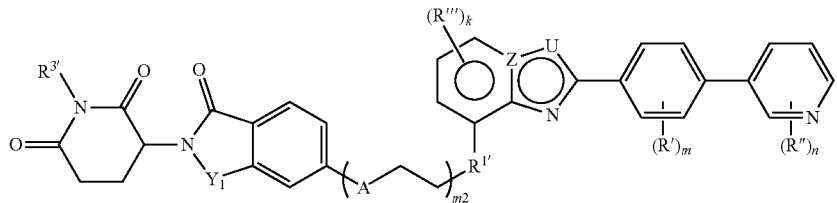

Formula 8

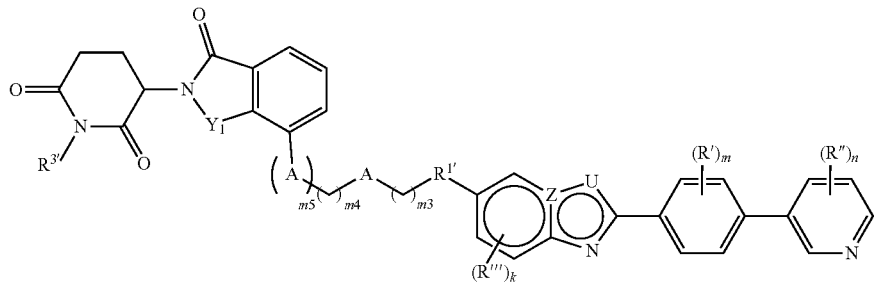

Formula 10

-continued

Formula 13

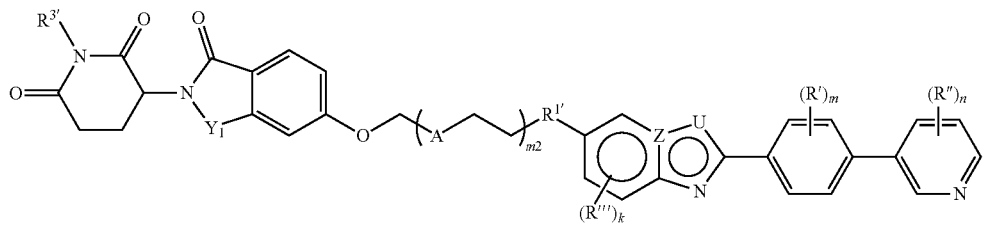

wherein
each A is independently O, NH,

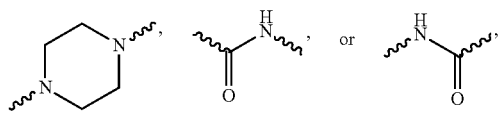

m2 is 1, 2, 3, 4, 5, 6, or 7;
m3 is 1, 2, 3, 4, 5, or 6;
m4 is 0, 1, 2, or 3;
m5 is 0, 1, 2, or 3; and
$R^{1'}$ is O, NH,

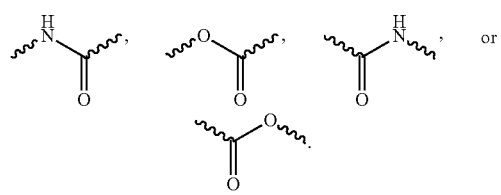

An embodiment of the disclosure is the compound of Formula 1, wherein R' is H, $C_{1-3}$ haloalkyl or $C_{1-3}$ alkoxy, preferably H, $CF_3$, $CCl_3$, methoxy or ethoxy, more preferably H, $CF_3$ or methoxy.

An embodiment of the disclosure is the compound of Formula 1, wherein m is 0, 1, 2, 3 or 4, preferably 0 or 1.

An embodiment of the disclosure is the compound of Formula 1, wherein R" is H, halo, OH, $NH_2$, $C_{1-3}$ alkoxy, $C_{1-3}$ alkylamino, $C_{3-5}$ cycloalkyl, $C_{3-5}$ cycloalkylamino and $C_{3-5}$ heterocycloalkyl, preferably H, F, Cl, $NH_2$, methoxy, ethoxy, methylamino, dimethylamino, ethylamino, diethylamino, cyclopropyl, cyclobutyl or cyclopentyl, more preferably H, F, dimethylamino or cyclopropyl.

An embodiment of the disclosure is the compound of Formula 1, wherein n is 0, 1 or 2, preferably 0 or 1.

An embodiment of the disclosure is the compound of Formula 1, wherein R''' is H, OH or halogen, preferably H, OH, F or Cl, more preferably H.

An embodiment of the disclosure is the compound of Formula 1, wherein k is 0, 1, 2 or 3, preferably 0 or 1.

An embodiment of the disclosure is the compound of Formula 1, wherein $R^{1'}$ is O, NH,

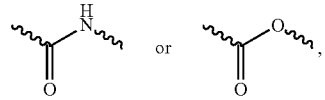

An embodiment of the disclosure is the compound of Formula 1, wherein $R^{1'}$ is O, NH,

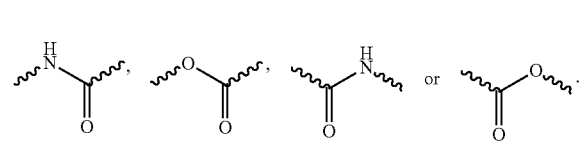

An embodiment of the disclosure is the compound of Formula 1, wherein A is O, NH,

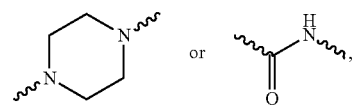

preferably O or

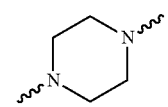

An embodiment of the disclosure is the compound of Formula 1, wherein m2 is 2, 3, 4 or 6, preferably 2 or 6.

An embodiment of the disclosure is the compound of Formula 1, wherein $R^{3'}$ is H or $C_{1-3}$ alkyl, preferably H or methyl, more preferably H.

An embodiment of the disclosure is the compound of Formula 1 having the structure as shown in Formula 1-1, Formula 1-1

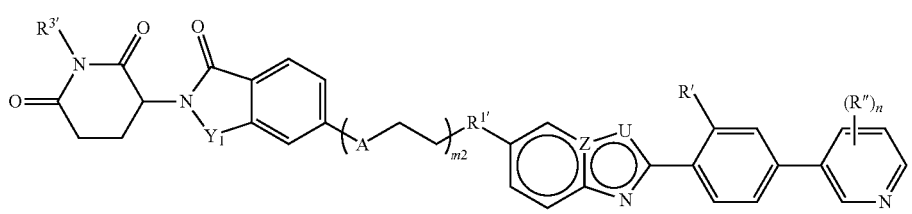

In Formula 1-1, $R^{3'}$ is H or $C_{1-3}$ alkyl; $Y_1$ is $CH_2$ or

;

A is O, NH,

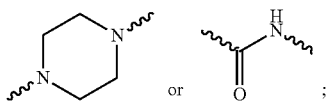

m2 is 1, 2, 3, 4, 5, 6 and 7; $R^{1'}$ is O, NH,

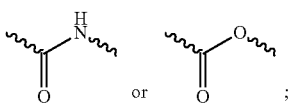;

U is O, S or CH; Z is C or N; where U and Z are not heteroatoms at the same time; R' is H, $C_{1-3}$ haloalkyl or $C_{1-3}$ alkoxy; R" is H, F, Cl, OH, $NH_2$, $C_{1-3}$ alkoxy, methylamino, dimethylamino, diethylamino or cyclopropylamino; n is 0, 1 or 2.

An embodiment of the disclosure is the compound of Formula 1-1, wherein m2 is 2, 3, 4 or 6, preferably 2 or 6.

An embodiment of the disclosure is the compound of Formula 1-1, wherein $R^{3'}$ is H or methyl.

An embodiment of the disclosure is the compound of Formula 1-1, wherein A is O or

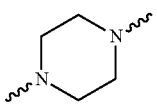.

An embodiment of the disclosure is the compound of Formula 1-1, wherein $R^{1'}$ is O, NH or

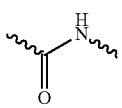.

An embodiment of the disclosure is the compound of Formula 1-1, wherein $R^{1'}$ is O, NH,

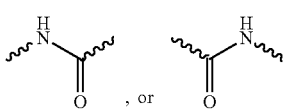.

An embodiment of the disclosure is the compound of Formula 1-1, wherein Z is N, U is CH.

An embodiment of the disclosure is the compound of Formula 1-1, wherein Z is C, U is S or O.

An embodiment of the disclosure is the compound of Formula 1-1, wherein R" is H, F, Cl, OH, $NH_2$, methoxy, methylamino, dimethylamino, diethylamino, cyclopropyl or cyclopropylamino, preferably H, F, methylamino, dimethylamino or cyclopropylamino.

An embodiment of the disclosure is the compound of Formula 1-1, wherein R' is H, $C_{1-3}$ fluoroalkyl, methoxy or ethoxy, preferably R' is H, methoxy or $CF_3$.

An embodiment of the disclosure is the compound of Formula 5, wherein $R^{3'}$ is H or $C_{1-3}$ alkyl, preferably H or methyl.

An embodiment of the disclosure is the compound of Formula 5, wherein A is O, NH or

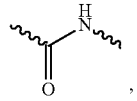, preferably O. An embodiment of the disclosure is the compound of Formula 5, wherein each A is independently O, NH,

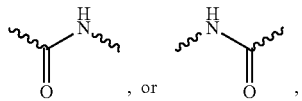,

An embodiment of the disclosure is the compound of Formula 5, wherein m4 is 0, 1, 2, or 3, preferably 0 or 3.

An embodiment of the disclosure is the compound of Formula 5, wherein m5 is 0, 1, 2 or 3, preferably 0 or 1.

An embodiment of the disclosure is the compound of Formula 5, wherein m3 is 1, 2, 3, 4, 5 or 6, preferably 3 or 5.

An embodiment of the disclosure is the compound of Formula 5, wherein $R^{1'}$ is O, NH or

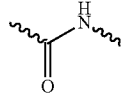.

An embodiment of the disclosure is the compound of Formula 5, wherein R'" is H, OH, $C_{1-3}$ alkyl, $C_{1-3}$ alkoxy or halogen, preferably H, methyl, methoxy or F, more preferably H.

An embodiment of the disclosure is the compound of Formula 5, wherein k is 0, 1, 2 or 3, preferably 0 or 1.

An embodiment of the disclosure is the compound of Formula 5, wherein Z is C, U is O or S.

An embodiment of the disclosure is the compound of Formula 5, wherein Z is N, U is CH.

An embodiment of the disclosure is the compound of Formula 5, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 5, wherein m is 0, 1, 2 or 3, preferably 0 or 1.

An embodiment of the disclosure is the compound of Formula 5, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, cyclopropyl or dimethylamino, more preferably H, F, $CF_3$, cyclopropyl, cyclopropylamino or dimethylamino.

An embodiment of the disclosure is the compound of Formula 5, wherein n is 0, 1 or 2, preferably 0 or 1.

An embodiment of the disclosure is the compound of Formula 5 having the structure as shown in Formula 5-1, Formula 5-1

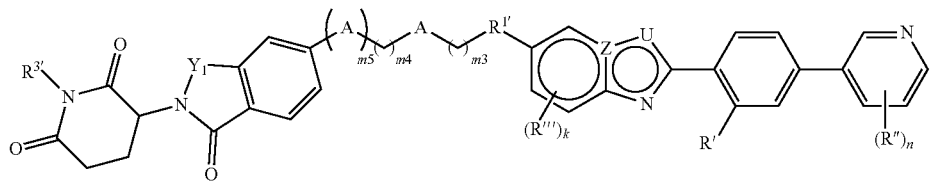

In Formula 5-1, R$^{3'}$ is H or C$_{1-3}$ alkyl; Y$_1$ is CH$_2$ or

A is O, NH,

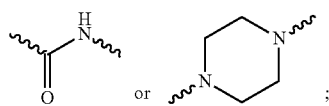

m5 is 0 or 1; m4 is 0, 1, 2, 3 or 4; m3 is 1, 2, 3, 4, 5 or 6; R$^{1'}$ is O, NH,

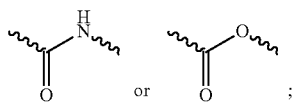

Z is C or N; U is O, S or CH; where Z and U are not heteroatoms at the same time; R''' is H, OH, C$_{1-3}$ alkyl, C$_{1-3}$ alkoxy or halogen; R' is H, halogen, OH, C$_{1-3}$ alkyl, C$_{1-3}$ haloalkyl or C$_{1-3}$ alkoxy; R'' is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino and C$_{3-5}$ heterocycloalkyl; n is 0, 1 or 2.

An embodiment of the disclosure is the compound of Formula 5-1, wherein A is O.

An embodiment of the disclosure is the compound of Formula 5-1, wherein m5 is 0 or 1.

An embodiment of the disclosure is the compound of Formula 5-1, wherein m4 is 0 or 3.

An embodiment of the disclosure is the compound of Formula 5-1, wherein m3 is 3, 5.

An embodiment of the disclosure is the compound of Formula 5-1, wherein R$^{1'}$ is O, NH or

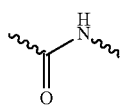

An embodiment of the disclosure is the compound of Formula 5-1, wherein Z is C, U is O or S.

An embodiment of the disclosure is the compound of Formula 5-1, wherein Z is N, U is CH.

An embodiment of the disclosure is the compound of Formula 5-1, wherein R' is H, halogen, C$_{1-3}$ alkyl, C$_{1-3}$ fluoroalkyl or C$_{1-3}$ alkoxy, preferably H, methyl, CF$_3$, methyl or methoxy, more preferably H or CF$_3$.

An embodiment of the disclosure is the compound of Formula 5-1, wherein R'' is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, CF$_3$, amino, methylamino, dimethylamino, cyclopropyl or cyclopropylamino, more preferably H, F, CF$_3$, dimethylamino, cyclopropylamino or cyclopropyl.

An embodiment of the disclosure is the compound of Formula 6, wherein R$^{3'}$ is H or C$_{1-3}$ alkyl, preferably H or methyl.

An embodiment of the disclosure is the compound of Formula 6, wherein A is O, NH or

preferably O or NH.

An embodiment of the disclosure is the compound of Formula 6, wherein m2 is 1, 2, 3, 4, 5, 6 or 7, preferably 2 or 6.

An embodiment of the disclosure is the compound of Formula 6, wherein R$^{1'}$ is O, NH or

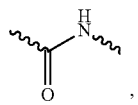

preferably O or NH.

An embodiment of the disclosure is the compound of Formula 6, wherein Z is C or N, and U is O, S or CH, where Z and U are not heteroatoms at the same time; preferably Z is C and U is S.

An embodiment of the disclosure is the compound of Formula 6, wherein R''' is H, OH, C$_{1-3}$ alkyl, C$_{1-3}$ alkoxy or halogen, preferably H, methyl, methoxy or F, more preferably H.

An embodiment of the disclosure is the compound of Formula 6, wherein R' is H, halogen, OH, C$_{1-3}$ alkyl, C$_{1-3}$ haloalkyl or C$_{1-3}$ alkoxy, preferably H, F, CF$_3$, CCl$_3$, methyl or methoxy, more preferably H or CF$_3$.

An embodiment of the disclosure is the compound of Formula 6, wherein m is 0, 1, 2 or 3, preferably 0 or 1.

An embodiment of the disclosure is the compound of Formula 6, wherein R" is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, OH, NH$_2$, methyl, methoxy, CF$_3$, CCl$_3$, methylamino, cyclopropyl, cyclopropylamino or dimethylamino, more preferably H, F, CF$_3$, dimethylamino, cyclopropyl or cyclopropylamino.

An embodiment of the disclosure is the compound of Formula 6, wherein n is 0 or 1.

An embodiment of the disclosure is the compound of Formula 6 having the structure as shown in Formula 6-1,

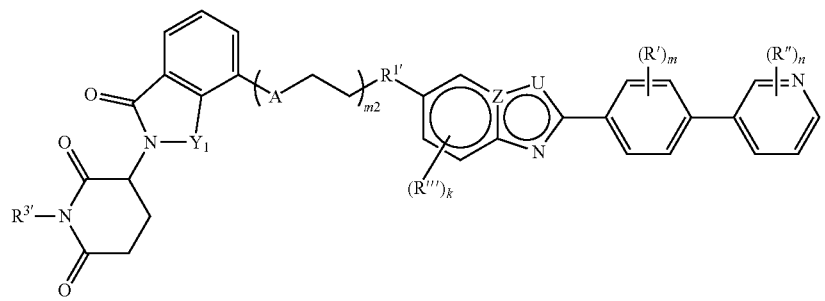

Formula 6-1

In Formula 6-1, R$^{3'}$ is H or C$_{1-3}$ alkyl; Y$_1$ is CH$_2$ or

A is O, NH,

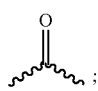

m2 is 1, 2, 3, 4, 5, 6 or 7; R$^{1'}$ is O, NH,

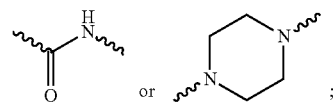

or

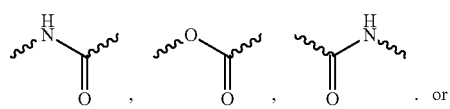

R'" is H, OH, C$_{1-3}$ alkyl, C$_{1-3}$ alkoxy or halogen; k is 0, 1, 2 or 3; Z is C or N; U is O, S or CH; where Z and U are not heteroatoms at the same time; R' is H, halogen, OH, C$_{1-3}$ alkyl, C$_{1-3}$ haloalkyl or C$_{1-3}$ alkoxy; m is 0, 1, 2 or 3; R" is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl; n is 0, 1 or 2.

In some embodiments of Formula 6-1, R$^{3'}$ is H or C$_{1-3}$ alkyl; Y$_1$ is CH$_2$ or

A is O, NH,

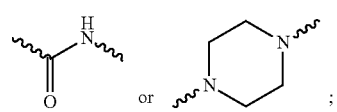

m2 is 1, 2, 3, 4, 5, 6 or 7; R$^{1'}$ is O, NH,

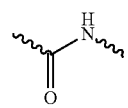

or

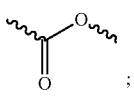

R'" is H, OH, C$_{1-3}$ alkyl, C$_{1-3}$ alkoxy or halogen; k is 0, 1, 2 or 3; Z is C or N; U is O, S or CH; where Z and U are not heteroatoms at the same time; R' is H, halogen, OH, C$_{1-3}$ alkyl, C$_{1-3}$ haloalkyl or C$_{1-3}$ alkoxy; m is 0, 1, 2 or 3; R" is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl; n is 0, 1 or 2.

An embodiment of the disclosure is the compound of Formula 6-1, wherein R$^{3'}$ is H or methyl.

An embodiment of the disclosure is the compound of Formula 6-1, wherein A is O or NH.

An embodiment of the disclosure is the compound of Formula 6-1, wherein m2 is 2 or 6.

An embodiment of the disclosure is the compound of Formula 6-1, wherein R$^{1'}$ is O, or NH.

An embodiment of the disclosure is the compound of Formula 6-1, wherein R' is H or CF$_3$.

An embodiment of the disclosure is the compound of Formula 6-1, wherein m is 0, 1, 2 or 3, preferably 0 or 1.

An embodiment of the disclosure is the compound of Formula 6-1, wherein R" is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, CF$_3$, methoxy, methyl, dimethylamino, cyclopropyl, cyclopropylamino or methylamino, more preferably H, CF$_3$, F, dimethylamino, cyclopropyl or cyclopropylamino, most preferably H, dimethylamino, cyclopropyl or cyclopropylamino.

An embodiment of the disclosure is the compound of Formula 6-1, wherein n is 0 or 1.

An embodiment of the disclosure is the compound of Formula 6-1, wherein R" substitutes at the adjacent position to the N atom.

An embodiment of the disclosure is the compound of Formula 8, wherein R$^{3'}$ is H or C$_{1-3}$ alkyl, preferably H or methyl.

An embodiment of the disclosure is the compound of Formula 8, wherein Y$_1$ is CH$_2$ or

, preferably CH$_2$.

An embodiment of the disclosure is the compound of Formula 8, wherein A is O, NH,

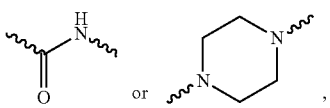, preferably O.

An embodiment of the disclosure is the compound of Formula 8, wherein m2 is 1, 2, 3 or 4, preferably 2.

An embodiment of the disclosure is the compound of Formula 8, wherein R$^{1'}$ is O, NH,

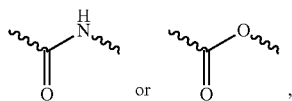, preferably O.

An embodiment of the disclosure is the compound of Formula 8, wherein R'" is H, OH, C$_{1-3}$ alkyl, C$_{1-3}$ alkoxy or halogen, preferably H, methyl, methoxy or F, more preferably H.

An embodiment of the disclosure is the compound of Formula 8, wherein k is 0 or 1.

An embodiment of the disclosure is the compound of Formula 8, wherein Z is C or N; U is O, S or CH; where Z and U are not heteroatoms at the same time; preferably Z is N and U is CH; preferably Z is C and U is S.

An embodiment of the disclosure is the compound of Formula 8, wherein R' is H, halogen, OH, C$_{1-3}$ alkyl, C$_{1-3}$ haloalkyl or C$_{1-3}$ alkoxy, preferably H, F, CF$_3$, CCl$_3$, methyl or methoxy, more preferably H or CF$_3$.

An embodiment of the disclosure is the compound of Formula 8, wherein m is 0, 1 or 2.

An embodiment of the disclosure is the compound of Formula 8, wherein R" is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, OH, NH$_2$, methyl, methoxy, CF$_3$, CCl$_3$, methylamino, dimethylamino, cyclopropyl or cyclopropylamino, more preferably H, F, CF$_3$, cyclopropyl or cyclopropylamino.

An embodiment of the disclosure is the compound of Formula 8, wherein n is 0, 1 or 2.

An embodiment of the disclosure is the compound of Formula 10, wherein R$^{3'}$ is H or C$_{1-3}$ alkyl, preferably H or methyl.

An embodiment of the disclosure is the compound of Formula 10, wherein Y$_1$ is CH$_2$ or

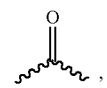, preferably CH$_2$.

An embodiment of the disclosure is the compound of Formula 10, wherein each A is independently O, NH,

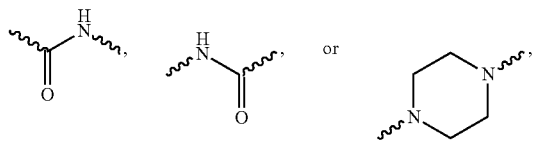

An embodiment of the disclosure is the compound of Formula 10, wherein A is O, NH,

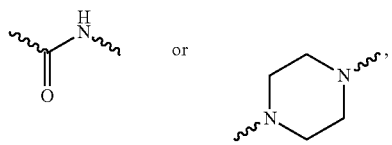

preferably

.

An embodiment of the disclosure is the compound of Formula 10, wherein m5 is 0 or 1.

An embodiment of the disclosure is the compound of Formula 10, wherein m4 is 0 or 1.

An embodiment of the disclosure is the compound of Formula 10, wherein m3 is 1, 2, 3, 4 or 5, preferably 4.

An embodiment of the disclosure is the compound of Formula 10, wherein R$^{1'}$ is O, NH,

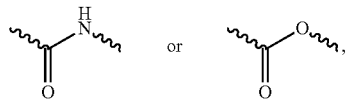

preferably O.

An embodiment of the disclosure is the compound of Formula 10, wherein R''' is H, OH, $C_{1-3}$ alkyl, $C_{1-3}$ alkoxy or halogen, preferably H, methyl, methoxy or F, more preferably H.

An embodiment of the disclosure is the compound of Formula 10, wherein k is 0 or 1.

An embodiment of the disclosure is the compound of Formula 10, wherein Z is C, U is S or O.

An embodiment of the disclosure is the compound of Formula 10, wherein Z is N, U is CH.

An embodiment of the disclosure is the compound of Formula 10, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 10, wherein m is 0 or 1.

An embodiment of the disclosure is the compound of Formula 10, wherein R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, cyclopropyl, cyclopropylamino or dimethylamino, more preferably H, F or $CF_3$.

An embodiment of the disclosure is the compound of Formula 10, wherein n is 0 or 1.

An embodiment of the disclosure is the compound of Formula 13, wherein $R^{3'}$ is H or $C_{1-3}$ alkyl, preferably H or methyl.

An embodiment of the disclosure is the compound of Formula 13, wherein $Y_1$ is $CH_2$ or

preferably $CH_2$.

An embodiment of the disclosure is the compound of Formula 13, wherein A is O,

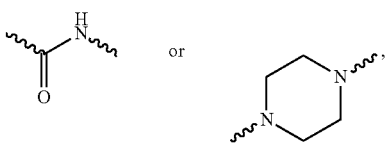

preferably

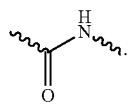

An embodiment of the disclosure is the compound of Formula 13, wherein m2 is 1, 2, 3 or 4, preferably 1.

An embodiment of the disclosure is the compound of Formula 13, wherein $R^{1'}$ is O, NH,

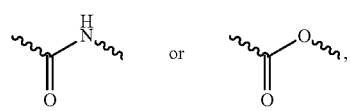

preferably NH.

An embodiment of the disclosure is the compound of Formula 13, wherein R''' is H, OH, $C_{1-3}$ alkyl, $C_{1-3}$ alkoxy or halogen, preferably H, methyl, methoxy or F, more preferably H.

An embodiment of the disclosure is the compound of Formula 13, wherein k is 0, 1, 2 or 3, preferably 0 or 1.

An embodiment of the disclosure is the compound of Formula 13, wherein Z is C, U is S or O.

An embodiment of the disclosure is the compound of Formula 13, wherein Z is N, U is CH.

An embodiment of the disclosure is the compound of Formula 13, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 13, wherein m is 0, 1, 2 or 3, preferably 0 or 1.

An embodiment of the disclosure is the compound of Formula 13, wherein R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, cyclopropyl, cyclopropylamino or dimethylamino, more preferably H, F, $CF_3$, dimethylamino, cyclopropyl or cyclopropylamino, most preferably dimethylamino.

An embodiment of the disclosure is the compound of Formula 13, wherein n is 0, 1 or 2, preferably 0 or 1.

An embodiment of the compound of Formula II-1 is of the following Formula 3,

Formula 3

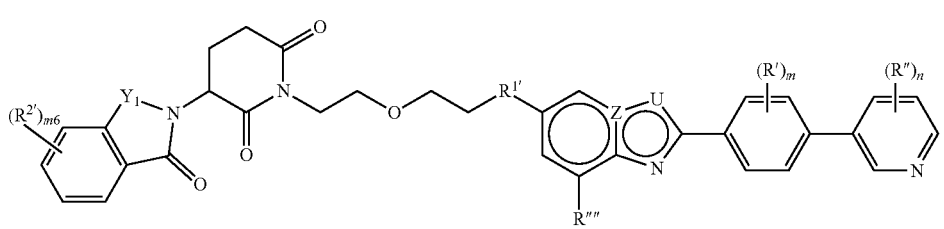

wherein $R^{1'}$ is O, NH,

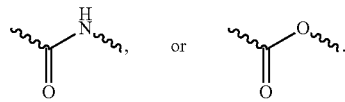

An embodiment of the disclosure is the compound of Formula 3, wherein $R^{2'}$ is H, OH, $C_{1-3}$ alkyl, $C_{1-3}$ alkoxy, $C_{1-3}$ alkylamino or $NH_2$, preferably H, OH or $NH_2$.

An embodiment of the disclosure is the compound of Formula 3, wherein m6 is 0, 1, 2 or 3, preferably 0 or 1.

An embodiment of the disclosure is the compound of Formula 3, wherein $R^{1'}$ is O or NH.

An embodiment of the disclosure is the compound of Formula 3, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 3, wherein m is 0, 1, 2, 3 or 4, preferably 0 or 1.

An embodiment of the disclosure is the compound of Formula 3, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 3, wherein n is 0, 1, 2 or 3, preferably 0, 1 or 2.

An embodiment of the disclosure is the compound of Formula 3, wherein Z is C, U is O or S.

An embodiment of the disclosure is the compound of Formula 3, wherein Z is N, U is CH.

An embodiment of the disclosure is the compound of Formula 3, wherein R'" is H, OH, $C_{1-3}$ alkyl, $C_{1-3}$ alkoxy or halogen, preferably H, F, methyl or methoxy, more preferably H.

An embodiment of the disclosure is the compound of Formula 3 having the structure as shown in Formula 3-1, wherein $R^{2'}$ is H, OH, $C_{1-3}$ alkyl, $C_{1-3}$ alkoxy, $C_{1-3}$ alkylamino or $NH_2$; m6 is 0, 1, 2 or 3; $Y_1$ is $CH_2$ or

$R^{1'}$ is O, NH,

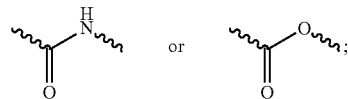

Z is C or N; U is O, S or CH; where Z and U are not heteroatoms at the same time; R" is H, halo, OH, $NH_2$, $C_{1-3}$ alkoxy, $C_{1-3}$ haloalkyl, $C_{3-5}$ cycloalkyl, $C_{3-5}$ cycloalkylamino or $C_{1-3}$ alkylamino; n is 0, 1 or 2.

An embodiment of the disclosure is the compound of Formula 3-1, wherein $R^{2'}$ is H, $NH_2$ or OH.

An embodiment of the disclosure is the compound of Formula 3-1, wherein m6 is 0 or 1.

An embodiment of the disclosure is the compound of Formula 3-1, wherein when m6 is 1, $R^{2'}$ is substituted at the following position in the phenyl:

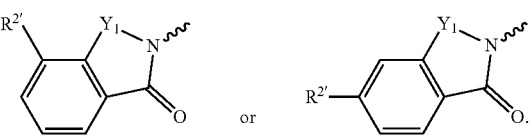

An embodiment of the disclosure is the compound of Formula 3-1, wherein $R^{1'}$ is O or NH.

An embodiment of the disclosure is the compound of Formula 3-1, wherein R" is F, dimethylamino, methylamino, cyclopropyl or cyclopropylamino.

An embodiment of the disclosure is the compound of Formula 3-1, wherein n is 0, 1, or 2.

An embodiment of the compound of Formula III-1 is of the following Formula 15,

Formula 3-1

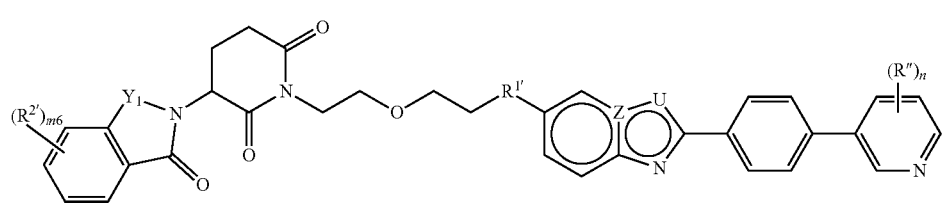

Formula 15

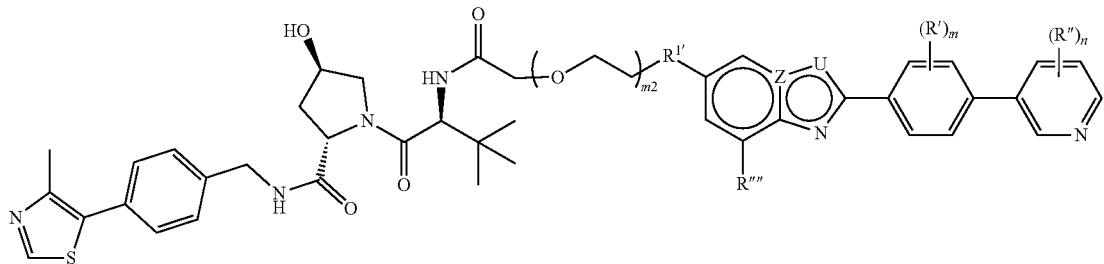

wherein m2 is 1, 2, 3, 4, 5, 6, or 7; and R is O, NH,

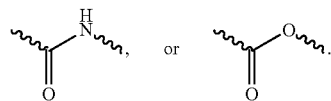

An embodiment of the disclosure is the compound of Formula 15, wherein m2 is 1, 2, 3, 4, 5, 6 or 7, preferably 1, 2, 3, 4, 5 or 6, more preferably 2 or 5.

An embodiment of the disclosure is the compound of Formula 15, wherein $R^{1'}$ is O, NH,

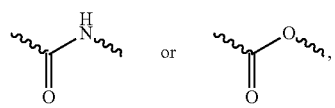

preferably O or NH.

An embodiment of the disclosure is the compound of Formula 15, wherein R''' is H, OH, $C_{1-3}$ alkyl, $C_{1-3}$ alkoxy or halogen, preferably H, F, methyl or methoxy, more preferably H.

An embodiment of the disclosure is the compound of Formula 15, wherein Z is C, U is O or S.

An embodiment of the disclosure is the compound of Formula 15, wherein Z is N, U is CH.

An embodiment of the disclosure is the compound of Formula 15, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H, $CF_3$ or F.

An embodiment of the disclosure is the compound of Formula 15, wherein m is 0, 1, 2 or 3, preferably 0, 1 or 2, more preferably 0 or 1.

An embodiment of the disclosure is the compound of Formula 15, wherein R'' is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F, methylamino, cyclopropylamino or dimethylamino, most preferably H or dimethylamino.

An embodiment of the disclosure is the compound of Formula 15, wherein n is 0, 1 or 2, preferably 0 or 1.

An embodiment of the compound of Formula IV-1 is of the following Formula 2, 7, 9, 11, 12 or 14, Formula 2

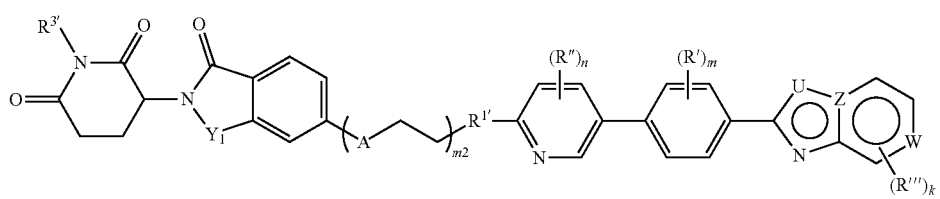

Formula 7

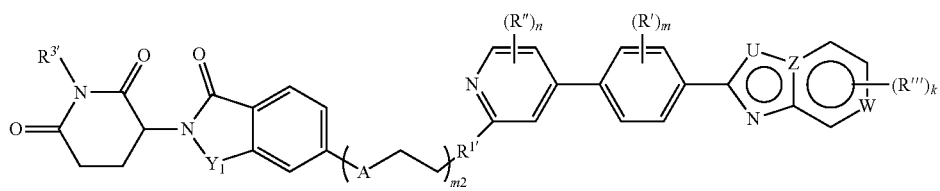

-continued
Formula 9
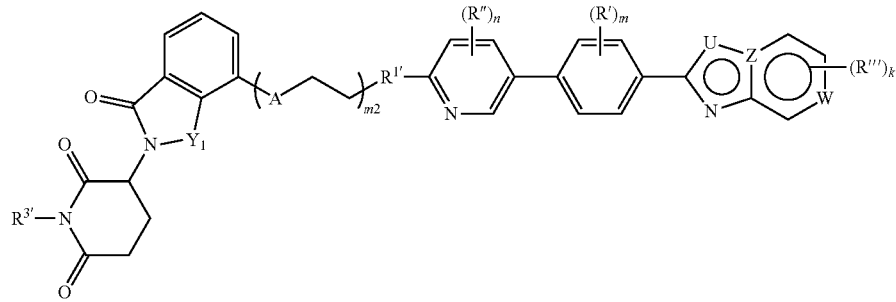
Formula 11
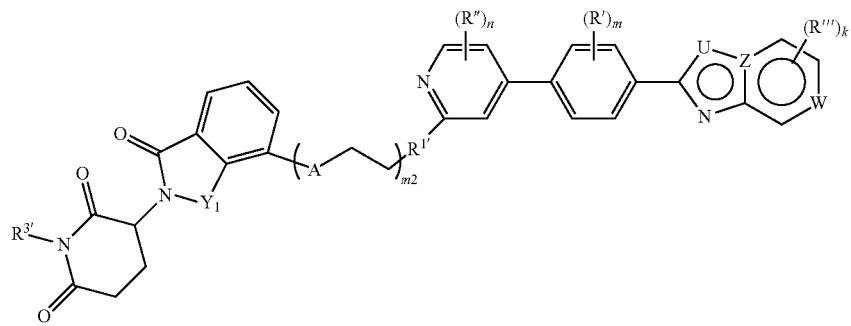
Formula 12
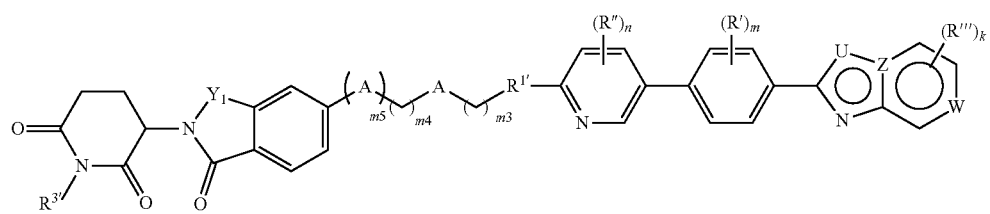
Formula 14
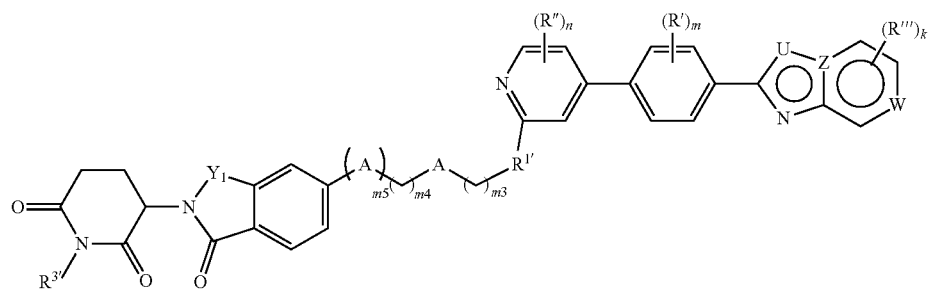
wherein
each A is independently O, NH,
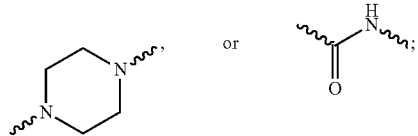 or 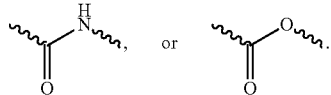.
m2 is 2, 3, 4, 5, or 6;
m3 is 1, 2, 3, 4, 5, or 6;
m4 is 0, 1, 2, 3, or 4;
m5 is 0, 1, 2, or 3; and
$R^{1'}$ is O, NH,
An embodiment of the disclosure is the compound of Formula 2, wherein $R^{3'}$ is H or $C_{1-3}$ alkyl, preferably H or methyl.
An embodiment of the disclosure is the compound of Formula 2, wherein $Y_1$ is $CH_2$ or
.

An embodiment of the disclosure is the compound of Formula 2, wherein A is O, NH,

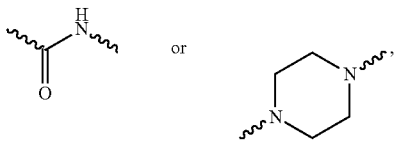 or preferably O.

An embodiment of the disclosure is the compound of Formula 2, wherein m2 is 2, 3, 4, 5 or 6, preferably 2 or 6.

An embodiment of the disclosure is the compound of Formula 2, wherein $R^{1'}$ is O, NH,

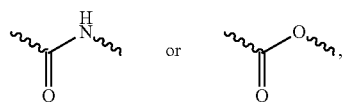

preferably NH.

An embodiment of the disclosure is the compound of Formula 2, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 2, wherein n is 0, 1 or 2, preferably 0 or 1.

An embodiment of the disclosure is the compound of Formula 2, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 2, wherein m is 0, 1, 2 or 3, preferably 0, 1 or 2.

An embodiment of the disclosure is the compound of Formula 2, wherein Z is C, U is O or S, W is CH.

An embodiment of the disclosure is the compound of Formula 2, wherein Z is N, U is CH, W is CH.

An embodiment of the disclosure is the compound of Formula 2, wherein Z is C, W is N, U is CH.

An embodiment of the disclosure is the compound of Formula 2, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 2, wherein k is 0, 1, 2 or 3, preferably 0, 1 or 2, more preferably 0 or 1.

An embodiment of the disclosure is the compound of Formula 7, wherein $R^{3'}$ is H or $C_{1-3}$ alkyl, preferably H or methyl.

An embodiment of the disclosure is the compound of Formula 7, wherein $Y_1$ is $CH_2$ or

An embodiment of the disclosure is the compound of Formula 7, wherein A is O, NH,

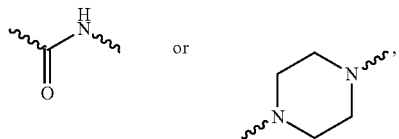 or preferably O.

An embodiment of the disclosure is the compound of Formula 7, wherein m2 is 2, 3, 4, 5 or 6, preferably 2 or 3.

An embodiment of the disclosure is the compound of Formula 7, wherein $R^{1'}$ is O, NH,

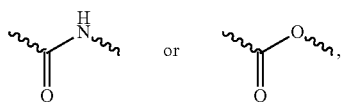

preferably NH.

An embodiment of the disclosure is the compound of Formula 7, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 7, wherein n is 0, 1, or 2, preferably 0 or 1.

An embodiment of the disclosure is the compound of Formula 7, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 7, wherein m is 0, 1, 2 or 3, preferably 0, 1 or 2.

An embodiment of the disclosure is the compound of Formula 7, wherein Z is C, U is O or S, W is CH.

An embodiment of the disclosure is the compound of Formula 7, wherein Z is N, U is CH, W is CH.

An embodiment of the disclosure is the compound of Formula 7, wherein Z is C, W is N, U is CH.

An embodiment of the disclosure is the compound of Formula 7, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 7, wherein k is 0, 1, 2 or 3, preferably 0, 1 or 2, more preferably 0 or 1.

An embodiment of the disclosure is the compound of Formula 9, wherein $R^{3'}$ is H or $C_{1-3}$ alkyl, preferably H or methyl.

An embodiment of the disclosure is the compound of Formula 9, wherein $Y_1$ is $CH_2$ or

An embodiment of the disclosure is the compound of Formula 9, wherein A is O, NH,

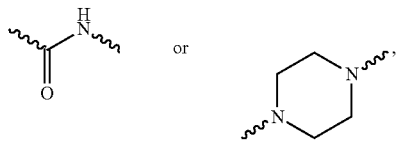 or preferably O.

An embodiment of the disclosure is the compound of Formula 9, wherein m2 is 2, 3, 4, 5 or 6, preferably 2 or 3.

An embodiment of the disclosure is the compound of Formula 9, wherein $R^{1'}$ is O, NH,

preferably NH.

An embodiment of the disclosure is the compound of Formula 9, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 9, wherein n is 0, 1, or 2, preferably 0 or 1.

An embodiment of the disclosure is the compound of Formula 9, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 9, wherein m is 0, 1, 2 or 3, preferably 0, 1 or 2.

An embodiment of the disclosure is the compound of Formula 9, wherein Z is C, U is O or S, W is CH.

An embodiment of the disclosure is the compound of Formula 9, wherein Z is N, U is CH, W is CH.

An embodiment of the disclosure is the compound of Formula 9, wherein Z is C, W is N, U is CH.

An embodiment of the disclosure is the compound of Formula 9, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 9, wherein k is 0, 1, 2 or 3, preferably 0, 1 or 2, more preferably 0 or 1.

An embodiment of the disclosure is the compound of Formula 11, wherein $R^{3'}$ is H or $C_{1-3}$ alkyl, preferably H or methyl.

An embodiment of the disclosure is the compound of Formula 11, wherein $Y_1$ is $CH_2$ or

An embodiment of the disclosure is the compound of Formula 11, wherein A is O, NH,

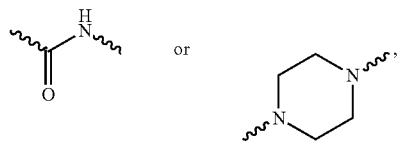 or preferably O.

An embodiment of the disclosure is the compound of Formula 11, wherein m2 is 2, 3, 4, 5 or 6, preferably 2 or 3.

An embodiment of the disclosure is the compound of Formula 11, wherein $R^{1'}$ is O, NH,

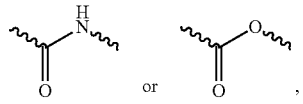

preferably NH.

An embodiment of the disclosure is the compound of Formula 11, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 11, wherein n is 0, 1 or 2, preferably 0 or 1.

An embodiment of the disclosure is the compound of Formula 11, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 11, wherein m is 0, 1, 2 or 3, preferably 0, 1 or 2.

An embodiment of the disclosure is the compound of Formula 11, wherein Z is C, U is O or S, W is CH.

An embodiment of the disclosure is the compound of Formula 11, wherein Z is N, U is CH, W is CH.

An embodiment of the disclosure is the compound of Formula 11, wherein Z is C, W is N, U is CH.

An embodiment of the disclosure is the compound of Formula 11, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 11, wherein k is 0, 1, 2 or 3, preferably 0, 1 or 2, more preferably 0 or 1.

An embodiment of the disclosure is the compound of Formula 12, wherein $R^{3'}$ is H or $C_{1-3}$ alkyl, preferably H or methyl.

An embodiment of the disclosure is the compound of Formula 12, wherein $Y_1$ is $CH_2$ or

preferably $CH_2$.

An embodiment of the disclosure is the compound of Formula 12, wherein each A is independently O, NH,

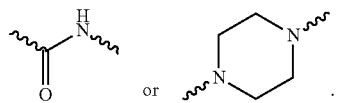

or

An embodiment of the disclosure is the compound of Formula 12, wherein A is O, NH,

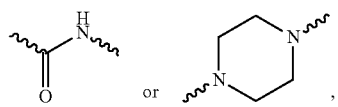

or, preferably O.

An embodiment of the disclosure is the compound of Formula 12, wherein m3 is 1, 2, 3, 4, 5 or 6, preferably 2 or 3.

An embodiment of the disclosure is the compound of Formula 12, wherein m4 is 0 or 1, 2 or 3, preferably 0 or 3.

An embodiment of the disclosure is the compound of Formula 12, wherein m5 is 0 or 1, 2 or 3, preferably 0 or 1.

An embodiment of the disclosure is the compound of Formula 12, wherein $R^{1'}$ is O, NH,

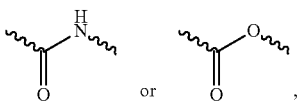

or, preferably NH.

An embodiment of the disclosure is the compound of Formula 12, wherein R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 12, wherein n is 0, 1 or 2, preferably 0 or 1.

An embodiment of the disclosure is the compound of Formula 12, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 12, wherein m is 0, 1 or 2, preferably 0, 1 or 2.

An embodiment of the disclosure is the compound of Formula 12, wherein Z is C, U is O or S, W is CH.

An embodiment of the disclosure is the compound of Formula 12, wherein Z is N, U is CH, W is CH.

An embodiment of the disclosure is the compound of Formula 12, wherein Z is C, W is N, U is CH.

An embodiment of the disclosure is the compound of Formula 12, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 12, wherein k is 0, 1, 2 or 3, preferably 0, 1 or 2, more preferably 0 or 1.

An embodiment of the disclosure is the compound of Formula 14, wherein $R^{3'}$ is H or $C_{1-3}$ alkyl, preferably H or methyl.

An embodiment of the disclosure is the compound of Formula 14, wherein $Y_1$ is $CH_2$ or

, preferably $CH_2$.

An embodiment of the disclosure is the compound of Formula 14, wherein each A is independently O, NH,

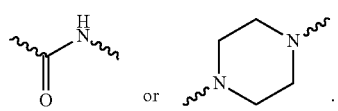

or.

An embodiment of the disclosure is the compound of Formula 14, wherein A is O, NH,

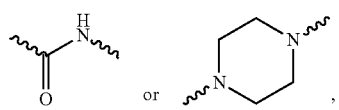

or, preferably O.

An embodiment of the disclosure is the compound of Formula 14, wherein m3 is 1, 2, 3, 4, 5 or 6, preferably 2, 3 or 4.

An embodiment of the disclosure is the compound of Formula 14, wherein m4 is 0, 1, 2, 3 or 4, preferably 0 or 3.

An embodiment of the disclosure is the compound of Formula 14, wherein m5 is 0 or 1, 2 or 3, preferably 0 or 1.

An embodiment of the disclosure is the compound of Formula 14, wherein $R^{1'}$ is O, NH,

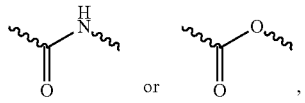

or, preferably

O

An embodiment of the disclosure is the compound of Formula 14, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 14, wherein n is 0, 1, or 2, preferably 0 or 1.

An embodiment of the disclosure is the compound of Formula 14, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 14, wherein m is 0, 1, 2 or 3, preferably 0, 1 or 2.

An embodiment of the disclosure is the compound of Formula 14, wherein Z is C, U is O or S, W is CH.

An embodiment of the disclosure is the compound of Formula 14, wherein Z is N, U is CH, W is CH.

An embodiment of the disclosure is the compound of Formula 14, wherein Z is C, W is N, U is CH.

An embodiment of the disclosure is the compound of Formula 14, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 14, wherein k is 0, 1, 2 or 3, preferably 0, 1 or 2, more preferably 0 or 1.

An embodiment of the compound of Formula V-1 is of the following Formula 4, wherein $R^{1'}$ is O, NH,

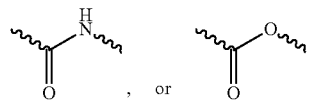

An embodiment of the disclosure is the compound of Formula 4, wherein $R^2$ is H, OH, $C_{1-3}$ alkyl, $C_{1-3}$ alkoxy, $C_{1-3}$ alkylamino or $NH_2$, preferably H, OH or $NH_2$.

An embodiment of the disclosure is the compound of Formula 4, wherein m6 is 0, 1, 2 or 3, preferably 0 or 1.

An embodiment of the disclosure is the compound of Formula 4, wherein $R^{1'}$ is O, NH,

preferably O or NH.

An embodiment of the disclosure is the compound of Formula 4, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 4, wherein m is 0, 1, 2, 3 or 4, preferably 0 or 1.

An embodiment of the disclosure is the compound of Formula 4, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 4, wherein n is 0, 1, or 2, preferably 0 or 1.

An embodiment of the disclosure is the compound of Formula 4, wherein Z is C, U is O or S, W is CH.

An embodiment of the disclosure is the compound of Formula 4, wherein Z is N, U is CH, W is CH.

An embodiment of the disclosure is the compound of Formula 4, wherein Z is C, U is CH, W is N.

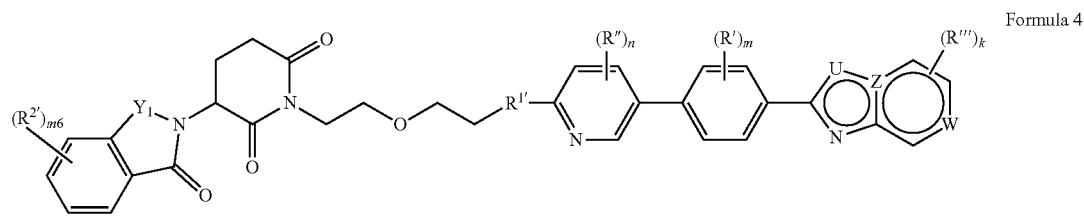

Formula 4

An embodiment of the disclosure is the compound of Formula 4, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 4, wherein k is 0, 1, 2 or 3, preferably 0, 1 or 2, more preferably 0 or 1.

An embodiment of the disclosure is the compound of Formula 4 having the structure as shown in Formula 4-1,

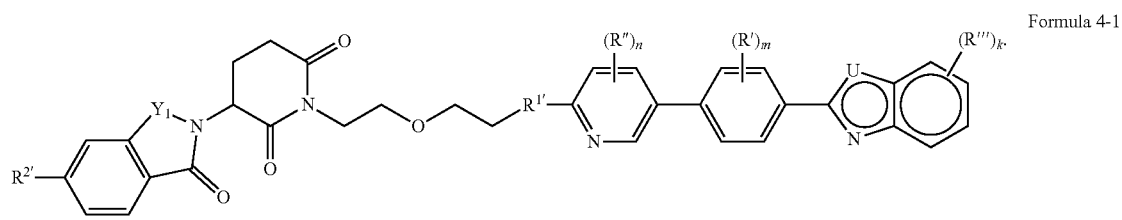

Formula 4-1

In Formula 4-1, $R^2$ is H, OH, $C_{1-3}$ alkyl, $C_{1-3}$ alkoxy, $C_{1-3}$ alkylamino or $NH_2$; $Y_1$ is $CH_2$ or

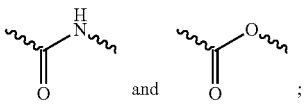

$R^{1'}$ is O, NH,

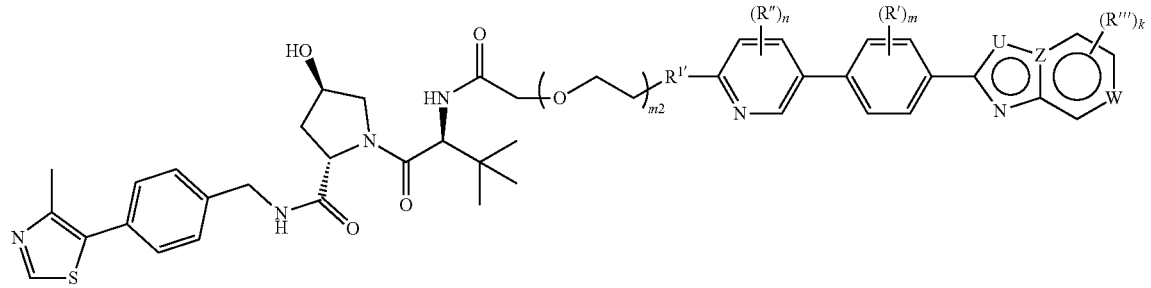

R'' is H, halo, OH, $NH_2$, $C_{1-3}$ alkoxy, $C_{1-3}$ haloalkyl, $C_{1-3}$ alkylamino or $C_{3-5}$ heterocycloalkyl; n is 0, 1 or 2; R' is H, halogen, OH, $C_{1-3}$ alkyl, $C_{1-3}$ haloalkyl or $C_{1-3}$ alkoxy; m is n is 0, 1 or 2; U is O or S; R''' is H, OH, $NH_2$, $C_{1-3}$ alkyl, $C_{1-3}$ alkylamino, $C_{1-3}$ alkoxy or halogen; k is 0, 1, 2, 3 or 4.

An embodiment of the disclosure is the compound of Formula 4-1, wherein $R^{1'}$ is NH.

An embodiment of the disclosure is the compound of Formula 4-1, wherein R'' is H.

An embodiment of the disclosure is the compound of Formula 4-1, wherein R' is H.

An embodiment of the disclosure is the compound of Formula 4-1, wherein $R^{2'}$ is OH.

An embodiment of the disclosure is the compound of Formula 4-1, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 4, wherein k is 0, 1, 2 or 3, preferably 0, 1 or 2, more preferably 0 or 1.

An embodiment of the disclosure is the compound of Formula 4, wherein U is S.

An embodiment of the compound of Formula VI-1 is of the following Formula 16 or 17, Formula 16

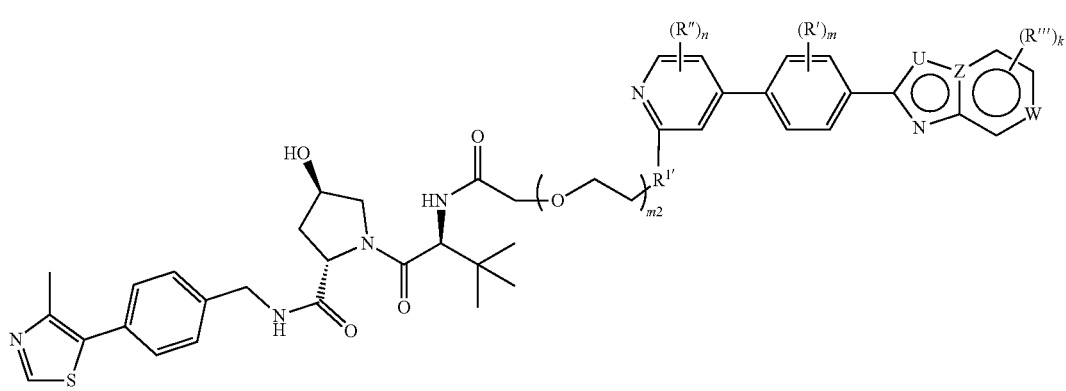

Formula 17 wherein m2 is 1, 2, 3, 4, 5, 6, or 7; and $R^{1'}$ is O, NH,

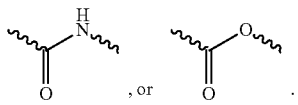, or

An embodiment of the disclosure is the compound of Formula 16, wherein m2 is 1, 2, 3, 4, 5 or 6, preferably 2 or 5.

An embodiment of the disclosure is the compound of Formula 16, wherein $R^{1'}$ is O, NH,

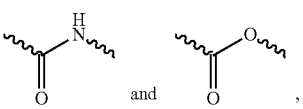 and preferably NH.

An embodiment of the disclosure is the compound of Formula 16, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 16, wherein m is 0, 1, 2, 3 or 4, preferably 0 or 1.

An embodiment of the disclosure is the compound of Formula 16, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 16, wherein n is 0, 1, or 2, preferably 0 or 1.

An embodiment of the disclosure is the compound of Formula 16, wherein Z is C, U is O or S, W is CH.

An embodiment of the disclosure is the compound of Formula 16, wherein Z is N, U is CH, W is CH.

An embodiment of the disclosure is the compound of Formula 16, wherein Z is C, U is CH, W is N.

An embodiment of the disclosure is the compound of Formula 16, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 16, wherein k is 0, 1, 2 or 3, preferably 0, 1 or 2, more preferably 0 or 1.

An embodiment of the disclosure is the compound of Formula 17, wherein m2 is 1, 2, 3, 4, 5 or 6, preferably 2 or 5.

An embodiment of the disclosure is the compound of Formula 17, wherein $R^{1'}$ is O, NH,

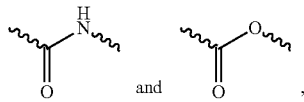

preferably NH.

An embodiment of the disclosure is the compound of Formula 17, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 17, wherein m is 0, 1, 2, 3 or 4, preferably 0 or 1.

An embodiment of the disclosure is the compound of Formula 17, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 17, wherein n is 0, 1, or 2, preferably 0 or 1.

An embodiment of the disclosure is the compound of Formula 17, wherein Z is C, U is O or S, W is CH.

An embodiment of the disclosure is the compound of Formula 17, wherein Z is N, U is CH, W is CH.

An embodiment of the disclosure is the compound of Formula 17, wherein Z is C, U is CH, W is N.

An embodiment of the disclosure is the compound of Formula 17, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 17, wherein k is 0, 1, 2 or 3, preferably 0, 1 or 2, more preferably 0 or 1.

Some embodiments of the disclosure are the compounds having a structure depicted in Table 2, or a pharmaceutical acceptable salt, an enantiomer, a non-enantiomer, a tautomer, a racemate, a solvate, a metabolic precursor, a prodrug thereof.

TABLE 2
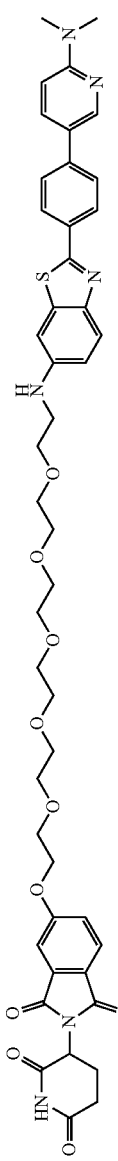

TABLE 2-continued
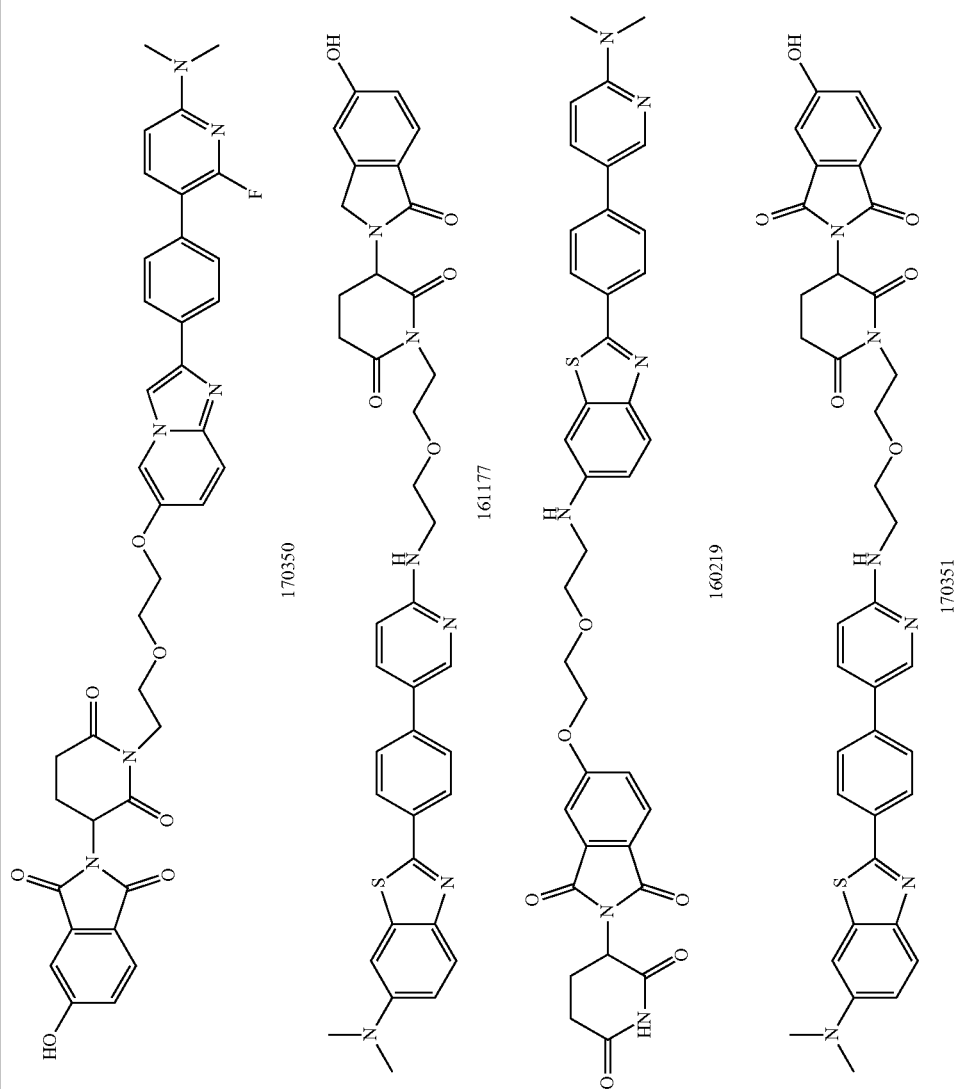

TABLE 2-continued
| | | | | |
|---|---|---|---|---|
| 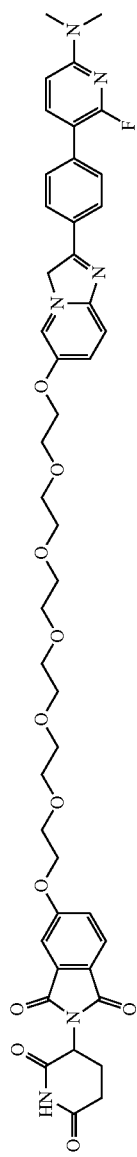 | 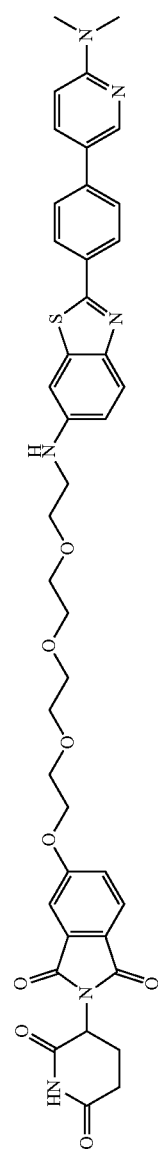 | 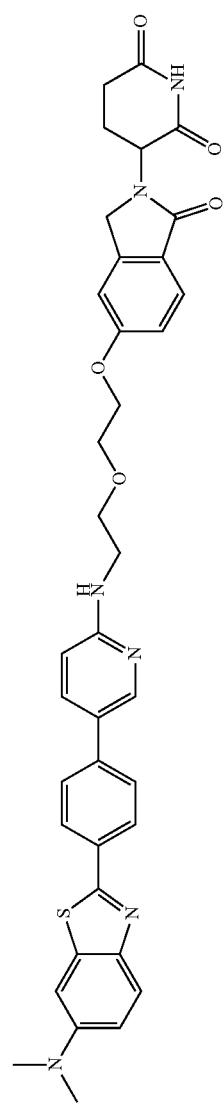 | 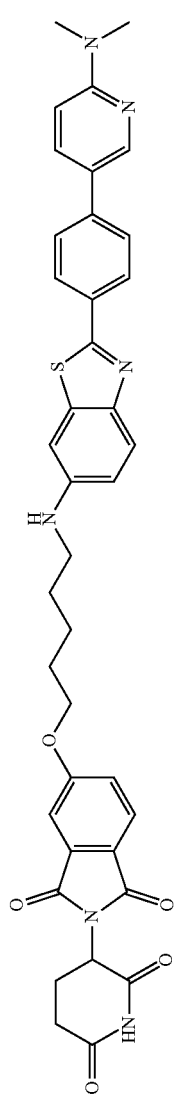 | 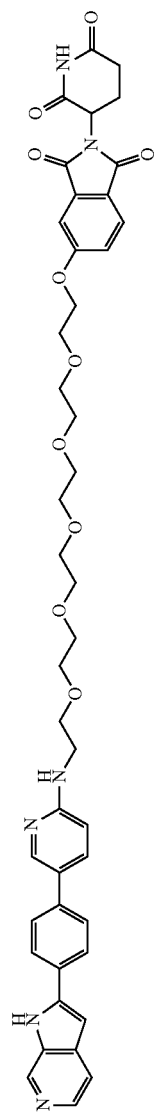 |
| 160744 | 160939 | 170352 | 161103 | 161104 |

TABLE 2-continued
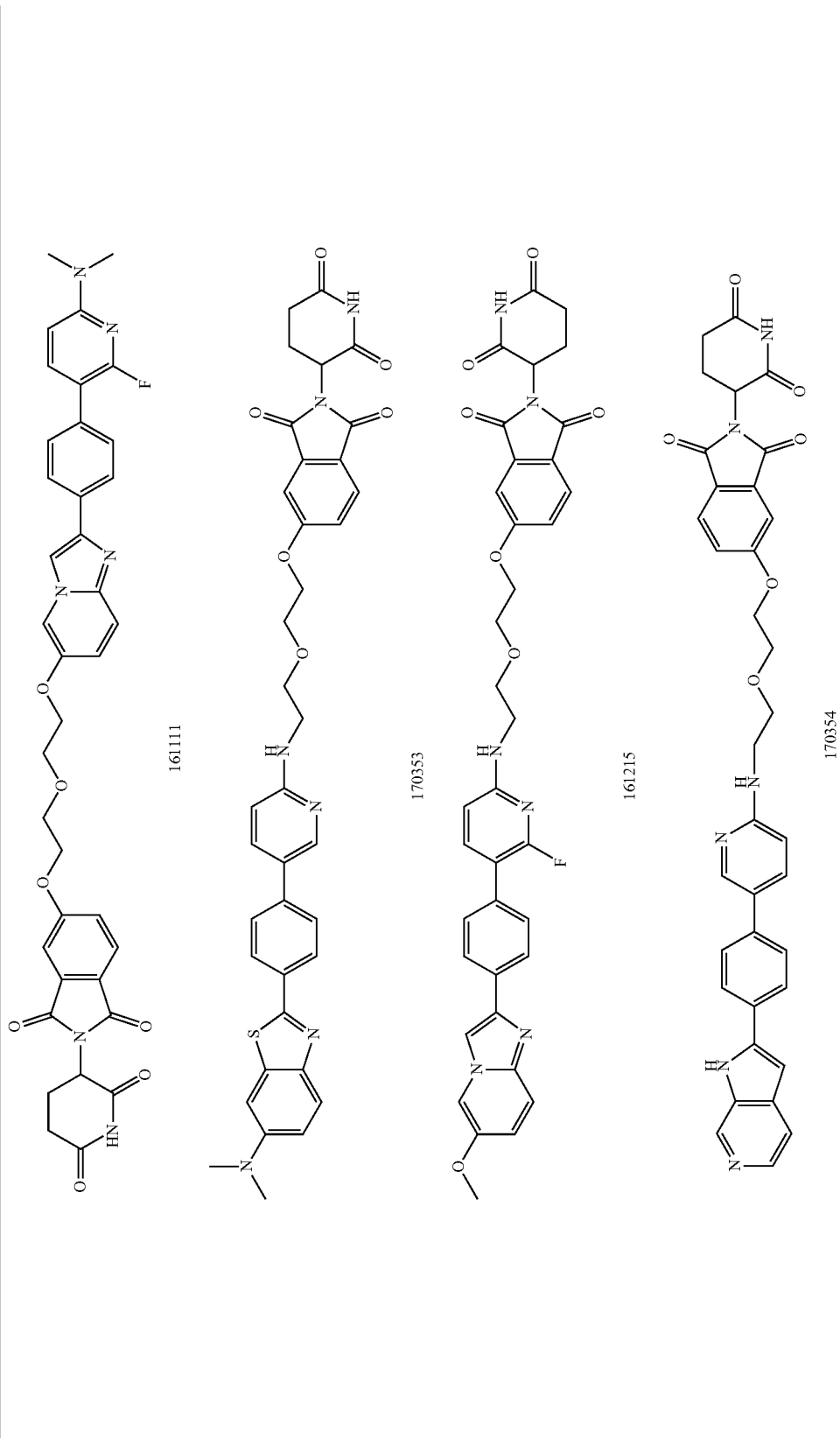

TABLE 2-continued
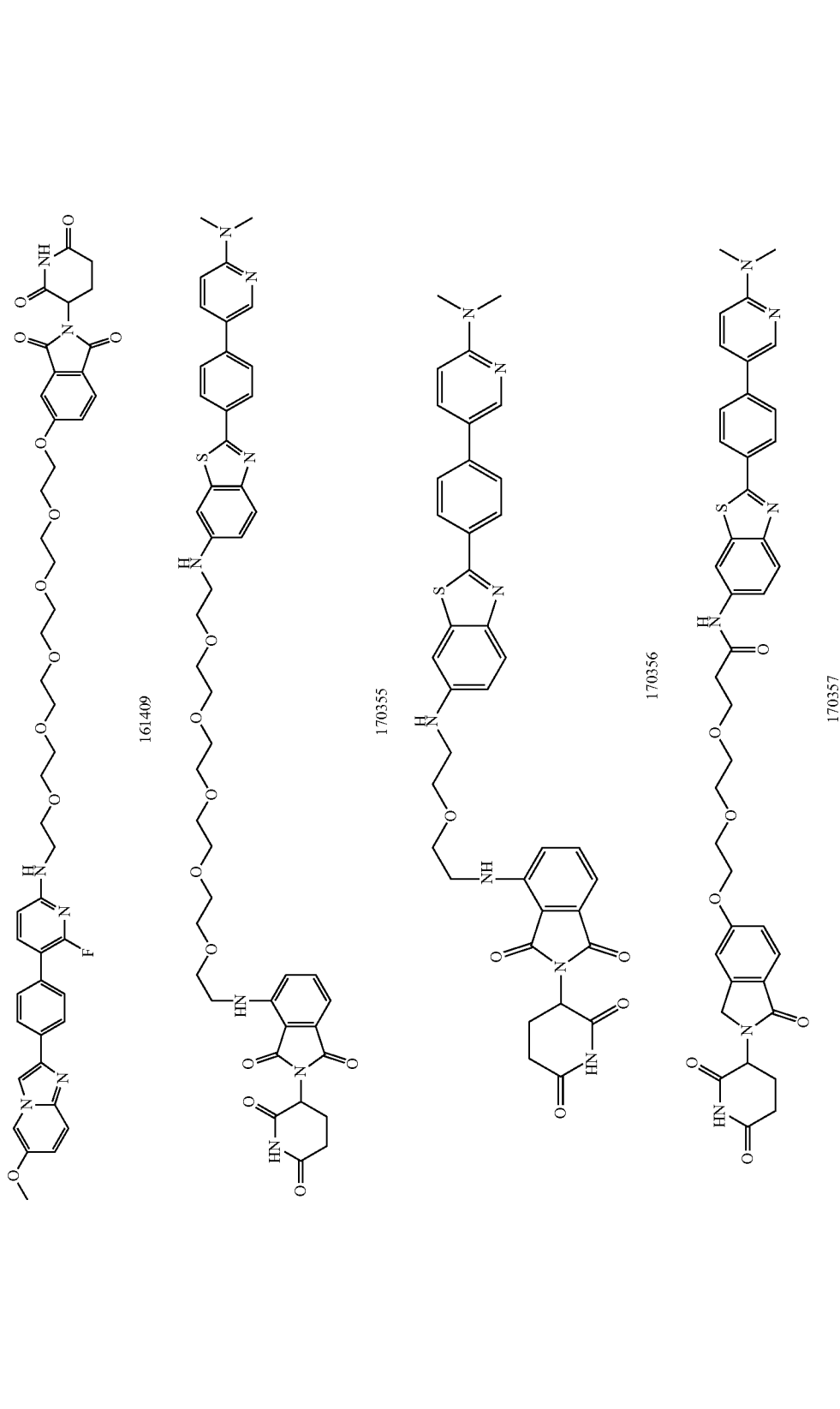

TABLE 2-continued
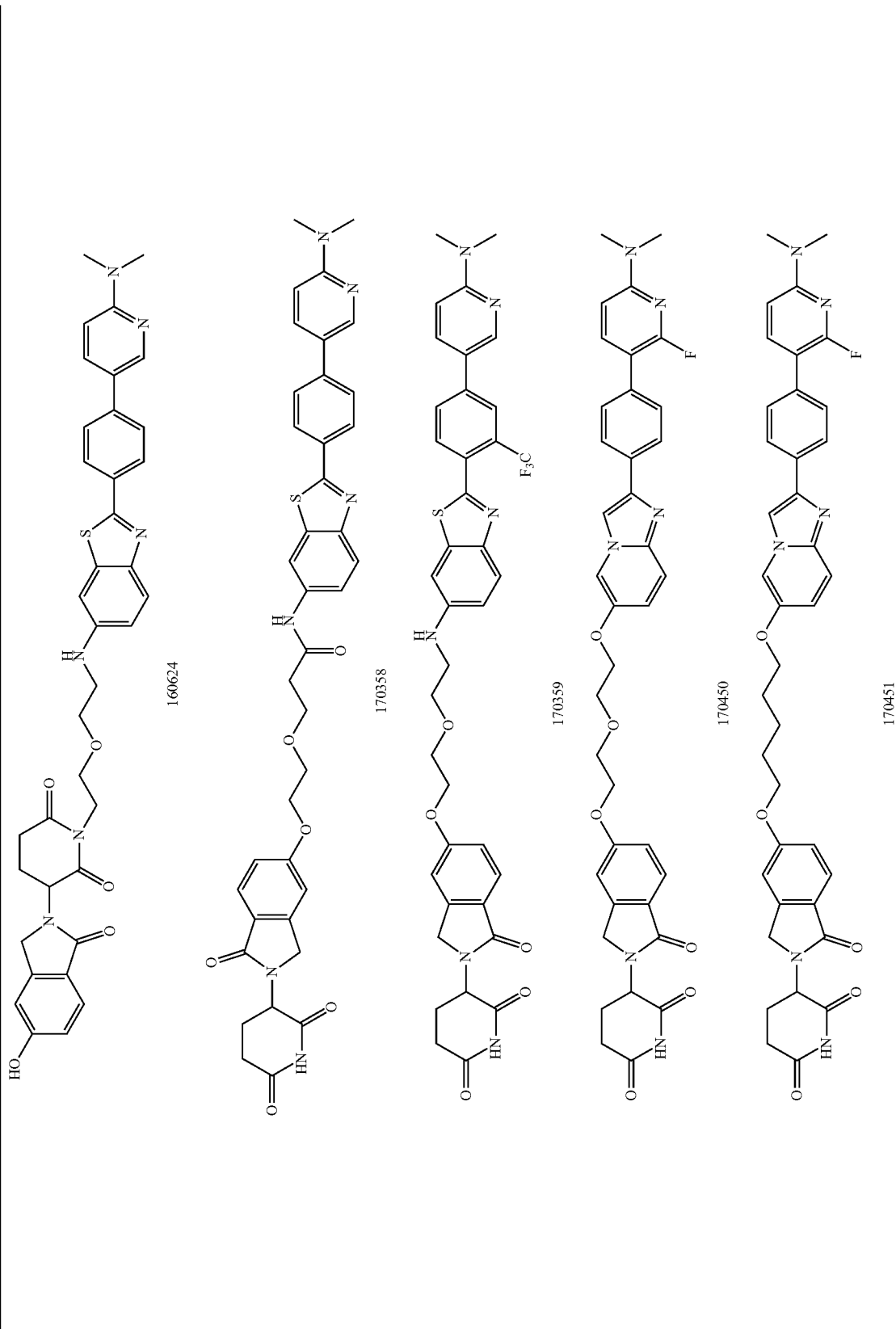

TABLE 2-continued
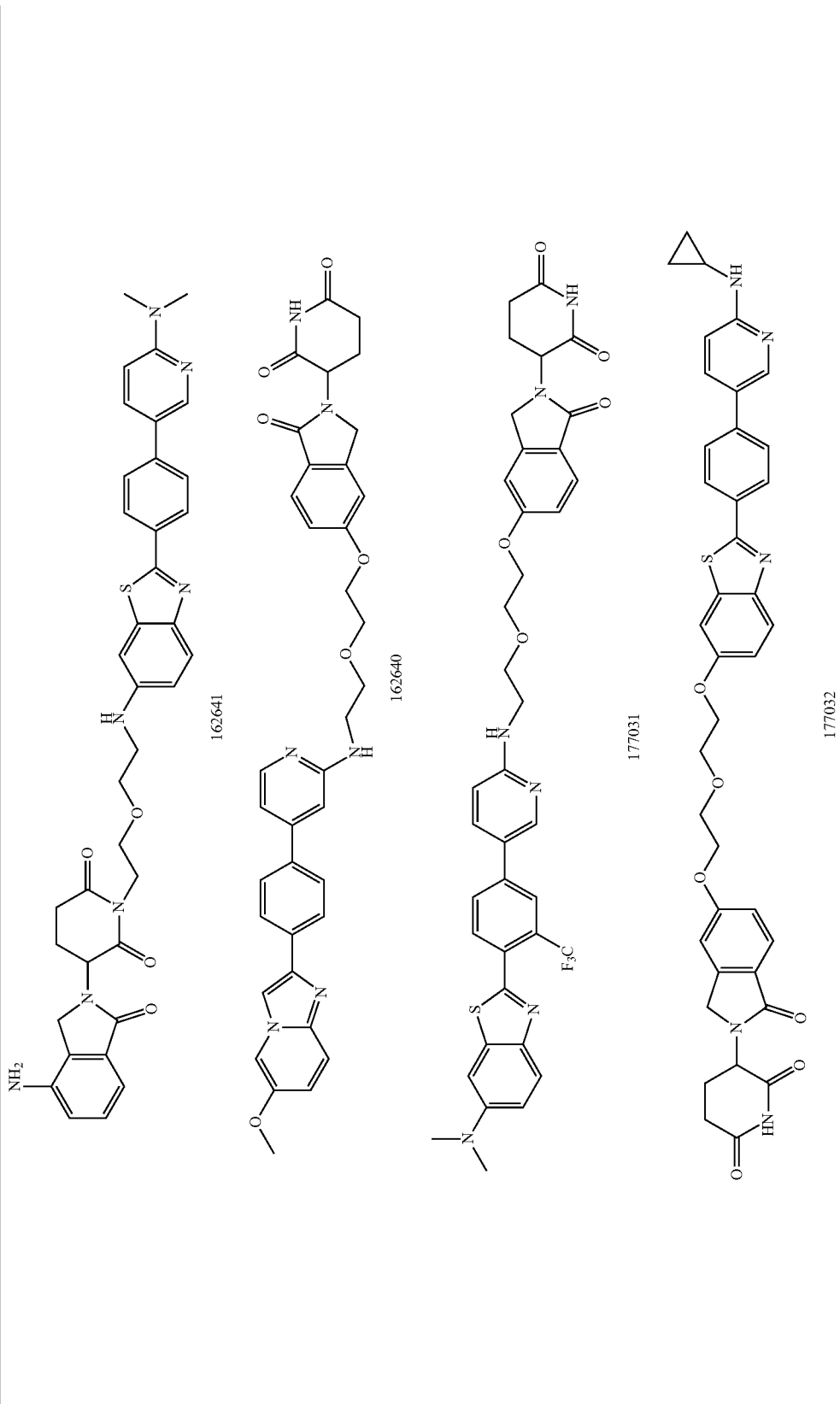

TABLE 2-continued
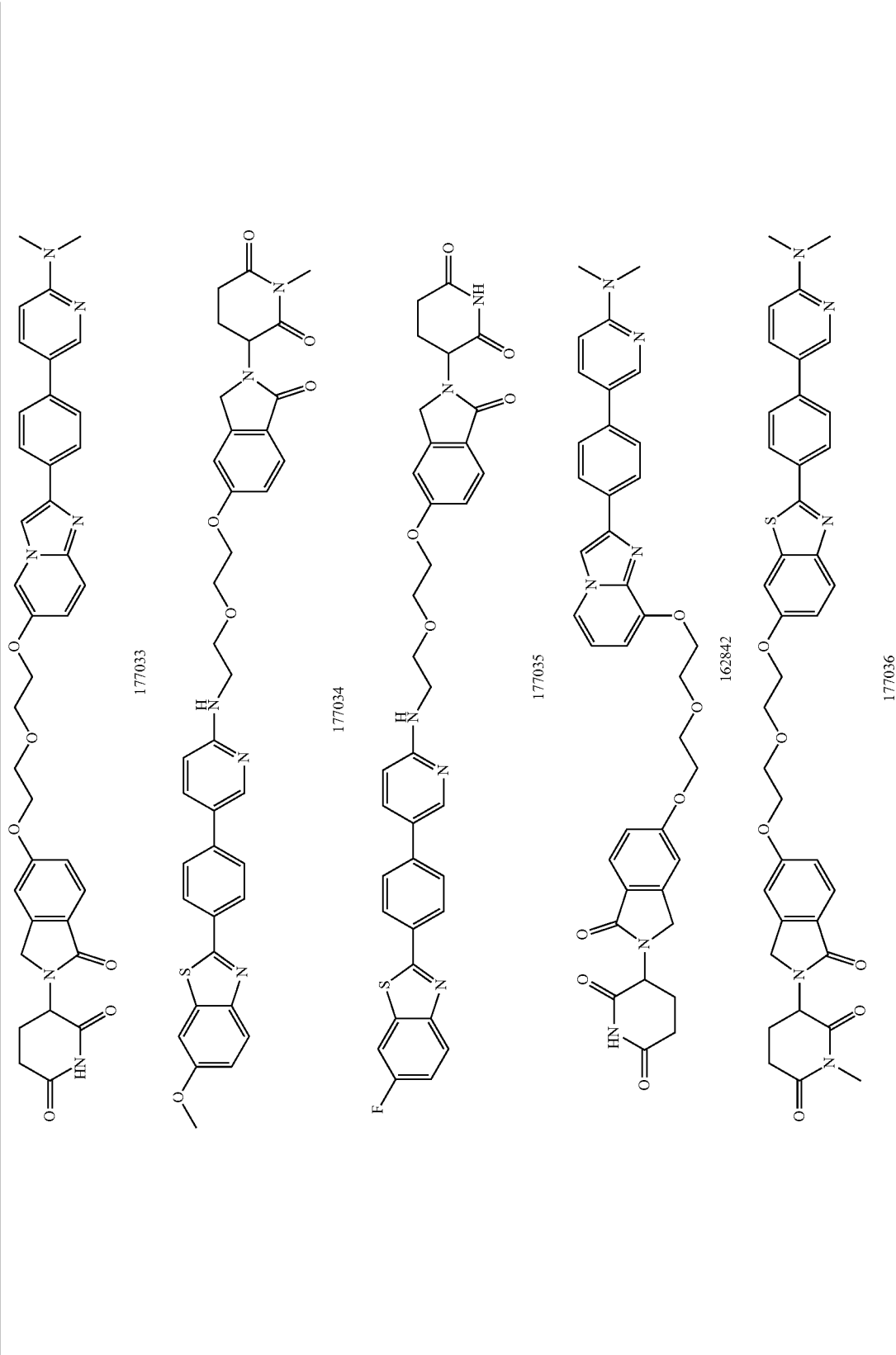

TABLE 2-continued
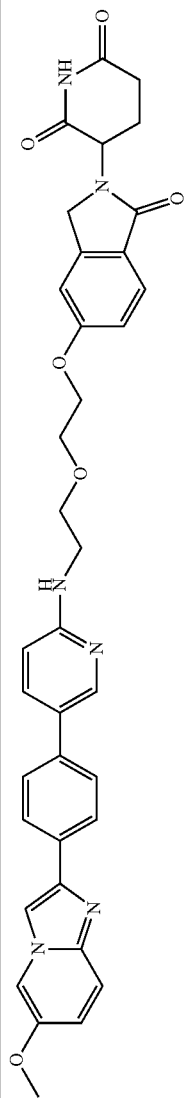
177037
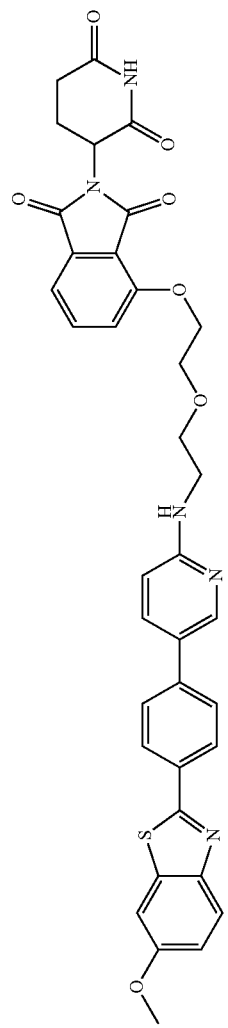
177038
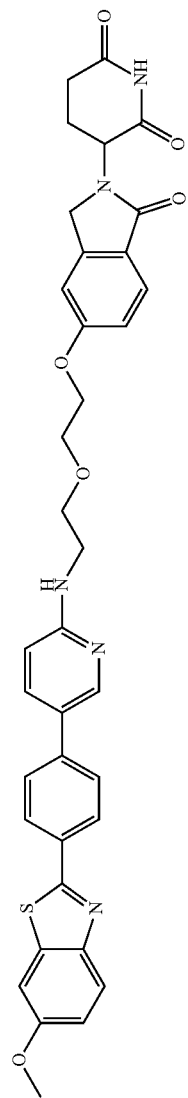
177039
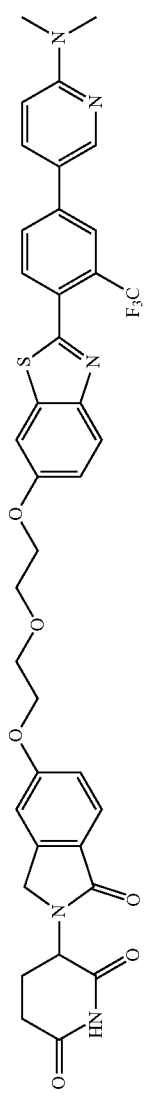
162903

TABLE 2-continued
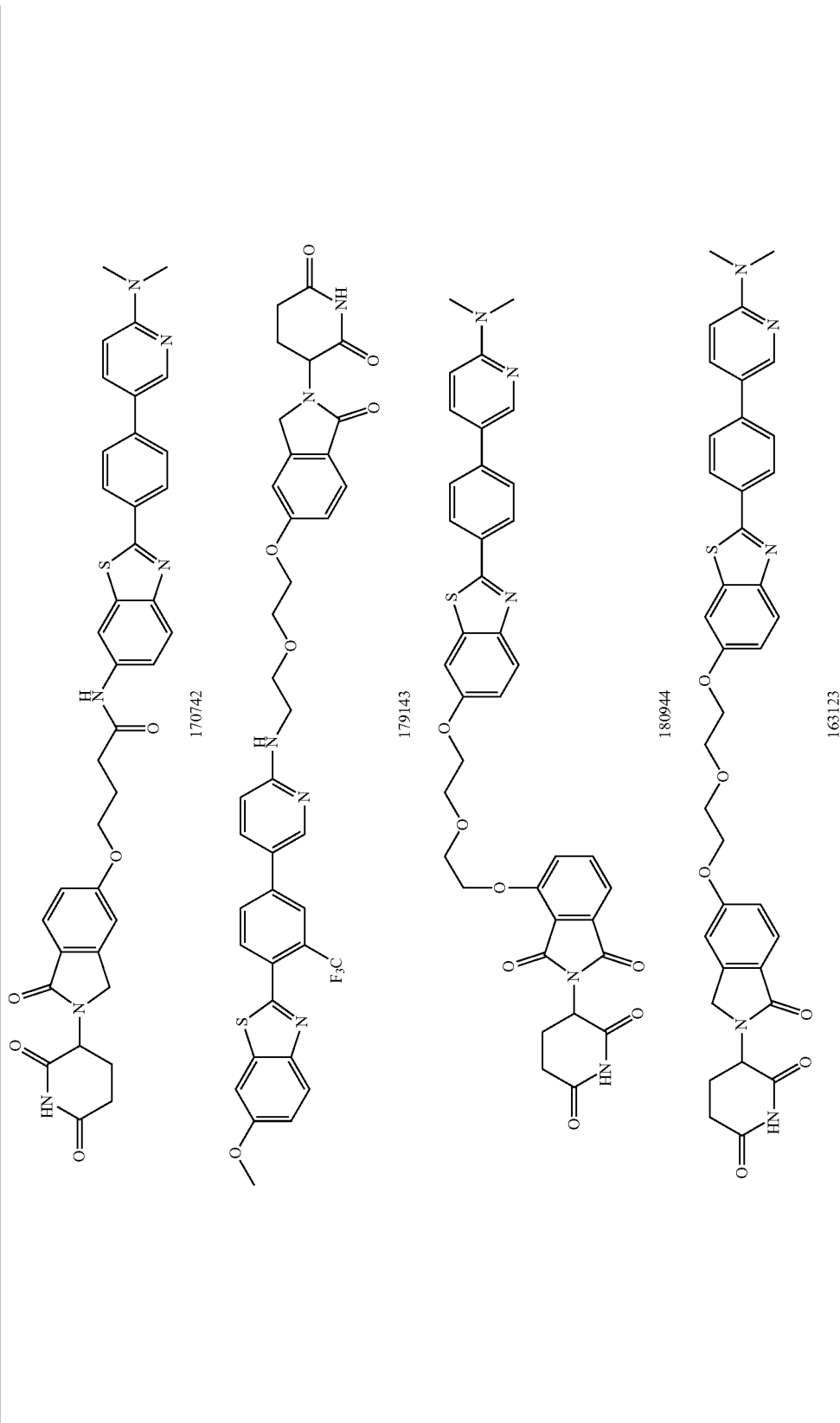

TABLE 2-continued
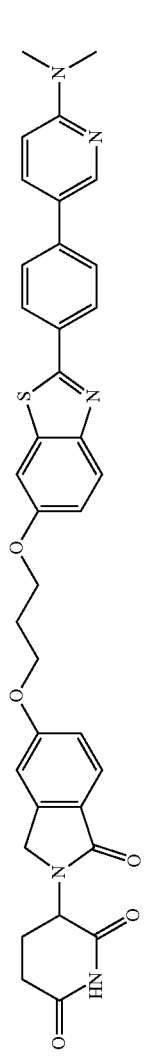
184605
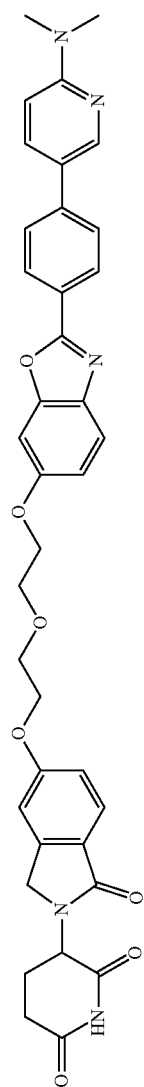
163365
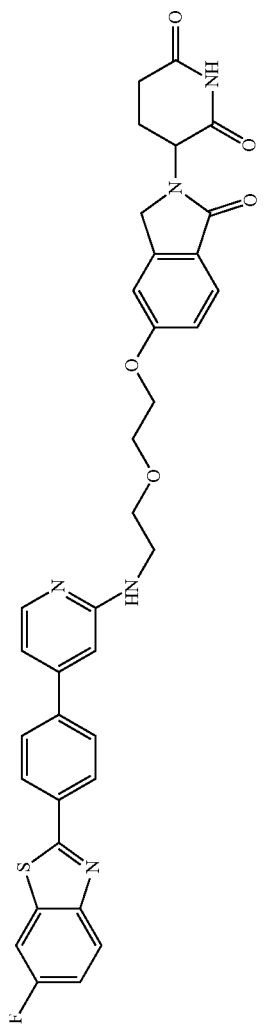
180948
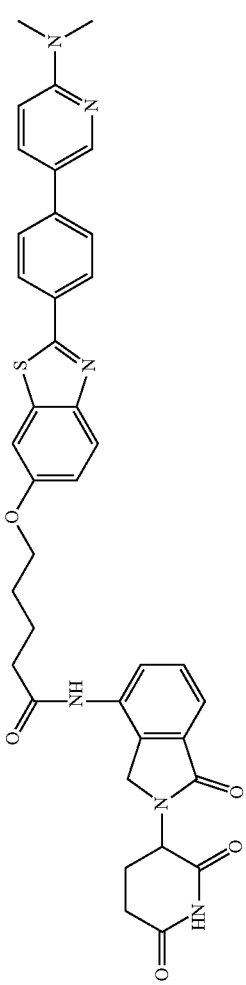
189149

TABLE 2-continued
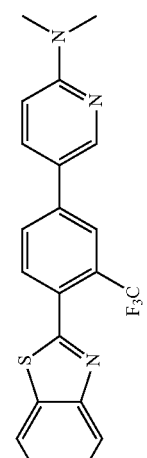
180950
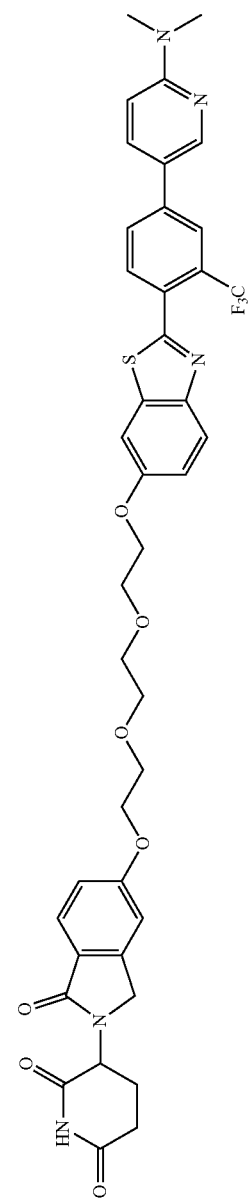
174251
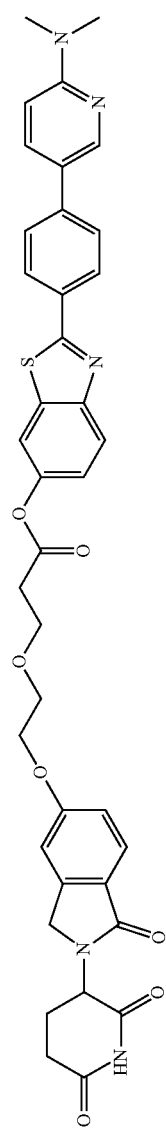
175552
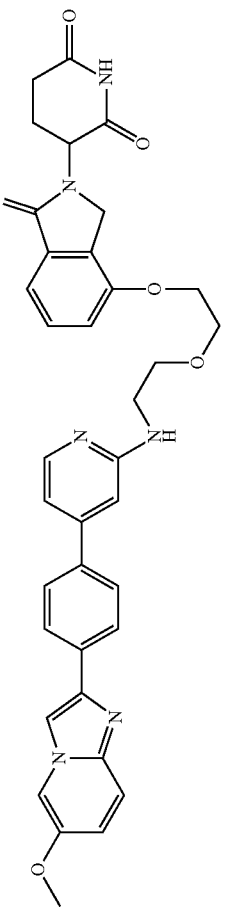
190753

TABLE 2-continued
| | | | |
|---|---|---|---|
| 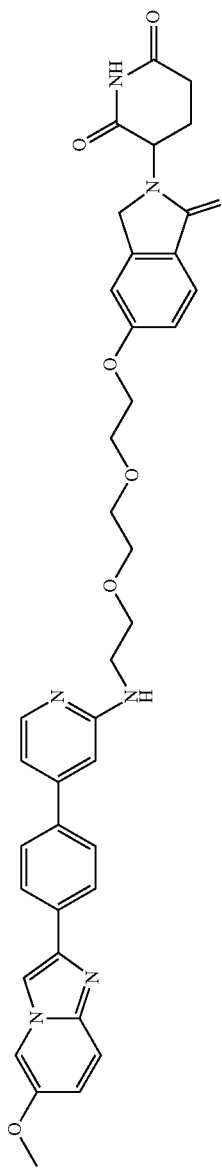 139854 | 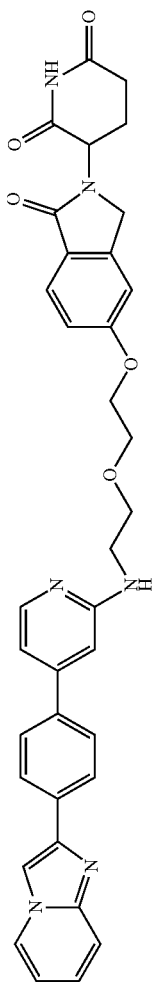 137955 | 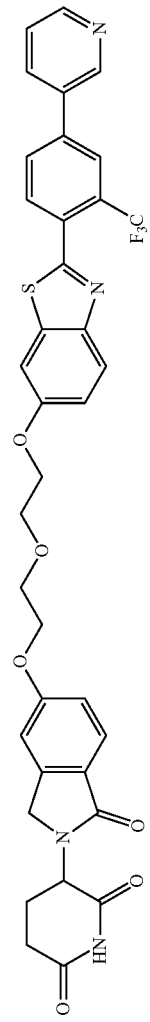 186756 | 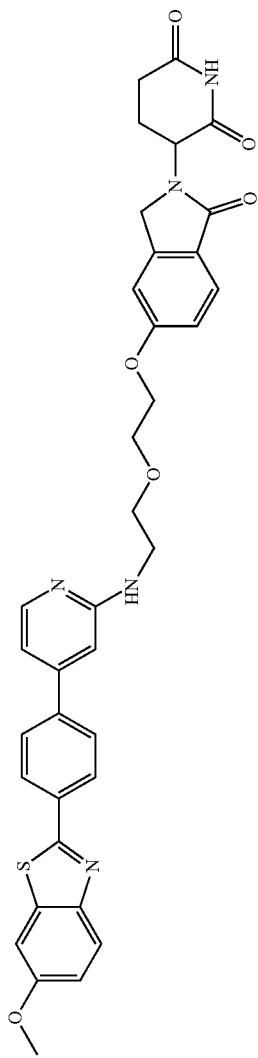 170257 |

TABLE 2-continued
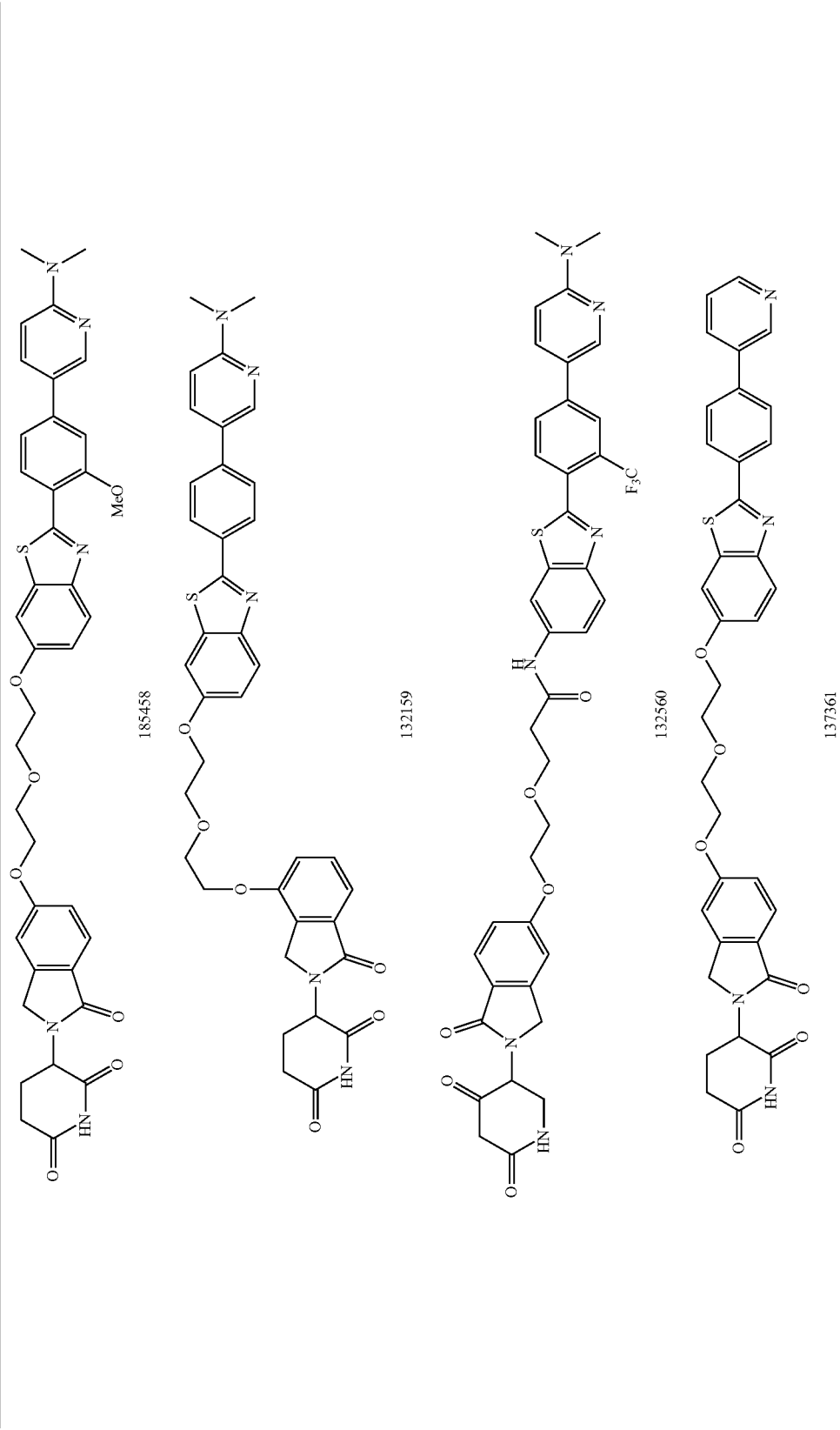

TABLE 2-continued
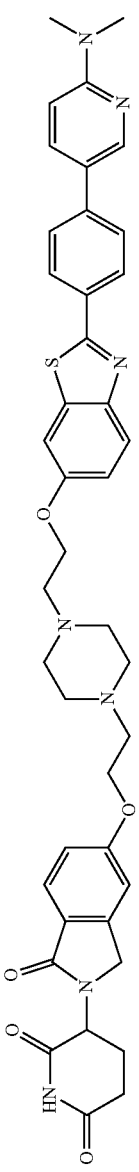 180262
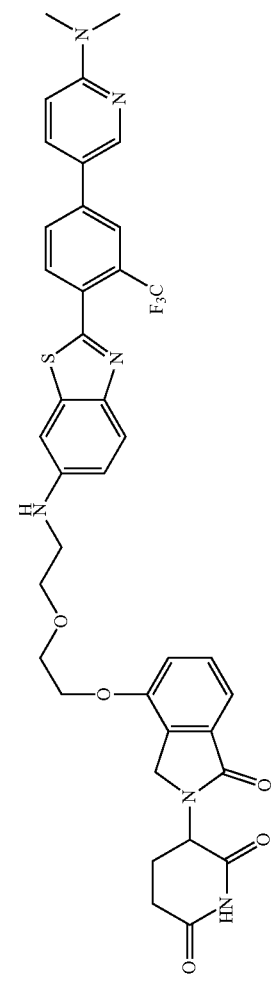 185563
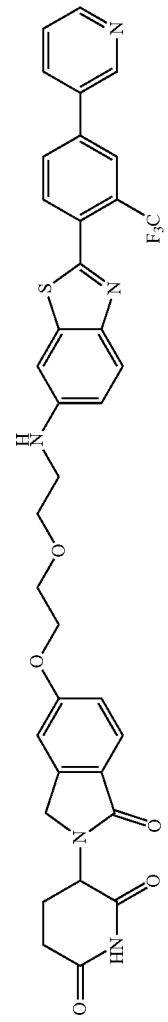 181964
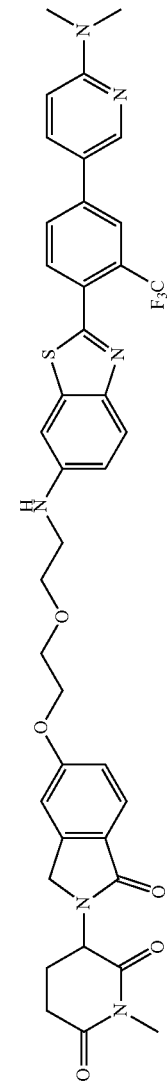 133065
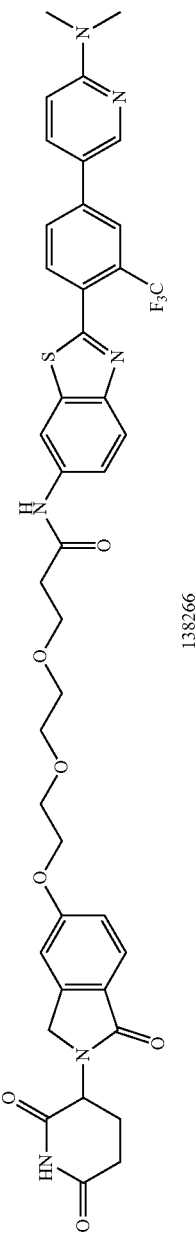 138266

TABLE 2-continued
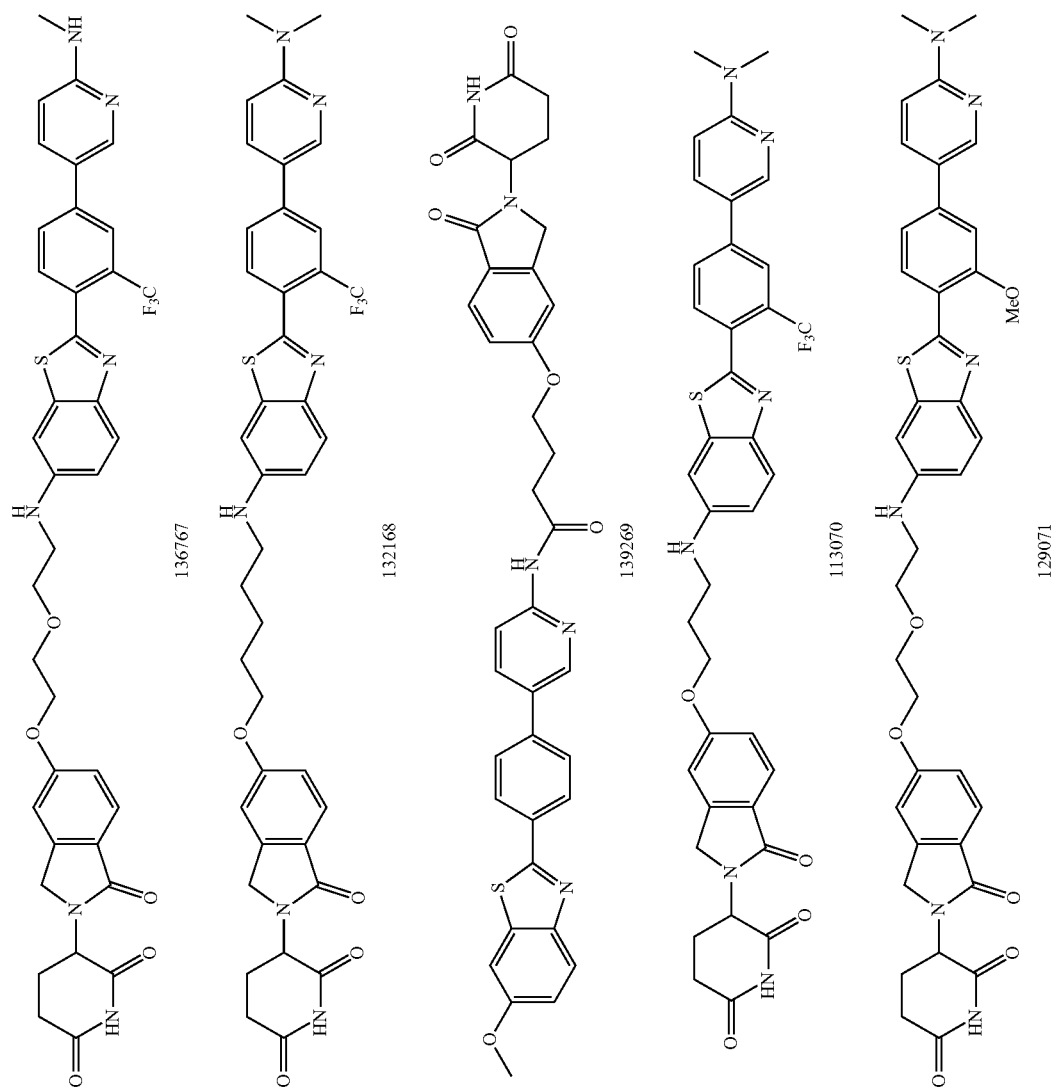

TABLE 2-continued
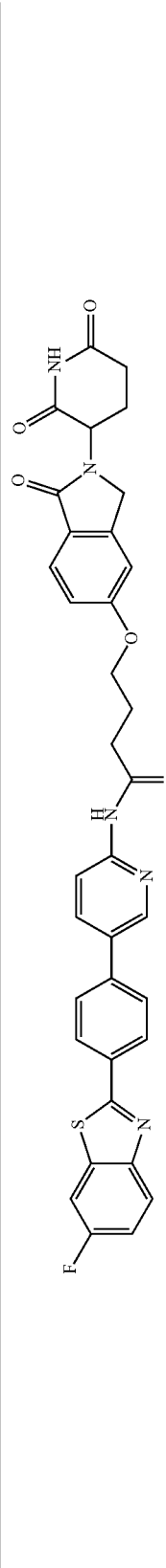

TABLE 2-continued
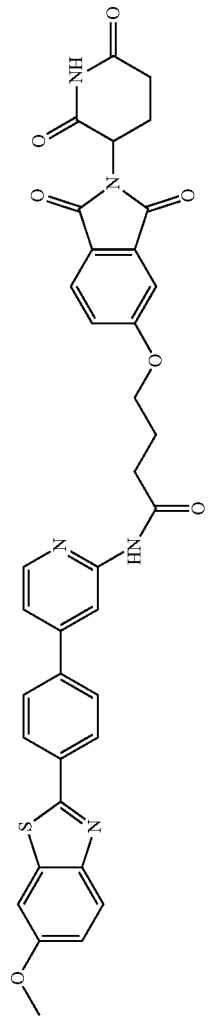 138876
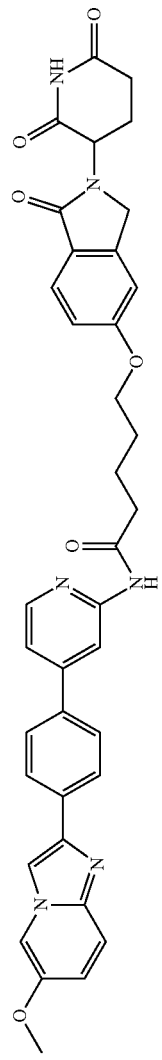 130177
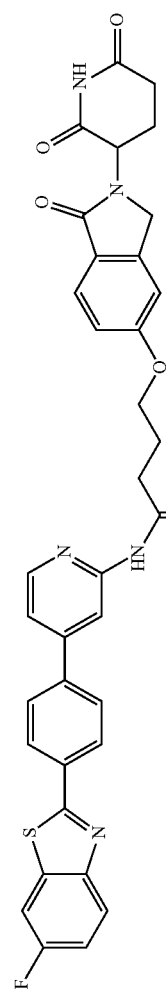 133678
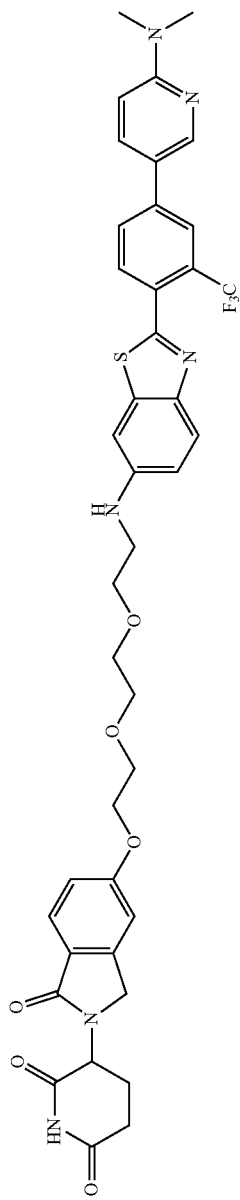 190279

TABLE 2-continued
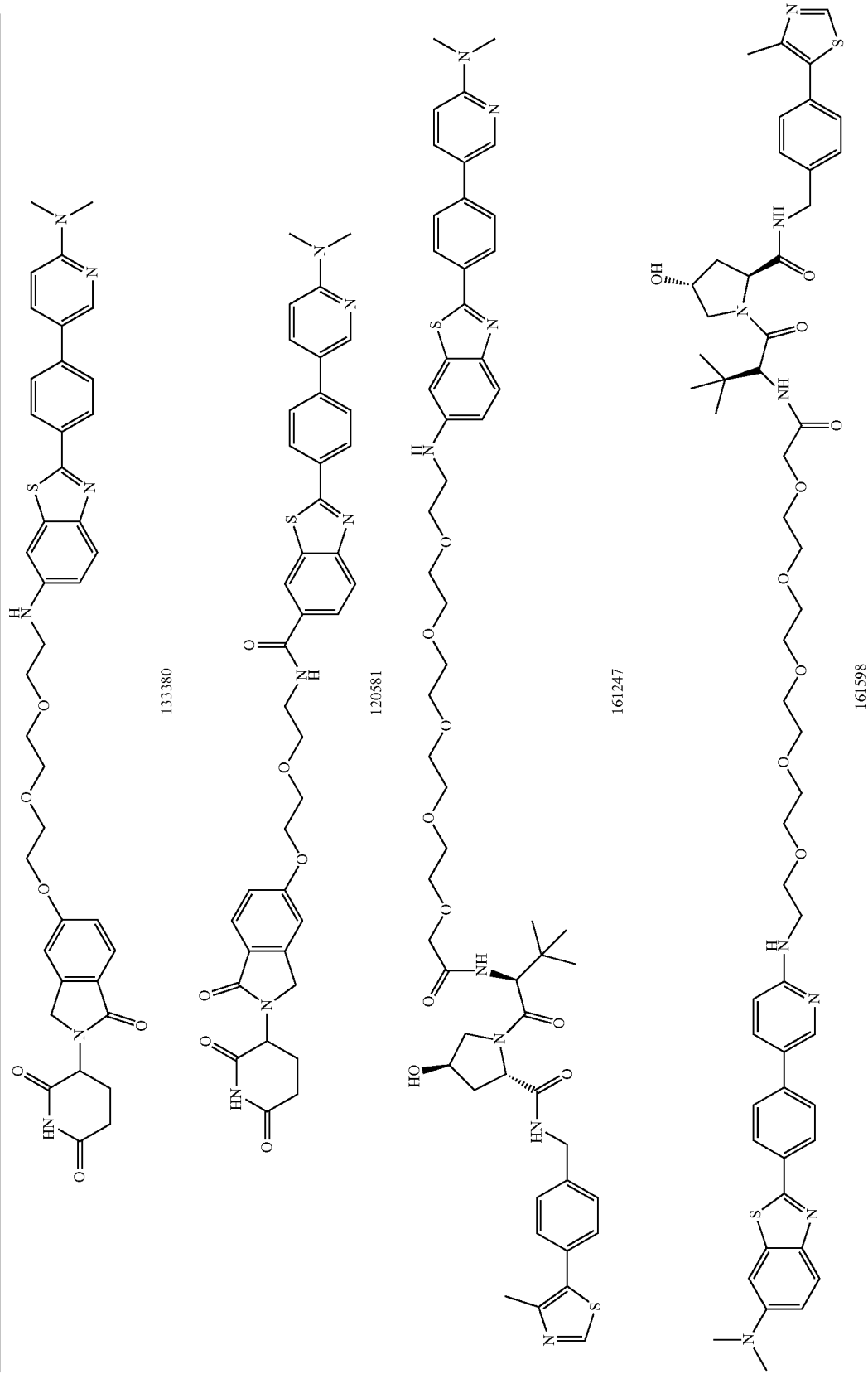

TABLE 2-continued
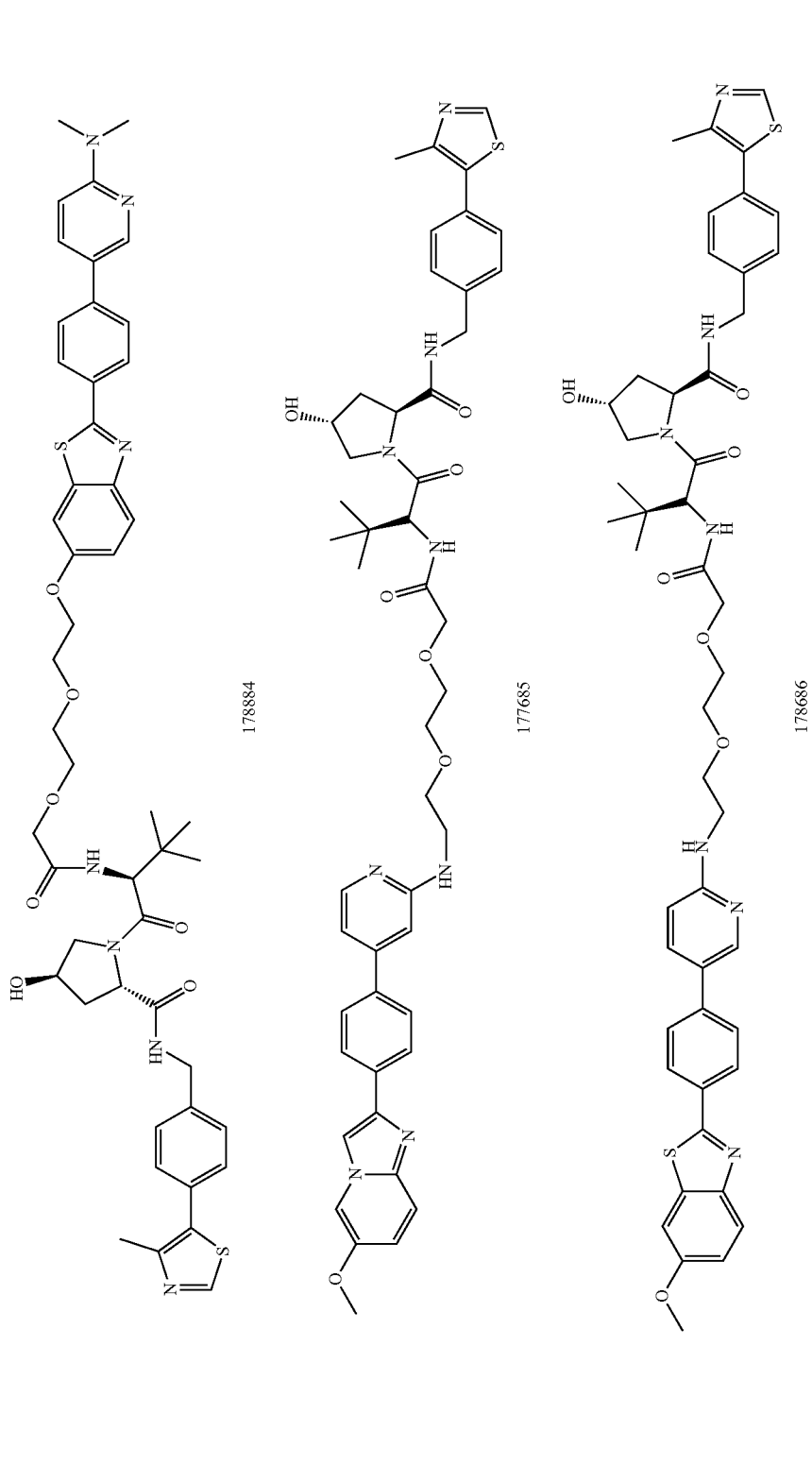

TABLE 2-continued
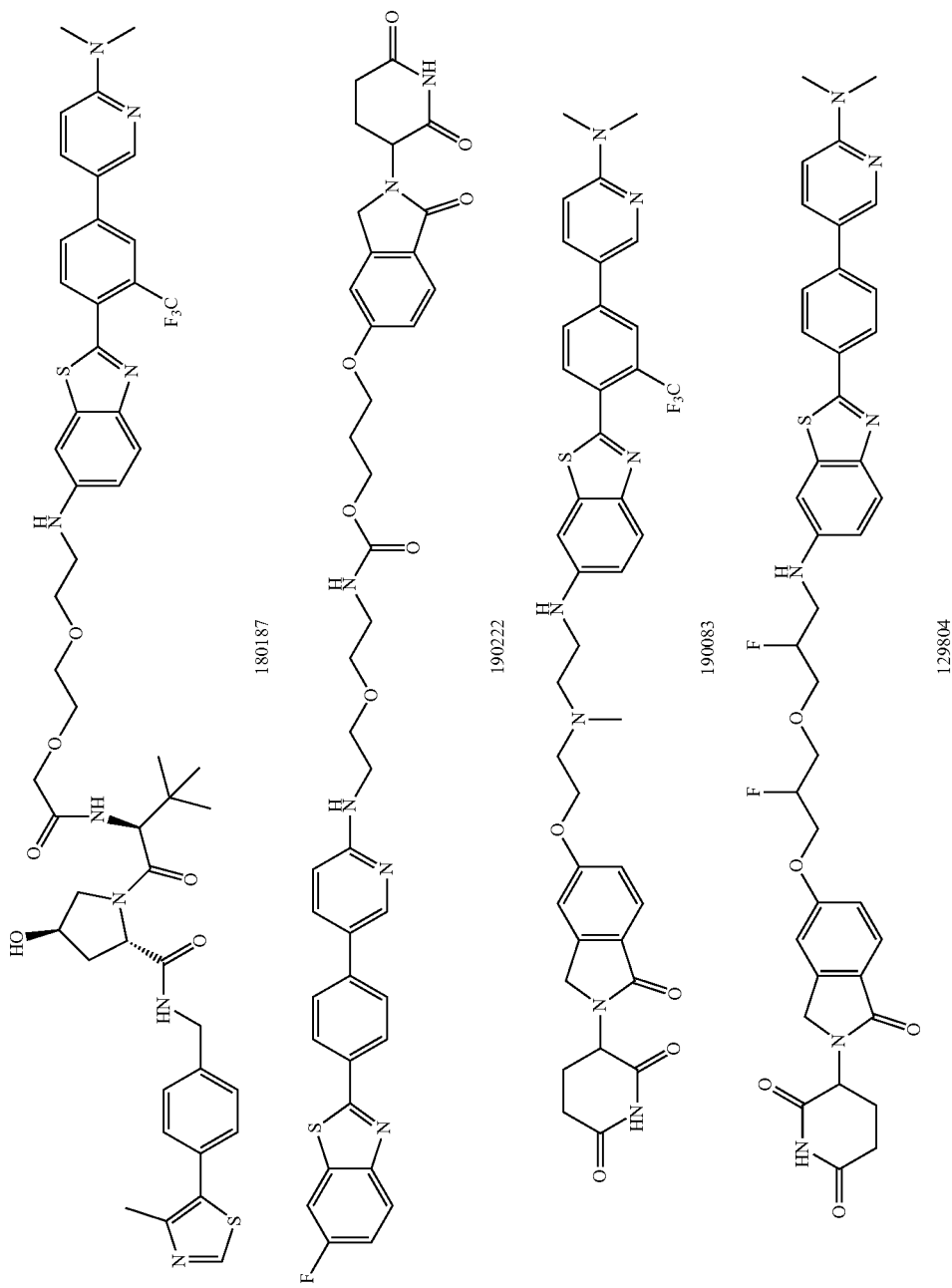

TABLE 2-continued
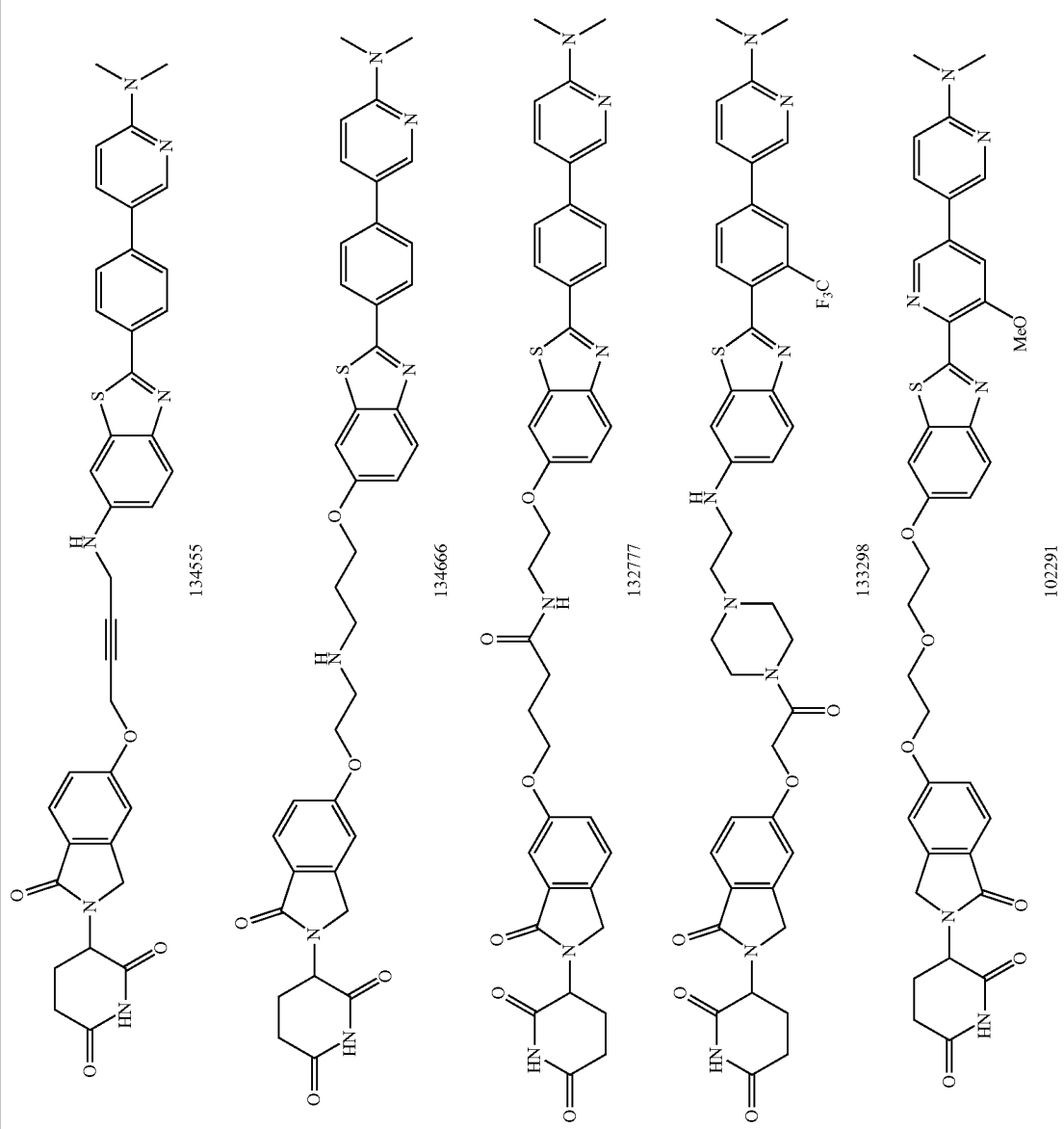

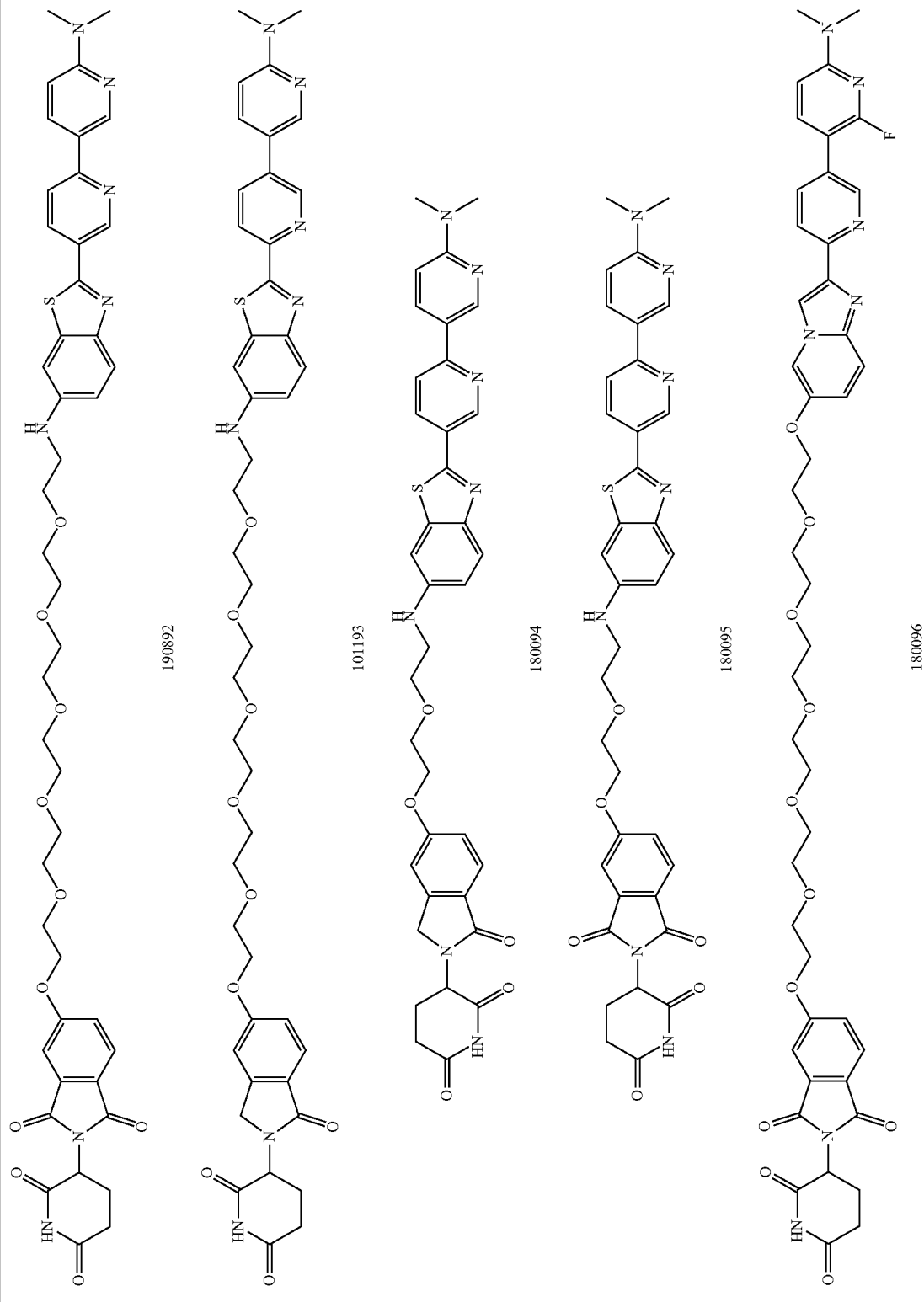

TABLE 2-continued
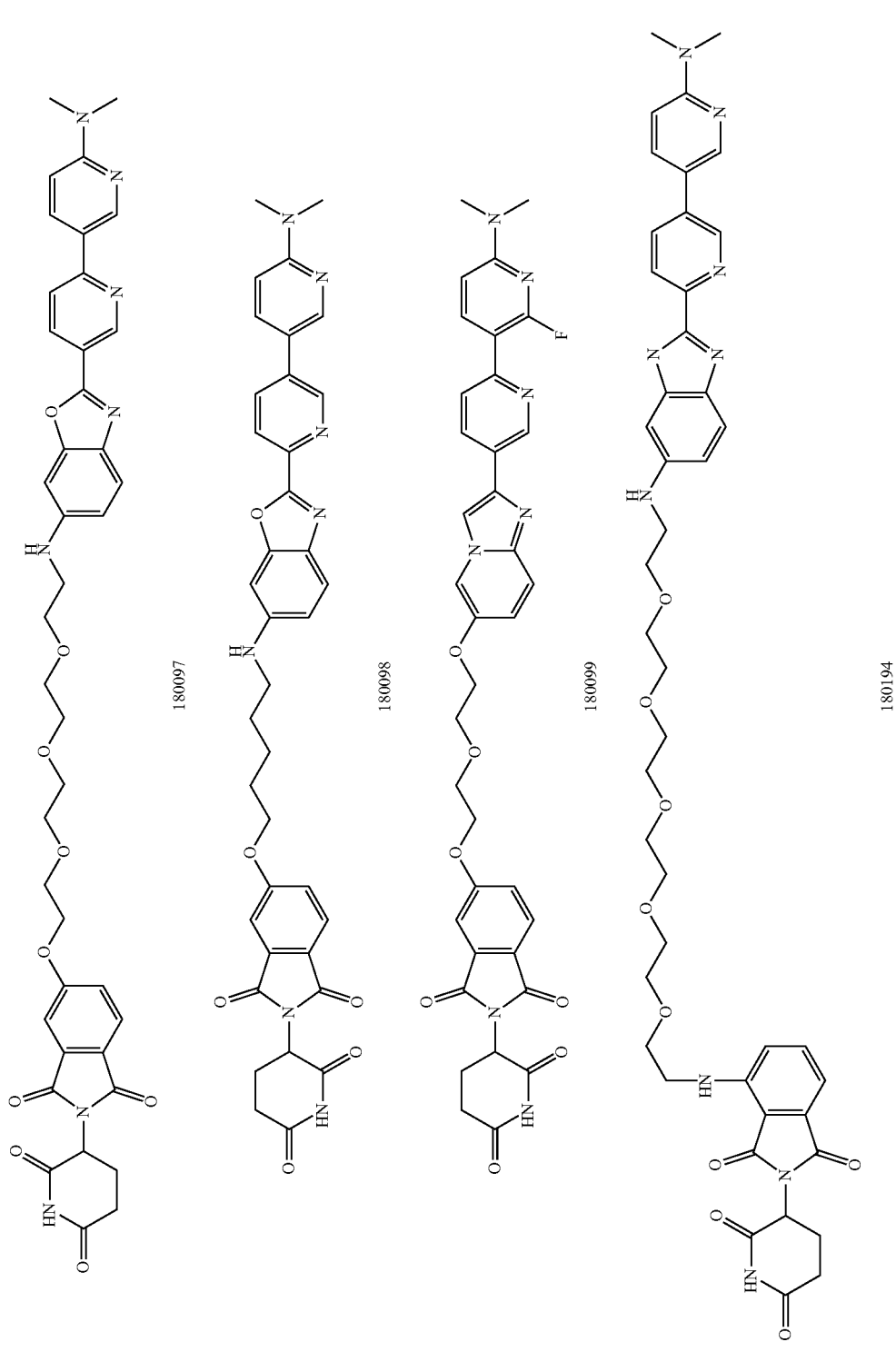

TABLE 2-continued
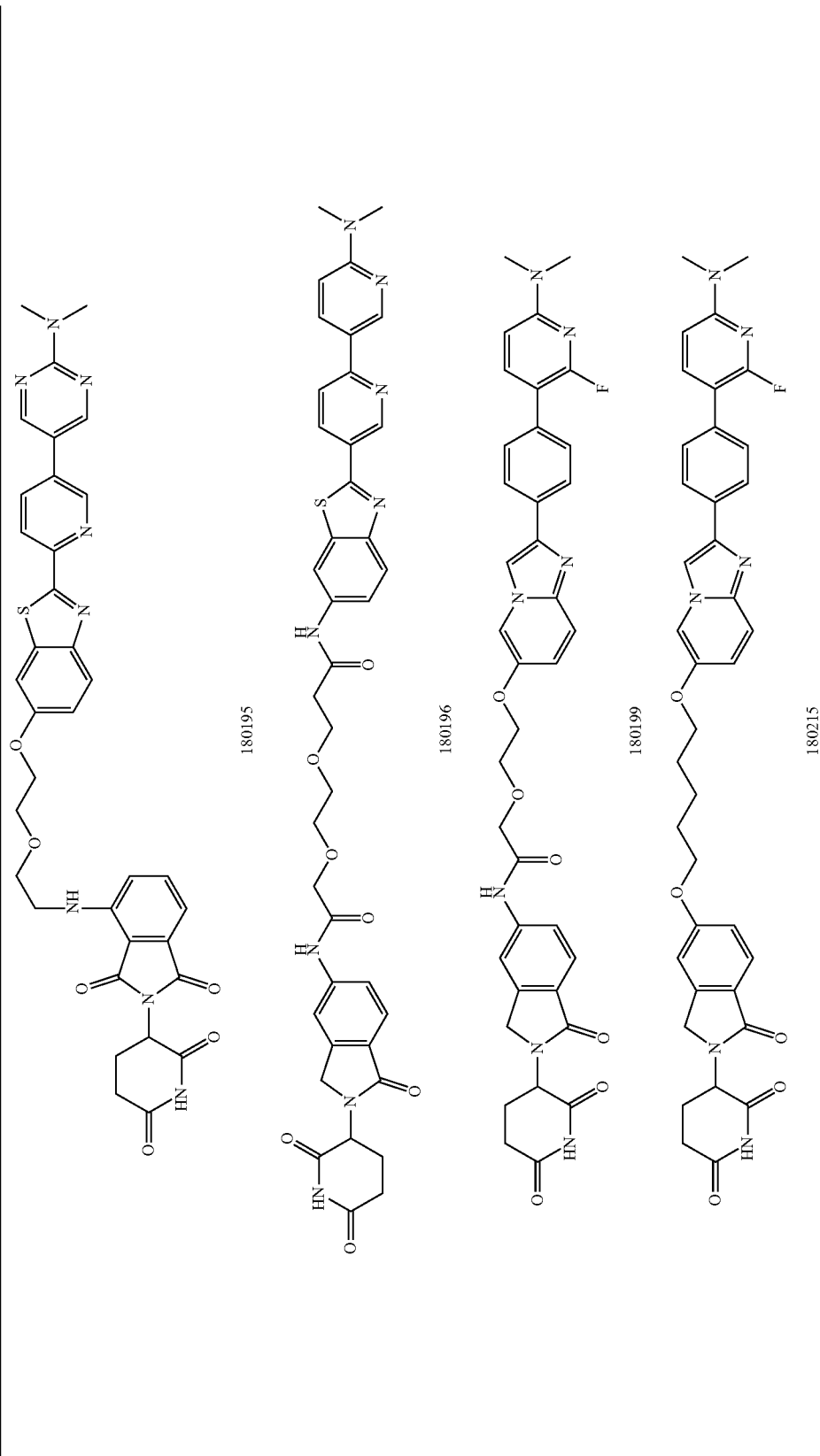

TABLE 2-continued
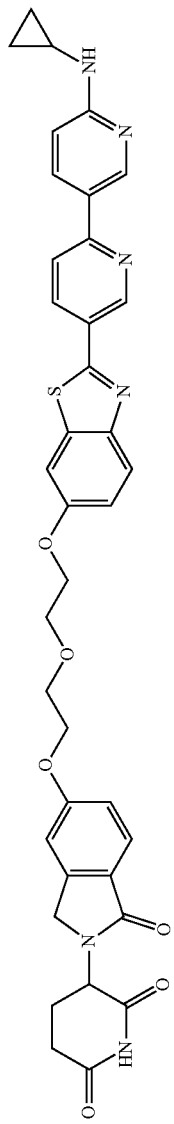 180216
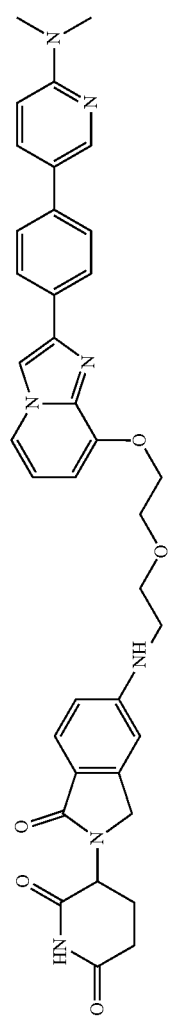 180218
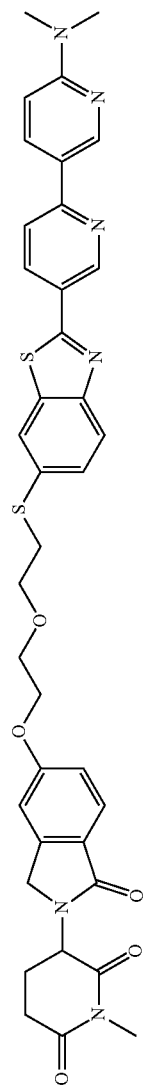 180219
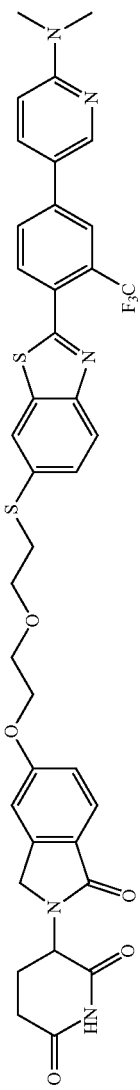 180310

TABLE 2-continued
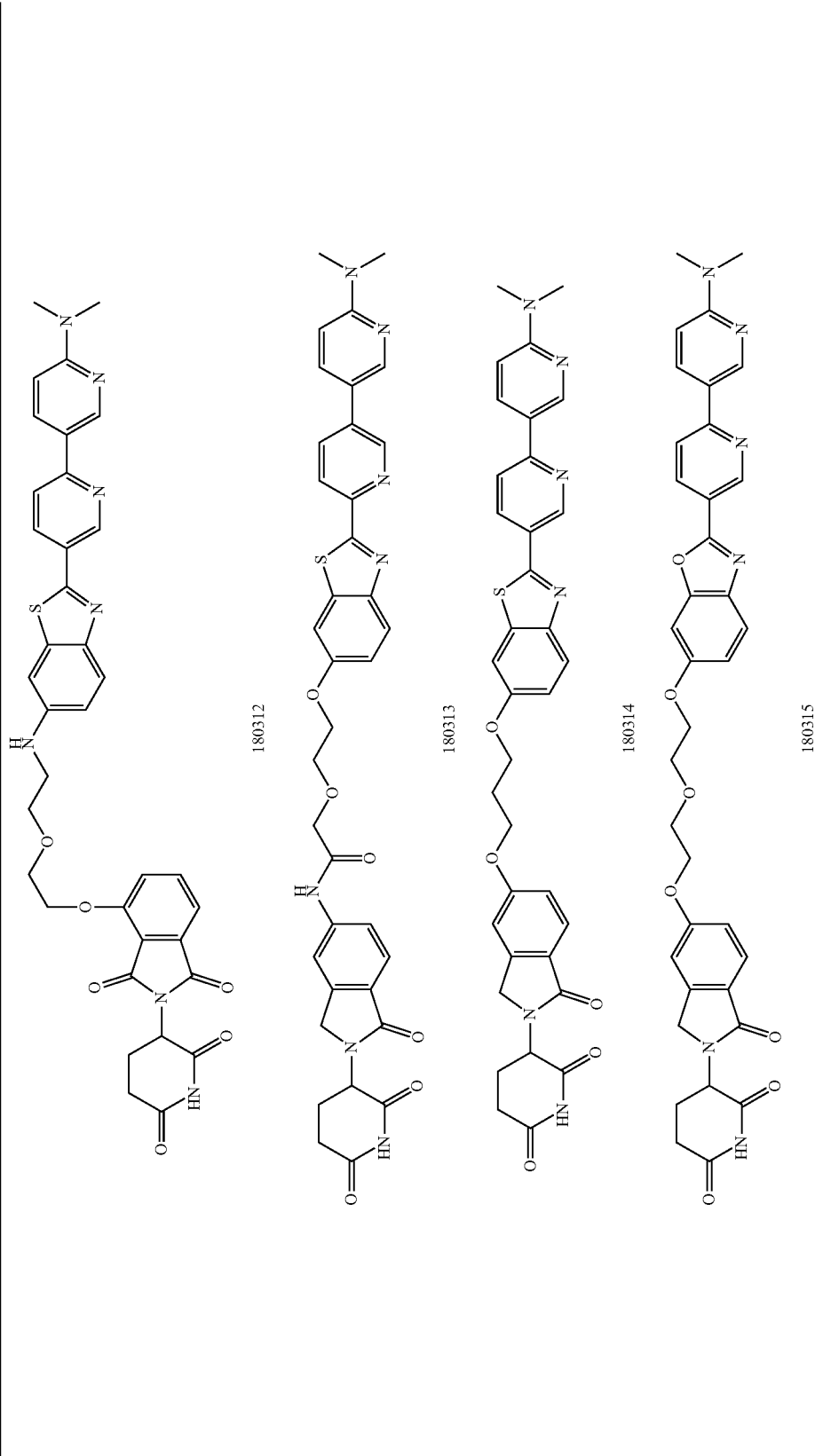

TABLE 2-continued
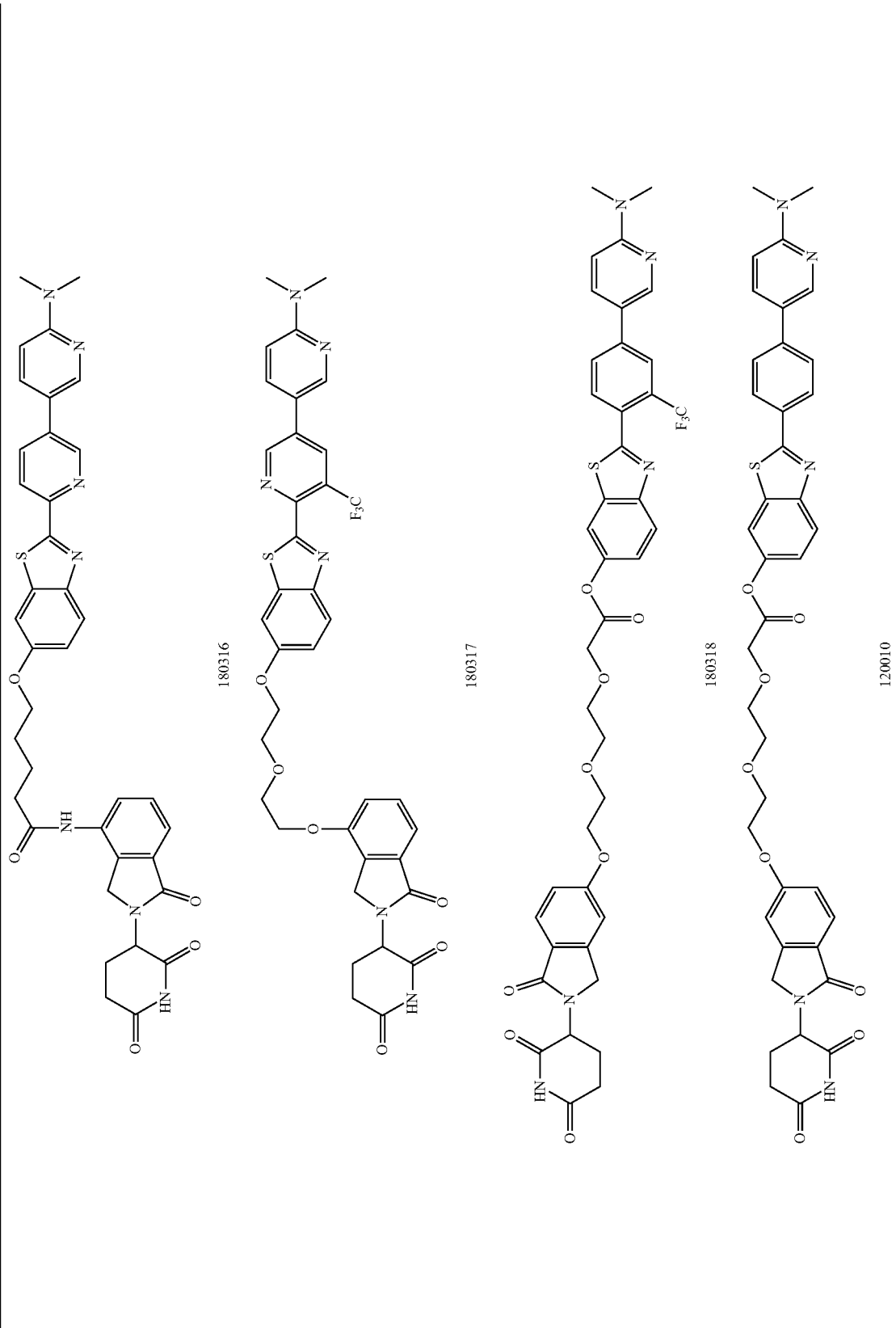

TABLE 2-continued
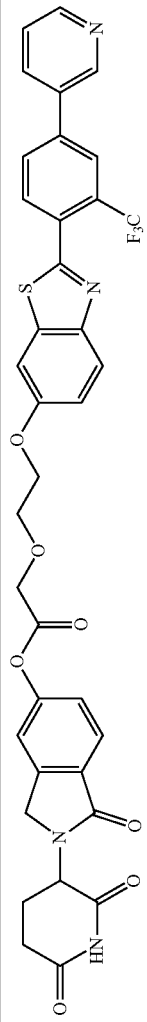
120011
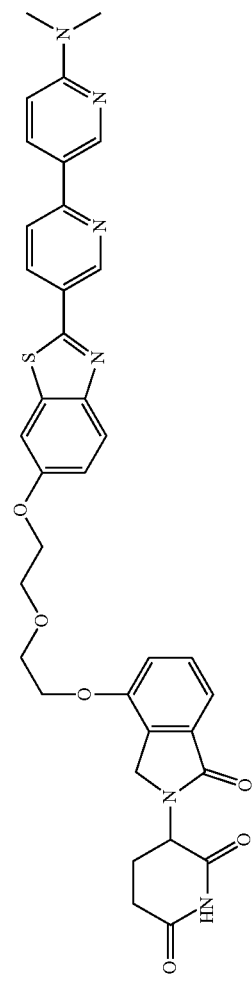
120012
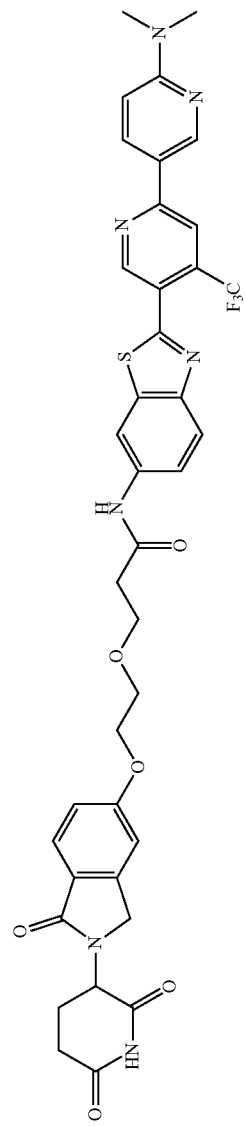
120013
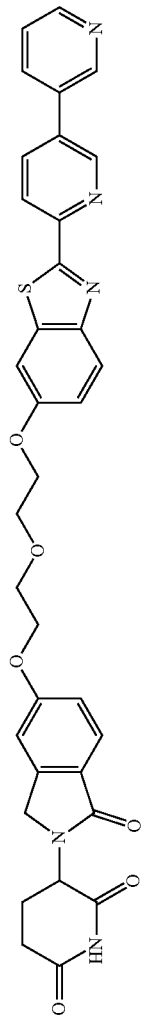
120014

TABLE 2-continued
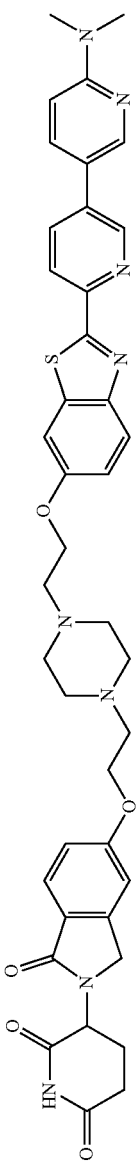
120015
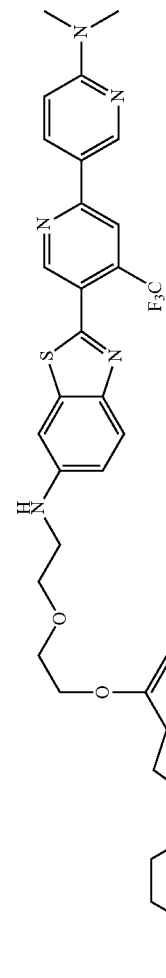
120016
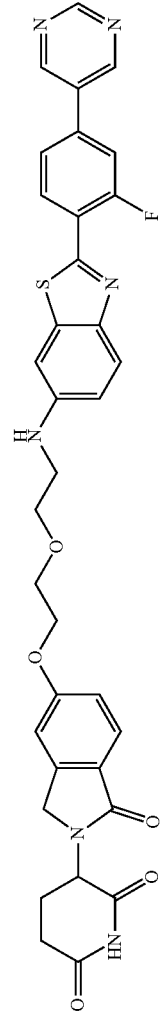
120017
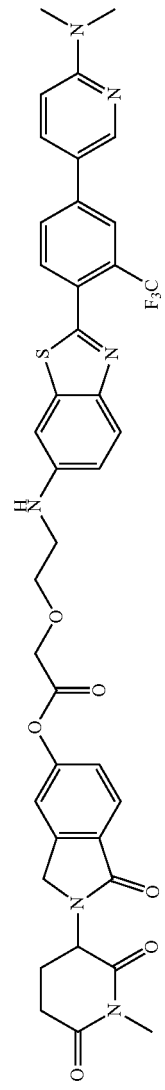
120018
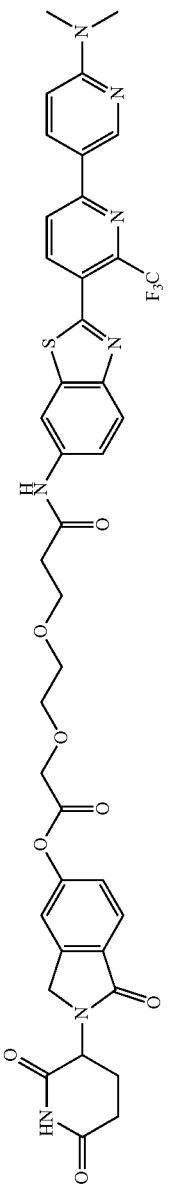
120019

TABLE 2-continued
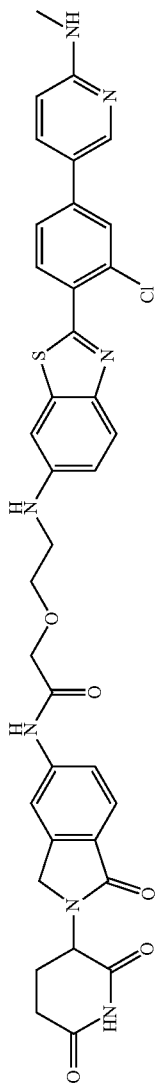
123013
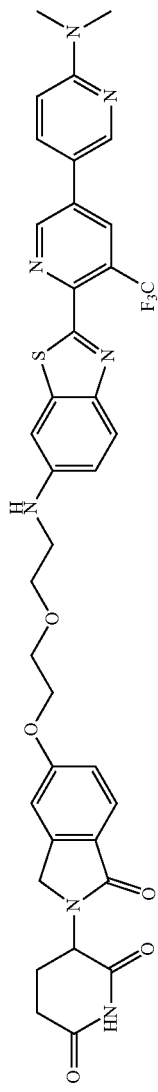
123014
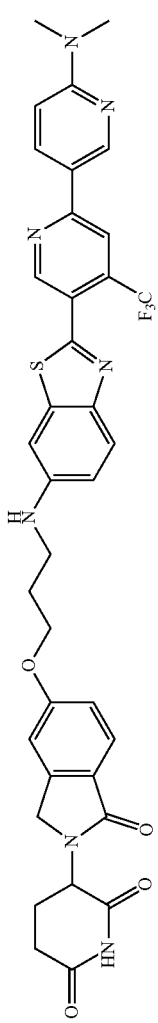
123015
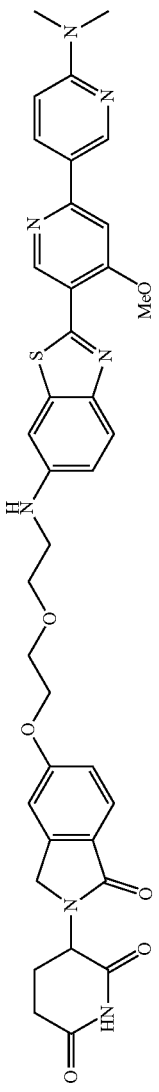
123016
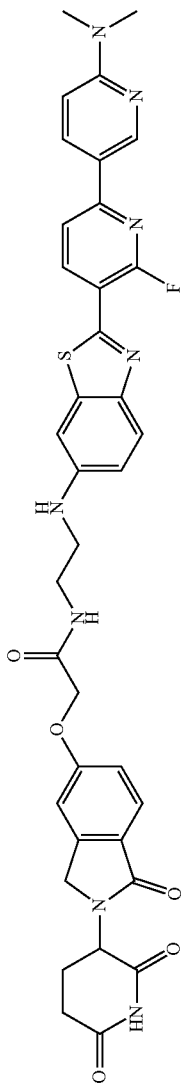
123017

TABLE 2-continued
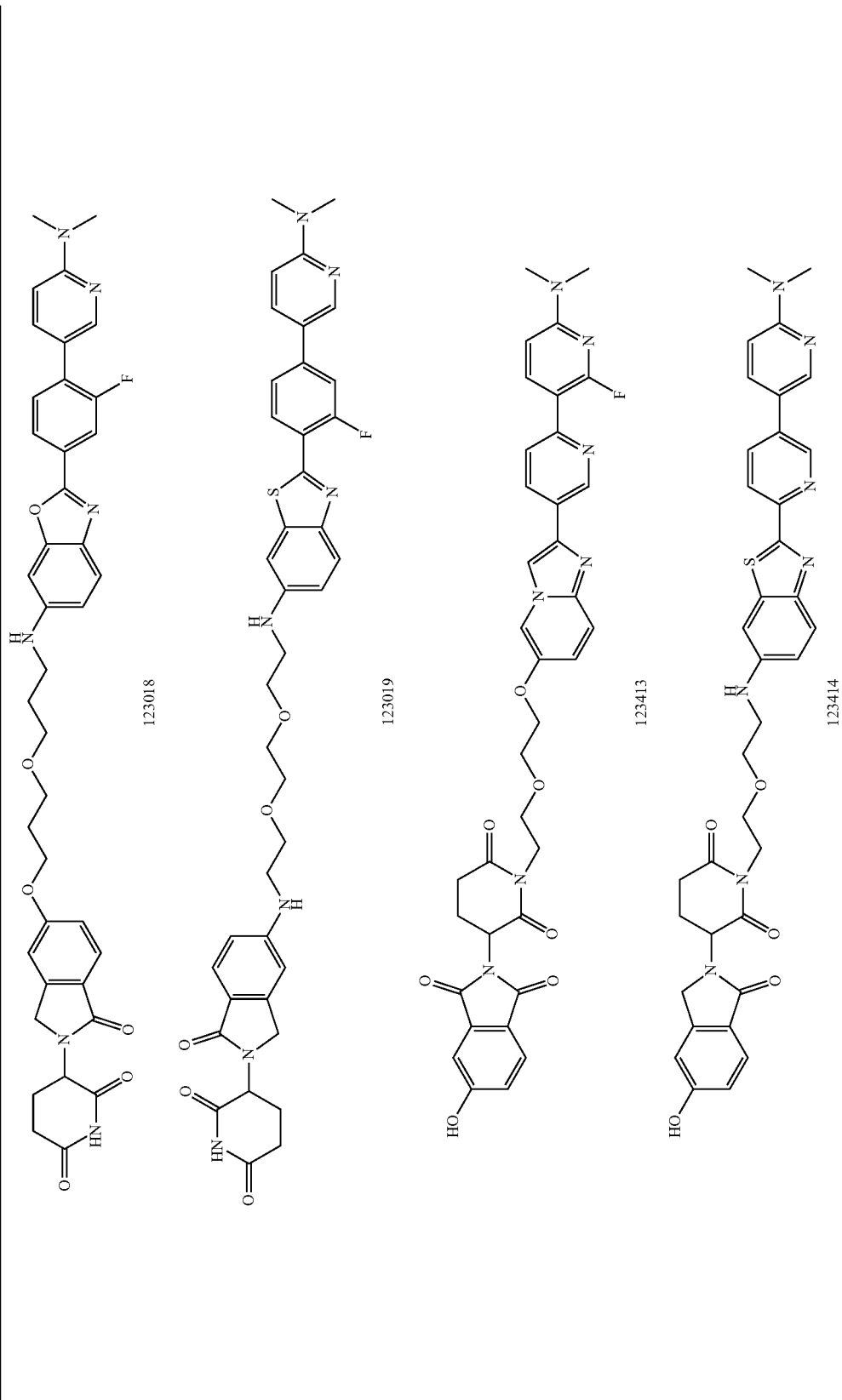

TABLE 2-continued
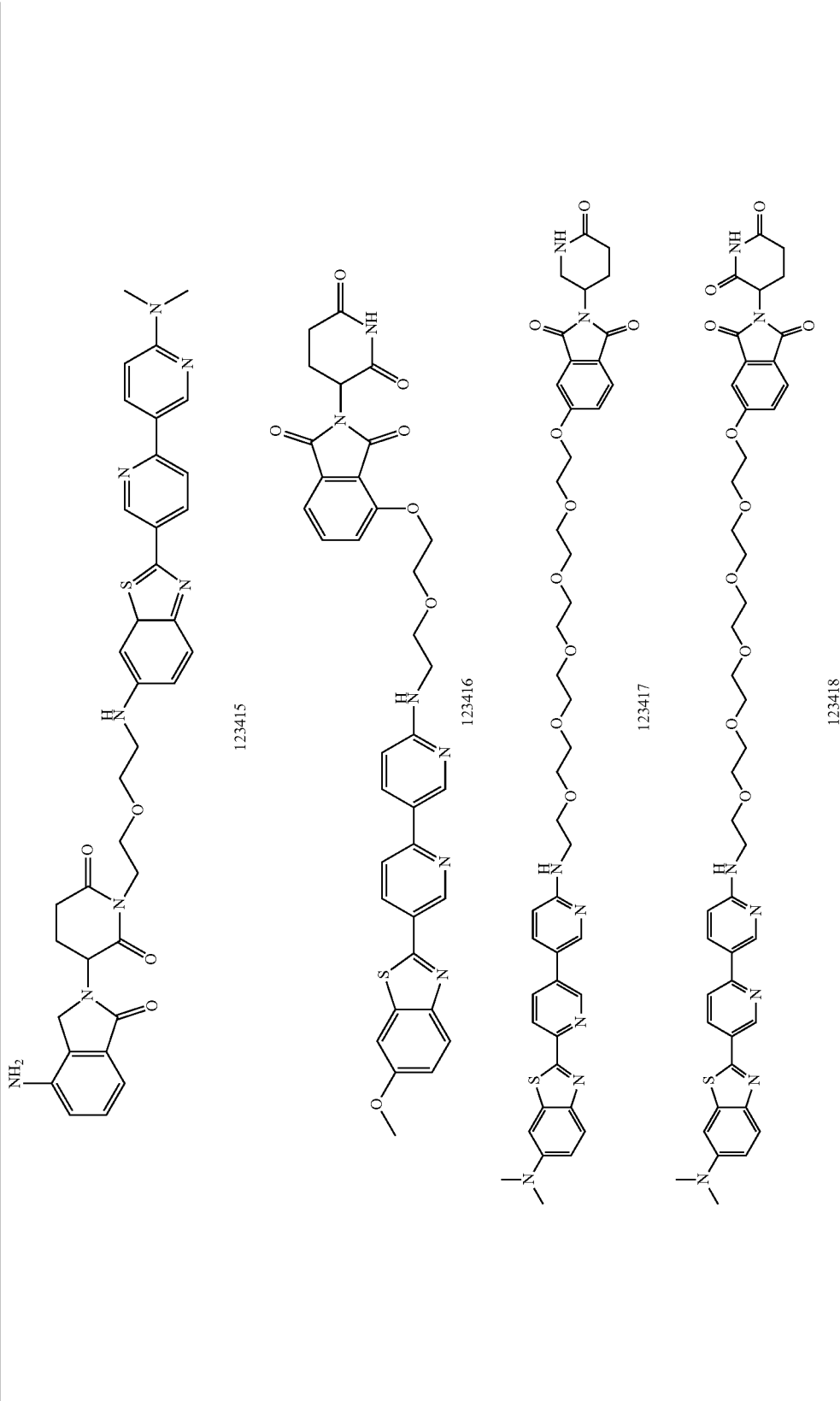

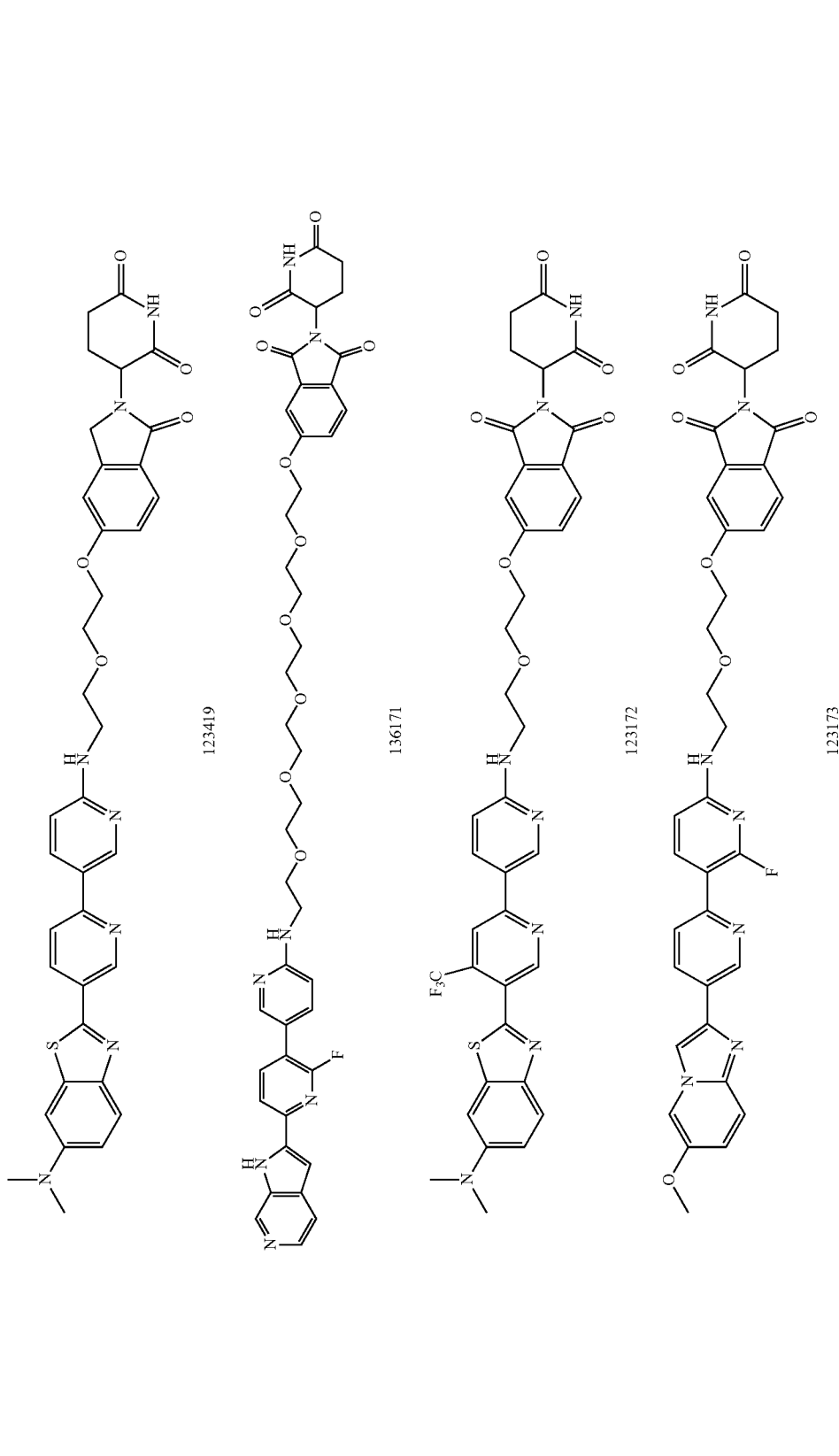

TABLE 2-continued

TABLE 2-continued
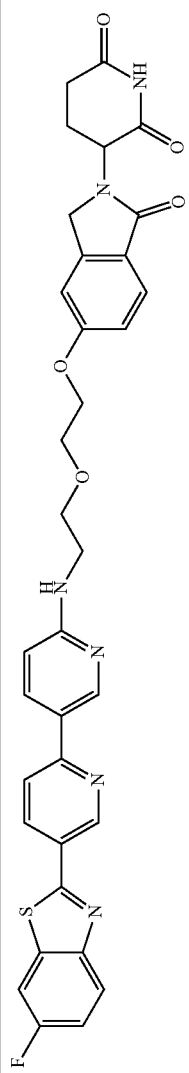
136179
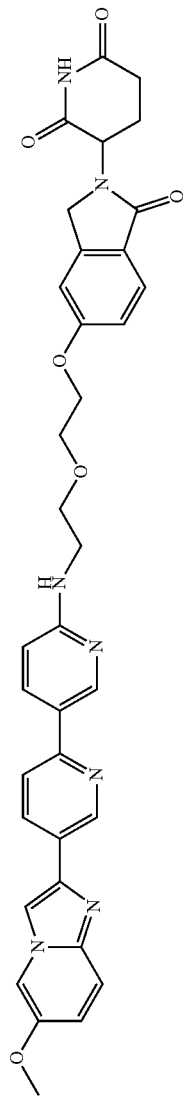
136571
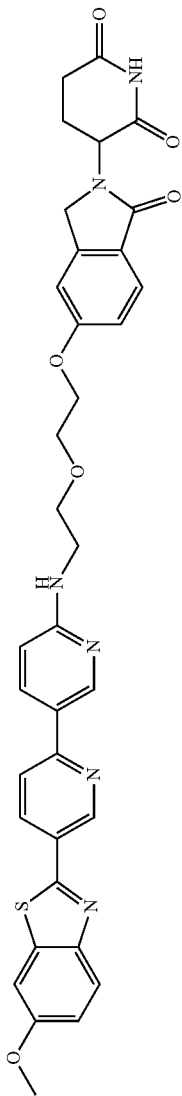
136572
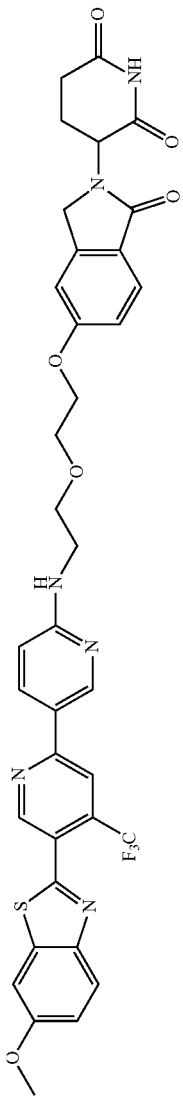
136573

TABLE 2-continued
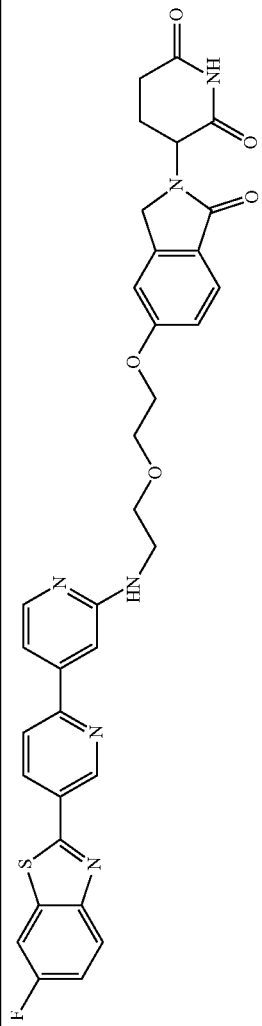
136574
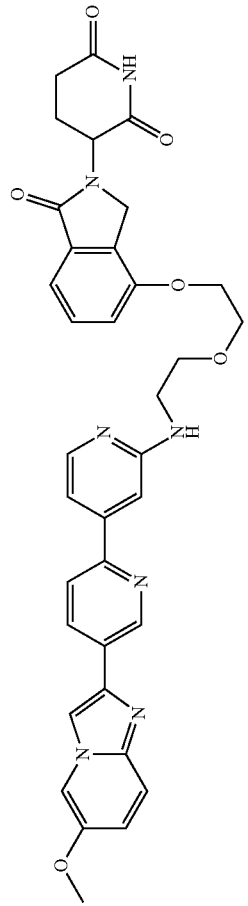
136575
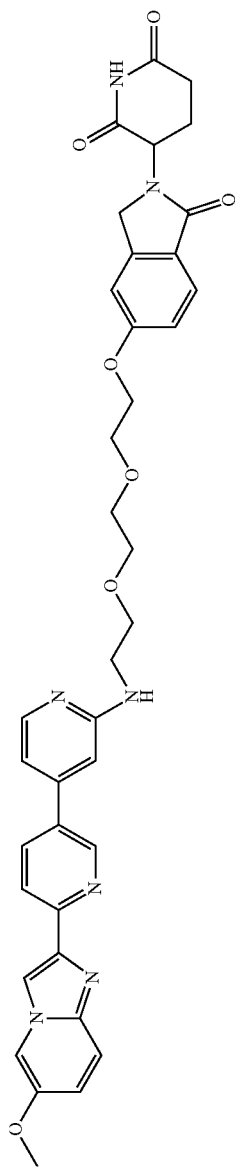
136576
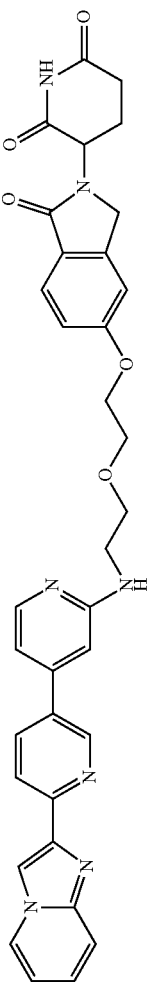
136577

TABLE 2-continued
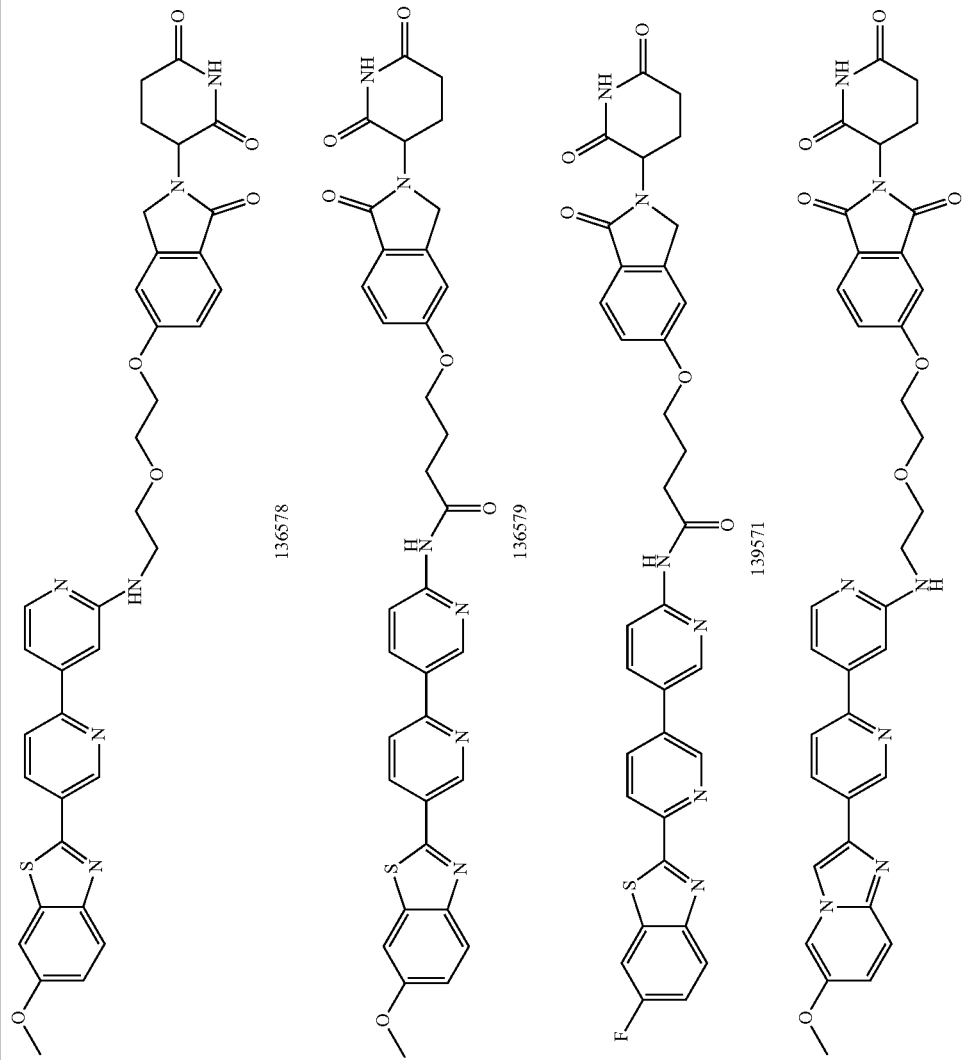

TABLE 2-continued
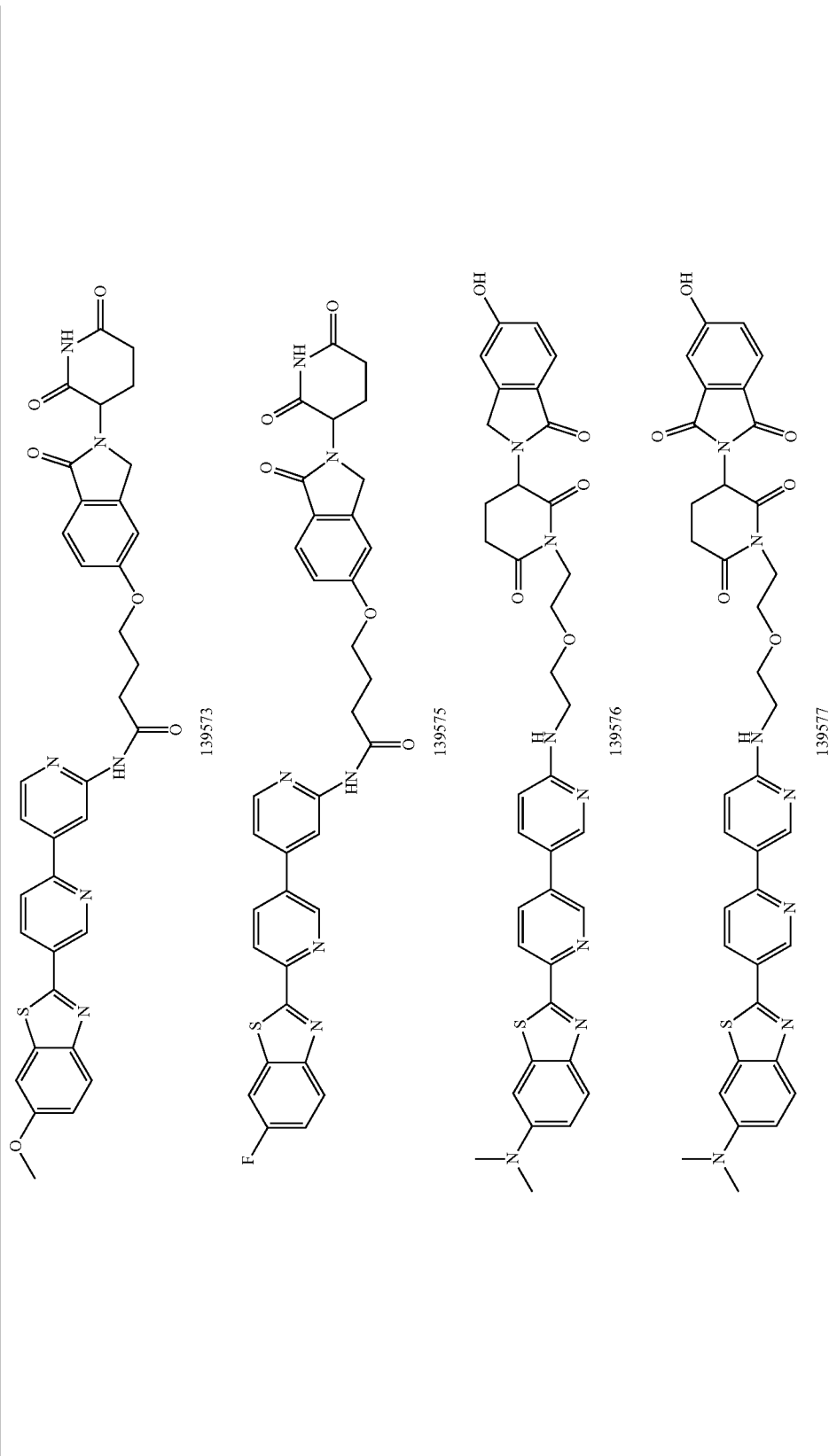

TABLE 2-continued
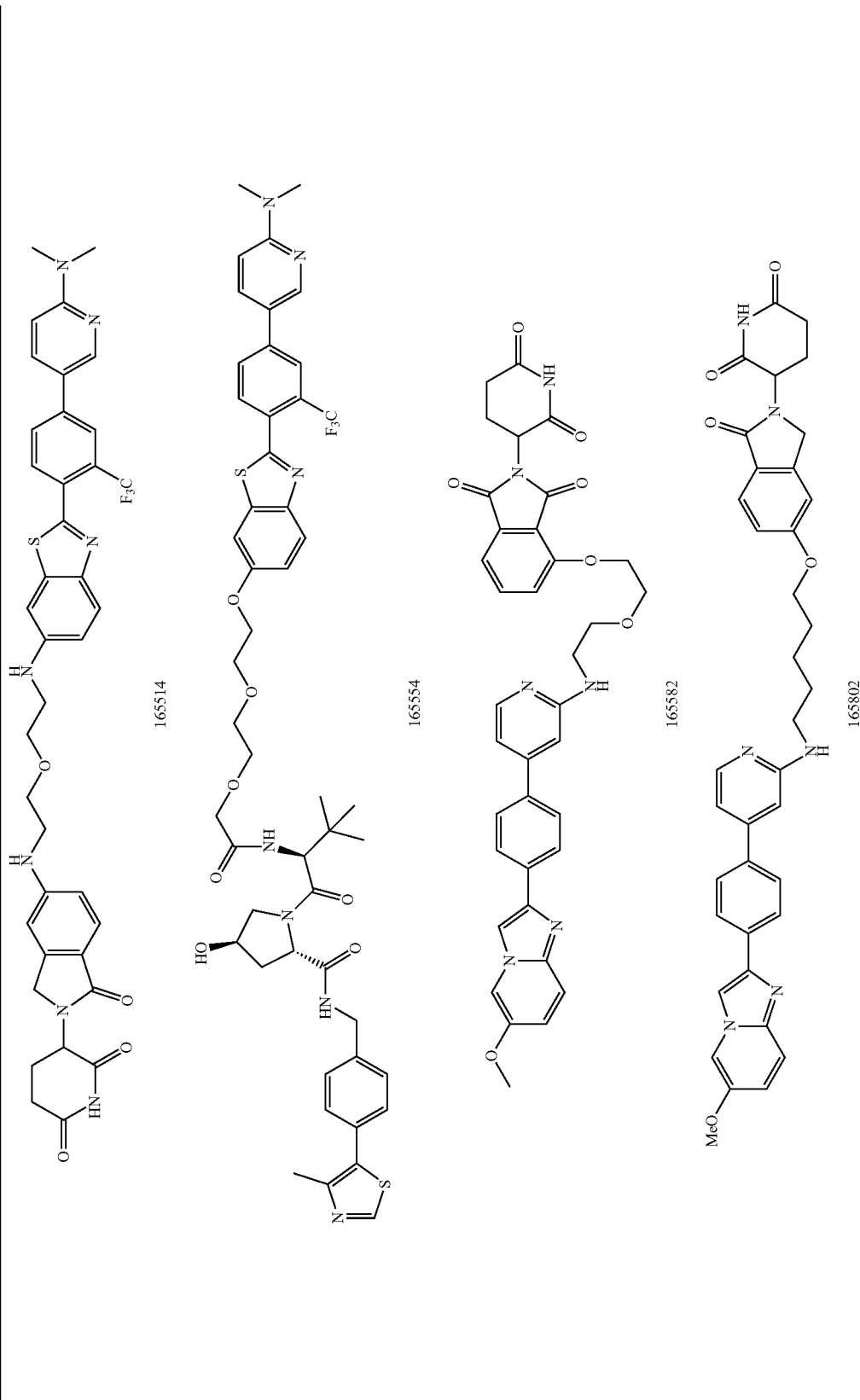

TABLE 2-continued
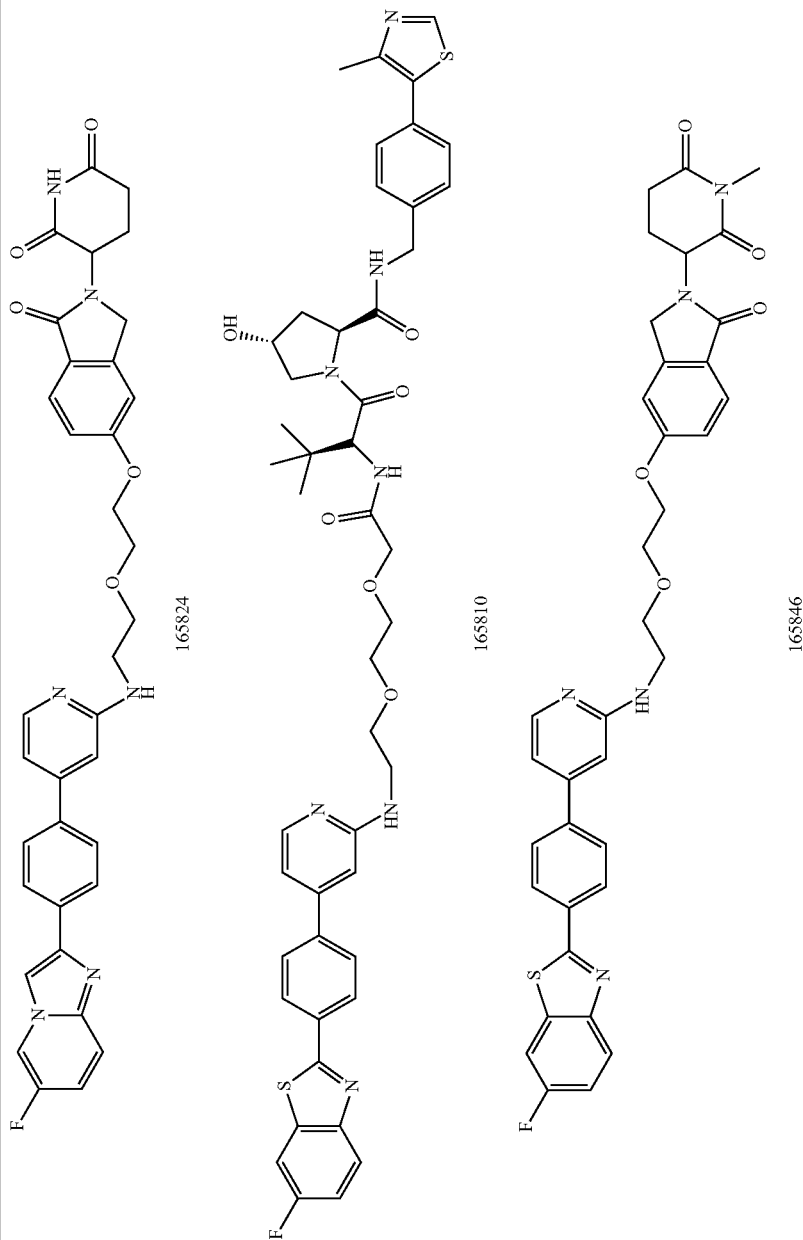

TABLE 2-continued
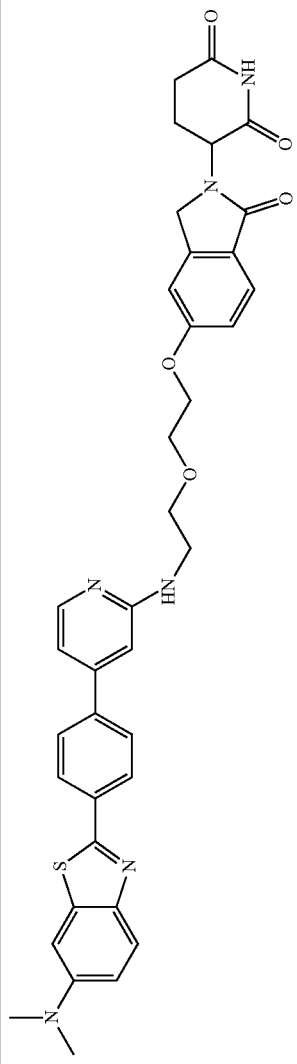
165950
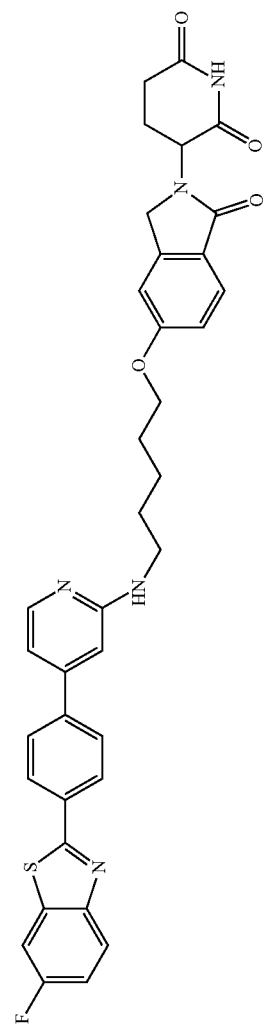
165825
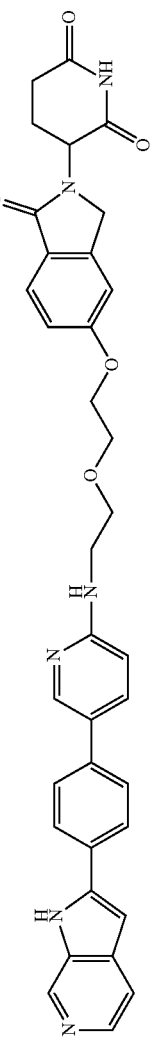
165954

TABLE 2-continued
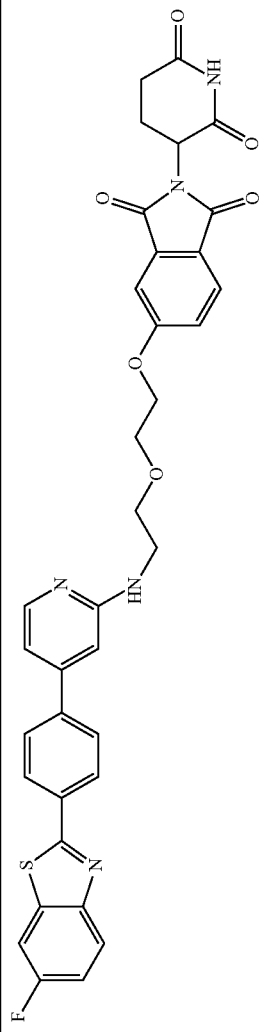
165952
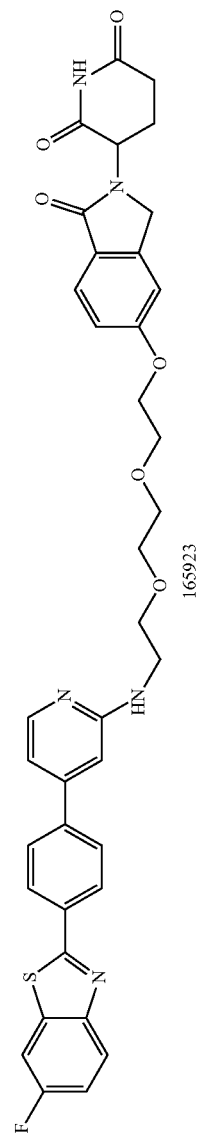
165923
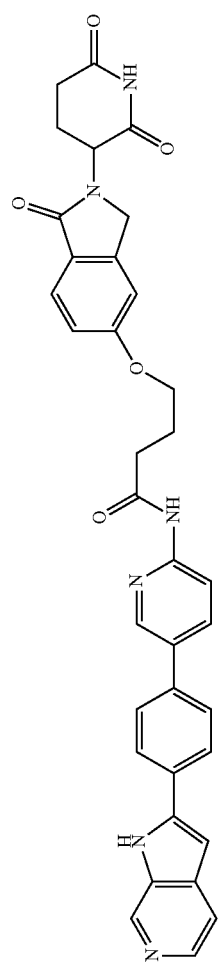
166099
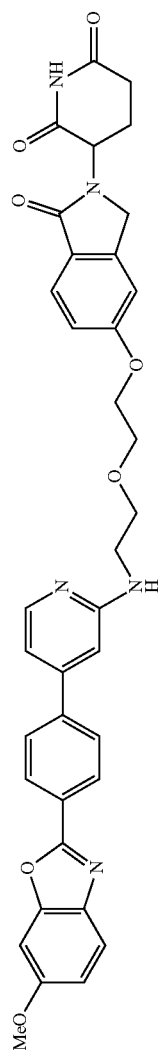
166123

TABLE 2-continued
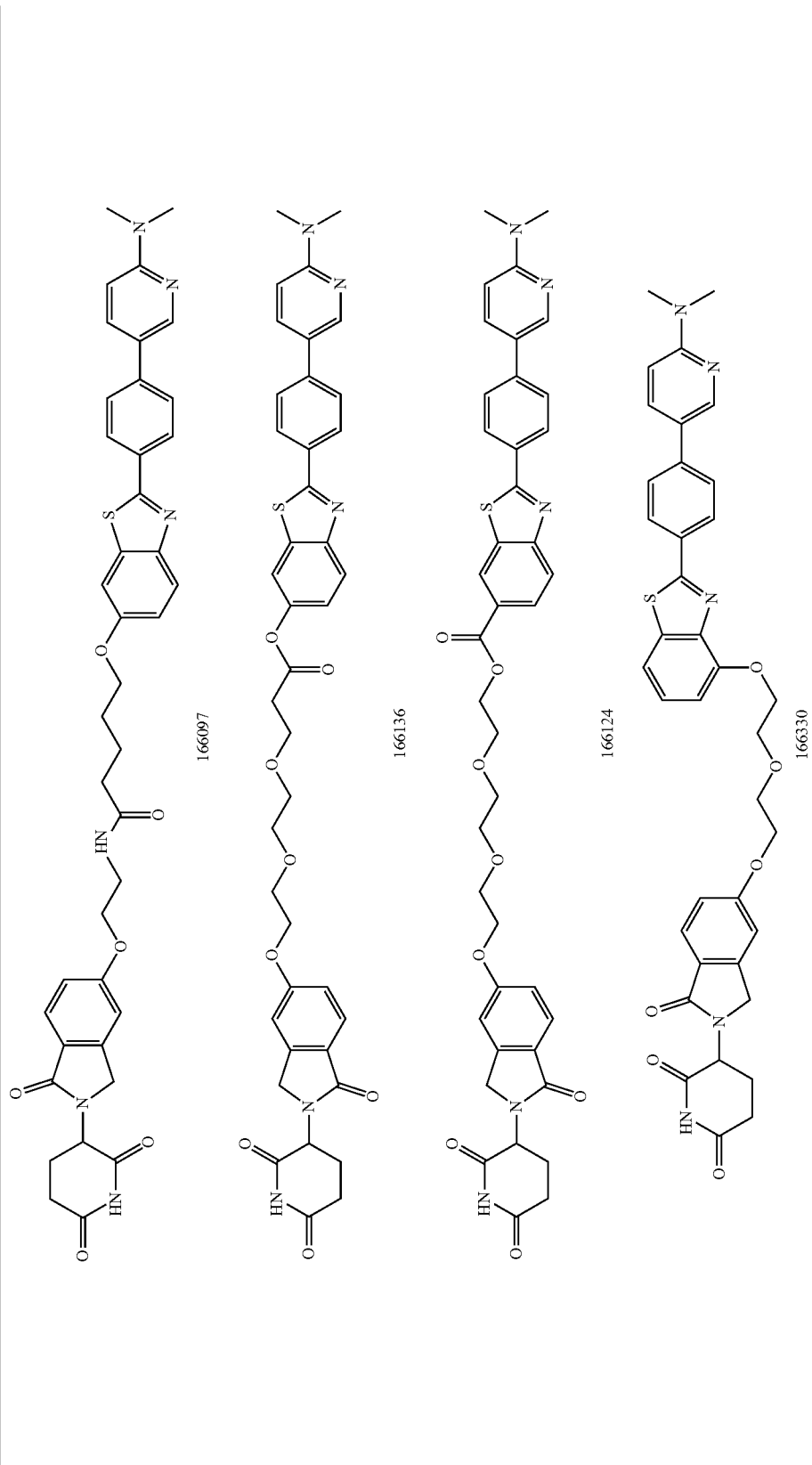

TABLE 2-continued
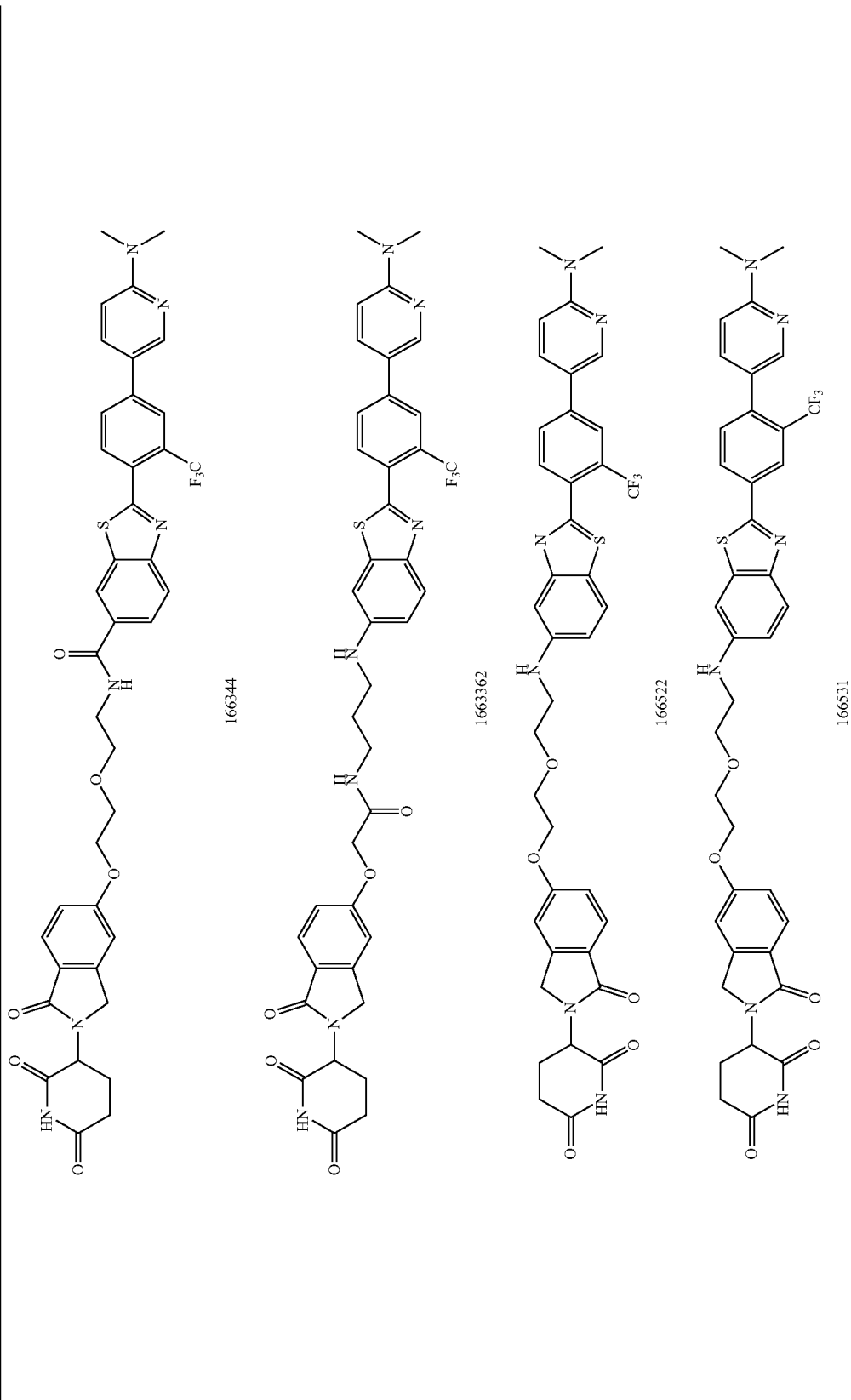

TABLE 2-continued
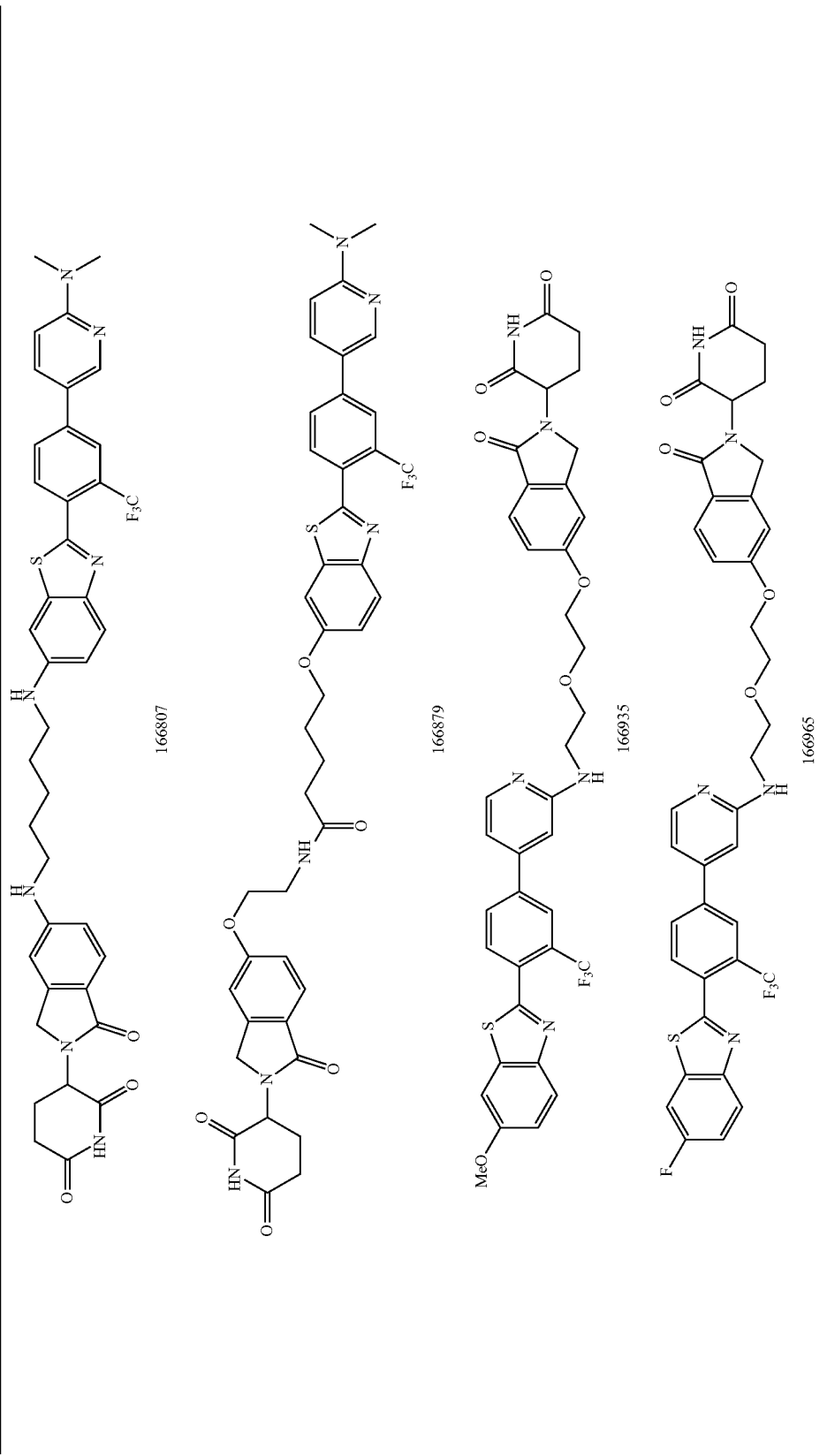

In some embodiments, provided herein is a solvate, hydrate, salt, or ester of a compound of the present disclosure.

An aspect of the disclosure is a composition, comprising a compound disclosed herein and at least one pharmaceutically acceptable excipient.

Definitions

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein. When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having indicated number of carbon atoms. In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), amyl ($C_5$), neopentyl ($C_5$), 3-methyl-2-butyl ($C_5$), tertiary amyl ($C_5$), and n-hexyl ($C_6$).

"Alkenyl" refers to an alkyl group with one or more carbon-carbon double bonds at any position of the chain, which can be monosubstituted or polysubstituted, and can be monovalent, divalent or multivalent. Examples of the alkenyl group include a vinyl group, a propenyl group, a butenyl group, a pentenyl group, a hexenyl group, a butadienyl group, a pentadienyl group, a hexadienyl group, etc.

"Alkynyl" refers to an alkyl group with one or more carbon-carbon triple bonds at any position of the chain, which can be monosubstituted or polysubstituted, and can be monovalent, divalent or multivalent. Examples of alkynyl groups include ethynyl, propynyl, butynyl, pentynyl, etc.

"Cycloalkyl" includes any stable cyclic or polycyclic hydrocarbon group and any carbon atom which is saturated, which can be monosubstituted or polysubstituted, and can be monovalent, divalent or multivalent. Examples of such cycloalkyl groups include, but are not limited to, cyclopropyl, norbornyl, [2.2.2]bicyclooctane, [4.4.0]bicyclononane, etc.

"Optionally" means that an event or situation described subsequently may, but not necessarily, occur, and the description includes the occurrence of the event or situation mentioned above and the absence of the event or situation described therein.

"Substituted" means that any one or more hydrogen atoms on a particular atom are replaced with substituents, including deuterium and hydrogen variants, as long as the valence of a particular atom is normal and the substituted compound is stable. When the substituent is a keto (i.e., =O), it means that two hydrogen atoms are substituted. Ketone substitution does not occur on aromatic groups. The term "optionally substituted" means that it may or may not be substituted. Unless otherwise specified, the type and number of substituents may be arbitrary on the basis of being chemically achievable.

When any variable (e.g., R) occurs more than one time in any constituents or formula for a compound, its definition at each occurrence is independent of its definition at every other occurrence. Thus, for example, if a group is shown to be substituted by 0-2 of R, then said group may optionally be substituted by up to two R groups and R at each occurrence is selected independently from the definition of R. Also, combinations of substituents and/or variables are permissible only if such combinations result in stable compounds.

When the number of a bonding group is zero, for example, -(A)$_0$-, then this bonding group is a single bond.

"Alkoxy" refers to refers to said alkyl group with a specified number of carbon atoms attached through an oxygen bridge. Unless otherwise specified, $C_{1-6}$ alkoxy includes $C_1$, $C_2$, $C_3$, $C_4$, $C_5$ and $C_6$ alkoxy group. Examples of alkoxy groups include, but are not limited to, methoxy, ethoxy, n-propoxy, isopropoxy, n-butoxy, sec-butoxy, tert-butoxy, n-pentyloxy and S-pentyloxy.

"Aryl" refers to a polyunsaturated, aromatic hydrocarbon substituent which can be monosubstituted or polysubstituted, and can be monovalent, divalent or polyvalent, and can be monocyclic or polycyclic (e.g., 1 to 3 rings; at least one of which is aromatic). They are fused together or covalently linked.

"Halo" or "halogen" by itself or as part of another substituent refers to a fluorine, chlorine, bromine or iodine atom.

"Haloalkyl" includes both monohaloalkyl and polyhaloalkyl. For example, the term "halo($C_{1-4}$)alkyl" includes, but is not limited to, trifluoromethyl, 2,2,2-trifluoroethyl, 4-chlorobutyl, 3-bromopropyl, etc. Unless otherwise specified, examples of haloalkyl include, but are not limited to, trifluoromethyl, trichloromethyl, pentafluoroethyl, and pentachloroethyl.

"Heterocyclo" refers to a radical of a 3- to 10-membered non-aromatic ring or aromatic ring system having indicated ring carbon atoms (such as 2 to 6 ring carbon atoms) and 1 to 4 ring heteroatoms, wherein each heteroatom is independently selected from nitrogen, oxygen and sulfur ("$C_{2-6}$ heterocyclo"). In heterocyclo groups that contain one or more nitrogen atoms, the point of attachment can be a carbon or nitrogen atom, as valency permits. A heterocyclo group can either be monocyclic ("monocyclic heterocyclo") or a fused, bridged or spiro ring system such as a bicyclic system ("bicyclic heterocyclo"), and can be saturated or partially unsaturated. Heterocyclo bicyclic ring systems can include one or more heteroatoms in one or both rings. "Heterocyclo" also includes ring systems wherein the heterocyclic ring, as defined above, is fused with one or more carbocyclic groups wherein the point of attachment is either on the carbocyclic or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

"Nitrogen protecting group" refers to a protecting group for preventing side reactions at the amino nitrogen position. Representative amino protecting groups include, but are not limited to formyl; acyl, such as alkanoyl (e.g., acetyl, trichloroacetyl or trifluoroacetyl); alkoxycarbonyl, such as tert-butoxycarbonyl (Boc); Arylmethoxycarbonyl, such as benzyloxycarbonyl (Cbz) and 9-fluorenylmethoxycarbonyl (Fmoc); arylmethyl, such as benzyl (Bn), trityl (Tr), 1,1-di-(4'-methoxyphenyl)methyl; silyl groups such as trimethylsilyl (TMS) and tert-butyldimethylsilyl (TBS), etc.

In some embodiments, a heterocyclo group is a 5-10 membered non-aromatic ring system or aromatic ring system having indicated ring carbon atoms and 1-4 ring heteroatoms, wherein each heteroatom is independently selected from nitrogen, oxygen, and sulfur. In some embodiments, a heterocyclo group is a 5-6 membered non-aromatic ring system or aromatic ring system having indicated ring carbon atoms and 1-4 ring heteroatoms, wherein each heteroatom is independently selected from nitrogen, oxygen, and sulfur ("5-6 membered heterocyclo"). In some embodiments, the 5-6 membered heterocyclo has 1-3 ring heteroatoms selected from nitrogen, oxygen, and sulfur. In some embodiments, the 5-6 membered heterocyclo has 1-2 ring heteroatoms selected from nitrogen, oxygen, and sulfur. In some embodiments, the 5-6 membered heterocyclo has one ring heteroatom selected from nitrogen, oxygen, and sulfur.

Exemplary 3-membered heterocyclo groups containing one heteroatom include, without limitation, azirdinyl, oxiranyl, and thiorenyl. Exemplary 4-membered heterocyclo groups containing one heteroatom include, without limitation, azetidinyl, oxetanyl, and thietanyl. Exemplary 5-membered heterocyclo groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclo groups containing two heteroatoms include, without limitation, dioxolanyl, oxasulfuranyl, disulfuranyl, and oxazolidin-2-one. Exemplary 5-membered heterocyclo groups containing three heteroatoms include, without limitation, triazolinyl, oxadiazolinyl, and thiadiazolinyl. Exemplary 6-membered heterocyclo groups containing one heteroatom include, without limitation, piperidinyl, tetrahydropyranyl, dihydropyridinyl, and thianyl. Exemplary 6-membered heterocyclo groups containing two heteroatoms include, without limitation, piperazinyl, morpholinyl, dithianyl, and dioxanyl. Exemplary 6-membered heterocyclo groups containing two heteroatoms include, without limitation, triazinanyl. Exemplary 7-membered heterocyclo groups containing one heteroatom include, without limitation, azepanyl, oxepanyl, and thiepanyl. Exemplary 8-membered heterocyclo groups containing one heteroatom include, without limitation, azocanyl, oxecanyl, and thiocanyl. Exemplary 5-membered heterocyclo groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclo groups fused to an aryl ring (also referred to herein as a 6,6-bicyclic heterocyclic ring) include, without limitation, tetrahydroquinolinyl, tetrahydroisoquinolinyl, and the like.

The term "pharmaceutically acceptable salt" means a salt that is not harmful to mammals, especially humans. Pharmaceutically acceptable salts can be formed using non-toxic acids or bases, including mineral acids or inorganic bases, or organic acids or organic bases. Examples of pharmaceutically acceptable salts include metal salts formed with aluminum, calcium, lithium, magnesium, potassium, sodium, zinc and so on, and organic salts formed with lysine, N,N'-dibenzylethylenediamine, chloroprocaine, choline, diethanolamine, ethylenediamine, meglumine (N-methylglucamine), procaine and so on. Also, pharmaceutically acceptable salts contain acid-addition salts and base-addition salts.

The term "solvate" means a solvent-containing compound that is formed by association of one or a plurality of solvent molecules to the compounds of the present disclosure. Solvates include, for example, monosolvates, disolvates, trisolvates, and tetrasolvates. Also, solvates include hydrates. The term "hydrate" means a compound further containing a stoichiometric or a non-stoichiometric amount of water constrained by non-covalent bonding intermolecular force, or a salt thereof. Hydrates include monohydrates, dihydrates, trihydrates, tetrahydrates, and the like.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If there are uses of the term which are not clear to persons of ordinary skill in the art, given the context in which it is used, "about" will mean up to plus or minus 10% of the particular term.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs)

and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms of the disease have developed or have been observed. In other embodiments, treatment may be administered in the absence of signs or symptoms of the disease or condition. For example, treatment may be administered to a susceptible subject prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound or a composition refers to an amount sufficient to elicit the desired biological response, i.e., treating the condition. As will be appreciated by those of ordinary skill in this art, the effective amount of a compound or a composition may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound or a composition is an amount sufficient to provide a therapeutic benefit in the treatment of a condition or to delay or minimize one or more symptoms associated with the condition. A therapeutically effective amount of a compound or a composition means an amount of therapeutic agent, alone or in combination with other therapies, which provides a therapeutic benefit in the treatment of the condition. The term "therapeutically effective amount" can encompass an amount that improves overall therapy, reduces, or avoids symptoms or causes of the condition, or enhances the therapeutic efficacy of another therapeutic agent.

The terms "alpha-synuclein", "α-synuclein" and "α-Syn" are used interchangeably herein and refer to a 140 amino acid polypeptide with the following amino acid sequence (wild-type human α-synuclein).

TABLE 1

GenBank Accession No. P37840

SEQ ID NO: 1
MDVFMKGLSKAKEGVVAAAEKTKQGVAEAAGKTKEGVLYVGSKTKEGV
VHGVATVAEKTKEQVTNVGGAV

VTGVTAVAQKTVEGAGSIAAATGFVKKDQLGKNEEGAPQEGILEDMPV
DPDNEAYEMPSEEGYQDYEPEA

The terms "aggregated α-synuclein", "α-synuclein aggregate" and "α-synuclein aggregates" are used interchangeably herein.

For E3 ubiquitin ligase, an exemplary amino acid sequence is shown in Table 2.

TABLE 2

E3 ubiquitin ligase [Homo sapiens]
GenBank Accession No. AAP47174.1

SEQ ID NO: 2
MEEGNNNEEVIHLNNFHCHRGQEWINLRDGPITISDSSDEERIPMLVT
PAPQQHEEEDLDDDVILTEDDS

EDDYGEFLDLGPPGISEFTKPSGQTEREPKPGPSHNQAANDIVNPRSE
QKVIILEEGSLLYTESDPLETA

NQSSEDSETELLSNLGESAALADDQAIEEDCWLDHPYFQSLNQQPREI
TNQVVPQERQPEAELGRLLFQH

EFPGPAFPRPEPQQGGISGPSSPQPAHPLGEFEDQQLASDDEEPGPAF
PMQESQEPNLENIWGQEAAEVD

QELVELLVKETEARFPDVANGFIEEIIHFKNYYDLNVLCNFLLENPDY
PKREDRIIINPSSSLLASQDET

KLPKIDFFDYSKLTPLDQRCFIQAADLLMADFKVLSSQDIKWALHELK
GHYAITRKALSDAIKKWQELSP

ETSGKRKKRKQMNQYSYIDFKFEQGDIKIEKRMFFLENKRRHCRSYDR
RALLPAVQQEQEFYEQKIKEMA

EHEDFLLALQMNEEQYQKDGQLIECRCCYGEFPFEELTQCADAHLFCK
ECLIRYAQEAVFGSGKLELSCM

EGSCTCSFPTSELEKVLPQTILYKYYERKAEEEVAAAYADELVRCPSC
SFPALLDSDVKRFSCPNPHCRK

ETCRKCQGLWKEHNGLTCEELAEKDDIKYRTSIEEKMTAARIRKCHKC
GTGLIKSEGCNRMSCRCGAQMC

YLCRVSINGYDHFCQHPRSPGAPCQECSRCSLWTDPTEDDEKLIEEIQ
KEAEEEQKRKNGENTFKRIGPP

LEKPVEKVQRVEALPRPVPQNLPQPQMPPYAFAHPPFPLPPVRPVFNN
FPLNMGPIPAPYVPPLPNVRVN

YDFGPIHMPLEHNLPMHFGPQPRHRF

For E3 ubiquitin ligase, another exemplary amino acid sequence is shown in Table 3.

TABLE 3

E3 ubiquitin ligase [Homo sapiens]
GenBank Accession No. AAP47175.1

SEQ ID NO: 3
MEEGNNNEEVIHLNNFHCHRGQEWINLRDGPITISDSSDEERIPMLVT
PAPQQHEEEDLDDDVILTETNK

PQRSRPNLIKPAAQWQDLKRLGEERPKKSRAAFESDKSSYFSVCNNP
LFDSGAQDDSEDDYGEFLDLGPP

GISEFTKPSGQTEREPKPGPSHNQAANDIVNPRSEQKVIILEEGSLL
YTESDPLETQNQSSEDSETELLS

NLGESAALADDQAIEEDCWLDHPYFQSLNQQPREITNQVVPQERQPEA
ELGRLLFQHEFPGPAFPRPEPA

QGGISGPSSPQPAHPLGEFEDQQLASDDEEPGPAFPMQESQEPNLENIW
GQEAAEVDQELVELLVKETEA

RFPDVANGFIEEIIHFKNYYDLNVLCNFLLENPDYPKREDRIIINPSSS
LLASQDETKLPKIDFFDYSKL

TPLDQRCFIQAADLLMADFKVLSSQDIKWALHELKGHYAITRKALSDAI
KKWQELSPETSGKRKKRKQMN

QYSYIDFKFEQGDIKIEKRMFFLENKRRHCRSYDRRALLPAVQQEQEFY
EQKIKEMAEHEDFLLALQMNE

TABLE 3-continued

E3 ubiquitin ligase [Homo sapiens]
GenBank Accession No. AAP47175.1

EQYQKDGQLIECRCCYGEFPFEELTQCADAHLFCKECLIRYAQEAVFGS
GKLELSCMEGSCTCSFPTSEL

EKVLPQTILYKYYERKAEEEVAAAYADELVRCPSCSFPALLDSDVKRFS
CPNPHCRKETCRKCQGLWKEH

NGLTCEELAEKDDIKYRTSIEEKMTAARIRKCHKCGTGLIKSEGCNRM
SCRCGAQMCYLCRVSINGYDHF

CQHPRSPGAPCQECSRCSLWTDPTEDDEKLIEEIQKEAEEEQKRKNGE
NTFKRIGPPLEKPVEKVQRVEA

LPRPVPQNLPQPQMPPYAFAHPPFPLPPVRPVFNNFPLNMGPIPAPYVP
PLPNVRVNYDFGPIHMPLEHN

LPMHFGPQPRHRF

The term "binder" refers to a compound that binds to a protein. The binder binds to a protein with a Kd of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

The term "proteasome" refers to a protease complex for carrying out degradation of proteins. Specifically, the proteasome is a multisubunit enzyme complex, which can also play a key role regulating proteins that control cell-cycle progression and apoptosis. The proteasome conducts proteolysis of selected proteins.

The term "pharmaceutically acceptable excipient" means pharmaceutically acceptable materials, compositions, or vehicles such as physiological saline solutions, liquid or solid fillers, diluents, solvents, or encapsulants. Examples of pharmaceutically acceptable excipients include water, saline water, physiological saline water or phosphate buffered saline water (PBS), sodium chloride injection solution, Ringer's injection solution, isotonic dextrose injection solution, sterile water injection solution, dextrose, and lactated Ringer's injection solution.

Synthesis of Compounds

The compounds of the present disclosure can be prepared by a variety of synthetic methods well known to those skilled in the art, including the embodiments listed below, combinations thereof with other chemical synthesis methods, and equivalent alternatives known to those skilled in the art.

The following synthetic procedures are provided as examples, using which one of ordinary skill in the art can synthesize the compounds of the disclosure.

Compounds of Formula (I)

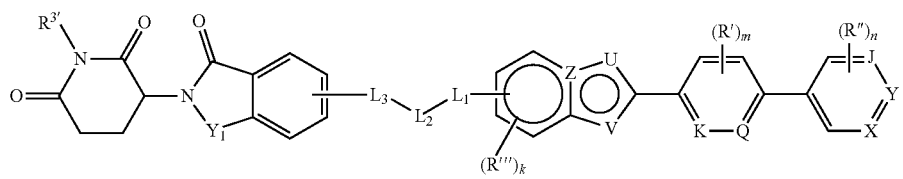

Formula I

Compounds of the general formula (I) are prepared as set forth in the Scheme below:

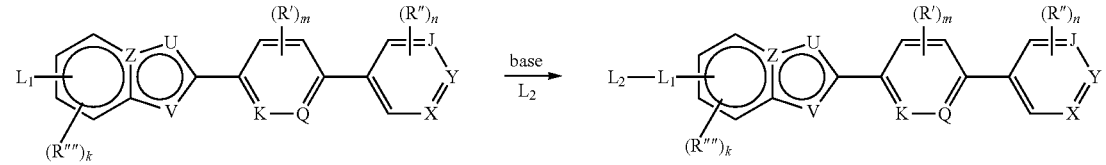

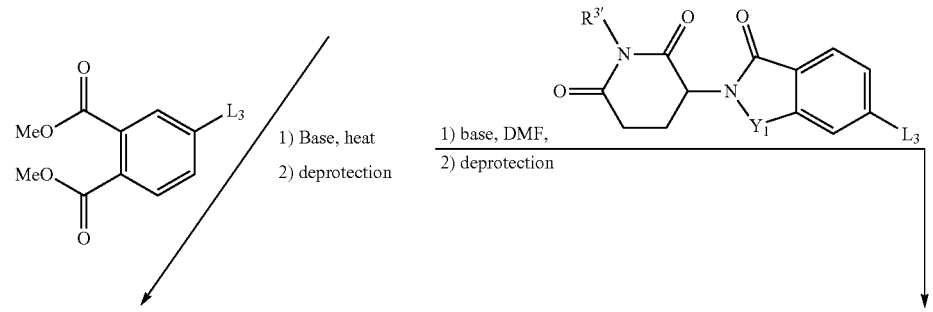

-continued
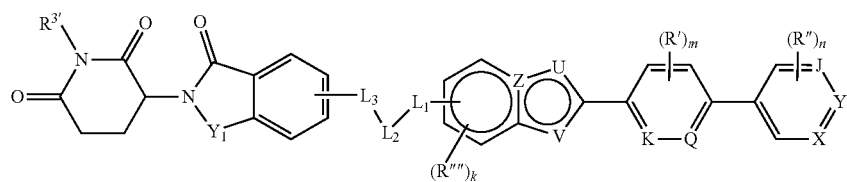
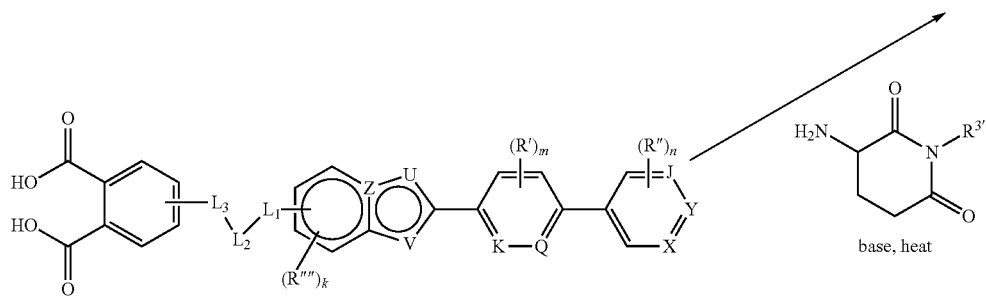
Compounds of Formula (II)
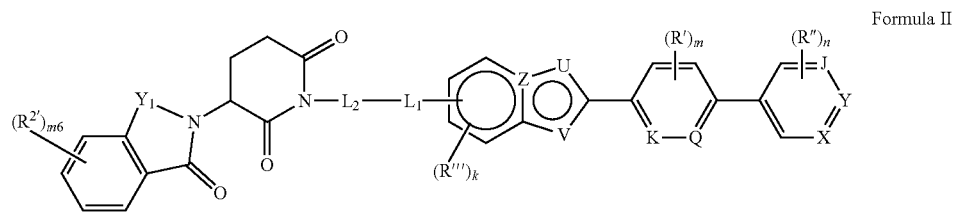
Formula II
Compounds of the general formula (II) are prepared as set forth in the Scheme below:
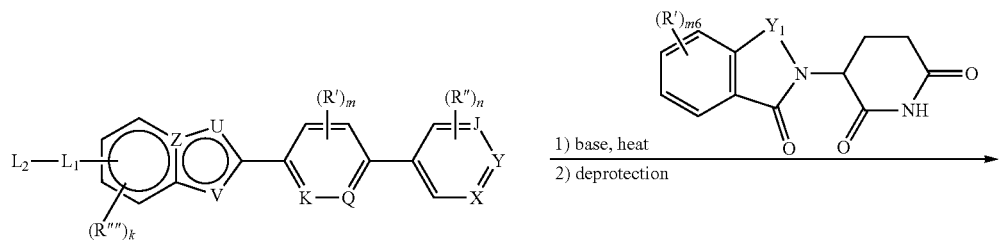
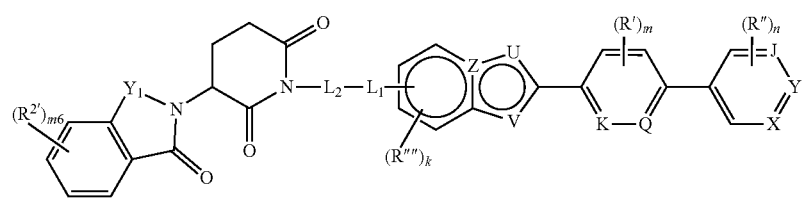

Compounds of Formula (III)
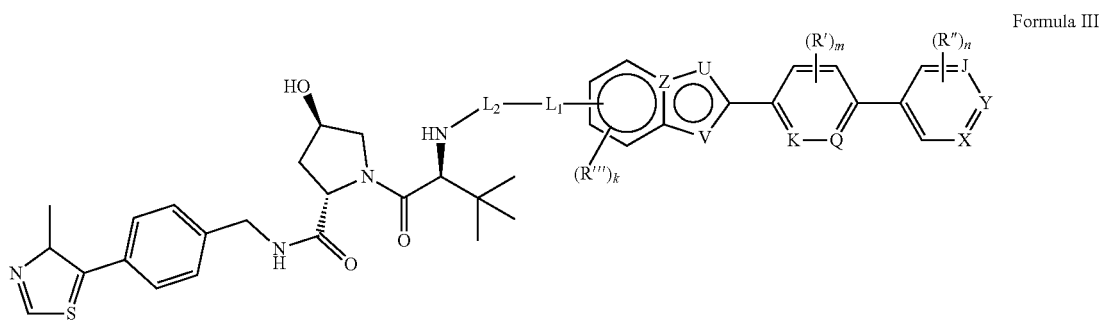
Formula III
Compounds of the general formula (III) are prepared as set forth in the Scheme below:
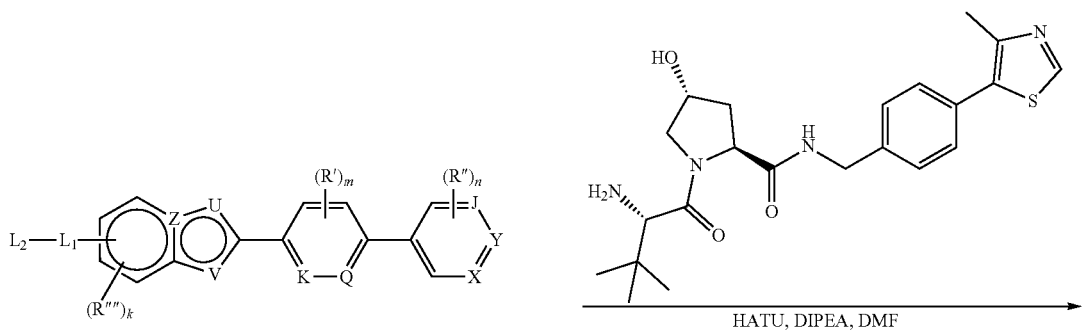
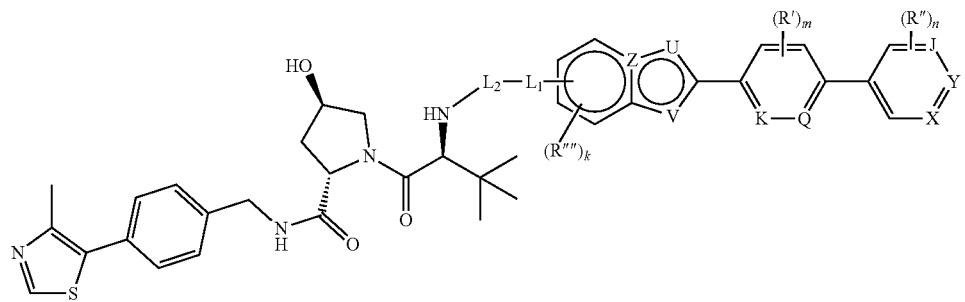
Compounds of Formula (IV)
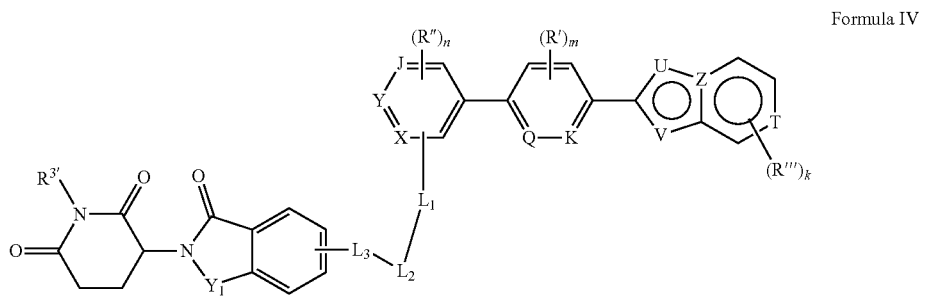
Formula IV Compounds of the general formula (IV) are prepared as set forth in the Scheme below:
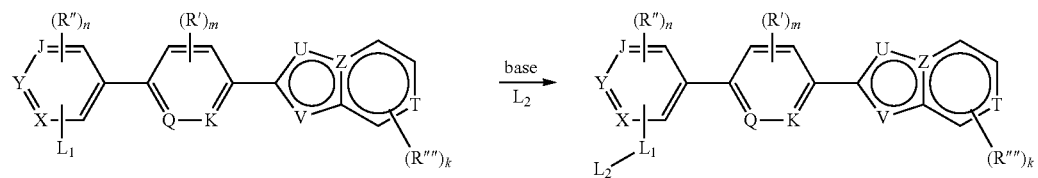
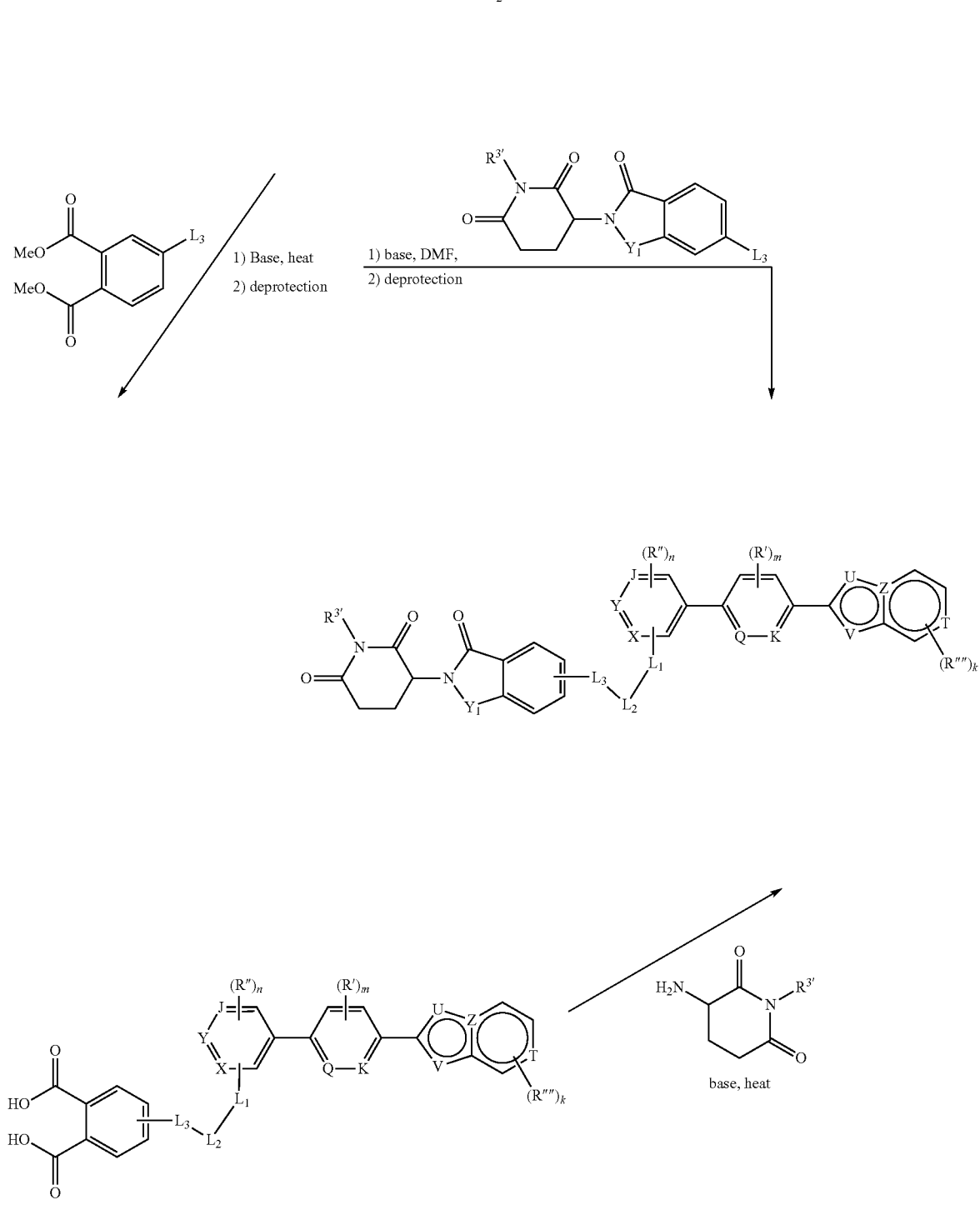

Compounds of Formula (V)
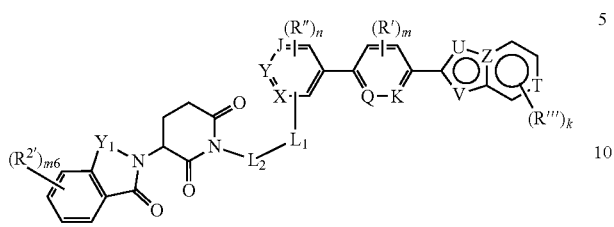
Formula V
Compounds of the general formula (V) are prepared as set forth in the Scheme below:
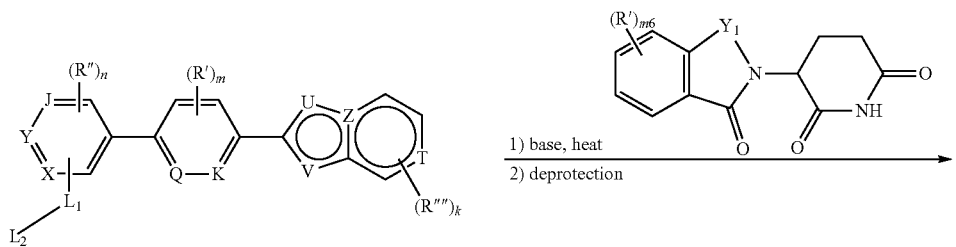
1) base, heat
2) deprotection
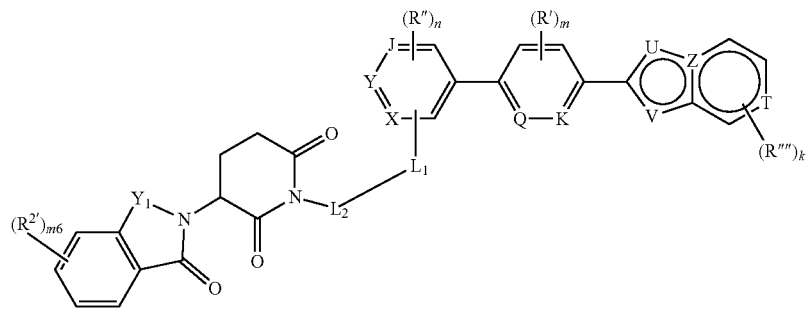
Compounds of Formula (VI)
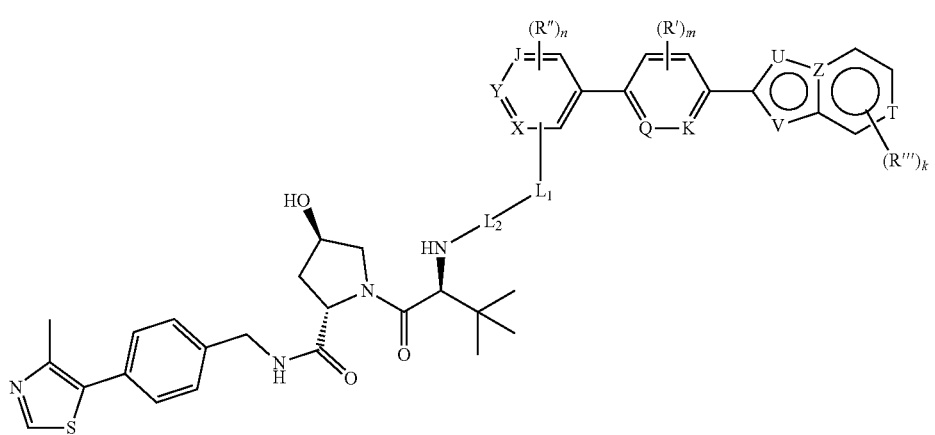
Formula VI Compounds of the general formula (VI) are prepared as set forth in the Scheme below:

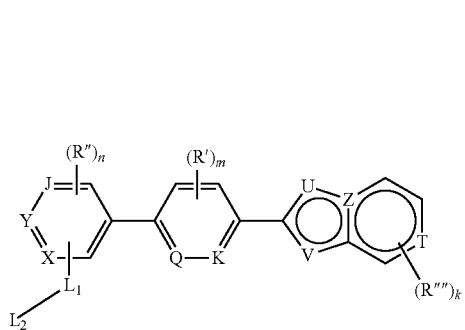
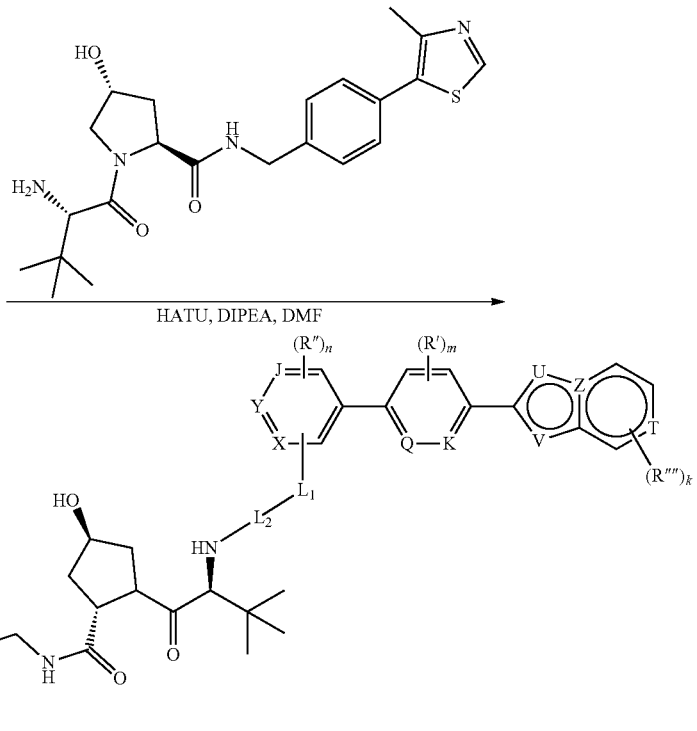

Other compounds within the scope of the disclosure are synthesized by methods like these, and by analogy with methods set forth in the Examples below. Additional synthetic methods can be found in WO2019214681, WO2018102067 and WO2019014429, all of which are incorporated herein by reference in full.

Methods of Treatment

Another aspect of the present disclosure is a method for aiding in the treatment of a synucleinopathy in a subject, the method comprising, consisting essentially of, or consisting of administering to the subject an effective amount of a compound as disclosed herein, or a composition as disclosed herein.

Another aspect of the present disclosure is a method of treating a subject (e.g., a human) suffering from a disease characterized by the presence of Lewy bodies or pathological aggregates of α-synuclein, the method comprising, consisting essentially of, or consisting of administering to the subject an effective amount of a compound as disclosed herein or a composition as disclosed herein.

Another aspect of the present disclosure is a method for prophylaxis of a disease characterized by the presence of Lewy bodies or pathological aggregates of α-synuclein in a subject, the method comprising, consisting essentially of, or consisting of administering to the subject an effective amount of a compound or a composition as disclosed herein.

In another aspect, provided herein are methods of treating a disease characterized by the presence of Lewy bodies or pathological aggregates of α-synuclein in a subject, the method comprising, consisting essentially of, or consisting of administering to the subject an effective amount of a compound or a pharmaceutical composition described herein.

In another aspect, provided herein are methods of lessening the severity of a disease characterized by the presence of Lewy bodies or pathological aggregates of α-synuclein in a subject, the methods comprising, consisting essentially of, or consisting of administering to the subject an effective amount of a compound or a pharmaceutical composition described herein.

In another aspect, provided herein are methods of delaying the progression of a disease characterized by the presence of Lewy bodies or pathological aggregates of α-synuclein in a subject, the methods comprising, consisting essentially of, or consisting of administering to the subject an effective amount of a compound or a pharmaceutical composition described herein.

In another aspect, provided herein are methods of reducing the risk of developing a disease characterized by the presence of Lewy bodies or pathological aggregates of α-synuclein in a subject, the methods comprising, consisting essentially of, or consisting of administering to the subject at risk of developing the disease an effective amount of a compound or a pharmaceutical composition described herein.

In another aspect, provided herein are methods of delaying the onset of a disease characterized by the presence of Lewy bodies or pathological aggregates of α-synuclein in a subject at risk of developing the disease, the methods comprising, consisting essentially of, or consisting of administering to the subject an effective amount of a compound or a pharmaceutical composition described herein.

In some embodiments, the subject to be treated exhibits one or more symptoms (signs) of synucleinopathies, such as neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia), or other signs and symptoms (fatigue, diplopia, blurred vision, seborrhea, weight loss/gain).

In some embodiments, the subject to be treated does not exhibit one or more symptoms of a synucleinopathy, but is known to have a genetic risk for developing a disease characterized by the presence of Lewy bodies or pathological aggregates of α-synuclein in the brain. For instance, such an individual may have one or more relatives with the disease, or their risk is determined by analysis of genetic or biochemical markers. For example, mutations in SNCA (PARK1, encoding α-synuclein), including A30P, E46K, H50Q, G51D, and A53T, as well as duplications and triplications of the entire SNCA gene cause autosomal dominant forms of PD. Mutations in LRRK2 (PARKS, Leucine-rich repeat kinase 2) and mutations in VPS35 (PARK17, vacuolar protein sorting 35) also cause autosomal dominant forms of PD (Hernandez et al., (2016) Genetics in Parkinson disease: Mendelian versus non-Mendelian inheritance. Journal of Neurochemistry 10.1111/jnc.13593). Mutations in PINK1 (PARK6, PTEN-induced kinase 1), DJ-1 (PARK7), Parkin (PARK2), ATP13A2 (PARK9, ATPase type 13A2), FBXO7 (PARK15, F-box only protein 7), and PLA2 GB (PARK14, phospholipase A2, group VI) have been shown to cause autosomal recessive PD/parkinonism. In addition, 28 different genetic risk loci associated with PD and related synucleinopathies have been identified including SNCA, LRRK2, GBA/SYT11, MAPT, HLA-DRB5, GAK, GCH1, NUCKS1/RAB7L1, SLC41A1, BST1, SIPA1L2, ACMSD/TMEM163, STK39, MCCC1, TMEM175/GAK/DGKQ, FAM47E/SCARB2, GPNMB, FGF20, INPP5F, MIR4697, CCDC62, GCH1, VPS13C, BCKDK/STX1B, SREBF/RAI1, RIT2 and DDRGK1 (Nails et al. (2014) Large-scale meta-analysis of genome-wide association data identifies six new risk loci for Parkinson's disease. Nature Genetics 46(9): 989-993). Accordingly, in prophylactic applications, the antibodies described herein, or pharmaceutical compositions comprising the same, are administered to a patient susceptible to, or otherwise at risk of the disease in a regime (dose, frequency and route of administration) effective to reduce the risk, lessen the severity, or delay the onset of at least one sign or symptom of the disease. In some prophylactic applications, the regime is effective to inhibit or delay accumulation of α-synuclein in the brain, and/or inhibit or delay its toxic effects and/or inhibit or delay development of behavioral deficits in the patient.

In some embodiments, the methods described above generate a beneficial therapeutic response in a patient (e.g., reduction of α-synuclein aggregates in the brain, improved cognitive function, and/or reversing, treating or preventing cognitive decline) in the subject. Accordingly, in some embodiments, the compounds or the pharmaceutical compositions described herein are administered to a patient suspected of, or already suffering from a disease characterized by the presence of Lewy bodies or pathological aggregates of α-synuclein in a regime (dose, frequency and route of administration) effective to ameliorate or at least inhibit further deterioration of at least one sign or symptom of the disease. In some therapeutic applications, the regime is effective to reduce or at least inhibit further increase of levels of α-synuclein, associated toxicities, and/or behavioral deficits. In certain embodiments, the treatments can result in, e.g., a reduction of α-synuclein aggregates in the brain by 10% or more, 20% or more, 30% or more, 40% or more, 50% or more, 60% or more, 70% or more, 80% or more, or 90% or more, relative to before initiating treatment or as compared to a population of untreated control patients.

In some embodiments, the disease characterized by the presence of Lewy bodies or pathological aggregates of α-synuclein in the brain is Parkinson's disease (including idiopathic Parkinson's disease), DLB, DLBD, LBVAD, pure autonomic failure, Lewy body dysphagia, incidental LBD, inherited LBD (e.g., mutations of SNCA (PARK1), LRRK2 (PARK8), VPS35 (PARK17), PINK1 (PARK6), DJ-1 (PARK7), Parkin (PARK2), ATP13A2 (PARK9), FBXO7 (PARK15) and PLA2 GB (PARK14)), or multiple system atrophy (MSA; e.g., olivopontocerebellar atrophy, striatonigral degeneration and Shy-Drageri syndrome).

Also provided are methods for preserving or increasing synaptic density and/or dentritic density, as measured using markers of synapse formation (synaptophysin) and/or dendrites (MAP2). Accordingly, in some embodiments, subjects treated with the compounds or the compositions described herein exhibit an elevation of synaptic or dendritic density of 10% or more, 20% or more, 30% or more, 40% or more, or 50% or more, relative to before initiating treatment or as compared to a population of untreated control patients.

A. Administration

After formulation with an appropriate pharmaceutically acceptable excipient in a desired dosage, the pharmaceutical compositions of the present disclosure can be administered to humans and other animals orally, parenterally, intracisternally, intraperitoneally, intrathecally, intraventricularly, topically, bucally, or the like, depending on the disease or condition being treated.

In certain embodiments, a pharmaceutical composition comprising a compound of the disclosure is administered orally or parenterally, at dosage levels sufficient to deliver from about 0.001 mg/kg to about 200 mg/kg in one or more doses for one or several days. In some embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In some embodiments, the compounds described herein are at dosages sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic and/or prophylactic effect. The desired dosage may be delivered three times a day, twice a day, once a day, every other day, every third day, every week, every two weeks, every three weeks, or every four weeks. In some embodiments, the dosage is delivered using multiple administrations (e.g., two, three, four, five, six, seven, eight, nine, ten, eleven, twelve, thirteen, fourteen, or more administrations). In some embodiments, the composition described herein is administered at a dose that is below the dose at which the agent causes non-specific effects.

B. Compositions

Pharmaceutical compositions described herein can be prepared by methods generally known in the art of pharmacology. In general, such methods include the steps of combining the compound of the disclosure with a carrier and/or one or more other accessory ingredients, and then shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Pharmaceutically acceptable excipients used in the manufacture of pharmaceutical compositions include inert diluents, dispersing and/or granulating agents, surface active agents and/or emulsifiers, disintegrating agents, binding agents, preservatives, stabilizers, buffering agents, lubricating agents, and/or oils. Excipients such as cocoa butter and suppository waxes, coloring agents, coating agents, sweetening, flavoring, and perfuming agents may also be present in the composition.

Suitable diluents include calcium carbonate, sodium carbonate, calcium phosphate, calcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Suitable granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

The following examples are provided as a further guide for those of ordinary skill in the art, and are not intended to limit the scope of the claimed invention in any way.

In general in the examples below, chemicals were purchased from Sinopharm Chemical Reagent Co. (SCRC), Sigma-Aldrich, Alfa, or other vendors. $^1$H NMR and $^{19}$F NMR spectra were recorded on a Bruker AVIII 400 or Bruker AVIII 500 spectrometer.

LCMS measurement was run on an Agilent 1200 HPLC/6100 SQ System using the following conditions: Method A: Mobile Phase: A: Water (0.01% TFA) B: CAN (0.01% TFA); Gradient Phase: 5% B increasing to 95% B within 1.4 min, 95% B with 1.6 min (total runtime: 3 min); Flow Rate: 2.3 mL/min; Column: SunFire C18, 4.6*50 mm, 3.5 µm; Column Temperature: 50° C. Detectors: ADC ELSD, DAD (214 nm and 254 nm), ES-API. Method B: Mobile Phase: A: Water (10 mM NH$_4$HCO$_3$) B: Acetonitrile; Gradient Phase: 5% to 95% B within 1.5 min, 95% B with 1.5 min (total runtime: 3 min); Flow Rate: 2.0 mL/min; Column: XBridge C18, 4.6*50 mm, 3.5 µm; Column Temperature: 40° C. Detectors: ADC ELSD, DAD (214 nm and 254 nm), MSD (ES-API). Method C: Mobile Phase: A: Water (10 mM NH$_4$HCO$_3$) B: Acetonitrile; Gradient Phase: 5% to 95% B within 1.5 min, 95% B with 1.5 min (total runtime: 3 min); Flow Rate: 2.0 mL/min; Column: XBridge C18, 4.6*50 mm, 3.5 µm; Column Temperature: 40° C. Detectors: ADC ELSD, DAD (214 nm and 254 nm), MSD (ES-API).

Abbreviations: THF—tetrahydrofuran; DMF—N,N-dimethylformamide; EtOAc—ethyl acetate; DCM—dichloromethane; MeOH—methanol; EtOH—ethanol; TEA—triethanol-amine; TFA—trifluoroacetic acid; RT—room temperature.

Additional embodiments are disclosed in further detail in the following examples, which are provided by way of illustration and are not in any way intended to limit the scope of this disclosure or the claims. While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

Example 1: Synthesis of Compound 159985

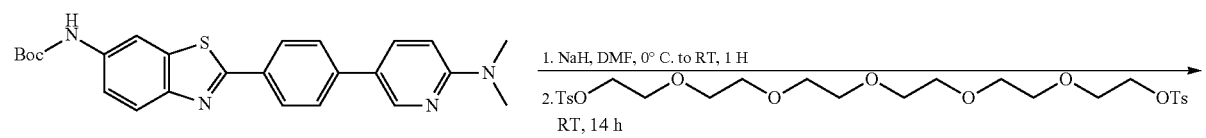

-continued

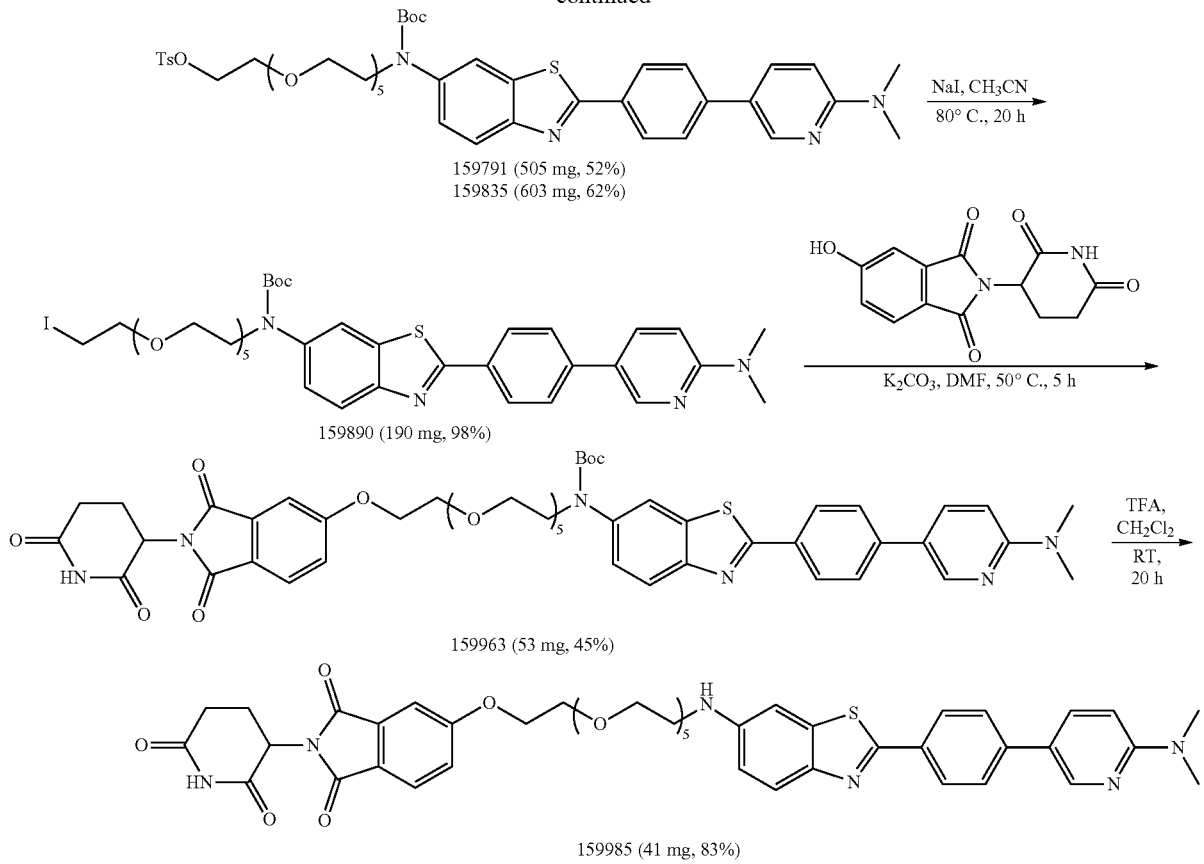

159791 (505 mg, 52%)
159835 (603 mg, 62%)

159890 (190 mg, 98%)

159963 (53 mg, 45%)

159985 (41 mg, 83%)

(A) 2-[2-[2-[2-[2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethoxy]ethoxy]ethoxy]ethyl 4-methylbenzenesulfonate: To a solution of tert-butyl N-[2-[4-[6-(dimethylamino)pyridin-3-yl]-phenyl]-1,3-benzothiazol-6-yl]carbamate (500 mg, 1.12 mmol) in DMF (10 mL) was added with NaH (107.49 mg, 4.48 mmol) at 0° C. and stirred at RT for 1 h. 2-[2-[2-[2-[2-[2-(4-methyl-phenyl)sulfonyloxyethoxy]ethoxy]ethoxy]ethoxy]ethyl 4-methylbenzenesulfonate (2.65 g, 4.48 mmol) in DMF (10 mL) was added to the reaction mixture and stirred at RT for 14 h. The mixture was quenched by adding water at 0° C. and then extracted with EtOAc (200 mL). The organic layer was washed with water (100 mL), brine (100 mL), dried over $Na_2SO_4$, concentrated and purified by column chromatography (DCM:MeOH=10:1, Rf=0.7) to give 2-[2-[2-[2-[2-[2-[[2-[4-[6-(dimethylamino)pyridin-3-yl]phenyl]-1,3-benzothiazol-6-yl]-[(2-methyl-propan-2-yl)oxycarbonyl]amino]ethoxy]ethoxy]ethoxy]ethoxy]ethyl 4-methylbenzenesulfonate (compound 159835, 603 mg, 0.70 mmol, 62% yield) as a pale-yellow solid.

(B) tert-butyl N-[2-[4-[6-(dimethylamino)pyridin-3-yl]phenyl]-1,3-benzothiazol-6-yl]-N-[2-[2-[2-[2-[2-(2-iodoethoxy)ethoxy]ethoxy]ethoxy]ethoxy]ethyl]carbamate: A mixture of 2-[2-[2-[2-[2-[2-[[2-[4-[6-(dimethylamino)pyridin-3-yl]phenyl]-1,3-benzothiazol-6-yl]-[(2-methyl-propan-2-yl)oxycarbonyl]amino]ethoxy]ethoxy]ethoxy]ethoxy]ethyl 4-methylbenzenesulfonate (200 mg, 0.23 mmol) and NaI (42 mg, 0.28 mmol) in $CH_3CN$ (5 mL) was heated at 80° C. for 20 h. The residue was taken up in DCM (50 mL) and water (50 mL). The organic layer was washed with water (50 mL), brine (50 mL) dried over $Na_2SO_4$ and concentrated to give tert-butyl N-[2-[4-[6-(dimethylamino)pyridin-3-yl]phenyl]-1,3-benzothiazol-6-yl]-N-[2-[2-[2-[2-(2-iodoethoxy)ethoxy]ethoxy]ethoxy]ethoxy]ethyl]carbamate (compound 159890, 185.1 mg, 0.23 mmol, 98% yield) as a yellow solid.

(C) tert-butyl N-[2-[2-[2-[2-[2-[2-[2-[2,6-bis(oxo)piperidin-3-yl]-1,3-bis(oxo)isoindol-5-yl]oxyethoxy]ethoxy]ethoxy]ethoxy]ethoxy]ethyl]-N-[2-[4-[6-(dimethylamino)pyridin-3-yl]-phenyl]-1,3-benzothiazol-6-yl]carbamate: A mixture of 2-[2,6-bis(oxo)piperidin-3-yl]-5-hydroxy-isoindole-1,3-dione (67 mg, 0.24 mmol), $K_2CO_3$ (51 mg, 0.37 mmol) and tert-butyl N-[2-[4-[6-(dimethylamino)pyridin-3-yl]phenyl]-1,3-benzothiazol-6-yl]-N-[2-[2-[2-[2-(2-iodo-ethoxy)ethoxy]ethoxy]ethoxy]ethoxy]ethyl]carbamate (100 mg, 0.12 mmol) in DMF (5 mL) was heated at 50° C. for 5 h. The mixture was quenched with water and then extracted with DCM (200 mL). The organic layer was dried over $Na_2SO_4$, concentrated, and purified by column chromatography on silica gel (DCM:MeOH=20:1, Rf=0.52) to give tert-butyl N-[2-[2-[2-[2-[2-[2-[2-[2,6-bis(oxo)piperidin-3-yl]-1,3-bis(oxo)isoindol-5-yl]oxyethoxy]ethoxy]ethoxy]-ethoxy]ethoxy]ethyl]-N-[2-[4-[6-(dimethylamino)pyridin-3-yl]phenyl]-1,3-benzothiazol-6-yl]-carbamate (53 mg, 0.05 mmol, 45% yield) as a pale-yellow solid.

(D) 2-[2,6-bis(oxo)piperidin-3-yl]-5-[2-[2-[2-[2-[2-[2-[[2-[4-[6-(dimethylamino)-pyridin-3-yl]phenyl]-1,3-benzothiazol-6-yl]amino]ethoxy]ethoxy]ethoxy]ethoxy]-ethoxy]isoindole-1,3-dione: To a solution of tert-butyl N-[2-[2-[2-[2-[2-[2-[2,6-bis(oxo)-piperidin-3-yl]-1,3-bis(oxo)isoindol-5-yl]oxyethoxy]ethoxy]ethoxy]ethoxy]ethoxy]

ethyl]-N-[2-[4-[6-(dimethylamino)pyridin-3-yl]phenyl]-1,3-benzothiazol-6-yl]carbamate (52 mg, 0.05 mmol) in DCM (5 mL) was added TFA (0.08 mL, 1.08 mmol) and stirred at RT for 20 h. The mixture was poured into ice water and neutralized with sat. NaHCO$_3$ solution to pH 8. The residue was taken up in DCM (20 mL) and water (10 mL). The organic layer was washed with water (10 mL), brine (10 mL), dried over Na$_2$SO$_4$ and concentrated to dryness to give 2-[2,6-bis(oxo)-piperidin-3-yl]-5-[2-[2-[2-[2-[2-[2-[[2-[4-[6-(dimethylamino)pyridin-3-yl]phenyl]-1,3-benzo-thiazol-6-yl]amino]ethoxy]ethoxy]ethoxy]ethoxy]ethoxy]ethoxy] isoindole-1,3-dione (compound 159985, 41 mg, 0.05 mmol, 83% yield) as a yellow solid. H NMR (400 MHz, DMSO-d$_6$). MS (ESI) m/z 867 (M+H)$^+$.

Example 2: Synthesis of Compound 160219 and stirred at room temperature for 14 h. The mixture was cooled to 0° C. and quenched with water. The precipitation was collected by filtration, washed with water and purified by column chromatography (DCM:MeOH=20:1, Rf=0.68) to give 2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethyl 4-methylbenzenesulfonate (595 mg, 0.86 mmol, 77% yield) as a yellow solid.

(B) Compound 160150: A mixture of 2-[2-[[2-[4-[6-(dimethylamino)pyridin-3-yl]-phenyl]-1,3-benzothiazol-6-yl]-[(2-methylpropan-2-yl)oxycarbonyl]amino]ethoxy]ethyl 4-methylbenzenesulfonate (595 mg, 0.86 mmol), NaI (156 mg, 1.04 mmol) in MeCN (15 mL) was heated at 80° C. for 17 h. The residue was taken up in DCM (50 mL) and water (50 mL). The organic layer was washed with water (50 mL), brine (50 mL), dried over Na$_2$SO$_4$ and concentrated to give tert-butyl N-[2-[4-[6-(dimethylamino)pyridin-3-yl]phenyl]-

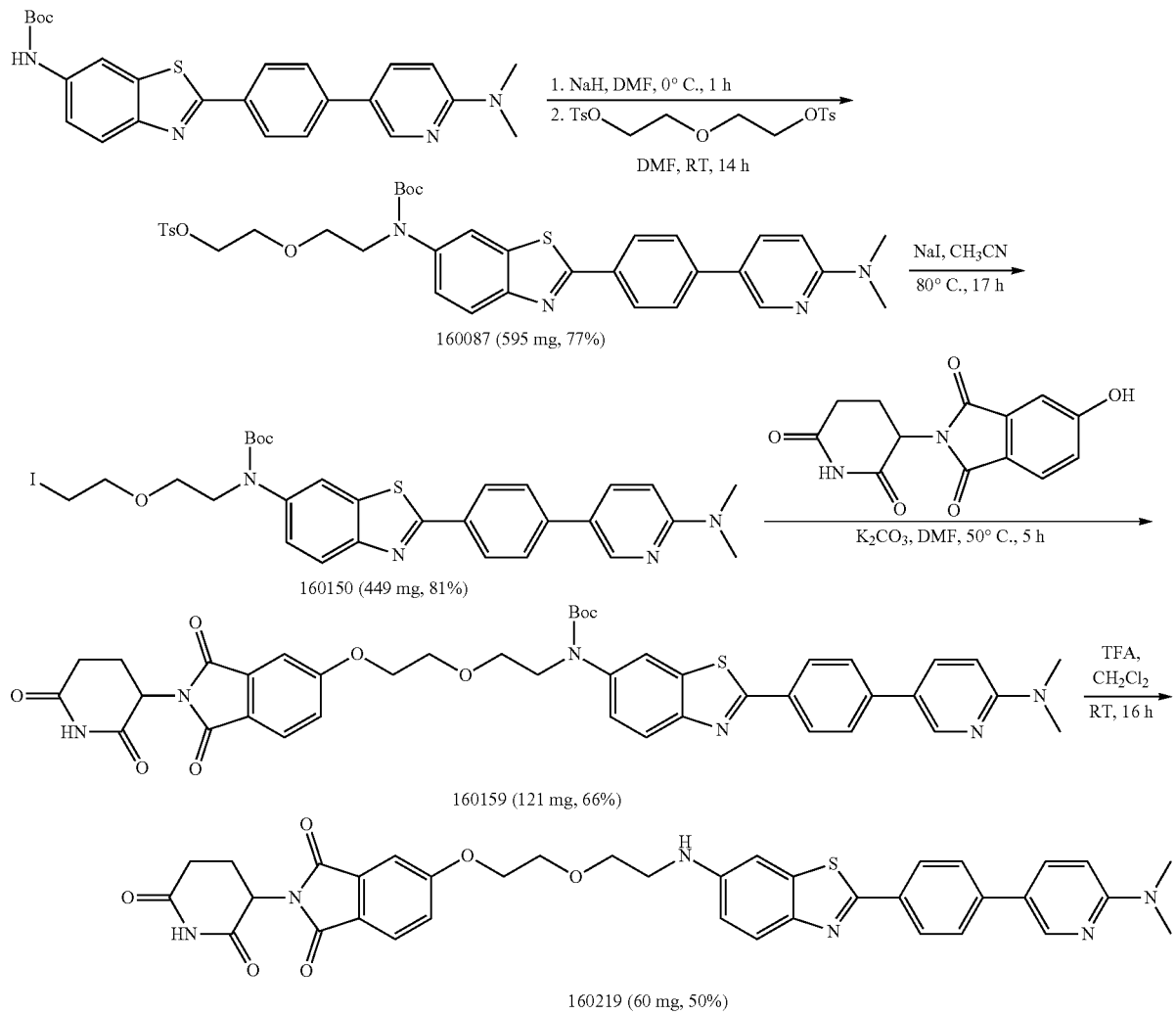

(A) Compound 160087: To a solution of tert-butyl N-[2-[4-[6-(dimethylamino)pyridin-3-yl]phenyl]-1,3-benzothiazol-6-yl]carbamate (500 mg, 1.12 mmol) in DMF (10 mL) was added NaH (107 mg, 4.48 mmol) at 0° C. and stirred at room temperature for 1 h. 2-[2-(4-Methyl-phenyl)sulfonyloxyethoxy]ethyl 4-methylbenzenesulfonate (1.86 g, 4.48 mmol) in DMF (10 mL) was added to the reaction mixture 1,3-benzo-thiazol-6-yl]-N-[2-(2-iodoethoxy)ethyl]carbamate (449 mg, 0.70 mmol, 81% yield) as a yellow solid.

(C) Compound 160159: A mixture of 2-[2,6-bis(oxo)piperidin-3-yl]-5-hydroxy-isoindole-1,3-dione (96 mg, 0.35 mmol), K$_2$CO$_3$ (96 mg, 0.70 mmol), tert-butyl N-[2-[4-[6-(di-methylamino)pyridin-3-yl]phenyl]-1,3-benzothiazol-6-yl]-N-[2-(2-iodoethoxy)ethyl]carbamate (150 mg, 0.23 mmol) in DMF (5 mL) was heated at 50° C. for 5 h. Water (10 mL) was added to the mixture and the resulting precipitation was collected by filtration. The residue was purified by column chromatography (DCM:EtOAc=5:2, Rf=0.32) to give tert-butyl N-[2-[2-[2-[2,6-bis(oxo)piperidin-3-yl]-1,3-bis(oxo)isoindol-5-yl]oxyethoxy]ethyl]-N-[2-[4-[6-(dimethylamino)-pyridin-3-yl]phenyl]-1,3-benzothiazol-6-yl]carbamate (121 mg, 0.15 mmol, 66% yield) as a yellow solid.

(D) Compound 160219: To a solution of tert-butyl N-[2-[2-[2-[2,6-bis(oxo)piperidin-3-yl]-1,3-bis(oxo)isoindol-5-yl]oxyethoxy]ethyl]-N-[2-[4-[6-(dimethylamino)pyridin-3-yl]phenyl]-1,3-benzothiazol-6-yl]carbamate (120 mg, 0.15 mmol) in DCM (5 mL) was added TFA (0.23 mL, 3.03 mmol), and the mixture stirred at room temperature for 20 h. The mixture was poured into ice water and neutralized with sat. NaHCO$_3$ to pH 8. The residue was taken up in DCM (20 mL) and water (10 mL). The organic layer was washed with water (10 mL), brine (10 mL), dried over Na$_2$SO$_4$, and concentrated to dryness to give 2-[2,6-bis(oxo)piperidin-3-yl]-5-[2-[2-[[2-[4-[6-(dimethylamino)pyridin-3-yl]phenyl]-1,3-benzothiazol-6-yl]amino]ethoxy]ethoxy]isoindole-1,3-dione (21 mg, 0.03 mmol, 18% yield) as a yellow solid.

Example 3: Synthesis of Compound 160939

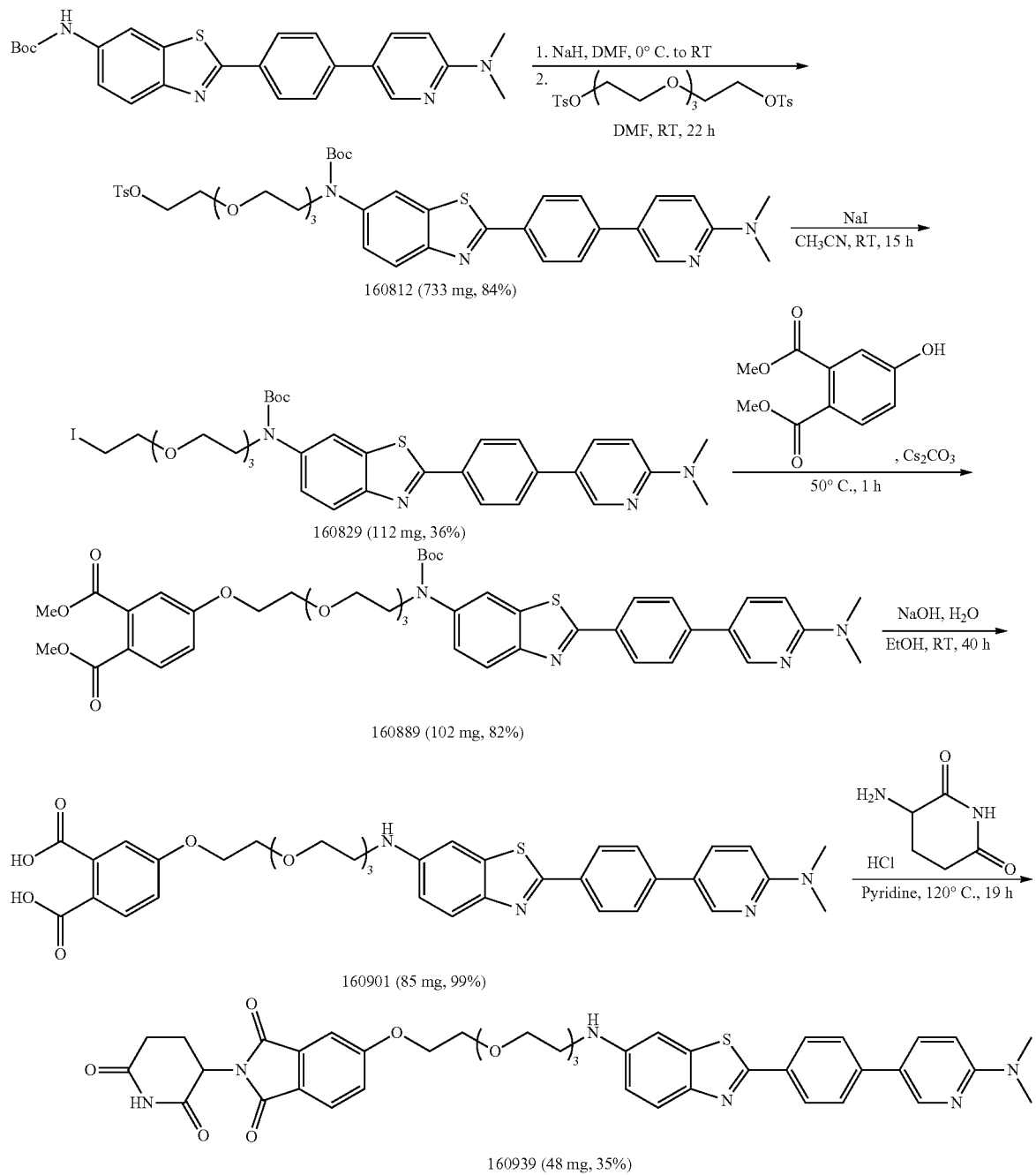

(A) Compound 160812: To a solution of tert-butyl N-[2-[4-[6-(dimethylamino)pyridin-3-yl]phenyl]-1,3-benzothiazol-6-yl]carbamate (500 mg, 1.12 mmol) in DMF (10 mL) was added NaH (107 mg, 4.48 mmol) at 0° C. and stirred at RT for 1 h. 2-[2-[2-[2-(4-methylphenyl)sulfonyloxyethoxy]ethoxy]ethoxy]ethyl 4-methylbenzenesulfonate (1125 mg, 2.24 mmol) in DMF (5 mL) was added to the reaction mixture and stirred at RT for 22 h. The mixture was taken up in water (50 mL) and DCM (50 mL). The organic layer was washed with water (50 mL), brine (50 mL) dried over Na₂SO₄, concentrated and purified by column chromatography on silica gel (EtOAc:DCM=1:5, Rf=0.13) to give 2-[2-[2-[2-[[2-[4-[6-(dimethylamino)pyridin-3-yl]-phenyl]-1,3-benzothiazol-6-yl]-[(2-methylpropan-2-yl)oxycarbonyl]amino]ethoxy]ethoxy]-ethoxy]ethyl 4-methylbenzenesulfonate (733 mg, 0.94 mmol, 84% yield) as a yellow solid.

(B) Compound 160829: A mixture of 2-[2-[2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethoxy]-ethoxy]ethyl 4-methylbenzenesulfonate (333 mg, 0.43 mmol) and NaI (109 mg, 0.73 mmol) in CH₃CN (10 mL) was heated at 80° C. for 15 h. The solvent was removed by vacuo and the residue was re-dissolved in EtOAc. The mixture was washed with water (50 mL), brine (50 mL), dried over MgSO₄ and concentrated to give tert-butyl N-[2-[4-[6-(dimethylamino)pyridin-3-yl]-phenyl]-1,3-benzothiazol-6-yl]-N-[2-[2-[2-(2-iodoethoxy)ethoxy]ethoxy]ethyl]carbamate (112 mg, 0.15 mmol, 36% yield) as a yellow solid.

(C) Compound 160889: A mixture of tert-butyl N-[2-[4-[6-(dimethylamino)pyridin-3-yl]phenyl]-3a,7a-dihydro-1,3-benzothiazol-6-yl]-N-[2-[2-[2-(2-iodoethoxy)ethoxy]ethoxy]-ethyl]carbamate (112 mg, 0.15 mmol), Cs₂CO₃ (149.09 mg, 0.46 mmol) and dimethyl 4-hydroxybenzene-1,2-dicarboxylate (64 mg, 0.30 mmol) in DMF (2 mL) was stirred at 50° C. for 1 h. The mixture was cooled to RT and added with water. The precipitation was collected by filtration and then purified by column chromatography (EtOAc:DCM=1:1, Rf=0.33) to give dimethyl 4-[2-[2-[2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethoxy]ethoxy]benzene-1,2-dicarboxylate (102 mg, 0.13 mmol, 82% yield) as a yellow solid.

(D) Compound 160901: To a solution of dimethyl 4-[2-[2-[2-[2-[[2-[4-[6-(dimethyl-amino)pyridin-3-yl]phenyl]-1,3-benzothiazol-6-yl]-[(2-methylpropan-2-yl)oxycarbonyl]amino]-ethoxy]ethoxy]ethoxy]ethoxy]benzene-1,2-dicarboxylate (102 mg, 0.13 mmol) in EtOH (2 mL) was added NaOH (40 mg, 1 mmol) in water (2 mL). The resulting mixture was stirred at RT for 40 h. The reaction was diluted with EtOAc (10 mL) and acidified with 1N HCl solution to pH 1. The organic layer was washed with water (10 mL), brine (10 mL) dried over Na₂SO₄ and concentrated to dryness to give 4-[2-[2-[2-[2-[[2-[4-[6-(dimethylamino)pyridin-3-yl]phenyl]-1,3-benzothiazol-6-yl]amino]ethoxy]ethoxy]ethoxy]ethoxy]phthalic acid (86 mg, 0.13 mmol, 99.9% yield) as an orange solid.

(E) Compound 160939: A mixture of 4-[2-[2-[2-[2-[[2-[4-[6-(dimethylamino)pyridin-3-yl]phenyl]-1,3-benzothiazol-6-yl]amino]ethoxy]ethoxy]ethoxy]ethoxy]phthalic acid (122 mg, 0.18 mmol) and 3-aminopiperidine-2,6-dione hydrochloride (32 mg, 0.20 mmol) in pyridine (5 mL) was heated at 120° C. for 19 h. The mixture was cooled to RT, diluted with DCM (100 mL) and washed with water (50 mL) and brine (50 mL). The organic layer was collected, dried over Na₂SO₄, concentrated and purified by column chromatography (MeOH:DCM=1:10, Rf=0.73) to afford 2-[2,6-bis(oxo)piperidin-3-yl]-5-[2-[2-[2-[2-[[2-[4-[6-(dimethyl-amino)pyridin-3-yl]-phenyl]-1,3-benzothiazol-6-yl]amino]ethoxy]ethoxy]ethoxy]ethoxy]isoindole-1,3-dione (49 mg, 0.06 mmol, 35% yield) as a yellow solid.

Example 4: Synthesis of Compound 161103

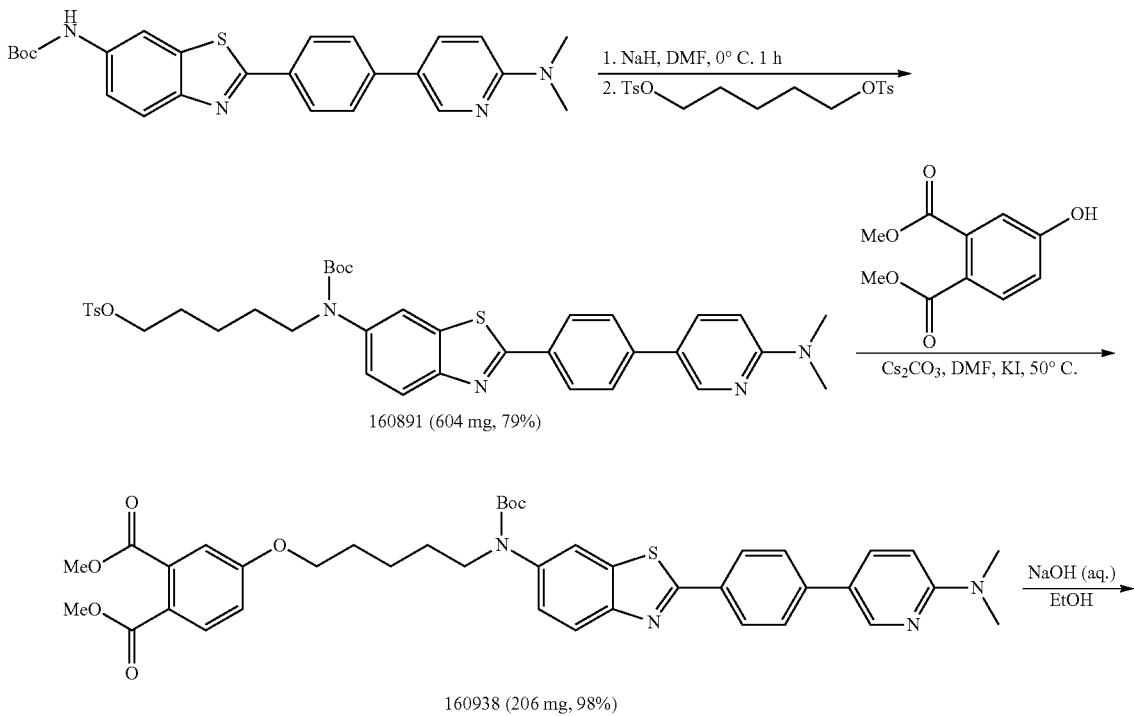

-continued

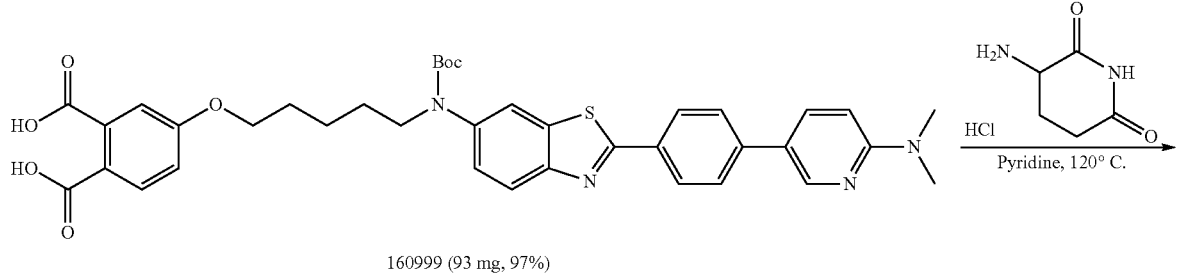

160999 (93 mg, 97%)

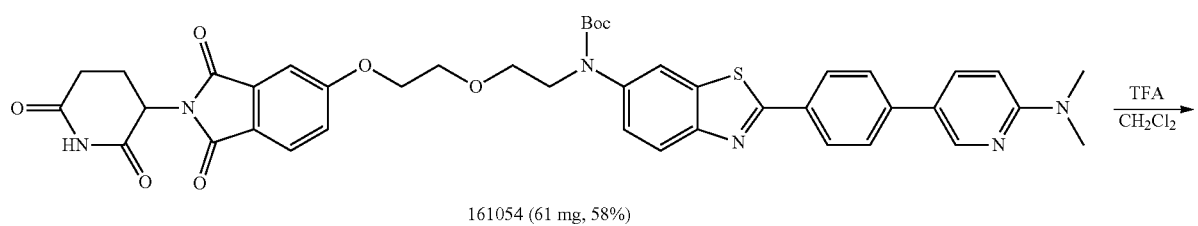

161054 (61 mg, 58%)

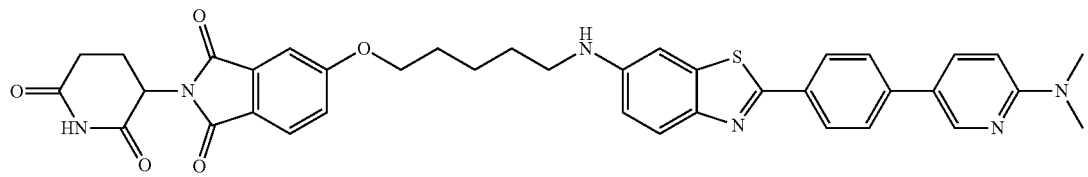

161103 (44 mg, 80%)

(A) Compound 160891: To a solution of tert-butyl N-[2-[4-[6-(dimethylamino)pyridin-3-yl]phenyl]-1,3-benzothiazol-6-yl]carbamate (500 mg, 1.12 mmol) in DMF (10 mL) was added NaH (107 mg, 4.48 mmol) at 0° C. and stirred at RT for 1 h. 5-(4-methylphenyl)sulfonyloxypentyl 4-methylbenzenesulfonate (1.85 g, 4.48 mmol) in DMF (10 mL) was added to the reaction mixture and stirred at RT for 17 h. The mixture was cooled to 0° C. and quenched with water. The resulting precipitation was collected by filtration and purified by column chromatography (DCM:EtOAc=4:1, Rf=0.7) to give 5-[[2-[4-[6-(dimethylamino)pyridin-3-yl]phenyl]-1,3-benzothiazol-6-yl]-[(2-methylpropan-2-yl)oxycarbonyl]amino]pentyl 4-methylbenzenesulfonate (604 mg, 0.88 mmol, 79% yield) as a yellow solid.

(B) Compound 160938: A mixture of dimethyl 4-hydroxybenzene-1,2-dicarboxylate (122 mg, 0.58 mmol), Cs$_2$CO$_3$ (285 mg, 0.87 mmol), KI (5 mg, 0.03 mmol) and 5-[[2-[4-[6-(di-methylamino)pyridin-3-yl]phenyl]-1,3-benzothiazol-6-yl]-[(2-methylpropan-2-yl)oxycarbonyl]amino]pentyl 4-methylbenzenesulfonate (200 mg, 0.29 mmol) in DMF (2 mL) was heated at 50° C. for 2 h. The reaction was quenched with water. The resulting solid was collected by filtration and washed with water to give dimethyl 4-[5-[[2-[4-[6-(dimethylamino)pyridin-3-yl]phenyl]-1,3-benzothiazol-6-yl]-[(2-methylpropan-2-yl)oxycarbonyl]amino]pentoxy]benzene-1,2-dicarboxylate (206 mg, 0.28 mmol, 98% yield) as a yellow solid.

(C) Compound 160999: A solution of dimethyl 4-[5-[[2-[4-[6-(dimethylamino) pyridin-3-yl]phenyl]-1,3-benzothiazol-6-yl]-[(2-methylpropan-2-yl)oxycarbonyl]amino]pentoxy]-benzene-1,2-dicarboxylate (100 mg, 0.14 mmol) in EtOH (2 mL) was added NaOH (110 mg, 2.76 mmol) in water (2 mL) and stirred at RT for 40 h. The reaction was neutralized to pH 1 with 1N HCl solution. The precipitation was collected by filtration and washed with water to afford 4-[5-[[2-[4-[6-(dimethylamino)pyridin-3-yl]phenyl]-1,3-benzothiazol-6-yl]-[(2-methylpropan-2-yl)oxycarbonyl]amino]pentoxy]phthalic acid (93 mg, 0.13 mmol, 97% yield) as a yellow solid.

(D) Compound 161054: A mixture of 4-[5-[[2-[4-[6-(dimethylamino)pyridin-3-yl]-phenyl]-1,3-benzothiazol-6-yl]-[(2-methylpropan-2-yl)oxycarbonyl]amino]pentoxy] phthalic acid (93 mg, 0.13 mmol), and 3-aminopiperidine-2,6-dione hydrochloride (48 mg, 0.29 mmol) in pyridine (3 mL) was heated at 120° C. for 40 h. Water was then added to the mixture. The precipitate was collected by filtration and purified by column chromatography (DCM:EtOAc=4:1, Rf=0.28) to afford tert-butyl N-[5-[2-[2,6-bis(oxo)piperidin-3-yl]-1,3-bis(oxo)isoindol-5-yl]oxypentyl]-N-[2-[4-[6-(dimethylamino)pyridin-3-yl]phenyl]-1,3-benzothiazol-6-yl]carbamate (61 mg, 0.08 mmol, 58% yield) as a yellow solid.

(E) Compound 161103: A solution of tert-butyl N-[5-[2-[2,6-bis(oxo)piperidin-3-yl]-1,3-bis(oxo)isoindol-5-yl]oxypentyl]-N-[2-[4-[6-(dimethylamino)pyridin-3-yl]phenyl]-1,3-benzothiazol-6-yl]carbamate (61 mg, 0.08 mmol) in DCM (5 mL) was added TFA (0.12 mL, 1.55 mmol) and stirred at RT for 6 h. The mixture was poured into iced water and neutralized with sat. NaHCO$_3$ solution to pH 8. The residue was taken up in DCM (20 mL) and water (10 mL). The organic layer was washed with water (10 mL), brine (10 mL), dried over Na$_2$SO$_4$, and concentrated to dryness to give 2-[2,6-bis(oxo)piperidin-3-yl]-5-[5-[[2-[4-[6-(dimethyl-amino)-pyridin-3-yl]phenyl]-1,3-benzothiazol-6-yl]amino]pentoxy]isoindole-1,3-dione (44 mg, 0.06 mmol, 80% yield) as a yellow solid.

Example 5: Synthesis of Compound 160273

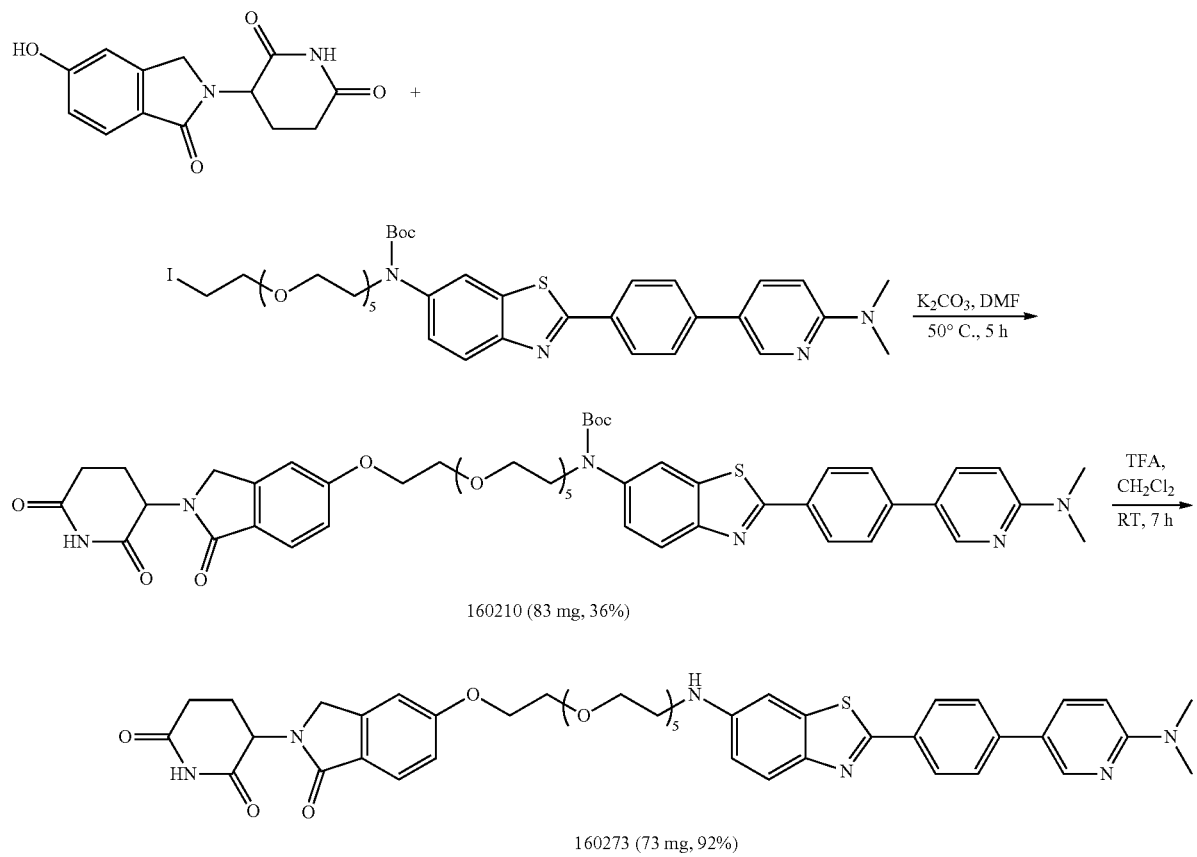

(A) Compound 160210: A mixture of 3-(6-hydroxy-3-oxo-1H-isoindol-2-yl)piperidine-2,6-dione (95 mg, 0.37 mmol), K₂CO₃ (101 mg, 0.73 mmol), tert-butyl N-[2-[4-[6-(dimethyl-amino)pyridin-3-yl]phenyl]-1,3-benzothiazol-6-yl]-N-[2-[2-[2-[2-[2-(2-iodoethoxy)ethoxy]-ethoxy]ethoxy]ethoxy]ethyl]carbamate (200 mg, 0.24 mmol) in DMF (5 mL) was heated at 50° C. for 5 h. The mixture was quenched with water and extracted with DCM (200 mL). The organic layer was collected, dried over Na₂SO₄, concentrated and purified by column chromatography (DCM:MeOH=20:1, Rf=0.48) to give tert-butyl N-[2-[2-[2-[2-[2-[2-[[2-[2,6-bis(oxo)piperidin-3-yl]-1-oxo-3H-isoindol-5-yl]-oxy]ethoxy]ethoxy]ethoxy]ethoxy]ethyl]-N-[2-[4-[6-(dimethyl-amino)pyridin-3-yl]phenyl]-1,3-benzothiazol-6-yl]carbamate (83 mg, 0.09 mmol, 36% yield) as a pale-yellow solid.

(B) Compound 160273: To a solution of tert-butyl N-[2-[2-[2-[2-[2-[2-[[2-[2,6-bis-(oxo)piperidin-3-yl]-1-oxo-3H-isoindol-5-yl]oxy]ethoxy]ethoxy]ethoxy]ethoxy]ethoxy]-ethyl]-N-[2-[4-[6-(dimethylamino)pyridin-3-yl]phenyl]-1,3-benzothiazol-6-yl]carbamate (83 mg, 0.09 mmol) in DCM (5 mL) was added TFA (0.13 mL, 1.74 mmol) and stirred at RT for 7 h. The mixture was poured into ice water and neutralized with sat. NaHCO₃ solution to pH 8. The residue was taken up in DCM (20 mL) and water (10 mL). The organic layer was washed with water (10 mL), brine (10 mL) dried over Na₂SO₄ and concentrated to dryness to give 3-[6-[2-[2-[2-[2-[2-[2-[[2-[4-[6-(dimethylamino)pyridin-3-yl]phenyl]-1,3-benzothiazol-6-yl]amino]ethoxy]-ethoxy]ethoxy]ethoxy]ethoxy]ethoxy]-3-oxo-1H-isoindol-2-yl]piperidine-2,6-dione (73 mg, 0.08 mmol, 92% yield) as a yellow solid.

Example 6: Synthesis of Compound 160313

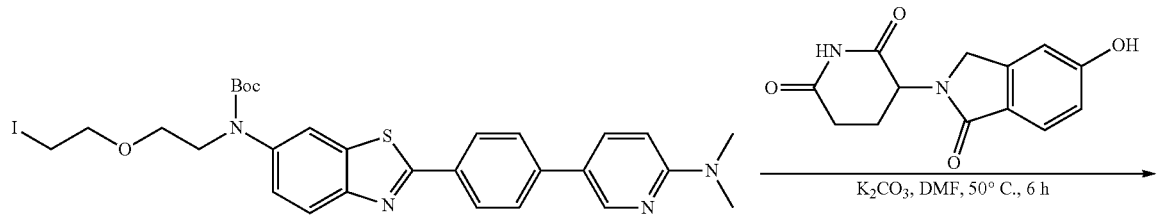

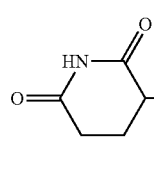 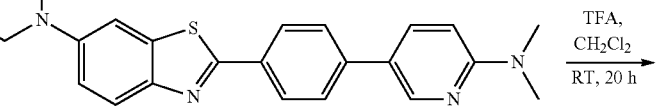

160284 (57 mg, 50%)

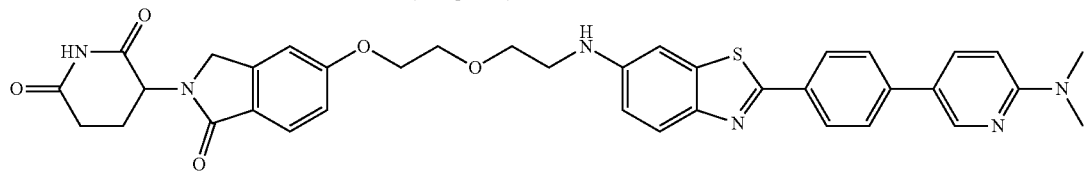

160313 (39 mg, 73%)

(A) Compound 160284: A mixture of 3-(6-hydroxy-3-oxo-1H-isoindol-2-yl)piperidine-2,6-dione (58 mg, 0.22 mmol), $K_2CO_3$ (61 mg, 0.44 mmol), tert-butyl N-[2-[4-[6-(dimethyl-amino)pyridin-3-yl]phenyl]-1,3-benzothiazol-6-yl]-N-[2-(2-iodoethoxy)ethyl]carbamate (95 mg, 0.15 mmol) in DMF (2 mL) was heated at 50° C. for 5 h. Water (10 mL) was added to the mixture. The resulting precipitate was collected by filtration and then purified by column chromatography (DCM:MeOH=20:1, Rf=0.52) to give tert-butyl N-[2-[2-[[2-[2,6-bis(oxo)piperidin-3-yl]-1-oxo-3H-isoindol-5-yl]oxy]ethoxy]-ethyl]-N-[2-[4-[6-(dimethyl-amino)pyridin-3-yl]phenyl]-1,3-benzothiazol-6-yl] carbamate (57 mg, 0.07 mmol, 50% yield) as a yellow solid.

(B) Compound 160313: To a solution of tert-butyl N-[2-[2-[[2-[2,6-bis(oxo)piperidin-3-yl]-1-oxo-3H-isoindol-5-yl]oxy]ethoxy]ethyl]-N-[2-[4-[6-(dimethylamino)pyridin-3-yl]-phenyl]-1,3-benzothiazol-6-yl]carbamate (54 mg, 0.07 mmol) in DCM (5 mL) was added TFA (0.11 mL, 1.39 mmol), and the mixture stirred at room temperature for 20 h. The mixture was poured into ice water and neutralized with sat. $NaHCO_3$ solution to pH 8. The residue was taken up in DCM (20 mL) and water (10 mL). The organic layer was washed with water (10 mL), brine (10 mL), dried over $Na_2SO_4$, and concentrated to dryness to give 3-[6-[2-[2-[[2-[4-[6-(dimethylamino)pyridin-3-yl]phenyl]-1,3-benzothiazol-6-yl]amino]ethoxy]ethoxy]-3-oxo-1H-isoindol-2-yl]piperidine-2,6-dione (39 mg, 0.05 mmol, 77% yield) as a yellow solid.

Example 7: Synthesis of Compound 162640

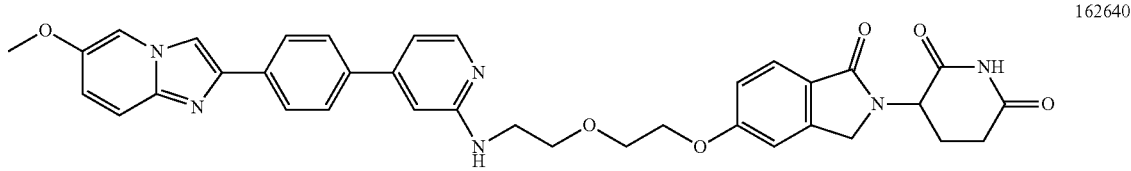 [SMILES: COc1ccc2nc(-c3ccc(-c4ccnc(NCCOCCOc5ccc6c(c5)CN(C5CCC(=O)NC5=O)C6=O)c4)cc3)cn2c1]

Compound 162640 were synthesized according to methods similar to Example 6.

$^1$H NMR (600 MHz, DMSO-d6) δ 10.97 (s, 1H), 8.36 (s, 1H), 8.24 (d, J=2.3 Hz, 1H), 8.01-8.05 (m, 4H), 7.72 (d, J=8.4 Hz, 2H), 7.62 (d, J=8.4 Hz, 1H), 7.52 (d, J=9.7 Hz, 1H), 7.17 (d, J=1.7 Hz, 1H), 7.05-7.09 (m, 2H), 6.81-6.85 (m, 2H), 6.61 (t, J=5.8 Hz, 1H), 5.07 (dd, J=13.2, 5.1 Hz, 1H), 4.36 (d, J=17.2 Hz, 1H), 4.19-4.27 (m, 4H), 3.79-3.85 (m, 7H), 3.66 (t, J=5.8 Hz, 3H), 3.48-3.54 (m, 3H), 2.85-2.93 (m, 1H), 1.92-1.99 (m, 1H).

Example 8: Synthesis of Compound 162842

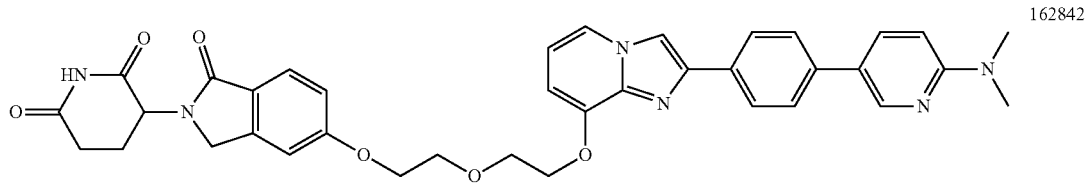 [SMILES: CN(C)c1ccc(-c2ccc(-c3cn4cccc(OCCOCCOc5ccc6c(c5)CN(C5CCC(=O)NC5=O)C6=O)c4n3)cc2)cn1]

Compound 162842 were synthesized according to methods similar to Example 6.

¹H NMR (600 MHz, DMSO-d6) δ 10.96 (s, 1H), 8.50 (d, J=2.5 Hz, 1H), 8.40 (s, 1H), 8.13 (d, J=6.6 Hz, 1H), 7.99 (d, J=8.2 Hz, 2H), 7.89 (dd, J=8.9, 2.5 Hz, 1H), 7.68 (d, J=8.2 Hz, 2H), 7.60 (d, J=8.4 Hz, 1H), 7.19 (s, 1H), 7.08 (d, J=8.4 Hz, 1H), 6.79 (t, J=7.4 Hz, 1H), 6.75 (d, J=8.9 Hz, 1H), 6.70 (d, J=7.4 Hz, 1H), 5.06 (dd, J=13.2, 5.1 Hz, 1H), 4.35-4.38 (m, 2H), 4.32 (d, J=17.2 Hz, 1H), 4.28 (dd, J=8.2, 4.5 Hz, 2H), 4.20 (d, J=17.2 Hz, 1H), 3.96-3.99 (m, 2H), 3.92-3.95 (m, 2H), 3.08 (s, 7H), 2.85-2.93 (m, 1H), 2.26-2.37 (m, 2H), 1.91-1.98 (m, 2H).

Example 9: Synthesis of Compound 162903

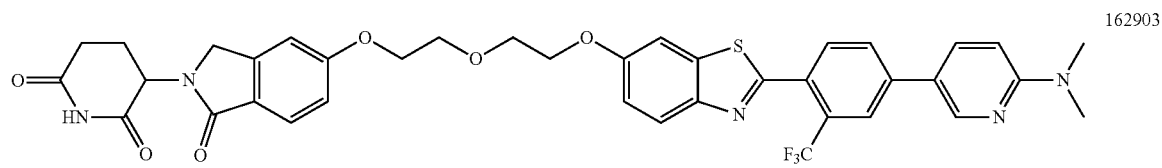 [SMILES: CN(C)c1ccc(-c2ccc(-c3nc4ccc(OCCOCCOc5ccc6c(c5)CN(C5CCC(=O)NC5=O)C6=O)cc4s3)c(C(F)(F)F)c2)cn1]

162903

Compound 162903 were synthesized according to methods similar to Example 6.

¹H NMR (600 MHz, DMS-d6) δ 10.97 (s, 1H), 8.63 (d, J=2.4 Hz, 1H), 8.12 (s, 1H), 8.08 (d, J=8.0 Hz, 1H), 8.03 (dd, J=8.9, 2.6 Hz, 1H), 7.99 (d, J=8.9 Hz, 1H), 7.87 (d, J=8.0 Hz, 1H), 7.78 (d, J=2.4 Hz, 1H), 7.63 (d, J=8.4 Hz, 1H), 7.18-7.21 (m, 1H), 7.08 (dd, J=8.4, 2.4 Hz, 1H), 6.79 (d, J=8.8 Hz, 1H), 5.08 (dd, J=13.4, 5.1 Hz, 1H), 4.38 (d, J=17.2 Hz, 1H), 4.22-4.29 (m, 4H), 3.89 (dd, J=9.2, 5.0 Hz, 3H), 3.11 (s, 3H), 2.56-2.63 (m, 1H), 2.33-2.40 (m, 1H).

Example 10: Synthesis of Compound 163123

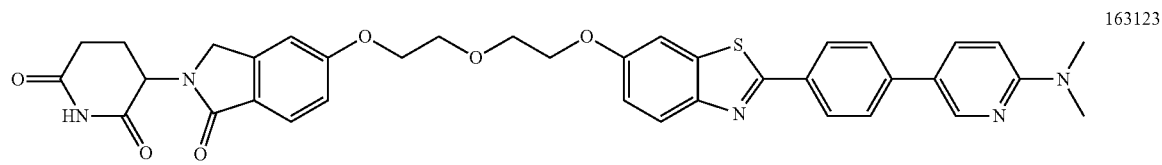 [SMILES: CN(C)c1ccc(-c2ccc(-c3nc4ccc(OCCOCCOc5ccc6c(c5)CN(C5CCC(=O)NC5=O)C6=O)cc4s3)cc2)cn1]

163123

Compound 163123 were synthesized according to methods similar to Example 6.

¹H NMR (600 MHz, DMSO-d6) δ 10.97 (s, 1H), 8.56 (d, J=2.5 Hz, 1H), 8.06 (d, J=8.4 Hz, 2H), 7.92-7.96 (m, 2H), 7.82 (d, J=8.4 Hz, 2H), 7.74 (d, J=2.5 Hz, 1H), 7.62 (d, J=8.4 Hz, 1H), 7.13-7.18 (m, 2H), 7.07 (dd, J=8.4, 2.1 Hz, 1H), 6.77 (d, J=9.0 Hz, 1H), 5.07 (dd, J=13.4, 5.2 Hz, 1H), 4.35 (d, J=17.1 Hz, 1H), 4.22-4.27 (m, 6H), 3.85-3.91 (m, 5H), 3.10 (s, 7H), 2.85-2.96 (m, 1H), 2.55-2.63 (m, 2H), 2.31-2.42 (m, 2H).

Example 11: Synthesis of Compound 163365

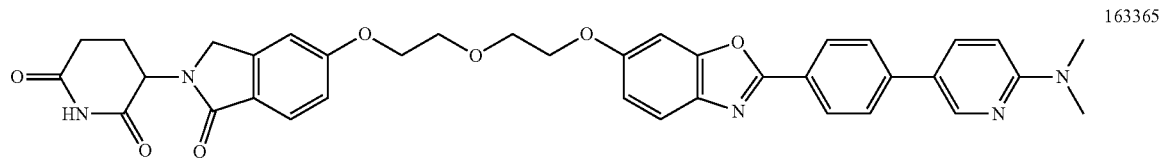 [SMILES: CN(C)c1ccc(-c2ccc(-c3nc4ccc(OCCOCCOc5ccc6c(c5)CN(C5CCC(=O)NC5=O)C6=O)cc4o3)cc2)cn1]

163365

Compound 163365 were synthesized according to methods similar to Example 6.

¹H NMR (600 MHz, DMSO-d6) δ 10.96 (s, 1H), 8.57 (d, J=2.5 Hz, 1H), 8.16 (d, J=8.4 Hz, 2H), 8.09 (s, 1H), 7.96 (dd, J=8.9, 2.4 Hz, 1H), 7.86 (d, J=8.4 Hz, 2H), 7.68 (d, J=8.7 Hz, 1H), 7.62 (d, J=8.4 Hz, 1H), 7.45 (d, J=2.1 Hz, 1H), 7.18 (s, 1H), 7.08 (d, J=8.3 Hz, 1H), 7.02 (dd, J=8.7, 2.2 Hz, 1H), 6.77 (d, J=8.9 Hz, 1H), 5.07 (dd, J=13.3, 5.2 Hz, 1H), 4.36 (d, J=17.2 Hz, 1H), 4.22-4.28 (m, 5H), 3.86-3.91 (m, 3H), 3.10 (s, 5H), 2.84-2.94 (m, 2H).

Example 12: Synthesis of Compound 161247 was added NaH (32 mg, 1.34 mmol) at 0° C. The resulting mixture was stirred at RT for 1 h. 2-[2-[2-[2-[2-[tert-butyl(dimethyl)silyl]oxyethoxy]ethoxy]ethoxy]ethoxy]ethyl 4-methylbenzenesulfonate (454 mg, 0.90 mmol) was added to the reaction mixture and stirred at RT for 22 h. The mixture was quenched with water. The precipitation was collected by filtration and purified by column chromatography (EtOAC:DCM=2:3, Rf=0.48) to give tert-butyl N-[2-[2-[2-[2-[2-[tert-butyl-(dimethyl)silyl]oxyethoxy]ethoxy]ethoxy]ethoxy]ethyl]-N-[2-[4-[6-(dimethylamino)pyridin-3-yl]phenyl]-1,3-benzothiazol-6-yl]carbamate (235 mg, 0.30 mmol, 67% yield) as a yellow solid.

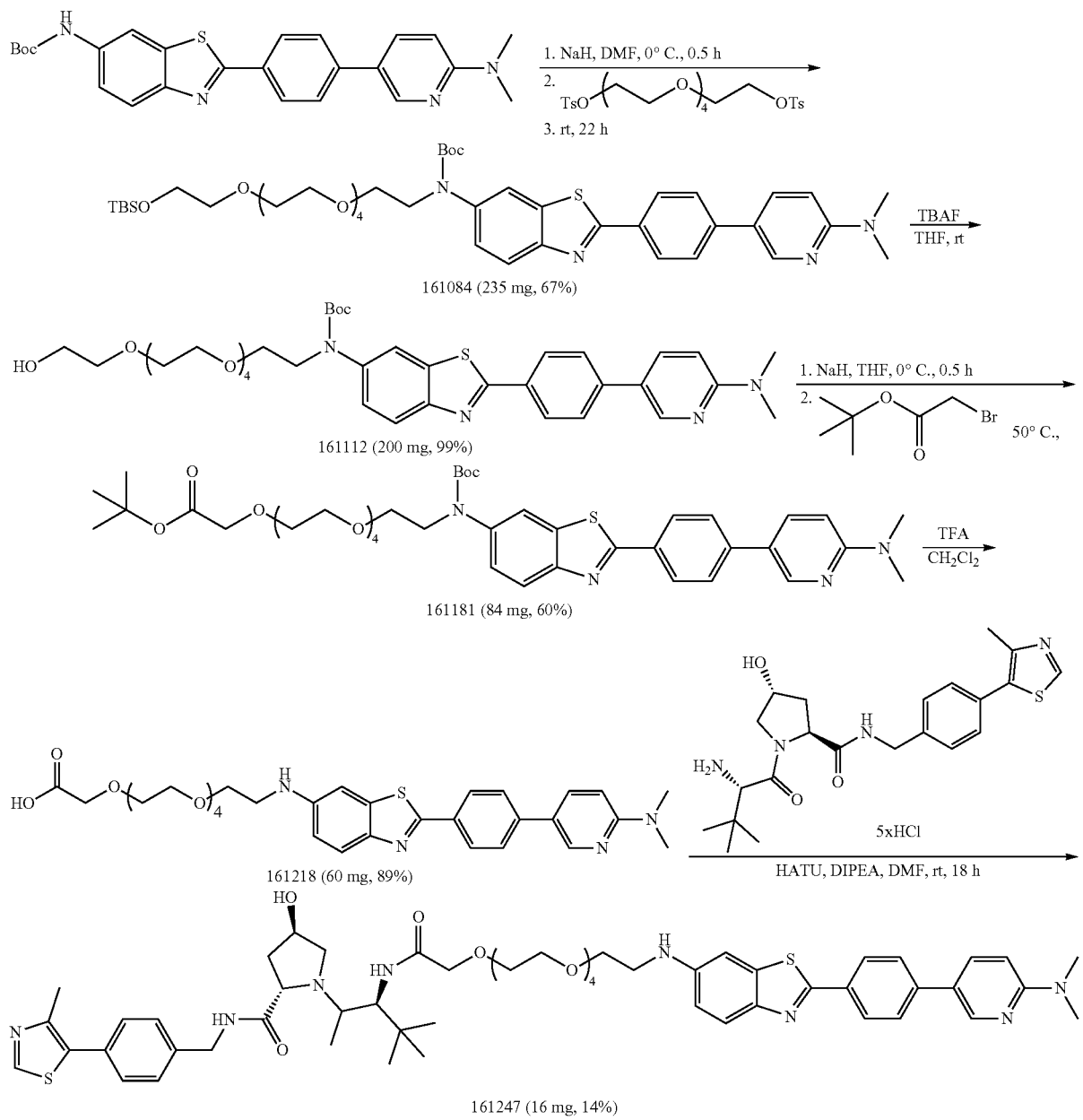

(A) Compound 161084: To a solution of tert-butyl N-[2-[4-[6-(dimethylamino)pyridin-3-yl]phenyl]-1,3-benzothiazol-6-yl]carbamate (200 mg, 0.45 mmol) in DMF (3 mL)

(B) Compound 161112: To a solution of tert-butyl N-[2-[2-[2-[2-[2-[tert-butyl-(di-methyl)silyl]oxyethoxy]ethoxy]ethoxy]ethoxy]ethyl]-N-[2-[4-[6-(dimethylamino)pyridin- 3-yl]-phenyl]-1,3-benzothiazol-6-yl]carbamate (235 mg, 0.30 mmol) in THF (5 mL) was added 1 M TBAF solution in THF (1.81 mL, 1.81 mmol) dropwise. The reaction mixture was stirred at RT for 7 h. The reaction mixture was concentrated to dryness and the residue was taken up in EtOAc (100 mL). The mixture was washed with water (100 mL) and brine (100 mL). The organic layer was collected, dried over $Na_2SO_4$ and concentrated to give tert-butyl N-[2-[4-[6-(dimethyl-amino)pyridin-3-yl]phenyl]-1,3-benzothiazol-6-yl]-N-[2-[2-[2-[2-(2-hydroxyethyloxy)ethoxy]-ethoxy]ethoxy]ethyl]carbamate (200 mg, 0.30 mmol, 99.7% yield) as a yellow solid.

(C) Compound 161181: To a solution of tert-butyl N-[2-[4-[6-(dimethylamino)pyridin-3-yl]phenyl]-1,3-benzothiazol-6-yl]-N-[2-[2-[2-[2-(2-hydroxyethyloxy)ethoxy] ethoxy]ethoxy]-ethyl]carbamate (120 mg, 0.18 mmol) in THF (3 mL) was added NaH (9 mg, 0.36 mmol) at 0° C. and stirred for 30 min. tert-Butyl 2-bromoethanoate (0.08 mL, 0.54 mmol) was then added and the mixture was heated at 50° C. for 8 h. The solvent was removed by vacuum. The residue was purified by column chromatography (EtOAc: DCM=2:3, Rf=0.35) to afford tert-butyl 2-[2-[2-[2-[2-[2-[[2-[4-[6-(dimethylamino)pyridin-3-yl]phenyl]-1,3-benzothiazol-6-yl]-[(2-methyl-propan-2-yl)oxycarbonyl]amino] ethoxy]ethoxy]ethoxy]ethoxy]ethanoate (84 mg, 0.11 mmol, 60% yield) as a yellow solid.

(D) Compound 161218: A mixture of tert-butyl 2-[2-[2-[2-[2-[2-[[2-[4-[6-(dimethyl-amino)pyridin-3-yl]phenyl]-1,3-benzothiazol-6-yl]-[(2-methylpropan-2-yl)oxycarbonyl]amino]-ethoxy]ethoxy]ethoxy]ethoxy]ethanoate (84 mg, 0.11 mmol) and TFA (0.12 mL, 1.61 mmol) in DCM (2 mL) was stirred at RT for 23 h. The mixture was acidified to pH 1 with 1N HCl solution. The mixture was extracted with DCM. The organic layer was washed with brine, dried over $Na_2SO_4$ and was concentrated to dryness to afford 2-[2-[2-[2-[2-[2-[[2-[4-[6-(di-methylamino)pyridin-3-yl]phenyl]-1,3-benzothiazol-6-yl]amino]ethoxy]ethoxy]ethoxy]-ethoxy]ethanoic acid (60 mg, 0.10 mmol, 89% yield) as a yellow solid.

(E) Compound 161247: A mixture of (2S,4R)-1-[(2S)-2-amino-3,3-dimethyl-butanoyl]-N-[[4-(4-methyl-1,3-thiazol-5-yl)phenyl]methyl]-4-hydroxy-pyrrolidine-2-carboxamide (45 mg, 0.11 mmol), 2-[2-[2-[2-[2-[2-[[2-[4-[6-(dimethyl-amino)pyridin-3-yl]phenyl]-1,3-benzothiazol-6-yl]amino] ethoxy]ethoxy]ethoxy]ethoxy]ethoxy]ethanoic acid (60 mg, 0.10 mmol), DIPEA (0.03 mL, 0.14 mmol) and HATU (73 mg, 0.19 mmol) in anhydrous DMF (3 mL) was stirred at RT for 18 h. The mixture was diluted with DCM, washed with water and brine, dried over $Na_2SO_4$, concentrated and purified by column chromatography on NH silica gel (MeOH:DCM=97:3, Rf=0.48) to give rac-(2R,4S)-N-[[4-(4-methyl-1,3-thiazol-5-yl)phenyl]methyl]-4-hydroxy-1-[rac-(2R)-2-[2-[2-[2-[2-[2-[[2-[4-[6-(dimethylamino)pyridin-3-yl]phenyl]-1,3-benzothiazol-6-yl]-amino]ethoxy]ethoxy] ethoxy]ethoxy]ethoxy]ethanoylamino]-3,3-dimethyl-butanoyl]pyrrolidine-2-carboxamide (16 mg, 0.01 mmol, 14% yield) as a yellow solid.

Example 13: Synthesis of Compound 160275

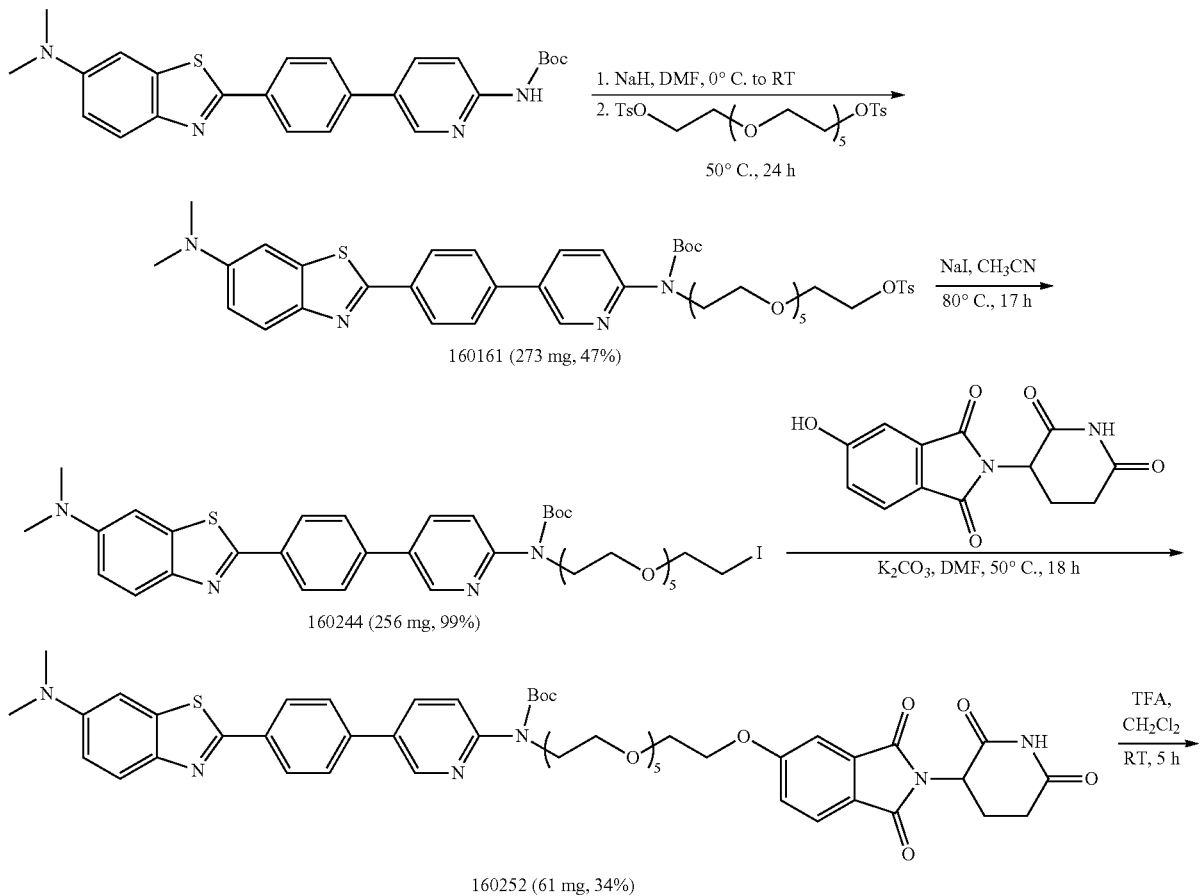

-continued

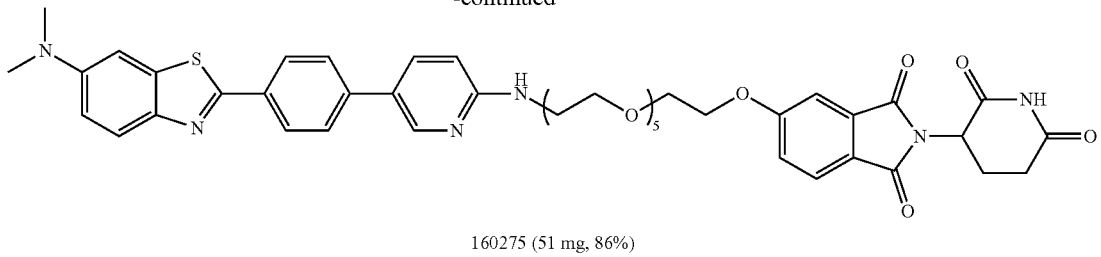

160275 (51 mg, 86%)

(A) Compound 160161: To a solution of NaH (81 mg, 2.02 mmol) in DMF (1 mL) was added tert-butyl N-[5-[4-[6-(dimethylamino)-1,3-benzothiazol-2-yl]phenyl]pyridin-2-yl]-carbamate (300 mg, 0.67 mmol) in DMF (6 mL) at 0° C. and stirred at 25° C. for 30 min. 2-[2-[2-[2-[2-[2-(4-methylphenyl)sulfonyloxyethoxy]ethoxy]ethoxy]ethoxy]ethyl 4-methylbenzenesulfonate (794 mg, 1.34 mmol) in DMF (3 mL) was added to the reaction mixture and heated at 50° C. for 2 h. The mixture was quenched with saturated NH4Cl solution and extracted with DCM. The organic layer was washed with brine, dried over MgSO4, concentrated and purified by column chromatography (MeOH:DCM=3:97, Rf=0.3) to afford 2-[2-[2-[2-[2-[2-[[5-[4-[6-(dimethylamino)-1,3-benzothiazol-2-yl]phenyl]pyridin-2-yl]-[(2-methylpropan-2-yl)-oxycarbonyl]amino]ethoxy]ethoxy]ethoxy]ethoxy]ethoxy]ethyl 4-methylbenzenesulfonate (273 mg, 0.32 mmol, 47% yield) as a yellow oil.

(B) Compound 160244: A mixture of 2-[2-[2-[2-[2-[2-[[5-[4-[6-(dimethylamino)-1,3-benzothiazol-2-yl]phenyl]pyridin-2-yl]-[(2-methylpropan-2-yl)oxycarbonyl]amino]ethoxy]-ethoxy]ethoxy]ethoxy]ethoxy]ethyl 4-methylbenzenesulfonate (270 mg, 0.31 mmol) and NaI (56.18 mg, 0.37 mmol) in CH3CN (5 mL) was heated at 80° C. for 19 h. The mixture was diluted with DCM and extracted with water (50 mL) and brine (50 mL). The organic layer was dried over MgSO4 and concentrated to dryness to afford tert-butyl N-[5-[4-[6-(dimethylamino)-1,3-benzothiazol-2-yl]phenyl]pyridin-2-yl]-N-[2-[2-[2-[2-[2-(2-iodoethoxy)ethoxy]ethoxy]ethoxy]-ethoxy]ethyl]carbamate (256 mg, 0.31 mmol, 99.9% yield) as an orange oil.

(C) Compound 160252: A mixture of 2-[2,6-bis(oxo)piperidin-3-yl]-5-hydroxy-isoindole-1,3-dione (102 mg, 0.37 mmol), K2CO3 (77 mg, 0.56 mmol) and tert-butyl N-[5-[4-[6-(dimethylamino)-1,3-benzothiazol-2-yl]phenyl]pyridin-2-yl]-N-[2-[2-[2-[2-[2-(2-iodoethoxy)-ethoxy]ethoxy]ethoxy]ethoxy]ethyl]carbamate (153 mg, 0.19 mmol) in DMF (4 mL) was heated at 50° C. for 18 h. The mixture was diluted with DCM (200 mL) and extracted with water. The organic layer was collected, dried over MgSO4, concentrated and purified by column chromatography (MeOH:DCM=5:95, Rf=0.3) to give tert-butyl N-[2-[2-[2-[2-[2-[2-[2,6-bis(oxo)-piperidin-3-yl]-1,3-bis(oxo)isoindol-5-yl]oxyethoxy]ethoxy]ethoxy]ethoxy]ethoxy]ethyl]-N-[5-[4-[6-(dimethylamino)-1,3-benzothiazol-2-yl]phenyl]pyridin-2-yl]carbamate (61 mg, 0.06 mmol, 34% yield) as a yellow solid.

(D) Compound 160275: To a solution of tert-butyl N-[2-[2-[2-[2-[2-[2-[2,6-bis(oxo)-piperidin-3-yl]-1,3-bis(oxo)isoindol-5-yl]oxyethoxy]ethoxy]ethoxy]ethoxy]ethoxy]ethyl]-N-[5-[4-[6-(dimethylamino)-1,3-benzothiazol-2-yl]phenyl]pyridin-2-yl]carbamate (61 mg, 0.06 mmol) in DCM (1 mL) was added TFA (0.5 mL, 6.53 mmol) at 0° C. The resulting mixture was stirred at RT for 5 h. The solution was neutralized with saturated NaHCO3 solution at 0° C. and extracted with DCM. The organic layer was washed with brine, dried over MgSO4, concentrated and purified by column chromatography on NH silica gel (MeOH:DCM=99:1, Rf=0.3) to afford 2-[2,6-bis(oxo)piperidin-3-yl]-5-[2-[2-[2-[2-[2-[[5-[4-[6-(dimethylamino)-1,3-benzothiazol-2-yl]phenyl]pyridin-2-yl]amino]ethoxy]ethoxy]ethoxy]ethoxy]ethoxy]isoindole-1,3-dione (51 mg, 0.05 mmol, 86% yield) as a yellow solid.

Example 14: Synthesis of Compound 161177

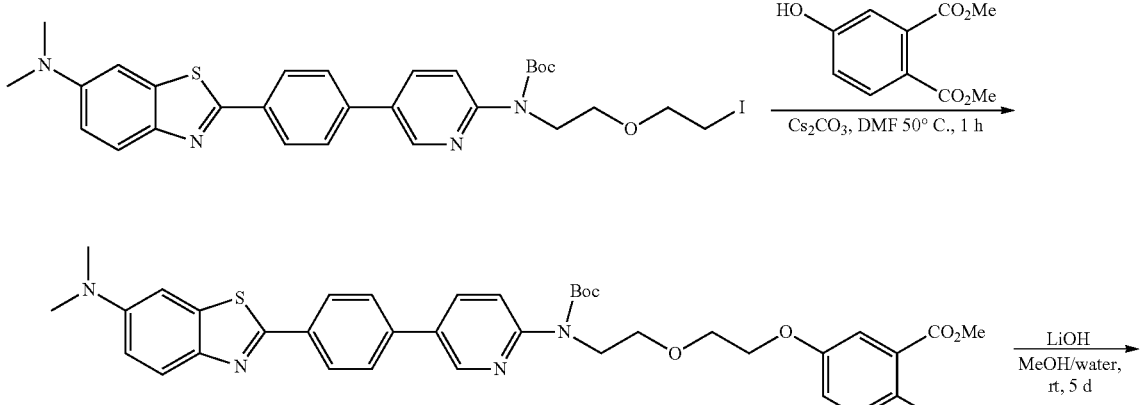

161026 (148 mg, 66%)

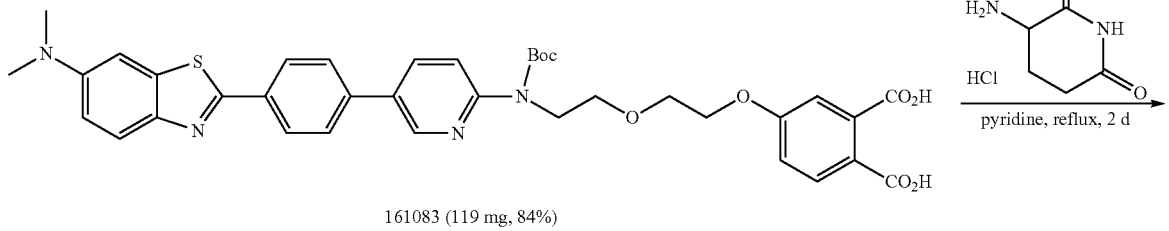

161083 (119 mg, 84%)

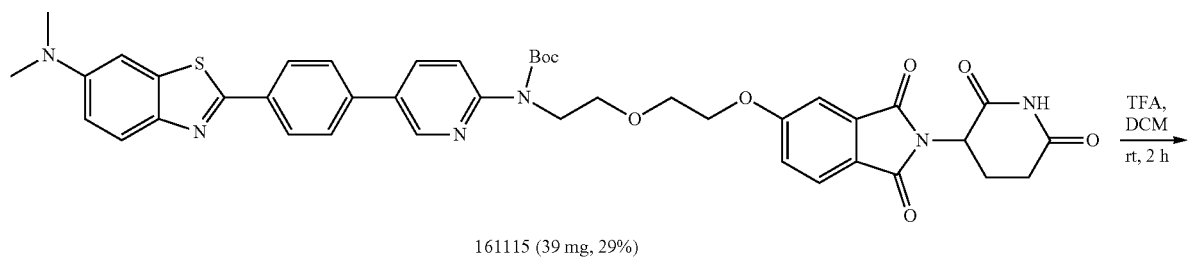

161115 (39 mg, 29%)

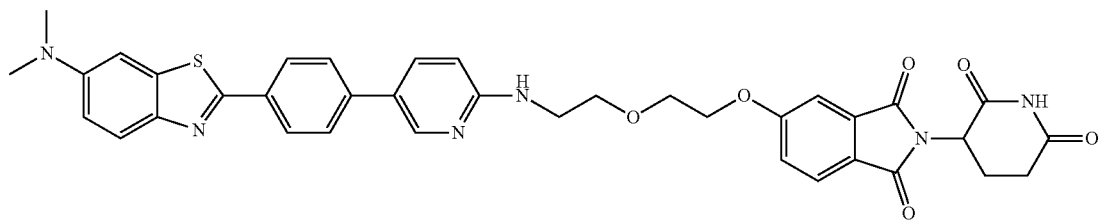

161177 (11 mg, 31%)

(A) Compound 161026: A mixture of dimethyl 4-hydroxyphthalate (139 mg, 0.62 mmol), Cs$_2$CO$_3$ (303 mg, 0.93 mmol), tert-butyl N-[5-[4-[6-(dimethylamino)-1,3-benzothiazol-2-yl]phenyl]pyridin-2-yl]-N-[2-(2-iodoethoxy)ethyl] carbamate (200 mg, 0.31 mmol) in DMF (5 mL) was heated at 50° C. for 1 h. The mixture was quenched with water and extracted with DCM. The organic layer was dried over MgSO$_4$, concentrated and purified by column chromatography (EtOAc:Hex=1:1, Rf=0.4) to give dimethyl 4-[2-[2-[[5-[4-[6-(dimethylamino)-1,3-benzo-thiazol-2-yl]phenyl]pyridin-2-yl]-[(2-methylpropan-2-yl)oxycarbonyl]amino]ethoxy]ethoxy]-benzene-1,2-dicarboxylate (148 mg, 0.20 mmol, 66% yield) as a yellow solid.

(B) Compound 161083: To a solution of dimethyl 4-[2-[2-[[5-[4-[6-(dimethylamino)-1,3-benzothiazol-2-yl]phenyl]pyridin-2-yl]-[(2-methylpropan-2-yl)oxycarbonyl]amino]ethoxy]-ethoxy]benzene-1,2-dicarboxylate (148 mg, 0.20 mmol) in MeOH (1 mL) and water (1 mL) was added LiOH (39 mg, 1.63 mmol). The reaction mixture was stirred at RT for 5 days. The solution was acidified with 1 N HCl to pH 4-5. The resulting precipitate was collected by filtration, washed with water and dried over vacuo to afford 4-[2-[2-[[5-[4-[6-(dimethylamino)-1,3-benzothiazol-2-yl]phenyl]pyridin-2-yl]-[(2-methylpropan-2-yl)oxycarbonyl]amino]ethoxy]-ethoxy]phthalic acid (119 mg, 0.17 mmol, 84% yield) as a yellow solid.

(C) Compound 161115: A mixture of 4-[2-[2-[[5-[4-[6-(dimethylamino)-1,3-benzo-thiazol-2-yl]phenyl]pyridin-2-yl]-[(2-methylpropan-2-yl)oxycarbonyl]amino]ethoxy] ethoxy]-phthalic acid (119 mg, 0.17 mmol) and 3-aminopiperidine-2,6-dione hydrochloride (31 mg, 0.19 mmol) in pyridine (2 mL) was heated at 120° C. for 2 days. The mixture was concentrated to dryness and purified by column chromatography (MeOH:DCM=5:95, Rf=0.3) to afford tert-butyl N-[2-[2-[2-[2,6-bis(oxo)piperidin-3-yl]-1,3-bis(oxo)isoindol-5-yl]oxyethoxy]ethyl]-N-[5-[4-[6-(dimethylamino)-1,3-benzothiazol-2-yl]phenyl]pyridin-2-yl]carbamate (39 mg, 0.05 mmol, 29% yield) as a yellow solid.

(D) Compound 161177: To a solution of tert-butyl N-[2-[2-[2-[2,6-bis(oxo)piperidin-3-yl]-1,3-bis(oxo)isoindol-5-yl]oxyethoxy]ethyl]-N-[5-[4-[6-(dimethylamino)-1,3-benzothiazol-2-yl]phenyl]pyridin-2-yl]carbamate (39 mg, 0.05 mmol) in DCM (1 mL) was added TFA (1 mL, 13.06 mmol) at 0° C. The resulting mixture was stirred at RT for 2 h. The solution was neutralized with sat. NaHCO$_3$ solution and extracted with DCM. The organic layer was washed with brine, dried over MgSO4, concentrated and purified by chromatography (MeOH:DCM=1:99, Rf=0.1) to afford 2-[2,6-bis(oxo)piperidin-3-yl]-5-[2-[2-[[5-[4-[6-(dimethylamino)-1,3-benzothiazol-2-yl]phenyl]pyridin-2-yl]amino]ethoxy]ethoxy]isoindole-1,3-dione (11 mg, 0.02 mmol, 31% yield) as a yellow solid.

Example 15: Synthesis of Compound 160383

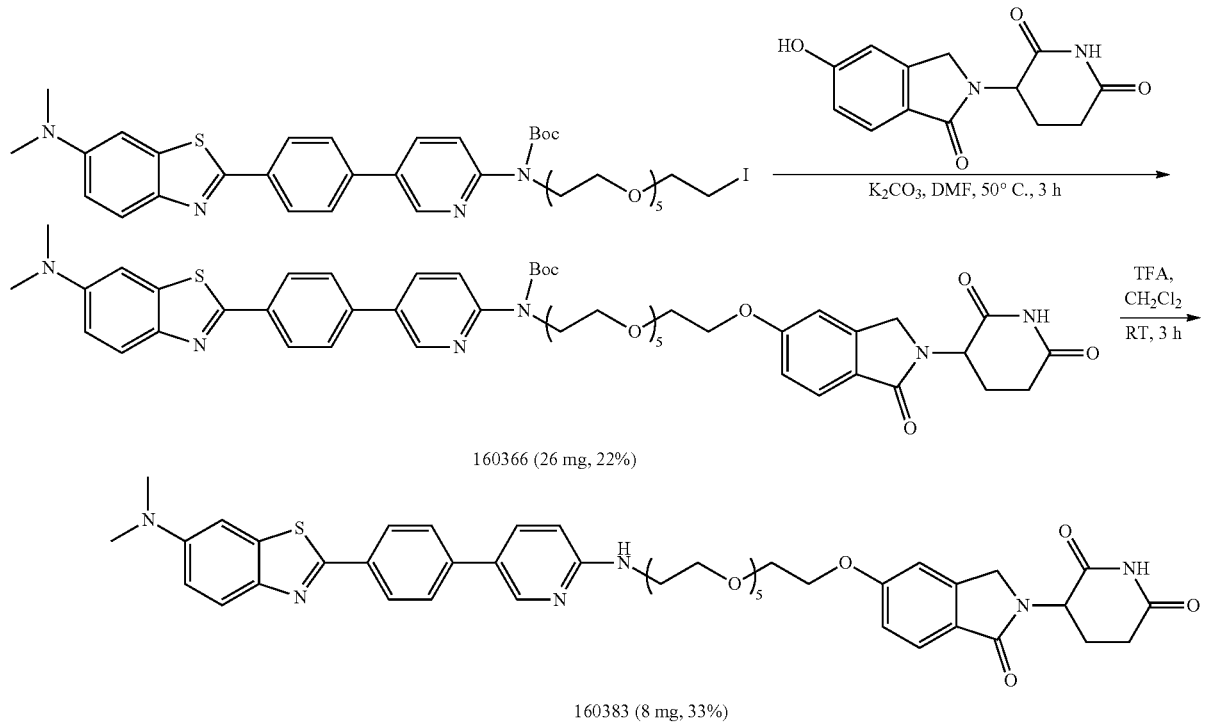

160366 (26 mg, 22%)

160383 (8 mg, 33%)

(A) Compound 160366: A mixture of 3-(6-hydroxy-3-oxo-1H-isoindol-2-yl)piperidine-2,6-dione (63 mg, 0.24 mmol), K₂CO₃ (51 mg, 0.37 mmol), tert-butyl N-[5-[4-[6-(dimethyl-amino)-1,3-benzothiazol-2-yl]phenyl]pyridin-2-yl]-N-[2-[2-[2-[2-[2-(2-iodoethoxy)ethoxy]-ethoxy]ethoxy]ethoxy]ethyl]carbamate (100 mg, 0.12 mmol) in DMF (2 mL) was heated at 50° C. for 3 h. The mixture was quenched with water, extracted with DCM (200 mL) dried over MgSO₄, concentrated and purified by chromatography (MeOH:DCM=5:95, Rf=0.3) to afford tert-butyl N-[2-[2-[2-[2-[2-[2-[[2-[2,6-bis(oxo)piperidin-3-yl]-1-oxo-3H-isoindol-5-yl]oxy]-ethoxy]ethoxy]ethoxy]ethoxy]ethyl]-N-[5-[4-[6-(dimethylamino)-1,3-benzothiazol-2-yl]-phenyl]pyridin-2-yl]carbamate (26 mg, 0.03 mmol, 22% yield) as a yellow solid.

(B) Compound 160383: To a solution of tert-butyl N-[2-[2-[2-[2-[2-[[2-[2,6-bis-(oxo)piperidin-3-yl]-1-oxo-3H-isoindol-5-yl]oxy]ethoxy]ethoxy]ethoxy]ethoxy]ethyl]-N-[5-[4-[6-(dimethylamino)-1,3-benzothiazol-2-yl]phenyl]pyridin-2-yl]carbamate (26 mg, 0.03 mmol) in DCM (1 mL) was added TFA (0.5 mL, 6.53 mmol) at 0° C. and the mixture was stirred at RT for 3 h. The solution was neutralized with sat. NaHCO₃ solution at 0° C. and then extracted with DCM. The organic layer was washed with brine, dried over MgSO₄, concentrated and purified by chromatography (MeOH:DCM=5:95, Rf=0.2) to afford 3-[6-[2-[2-[2-[2-[2-[2-[[5-[4-[6-(dimethylamino)-1,3-benzothiazol-2-yl]phenyl]pyridin-2-yl]amino]ethoxy]ethoxy]ethoxy]-ethoxy]ethoxy]ethoxy]-3-oxo-1H-isoindol-2-yl]piperidine-2,6-dione (9 mg, 0.01 mmol, 33% yield) as a yellow solid.

Example 16: Synthesis of Compound 160744

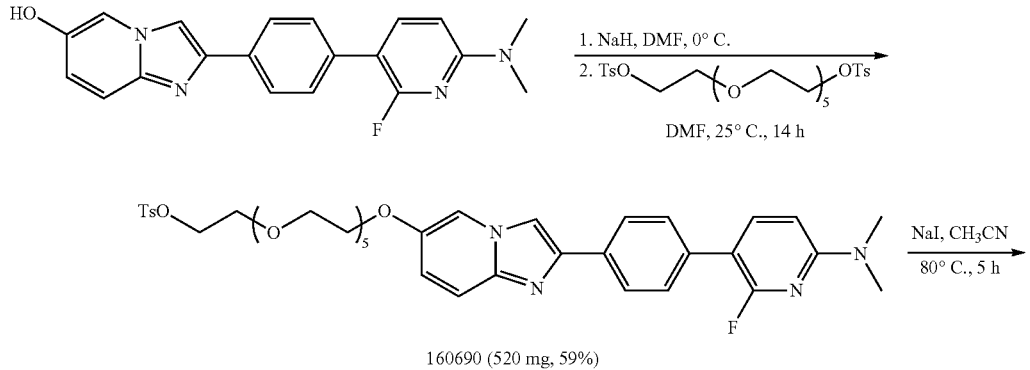

160690 (520 mg, 59%)

-continued

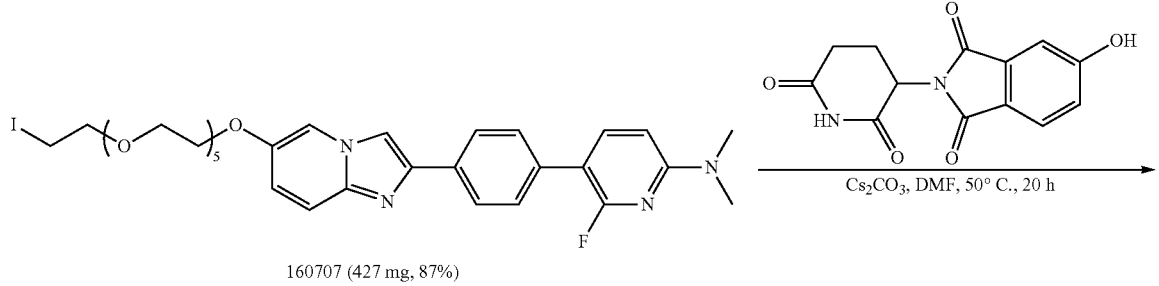

160707 (427 mg, 87%)

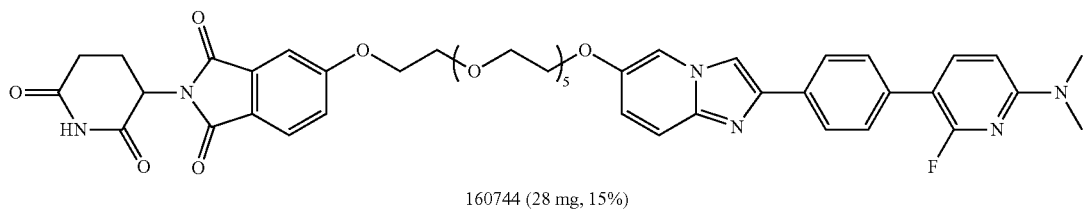

160744 (28 mg, 15%)

(A) Compound 160690: To a solution of 2-[4-[6-(dimethylamino)-2-fluoro-pyridin-3-yl]phenyl]imidazo[1,2-a]pyridin-6-ol (400 mg, 1.15 mmol) in DMF (10 mL) was added NaH (184 mg, 4.59 mmol) at 0° C. and stirred at RT for 1 h. 2-[2-[2-[2-[2-[2-(4-methylphenyl)sulfonyloxyethoxy]ethoxy]ethoxy]ethoxy]ethyl 4-methylbenzenesulfonate (2 mL, 4.13 mmol) was added to the mixture and stirred at RT for 14 h under argon. The mixture was diluted with DCM (10 mL), washed with water (10 mL) and brine (10 mL). The organic layer was collected, dried over Na₂SO₄, concentrated and purified by column chromatography (DCM:MeOH=50:1, Rf=0.29) to give 2-[2-[2-[2-[2-[2-[2-[4-[6-(dimethylamino)-2-fluoro-pyridin-3-yl]phenyl]-imidazo[1,2-a]pyridin-6-yl]oxyethoxy]ethoxy]ethoxy]ethoxy]ethyl 4-methylbenzenesulfonate (520 mg, 0.68 mmol, 59% yield) as pale yellow solid.

(B) Compound 160707: A mixture of 2-[2-[2-[2-[2-[2-[2-[4-[6-(dimethylamino)-2-fluoro-pyridin-3-yl]phenyl]imidazo[1,2-a]pyridin-6-yl]oxyethoxy]ethoxy]ethoxy]ethoxy]ethyl 4-methylbenzenesulfonate (520 mg, 0.68 mmol) and NaI (122 mg, 0.81 mmol) in CH₃CN (6 mL) was heated at 80° C. for 5 h. The mixture was added water and extracted with DCM. The organic layer was washed with water (20 mL), brine (20 mL), dried over Na₂SO₄, concentrated and purified by chromatography (MeOH:DCM=1:50, Rf=0.39) to give 6-fluoro-5-[4-[6-[2-[2-[2-[2-[2-(2-iodoethoxy)ethoxy]ethoxy]ethoxy]ethoxy]imidazo[1,2-a]-pyridin-2-yl]phenyl]-N,N-dimethyl-pyridin-2-amine (427 mg, 0.59 mmol, 87% yield) as pale-yellow solid.

(C) Compound 160744: A mixture of 2-[2,6-bis(oxo)piperidin-3-yl]-5-hydroxy-isoindole-1,3-dione (114 mg, 0.41 mmol), Cs₂CO₃ (202 mg, 0.62 mmol) and 6-fluoro-5-[4-[6-[2-[2-[2-[2-[2-(2-iodoethoxy)ethoxy]ethoxy]ethoxy]ethoxy]-3,8a-dihydroimidazo[1,2-a]-pyridin-2-yl]phenyl]-N,N-dimethyl-pyridin-2-amine (150 mg, 0.21 mmol) in DMF (3 mL) was heated at 50° C. for 20 h. The mixture was quenched with water and the resulting precipitation was collected by filtration. The residue was purified by column chromatography (MeOH:DCM=1:20, Rf=0.34) to give 2-[2,6-bis(oxo)piperidin-3-yl]-5-[2-[2-[2-[2-[2-[2-[4-[6-(dimethyl-amino)-2-fluoro-pyridin-3-yl]phenyl]imidazo[1,2-a]pyridin-6-yl]oxyethoxy]ethoxy]ethoxy]-ethoxy]ethoxy]ethoxy]isoindole-1,3-dione (28 mg, 0.03 mmol, 15% yield) as brown solid.

¹H NMR (400 MHz, DMSO-d6) δ 11.09 (s, 1H), 8.28 (s, 1H), 8.23 (d, J=2.3 Hz, 1H), 7.97 (d, J=7.8, 2H), 7.87 (dd, J=10.8, 8.4 Hz, 1H), 7.81 (d, J=8.4 Hz, 1H), 7.57 (d, J=7.8 Hz, 2H), 7.50 (d, J=9.7 Hz, 1H), 7.43 (d, J=2.3 Hz, 1H), 7.34 (dd, J=8.4, 2.3 Hz, 1H), 7.05 (dd, J=9.7, 2.3 Hz, 1H), 6.63 (dd, J=8.4, 2.0 Hz, 1H), 5.11 (dd, J=12.9, 5.5 Hz, 1H), 4.25-4.32 (m, 2H), 4.06-4.14 (m, 2H), 3.74-3.79 (m, 4H), 3.47-3.63 (m, 18H), 3.06 (s, 6H), 2.80-2.96 (m, 2H).

Example 17: Synthesis of Compound 161111

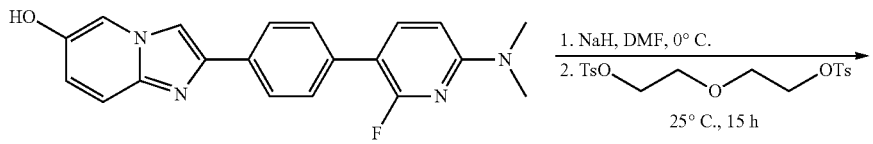

25° C., 15 h

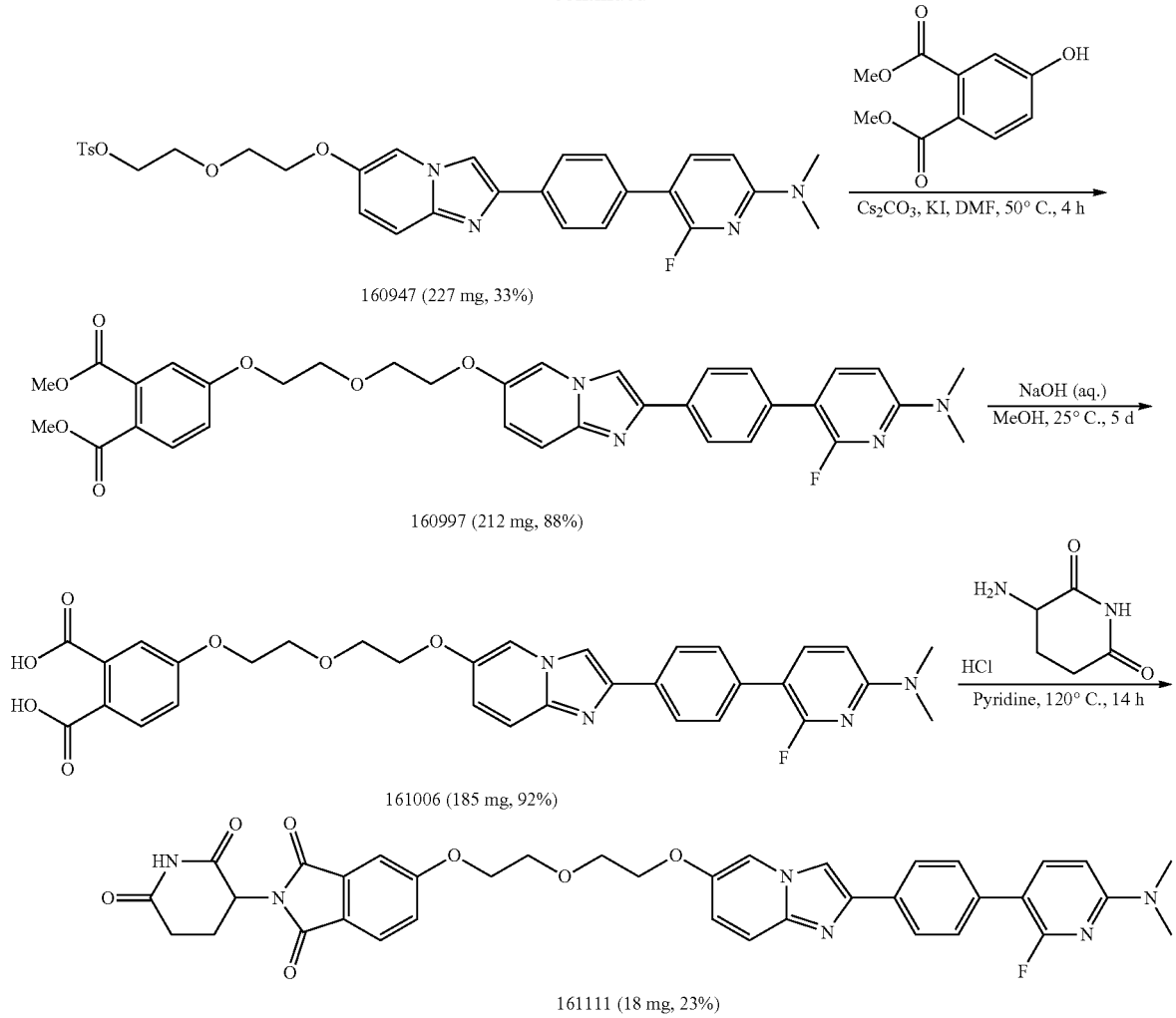

160947 (227 mg, 33%)

160997 (212 mg, 88%)

161006 (185 mg, 92%)

161111 (18 mg, 23%)

(A) Compound 160947: To a solution of 2-[4-[6-(dimethylamino)-2-fluoro-pyridin-3-yl]phenyl]imidazo[1,2-a]pyridin-6-ol (400 mg, 1.15 mmol) in dry DMF (8 mL) was added NaH (0.14 g, 3.44 mmol) at 0° C. and stirred at RT for 1 h. 2-[2-(4-methylphenyl)sulfonyloxyethoxy]-ethyl 4-methyl-benzenesulfonate (1.43 g, 3.44 mmol) was added to the mixture and stirred at the same temperature for 16 h. The reaction was quenched with water and extracted with DCM. The organic layer was washed with water, brine, dried over Na₂SO₄, concentrated and purified by column chromatography on silica gel (EtOAc:DCM=1:5, Rf=0.33) to give 2-[2-[2-[4-[6-(di-methylamino)-2-fluoro-pyridin-3-yl]phenyl]imidazo[1,2-a]pyridin-6-yl]oxyethoxy]ethyl 4-methyl-benzenesulfonate (227 mg, 0.38 mmol, 33% yield) as orange solid.

(B) Compound 160997: A mixture of dimethyl 4-hydroxybenzene-1,2-dicarboxylate (161 mg, 0.77 mmol), Cs₂CO₃ (374.2 mg, 1.15 mmol), KI (6 mg, 0.04 mmol) and 2-[2-[2-[4-[6-(dimethylamino)-2-fluoro-pyridin-3-yl]phenyl]imidazo[1,2-a]pyridin-6-yl]oxyethoxy]ethyl 4-methyl-benzenesulfonate (226 mg, 0.38 mmol) in DMF (4 mL) was heated at 50° C. for 4 h. The mixture was quenched with water and the resulting precipitation was collected by filtration and washed with water to give dimethyl 4-[2-[2-[2-[4-[6-(dimethylamino)-2-fluoro-pyridin-3-yl]-phenyl]imidazo[1,2-a]pyridin-6-yl]oxyethoxy]ethoxy]benzene-1,2-dicarboxylate (212 mg, 0.34 mmol, 88% yield) as an orange solid.

(C) Compound 161006: To a solution of dimethyl 4-[2-[2-[2-[4-[6-(dimethylamino)-2-fluoro-pyridin-3-yl]phenyl]imidazo[1,2-a]pyridin-6-yl]oxyethoxy]ethoxy]benzene-1,2-dicarboxylate (211 mg, 0.34 mmol) in MeOH (2 mL) was added NaOH (443 mg, 11.08 mmol) in water (2 mL) and stirred at RT for 5 days. The reaction was diluted with EtOAc (50 mL) and acidified with 1 N HCl solution to pH 1. The organic layer was washed with water (50 mL), brine (50 mL) dried over Na₂SO₄ and concentrated to give 4-[2-[2-[2-[4-[6-(dimethylamino)-2-fluoro-pyridin-3-yl]phenyl]imidazo[1,2-a]pyridin-6-yl]oxyethoxy]ethoxy]phthalic acid (185 mg, 0.31 mmol, 92% yield) as a yellow solid.

(D) Compound 161111: A mixture of 4-[2-[2-[2-[4-[6-(dimethylamino)-2-fluoro-pyridin-3-yl]phenyl]imidazo[1,2-a]pyridin-6-yl]oxyethoxy]ethoxy]phthalic acid (67 mg, 0.11 mmol), and 3-aminopiperidine-2,6-dione hydrochloride (20 mg, 0.15 mmol) in pyridine (3 mL) was heated at 120° C. for 14 h. The solvent was removed by vacuum. The residue was redissolved in DCM and water was added. The resulting precipitate was collected by filtration and purified by column chromatography (MeOH:DCM=1:100, Rf=0.19) to afford 2-[2,6-bis(oxo)piperidin-3-yl]-5-[2-[2-[2-[4-[6-(dimethylamino)-2-fluoro-pyridin-3-yl]phenyl]imidazo[1,2-a]pyridin-6-yl]oxyethoxy]ethoxy]isoindole-1,3-dione (18 mg, 0.02 mmol, 22% yield) as a yellow solid.

Example 18: Synthesis of Compound 161215 pyridin-2-yl]carbamate (500 mg, 1.15 mmol) in DMF (10 mL) at 0° C. The resulting mixture was stirred at room temperature for 30 min. 2-[2-(4-Methylphenyl)sulfonyloxyethoxy]ethyl 4-methylbenzenesulfonate (954 mg, 2.30 mmol) in DMF (3 mL) was added to the reaction mixture and stirred at room temperature for 21 h. The mixture was

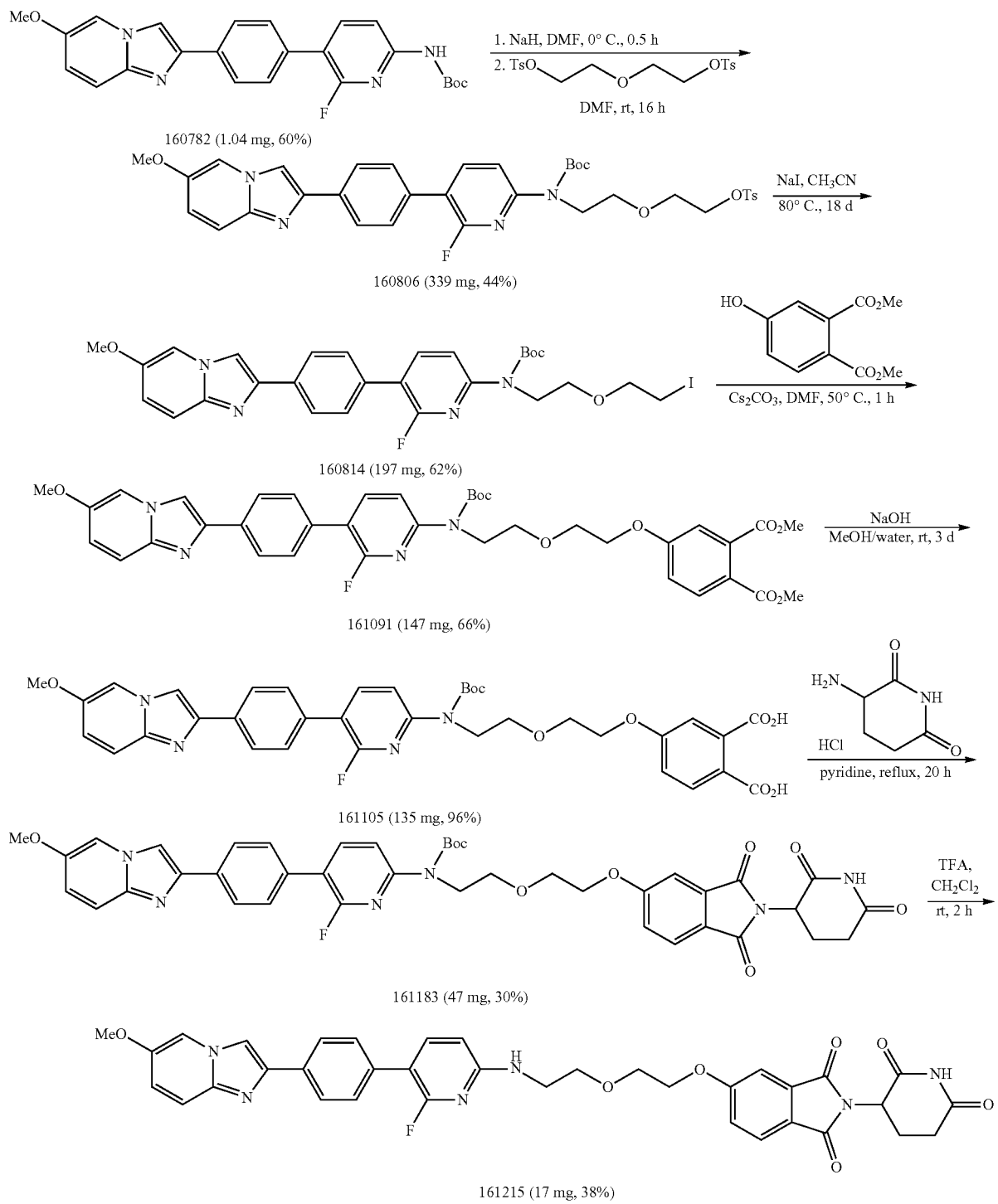

(A) Compound 160806: To a solution of NaH (138 mg, 3.45 mmol) in DMF (2 mL) was added tert-butyl N-[6-fluoro-5-[4-(6-methoxyimidazo[1,2-a]pyridin-2-yl)phenyl]

quenched with saturated NH₄Cl solution and extracted with EtOAc. The organic layer was washed with brine, dried over MgSO₄, concentrated and purified by column chromatography (EtOAc:DCM=3:17, Rf=0.3) to afford 2-[2-[[6-fluoro-5-[4-(6-methoxyimidazo[1,2-a]pyridin-2-yl)phenyl]pyridin-2-yl]-[(2-methyl-propan-2-yl)oxycarbonyl]amino]ethoxy]ethyl 4-methylbenzenesulfonate (339 mg, 0.50 mmol, 44% yield) as a yellow solid.

(B) Compound 160814: A mixture of 2-[2-[[6-fluoro-5-[4-(6-methoxyimidazo[1,2-a]-pyridin-2-yl)phenyl]pyridin-2-yl]-[(2-methylpropan-2-yl)oxycarbonyl]amino]ethoxy]ethyl 4-methylbenzenesulfonate (339 mg, 0.50 mmol) and NaI (90 mg, 0.60 mmol) in MeCN (10 mL) was heated at 80° C. for 19 h. The mixture was added to water and extracted with EtOAc. The organic layer was washed with water (50 mL), brine (50 mL), dried over MgSO₄, concentrated, and purified by column chromatography (EtOAc:DCM=1:9, Rf=0.3) to afford tert-butyl N-[6-fluoro-5-[4-(6-methoxyimidazo[1,2-a]pyridin-2-yl)phenyl]pyridin-2-yl]-N-[2-(2-iodoethoxy)-ethyl]carbamate (197 mg, 0.31 mmol, 62% yield) as a yellow solid.

(C) Compound 161091: A mixture of dimethyl 4-oxobenzene-1,2-dicarboxylate (131 mg, 0.62 mmol), Cs₂CO₃ (305 mg, 0.93 mmol), tert-butyl N-[6-fluoro-5-[4-(6-methoxyimidazo-[1,2-a]pyridin-2-yl)phenyl]pyridin-2-yl]-N-[2-(2-iodoethoxy)ethyl]carbamate (197 mg, 0.31 mmol) in DMF (5 mL) was heated at 50° C. for 1 h. The mixture was quenched with water, extracted with DCM, dried over MgSO₄, concentrated, and purified by column chromatography (EtOAc:hexane=1:1, Rf=0.3) to give dimethyl 4-[2-[2-[[6-fluoro-5-[4-(6-methoxyimidazo-[1,2-a]pyridin-2-yl)phenyl]pyridin-2-yl]-[(2-methylpropan-2-yl)oxycarbonyl]amino]ethoxy]-ethoxy]benzene-1,2-dicarboxylate (147 mg, 0.21 mmol, 66% yield) as a yellow solid.

(D) Compound 161105: To a solution of dimethyl 4-[2-[2-[[6-fluoro-5-[4-(6-methoxyimidazo[1,2-a]pyridin-2-yl)phenyl]pyridin-2-yl]-[(2-methylpropan-2-yl)oxycarbonyl]amino]-ethoxy]ethoxy]benzene-1,2-dicarboxylate (147 mg, 0.21 mmol) in MeOH (2 mL) was added NaOH (66 mg, 1.65 mmol) in water (2 mL), and the mixture stirred at room temperature for 3 days. The reaction was neutralized with 1N HCl solution to pH 1. The precipitate was collected by filtration and washed with water to give 4-[2-[2-[[6-fluoro-5-[4-(6-methoxyimidazo[1,2-a]-pyridin-2-yl)phenyl]pyridin-2-yl]-[(2-methylpropan-2-yl)oxycarbonyl]amino]ethoxy]ethoxy]-phthalic acid (135 mg, 0.20 mmol, 96% yield) as a white solid.

(E) Compound 161183: A mixture of 4-[2-[2-[[6-fluoro-5-[4-(6-methoxyimidazo[1,2-a]pyridin-2-yl)phenyl]pyridin-2-yl]-[(2-methylpropan-2-yl)oxycarbonyl]amino]ethoxy]ethoxy]-phthalic acid (135 mg, 0.20 mmol) and 3-aminopiperidine-2,6-dione hydrochloride (49 mg, 0.29 mmol) in pyridine (2 mL) was heated at 120° C. for 20 h. The mixture was concentrated to dryness, and purified by column chromatography on NH silica gel (MeOH:DCM=1:99, Rf=0.1) to afford tert-butyl N-[2-[2-[2-[2,6-bis(oxo)piperidin-3-yl]-1,3-bis(oxo)isoindol-5-yl]oxyethoxy]ethyl]-N-[6-fluoro-5-[4-(6-methoxyimidazo[1,2-a]pyridin-2-yl)phenyl]pyridin-2-yl]-carbamate (47 mg, 0.06 mmol, 30% yield) as a yellow solid.

(F) Compound 161215: To a solution of tert-butyl N-[2-[2-[2-[2,6-bis(oxo)piperidin-3-yl]-1,3-bis(oxo)isoindol-5-yl]oxyethoxy]ethyl]-N-[6-fluoro-5-[4-(6-methoxyimidazo[1,2-a]pyridin-2-yl)phenyl]pyridin-2-yl]carbamate (47 mg, 0.06 mmol) in DCM (1 mL) was added TFA (1 mL, 13 mmol) at 0° C., and the mixture stirred at room temperature for 2 h. The solution was neutralized with saturated NaHCO₃ solution and extracted with DCM. The organic layer was washed with brine, dried over MgSO₄, concentrated and purified by chromatography on NH silica gel (MeOH:DCM=1:99, Rf=0.1) to afford 2-[2,6-bis(oxo)piperidin-3-yl]-5-[2-[2-[[6-fluoro-5-[4-(6-methoxyimidazo[1,2-a]pyridin-2-yl)phenyl]pyridin-2-yl]amino]ethoxy]ethoxy]-isoindole-1,3-dione (17 mg, 0.02 mmol, 38% yield) as a yellow solid. ¹H NMR (400 MHz, DMSO-d6) δ 11.07 (s, 1H), 8.28 (s, 1H), 8.19 (d, J=2.3 Hz, 1H), 7.92 (d, J=8.3 Hz, 2H), 7.79 (d, J=8.3 Hz, 1H), 7.70 (dd, J=10.3, 8.2 Hz, 1H), 7.46-7.52 (m, 3H), 7.43 (d, J=2.2 Hz, 1H), 7.34 (dd, J=8.2, 2.3 Hz, 1H), 7.14 (t, J=5.7 Hz, 1H), 7.01 (dd, J=10.3, 2.2 Hz, 1H), 6.49 (d, J=8.5 Hz, 1H), 5.08 (dd, J=13.1, 5.3 Hz, 1H), 4.34-4.28 (m, 2H), 3.75-3.83 (m, 5H), 3.62 (t, J=5.5 Hz, 2H), 3.39-3.44 (m, 2H), 2.77-2.91 (m, 1H), 2.49-2.66 (m, 2).

Example 19: Synthesis of Compound 161409

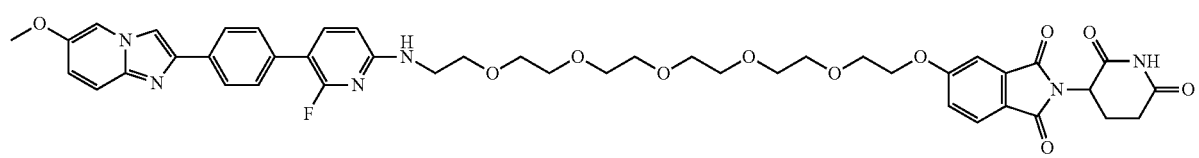

161409

Compound 161409 could be synthesized by method similar to example 19. H NMR (400 MHz, DMSO-d6) δ 11.09 (s, 1H), 8.27 (s, 1H), 8.19 (d, J=2.5 Hz, 1H), 7.92 (d, J=8.0 Hz, 2H), 7.78 (d, J=8.4 Hz, 1H), 7.71 (dd, J=10.2, 8.6 Hz, 1H), 7.45-7.53 (m, 3H), 7.41 (d, J=2.0 Hz, 1H), 7.32 (dd, J=8.6, 2.1 Hz, 1H), 7.13 (t, J=5.3 Hz, 1H), 7.00 (dd, J=9.7, 1.6 Hz, 1H), 6.49 (d, J=9.2 Hz, 1H), 5.07 (dd, J=12.8, 5.3 Hz, 1H), 4.24-4.29 (m, 2H), 3.77 (s, 3H), 3.72-3.76 (m, 2H), 3.44-3.58 (m, 20H), 3.34-3.41 (m, 3H), 2.77-2.91 (m, 2H).

Example 20: Synthesis of Compound 161104

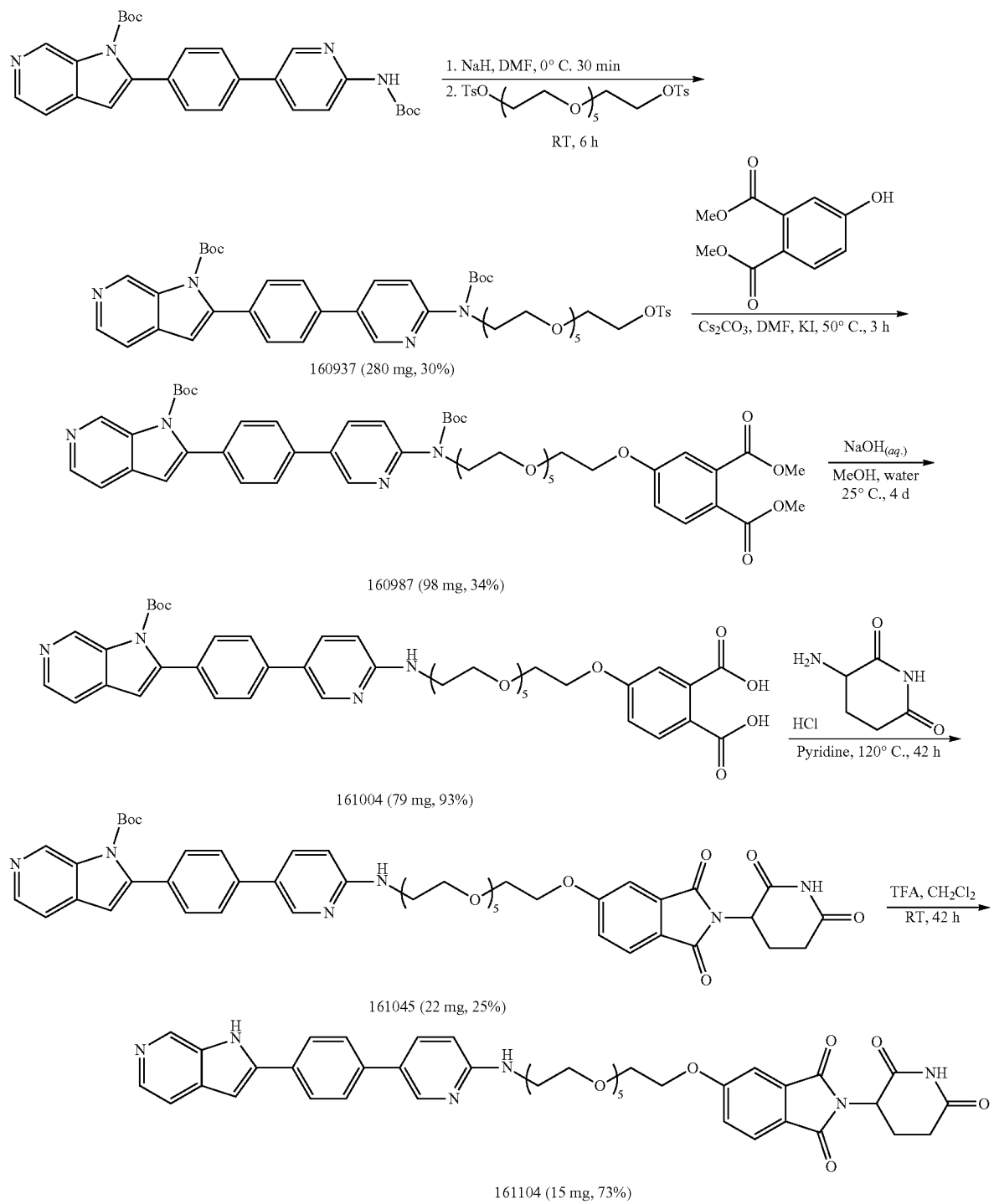

(A) Compound 160937: To a solution of tert-butyl 2-[4-[6-[(2-methylpropan-2-yl)oxycarbonylamino]pyridin-3-yl]phenyl]pyrrolo[2,3-c]-pyridine-1-carboxylate (500 mg, 1.03 mmol) in DMF (10 mL) was added NaH (49 mg, 1.23 mmol) at 0° C. and stirred at RT for 30 min. 2-[2-[2-[2-[2-[2-(4-methylphenyl)sulfonyloxyethoxy]ethoxy]ethoxy]ethoxy]ethyl 4-methylbenzenesulfonate (789 mg, 1.34 mmol) was added to the reaction mixture and stirred at RT for 6 h. The mixture was quenched with sat. NH₄Cl solution and extracted with DCM. The organic layer was washed with brine, dried over MgSO₄, concentrated and purified by column chromatography (EtOAc:DCM=1:4, Rf=0.33) to afford tert-butyl 2-[4-[6-[2-[2-[2-[2-[2-[2-(4-methylphenyl)sulfonyloxyethoxy]ethoxy]ethoxy]ethoxy]ethyl-[(2- methylpropan-2-yl)-oxycarbonyl]amino]pyridin-3-yl]phenyl]pyrrolo[2,3-c]pyridine-1-carboxylate (280 mg, 0.31 mmol, 30% yield) as pale-yellow oil.

(B) Compound 160987: A solution of dimethyl 4-hydroxybenzene-1,2-dicarboxylate (130.05 mg, 0.62 mmol), $Cs_2CO_3$ (303 mg, 0.93 mmol), and tert-butyl 2-[4-[6-[2-[2-[2-[2-[2-(4-methylphenyl)sulfonyloxyethoxy]ethoxy]ethoxy]ethoxy]ethyl-[(2-methylpropan-2-yl)oxycarbonyl]amino]pyridin-3-yl]phenyl]pyrrolo[2,3-c]pyridine-1-carboxylate (280 mg, 0.31 mmol) in DMF (3 mL) was heated at 50° C. for 3 h. The mixture was quenched with water and the resulting precipitation was collected by filtration. The solid was then purified by column chromatography (EtOAc:DCM=4:1, Rf=0.32) to provide dimethyl 4-[2-[2-[2-[2-[2-[2-[(2-methylpropan-2-yl)oxycarbonyl-[5-[4-[1-[(2-methylpropan-2-yl)oxycarbonyl]pyrrolo[2,3-c]-pyridin-2-yl]phenyl]pyridin-2-yl]amino]ethoxy]ethoxy]ethoxy]ethoxy]ethoxy]benzene-1,2-dicarboxylate (98 mg, 0.10 mmol, 34% yield) as pale-yellow oil.

(C) Compound 161004: To a solution of dimethyl 4-[2-[2-[2-[2-[2-[2-[(2-methyl-propan-2-yl)oxycarbonyl-[5-[4-[1-[(2-methylpropan-2-yl)oxycarbonyl]pyrrolo[2,3-c]pyridin-2-yl]phenyl]pyridin-2-yl]amino]ethoxy]ethoxy]ethoxy]ethoxy]ethoxy]benzene-1,2-dicarboxylate (98 mg, 0.10 mmol) in EtOH (5 mL) was added NaOH (33 mg, 0.83 mmol) in water (5 mL) and stirred at RT for 4 days. The reaction was diluted with DCM (10 mL) and acidified with 1 N HCl solution to pH 1. The organic layer was washed with water (10 mL), brine (10 mL) dried over $Na_2SO_4$ and concentrated to dryness to give 4-[2-[2-[2-[2-[2-[2-[[5-[4-[1-[(2-methyl-propan-2-yl)oxycarbonyl]pyrrolo[2,3-c]pyridin-2-yl]phenyl]pyridin-2-yl]amino]ethoxy]ethoxy]-ethoxy]ethoxy]ethoxy]ethoxy]phthalic acid (79 mg, 0.10 mmol, 93% yield) as pale-yellow solid.

(D) Compound 161045: A mixture of 4-[2-[2-[2-[2-[2-[2-[[5-[4-[1-[(2-methylpropan-2-yl)oxycarbonyl]pyrrolo[2,3-c]pyridin-2-yl]phenyl]pyridin-2-yl]amino]ethoxy]ethoxy]ethoxy]-ethoxy]ethoxy]ethoxy]phthalic acid (79 mg, 0.10 mmol) and 3-aminopiperidine-2,6-dione HCl (18 mg, 0.11 mmol) in pyridine (3 mL) was heated at 120° C. for 42 h. The solvent was removed in vacuo. The residue was re-dissolved in with DCM (10 mL), washed with brine, dried over $Na_2SO_4$, concentrated and purified by column chromatography (MeOH:DCM=1:19, Rf=0.3) to give tert-butyl 2-[4-[6-[2-[2-[2-[2-[2-[2-[2-[2,6-bis(oxo)piperidin-3-yl]-1,3-bis(oxo)isoindol-5-yl]oxyethoxy]ethoxy]ethoxy]ethoxy]ethoxy]ethylamino]pyridin-3-yl]phenyl]pyrrolo[2,3-c]-pyridine-1-carboxylate (22 mg, 0.02 mmol, 25% yield) as a yellow solid.

(E) Compound 161104: To a solution of tert-butyl 2-[4-[6-[2-[2-[2-[2-[2-[2-[2-[2,6-bis-(oxo)piperidin-3-yl]-1,3-bis(oxo)isoindol-5-yl]oxyethoxy]ethoxy]ethoxy]ethoxy]ethoxy]ethylamino]pyridin-3-yl]phenyl]pyrrolo[2,3-c]pyridine-1-carboxylate (22 mg, 0.02 mmol) in DCM (3 mL) was added TFA (0.03 mL, 0.36 mmol), and the mixture stirred at RT for 42 h. The mixture was neutralized with sat. $NaHCO_3$ to pH 8 and extracted with DCM (10 mL). The organic layer was washed with brine, dried over $Na_2SO_4$ and concentrated to dryness to give 2-[2,6-bis(oxo)-piperidin-3-yl]-5-[2-[2-[2-[2-[2-[2-[[5-[4-(1H-pyrrolo[2,3-c]pyridin-2-yl)phenyl]pyridin-2-yl]-amino]ethoxy]ethoxy]ethoxy]ethoxy]ethoxy]isoindole-1,3-dione (15 mg, 0.02 mmol, 73% yield) as a yellow solid.

Example 21: Synthesis of Compound 160624

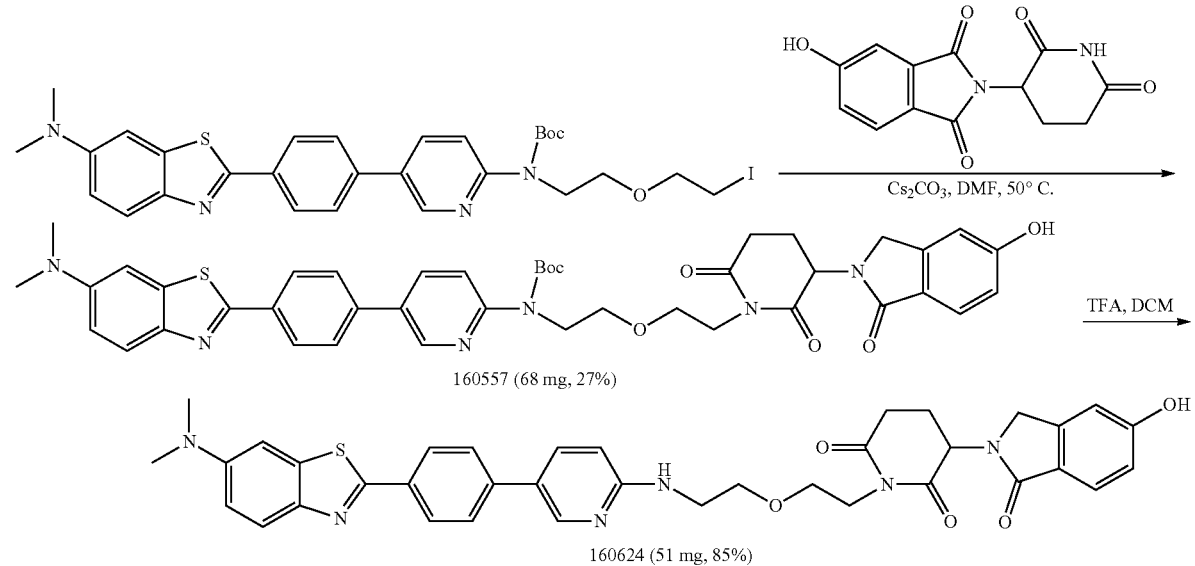

Compound 160557: A mixture of 3-(6-oxidanyl-3-oxidanylidene-1H-isoindol-2-yl)piperidine-2,6-dione (169 mg, 0.65 mmol), $Cs_2CO_3$ (317 mg, 0.97 mmol), tert-butyl N-[5-[4-[6-(dimethylamino)-1,3-benzothiazol-2-yl]phenyl]pyridin-2-yl]-N-[2-(2-iodanylethoxy)ethyl]carbamate (209 mg, 0.32 mmol) in DMF (5 mL) was heated at 50° C. for 1 h. The mixture was quenched with water, extracted with DCM, dried over $MgSO_4$, concentrated and purified by column chromatography (solvent gradient 0% to 3% MeOH in DCM, Rf=0.2) to give tert-butyl (5-(4-(6-(dimethylamino)benzo[d]thiazol-2-yl)phenyl)pyridin-2-yl)(2-(2-(3-(5-hydroxy-1-oxoisoindolin-2-yl)-2,6-dioxopiperidin-1-yl)ethoxy)ethyl)carbamate (68 mg, 0.09 mmol, 27% yield) as a yellow solid.

Compound 160624: To a solution of tert-butyl (5-(4-(6-(dimethylamino)benzo[d]thiazol-2-yl)phenyl)pyridin-2-yl)

(2-(2-(3-(5-hydroxy-1-oxoisoindolin-2-yl)-2,6-dioxopiperidin-1-yl)ethoxy)ethyl)carbamate (68 mg, 0.09 mmol) in DCM (2 mL) was added TFA (1 mL, 13.06 mmol) at 0° C. and stirred at room temperature for 6 h. The solution was neutralized with saturated NaHCO₃ solution at 0° C. and the solution was extracted with DCM. The organic layer was washed with brine, dried over MgSO₄ and concentrated to dryness to afford 1-(2-(2-((5-(4-(6-(dimethylamino)benzo[d]thiazol-2-yl)phenyl)pyridin-2-yl)amino)ethoxy)ethyl)-3-(5-hydroxy-1-oxoisoindolin-2-yl)piperidine-2,6-dione (51 mg, 0.07 mmol, 85% yield) as a yellow solid.

Example 22: Synthesis of Compound 162641 purified by column chromatography (MeOH:DCM=1:20, Rf=0.3) to give tert-butyl N-[2-[2-[3-(7-azanyl-3-oxidanylidene-1H-isoindol-2-yl)-2,6-bis(oxidanylidene)piperidin-1-yl]ethoxy]ethyl]-N-[2-[4-[6-(dimethylamino)pyridin-3-yl]phenyl]-1,3-benzothiazol-6-yl]carbamate (70 mg, 0.09 mmol, 58% yield) as a yellow solid.

Compound 162641: To a solution of tert-butyl N-[2-[2-[3-(7-azanyl-3-oxidanylidene-1H-isoindol-2-yl)-2,6-bis(oxidanylidene)piperidin-1-yl]ethoxy]ethyl]-N-[2-[4-[6-(dimethylamino)pyridin-3-yl]phenyl]-1,3-benzothiazol-6-yl]carbamate (70 mg, 0.09 mmol) in DCM (2 mL) was added TFA (0.1 mL, 1.35 mmol) and stirred at room temperature for 20 h. The mixture was neutralized with sat. NaHCO₃ solution to pH 8. The residue was taken up in DCM (20 mL)

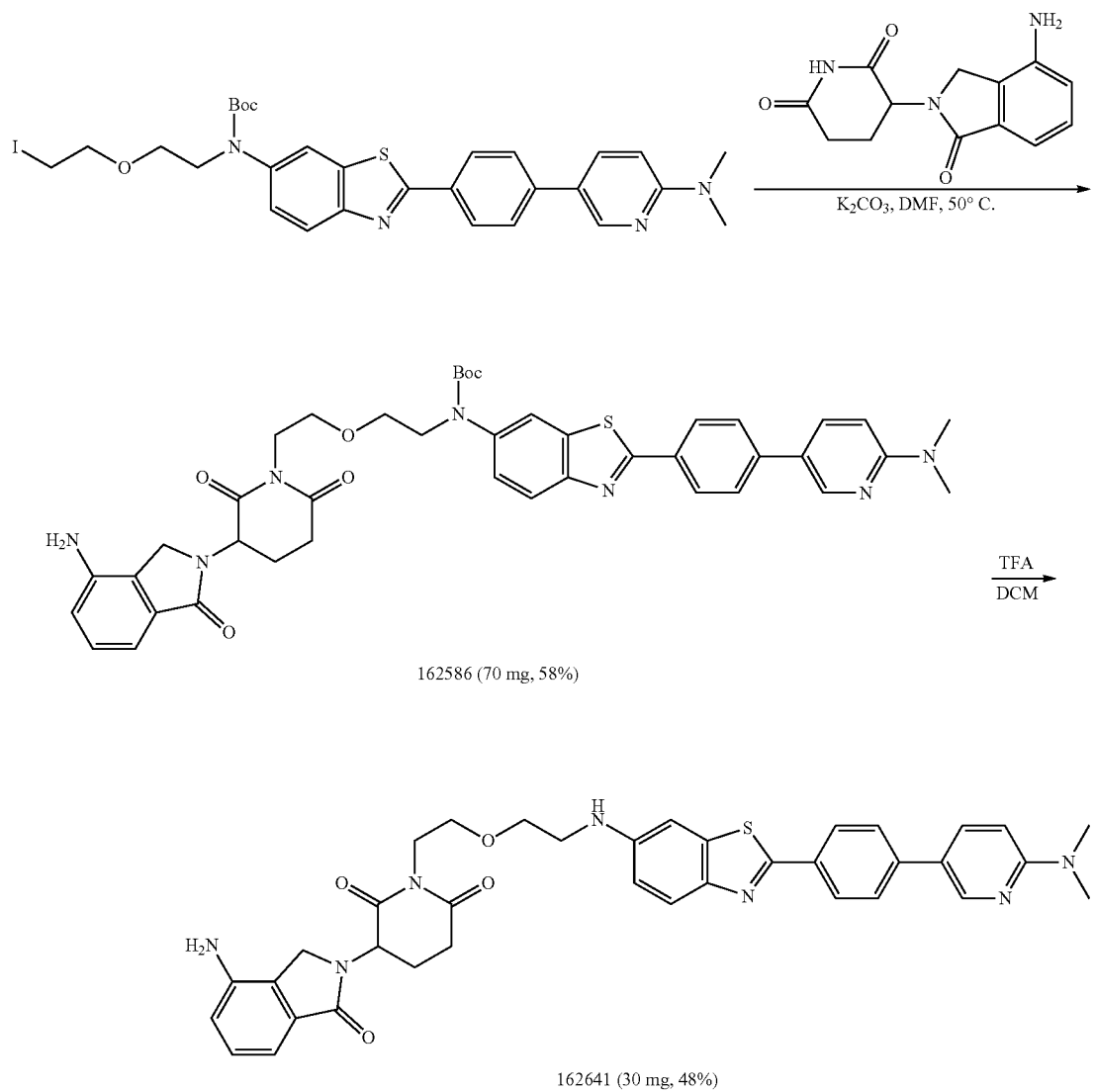 [SMILES: CN(C)c1ccc(-c2ccc(-c3nc4ccc(N(CCOCCI)C(=O)OC(C)(C)C)cc4s3)cc2)cn1 ; Nc1cccc2c1CN(C1CCC(=O)NC1=O)C2=O ; CN(C)c1ccc(-c2ccc(-c3nc4ccc(N(CCOCCN5C(=O)CCC(N6Cc7c(N)cccc7C6=O)C5=O)C(=O)OC(C)(C)C)cc4s3)cc2)cn1 ; CN(C)c1ccc(-c2ccc(-c3nc4ccc(NCCOCCN5C(=O)CCC(N6Cc7c(N)cccc7C6=O)C5=O)cc4s3)cc2)cn1]

162586 (70 mg, 58%)

162641 (30 mg, 48%)

Compound 162586: A solution of tert-butyl N-[2-[4-[6-(dimethylamino)pyridin-3-yl]phenyl]-1,3-benzothiazol-6-yl]-N-[2-(2-iodanylethoxy)ethyl]carbamate (100 mg, 0.16 mmol) in DMF (5 mL) was added 3-(7-azanyl-3-oxidanylidene-1H-isoindol-2-yl)piperidine-2,6-dione (48 mg, 0.19 mmol) and K₂CO₃ (101 mg, 0.31 mmol) and heated at 80° C. for 3 h. The mixture was diluted with DCM, washed with water and brine, dried over Na₂SO₄, concentrated and and water (10 mL). The organic layer was washed with water (10 mL) and brine (10 mL), dried over Na₂SO₄ and concentrated to give 3-(7-azanyl-3-oxidanylidene-1H-isoindol-2-yl)-1-[2-[2-[[2-[4-[6-(dimethylamino)pyridin-3-yl]phenyl]-1,3-benzothiazol-6-yl]amino]ethoxy]ethyl]piperidine-2,6-dione (30 mg, 0.04 mmol, 46% yield) as a yellow solid.

Example 23: Synthesis of Compound 161598

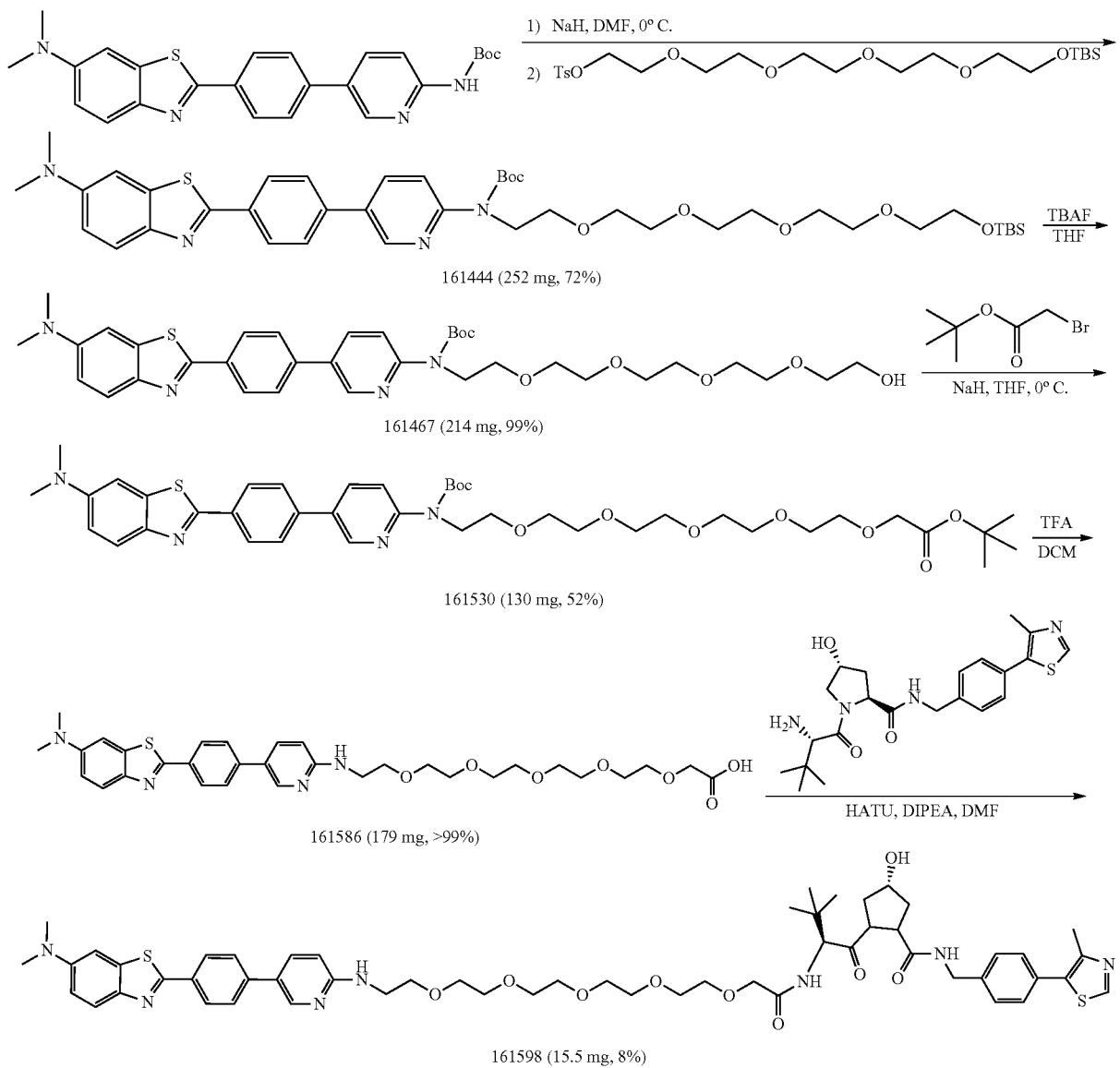

Compound 161444: To a solution of tert-butyl N-[5-[4-[6-(dimethylamino)-1,3-benzothiazol-2-yl]phenyl]pyridin-2-yl]carbamate (200 mg, 0.45 mmol) in DMF (5 mL) was added NaH (43 mg, 1.79 mmol) at 0° C. and stirred at room temperature for 1 h. The mixture was added 2-[2-[2-[2-[2-[tert-butyl(dimethyl)silyl]oxyethoxy]ethoxy]ethoxy]ethoxy]ethyl 4-methylbenzenesulfonate (681 mg, 1.34 mmol) and stirred at the same temperature for 24 h. The reaction was quenched by adding water. The resulting solid was collected by filtration and purified by column chromatography (EtOAc:DCM=7:3, Rf=0.4) to give tert-butyl N-[2-[2-[2-[2-[2-[tert-butyl(dimethyl)silyl]oxyethoxy]ethoxy]ethoxy]ethoxy]ethyl]-N-[5-[4-[6-(dimethylamino)-1,3-benzothiazol-2-yl]phenyl]pyridin-2-yl]carbamate (252 mg, 0.32 mmol, 72% yield) as a yellow oil.

Compound 161467: A solution of tert-butyl N-[2-[2-[2-[2-[2-[tert-butyl(dimethyl)silyl]oxyethoxy]ethoxy]ethoxy]ethoxy]ethyl]-N-[5-[4-[6-(dimethylamino)-1,3-benzothiazol-2-yl]phenyl]pyridin-2-yl]carbamate (252 mg, 0.32 mmol) in THF (5 mL) was added TBAF (1M in THF, 1.94 mL, 1.94 mmol) dropwise and stirred at room temperature for 19 h. The reaction mixture was concentrated to dryness and the residue was taken up in EtOAc (50 mL). The mixture was washed with water (50 mL) and brine (50 mL), dried over $Na_2SO_4$. And concentrated to dryness to give tert-butyl N-[5-[4-[6-(dimethylamino)-1,3-benzothiazol-2-yl]phenyl]pyridin-2-yl]-N-[2-[2-[2-[2-(2-hydroxyethyloxy)ethoxy]ethoxy]ethoxy]ethyl]carbamate (214 mg, 0.32 mmol, 99% yield) as a yellow oil.

Compound 161530: A mixture of tert-butyl N-[5-[4-[6-(dimethylamino)-1,3-benzothiazol-2-yl]phenyl]pyridin-2-yl]-N-[2-[2-[2-[2-(2-hydroxyethyloxy)ethoxy]ethoxy]ethoxy]ethyl]carbamate (214 mg, 0.32 mmol) and tert-butyl 2-bromanylethanoate (0.14 mL, 0.96 mmol) in THF (3 mL)

was added NaH (19 mg, 0.80 mmol) at 0° C. and stirred at room temperature for 42 h. The reaction was quenched by adding water. The mixture was diluted with DCM (50 mL), washed with water (50 mL) and brine (50 mL), dried over Na$_2$SO$_4$, concentrated to dryness and purified by column chromatography (EtOAc:Hex=1:1, Rf=0.35) to afford tert-butyl 2-[2-[2-[2-[2-[2-[[5-[4-[6-(dimethylamino)-1,3-benzothiazol-2-yl]phenyl]pyridin-2-yl]-[(2-methylpropan-2-yl)oxycarbonyl]amino]ethoxy]ethoxy]ethoxy]ethoxy]ethanoate (130 mg, 0.17 mmol, 52% yield) as a yellow oil.

raphy (MeOH:DCM=3:100, Rf=0.32) to give rac-(2R,4S)-N-[[4-(4-methyl-1,3-thiazol-5-yl)phenyl]methyl]-4-oxidanyl-1-[rac-(2R)-2-[2-[2-[2-[2-[2-[[5-[4-[6-(dimethylamino)-1,3-benzothiazol-2-yl]phenyl]pyridin-2-yl]amino]ethoxy]ethoxy]ethoxy]ethoxy]ethoxy]ethanoylamino]-3,3-dimethyl-butanoyl]pyrrolidine-2-carboxamide (16 mg, 0.01 mmol, 8% yield) as a yellow solid.

Example 24: Synthesis of Compound 160570

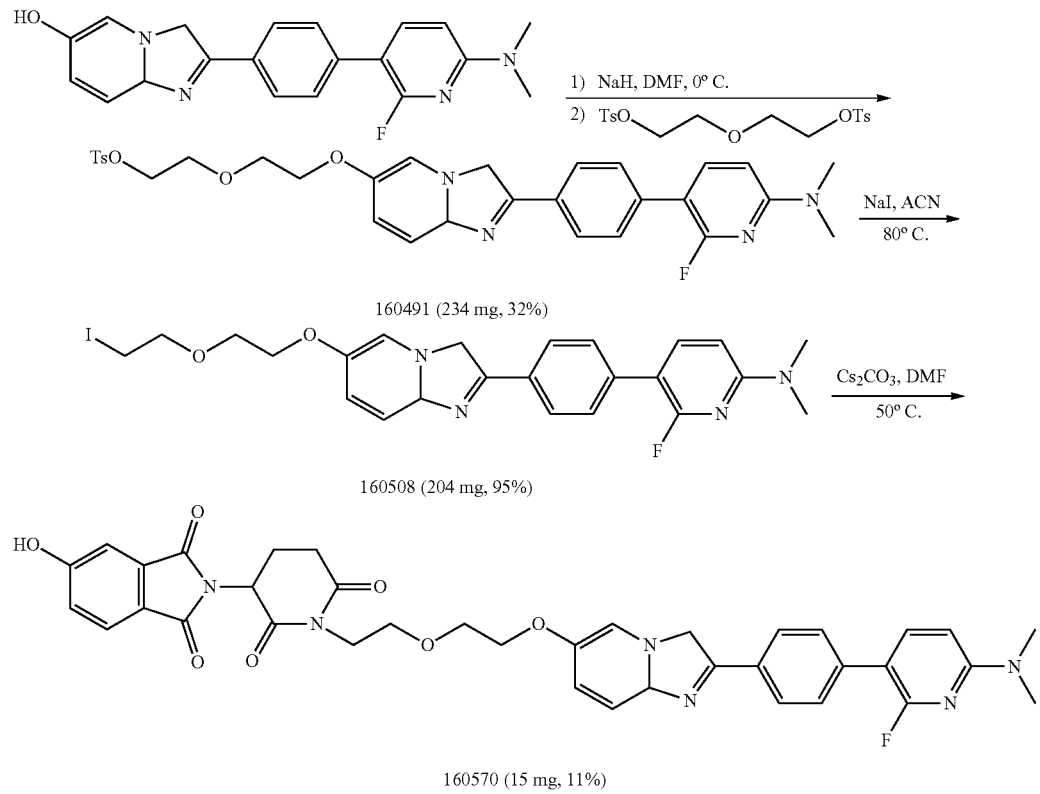

160491 (234 mg, 32%)

160508 (204 mg, 95%)

160570 (15 mg, 11%)

Compound 161586: To a solution of tert-butyl 2-[2-[2-[2-[2-[2-[[5-[4-[6-(dimethylamino)-1,3-benzothiazol-2-yl]phenyl]pyridin-2-yl]-[(2-methylpropan-2-yl)oxycarbonyl]amino]ethoxy]ethoxy]ethoxy]ethoxy]ethanoate (130 mg, 0.17 mmol) in DCM (2 mL) was added TFA (0.38 mL, 4.99 mmol) and stirred at room temperature for 22 h. The mixture was concentrated to dryness to afford 2-[2-[2-[2-[2-[2-[[5-[4-[6-(dimethylamino)-1,3-benzothiazol-2-yl]phenyl]pyridin-2-yl]amino]ethoxy]ethoxy]ethoxy]ethoxy]ethanoic acid TFA salt (179 mg, 0.29 mmol, >99% yield) as an orange oil.

Compound 161598: A mixture of (2S,4R)-1-[(2S)-2-azanyl-3,3-dimethyl-butanoyl]-N-[[4-(4-methyl-1,3-thiazol-5-yl)phenyl]methyl]-4-oxidanyl-pyrrolidine-2-carboxamide (79 mg, 0.18 mmol), 2-[2-[2-[2-[2-[2-[[5-[4-[6-(dimethylamino)-1,3-benzothiazol-2-yl]phenyl]pyridin-2-yl]amino]ethoxy]ethoxy]ethoxy]ethoxy]ethoxy]ethanoic acid (104 mg, 0.17 mmol), DIPEA (0.04 mL, 0.25 mmol) and HATU (127 mg, 0.33 mmol) in anhydrous DMF (3 mL) was stirred at room temperature for 18 h. The mixture was taken up in DCM, washed with water and brine, dried over anhydrous Na$_2$SO$_4$, concentrated and purified by column chromatog- Compound 160491: To a solution of 2-[4-[6-(dimethylamino)-2-fluoranyl-pyridin-3-yl]phenyl]imidazo[1,2-a]pyridin-6-ol (0.43 g, 1.24 mmol) in dry DMF (4 mL) was added NaH (0.10 g, 2.48 mmol) at 0° C. and stirred at room temperature for 1 h. 2-[2-(4-methylphenyl)sulfonyloxyethoxy]ethyl 4-methylbenzenesulfonate (1.54 g, 3.72 mmol) in dry DMF (4 mL) was added to the reaction mixture and stirred at the same temperature for 14 h. The mixture was cooled to 0° C., quenched with water (30 mL) and extracted with DCM (30 mL) was added. The organic layer was washed with water (30 mL) and brine (30 mL), dried over anhydrous Na$_2$SO$_4$, concentrated and purified by column chromatography (EtOAc:DCM=1:5, Rf=0.33) to give 2-[2-[2-[4-[6-(dimethylamino)-2-fluoranyl-pyridin-3-yl]phenyl]imidazo[1,2-a]pyridin-6-yl]oxyethoxy]ethyl 4-methylbenzenesulfonate (234 mg, 0.40 mmol, 32% yield) as an orange solid.

Compound 160508: A mixture of 2-[2-[[2-[4-[6-(dimethylamino)-2-fluoranyl-pyridin-3-yl]phenyl]-3,8a-dihydro-imidazo[1,2-a]pyridin-6-yl]oxy]ethoxy]ethyl 4-methylbenzenesulfonate (232 mg, 0.39 mmol) and NaI (70 mg, 0.47 mmol) in ACN (2 mL) was heated at 80° C. for 14 h. The mixture was added water and extracted with DCM. The organic layer was washed with water (20 mL) and brine (20 mL), dried over Na₂SO₄, concentrated and purified by chromatography (EtOAc:DCM=1:10, Rf=0.20) to give 6-fluoranyl-5-[4-[6-[2-(2-iodanylethoxy)ethoxy]-3,8a-dihydroimidazo[1,2-a]pyridin-2-yl]phenyl]-N,N-dimethyl-pyridin-2-amine (204 mg, 0.37 mmol, 95% yield) as a pale-yellow solid.

Compound 160570: A mixture of 2-[2,6-bis(oxidanylidene)piperidin-3-yl]-5-oxidanyl-isoindole-1,3-dione (101 mg, 0.37 mmol), Cs₂CO₃ (180 mg, 0.55 mmol) and 6-fluoranyl-5-[4-[6-[2-(2-iodanylethoxy)ethoxy]-3,8a-dihydroimidazo[1,2-a]pyridin-2-yl]phenyl]-N,N-dimethyl-pyridin-2-amine (101 mg, 0.18 mmol) in DMF (3 mL) was heated at 50° C. for 4 h and then stirred at room temperature for 3 days. The mixture was triturated with water and the resulting precipitate was collected and purified by column chromatography (EtOAc:DCM=1:4, Rf=0.05) to give 2-[1-[2-[2-[2-[4-[6-(dimethylamino)-2-fluoranyl-pyridin-3-yl]phenyl]imidazo[1,2-a]pyridin-6-yl]oxyethoxy]ethyl]-2,6-bis(oxidanylidene)piperidin-3-yl]-5-oxidanyl-isoindole-1,3-dione (15 mg, 0.02 mmol, 11% yield) as a brown solid.

Example 25: Synthesis of Compound 160703

Compound 160686: A mixture of 2-[2,6-bis(oxidanylidene)piperidin-3-yl]-5-oxidanyl-isoindole-1,3-dione (68 mg, 0.25 mmol), Cs₂CO₃ (121 mg, 0.37 mmol) and tert-butyl N-[5-[4-[6-(dimethylamino)-1,3-benzothiazol-2-yl]phenyl]pyridin-2-yl]-N-[2-(2-iodanylethoxy)ethyl]carbamate (80 mg, 0.12 mmol) in DMF (5 mL) was heated at 50° C. for 3 h. The mixture was diluted with DCM, extracted with water, dried over MgSO₄, concentrated and purified by column chromatography on NH silica gel (MeOH:DCM=1:20, Rf=0.2) to give tert-butyl N-[2-[2-[2-[2,6-bis(oxidanylidene)piperidin-3-yl]-1,3-bis(oxidanylidene)isoindol-5-yl]oxyethoxy]ethyl]-N-[5-[4-[6-(dimethylamino)-1,3-benzothiazol-2-yl]phenyl]pyridin-2-yl]carbamate (25 mg, 0.03 mmol, 25% yield) as a yellow solid.

Compound 160703: To a solution of tert-butyl N-[2-[2-[2-[2,6-bis(oxidanylidene)piperidin-3-yl]-1,3-bis(oxidanylidene)isoindol-5-yl]oxyethoxy]ethyl]-N-[5-[4-[6-(dimethylamino)-1,3-benzothiazol-2-yl]phenyl]pyridin-2-yl]carbamate (42 mg, 0.05 mmol) in DCM (5 mL) was added TFA (0.04 mL, 0.53 mmol) at 0° C. and stirred at room temperature for 23 h. The mixture was neutralized with sat. NaHCO₃ solution to pH 8 and extracted with DCM. The organic layer was dried over Na₂SO₄ and concentrated to dryness to give 2-[1-[2-[2-[[5-[4-[6-(dimethylamino)-1,3-

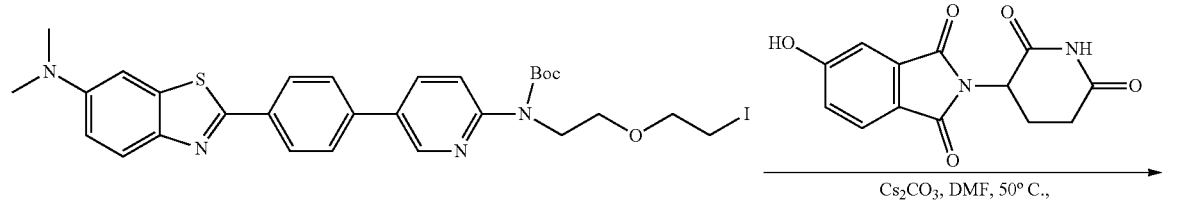

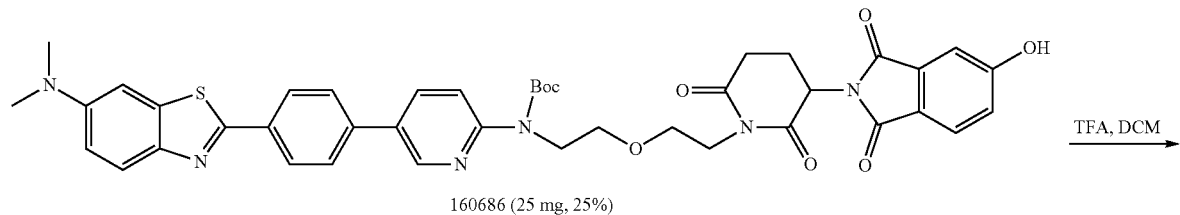

160686 (25 mg, 25%)

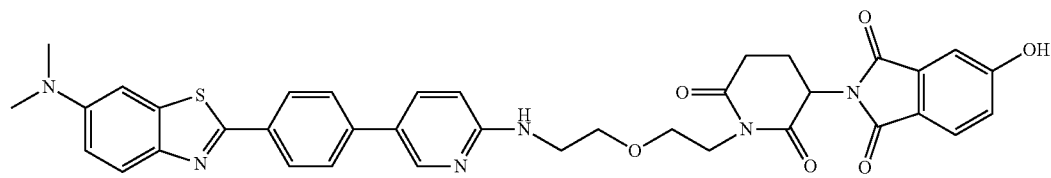

160703 (34 mg, 88%)

benzothiazol-2-yl]phenyl]pyridin-2-yl]amino]ethoxy]ethyl]-2,6-bis(oxidanylidene)piperidin-3-yl]-5-oxidanyl-isoindole-1,3-dione (34 mg, 0.05 mmol, 88% yield) as a yellow solid.

Example 26: Synthesis of Compound 161262 ethoxy]benzene-1,2-dicarboxylate (302 mg, 0.67 mmol) was added to the reaction mixture and stirred at room temperature for 20 h and heated to 50° C. for 20 h. The mixture was quenched with water and extracted with DCM. The organic layer was washed with brine, dried over MgSO₄, concentrated and purified by column chromatogra-

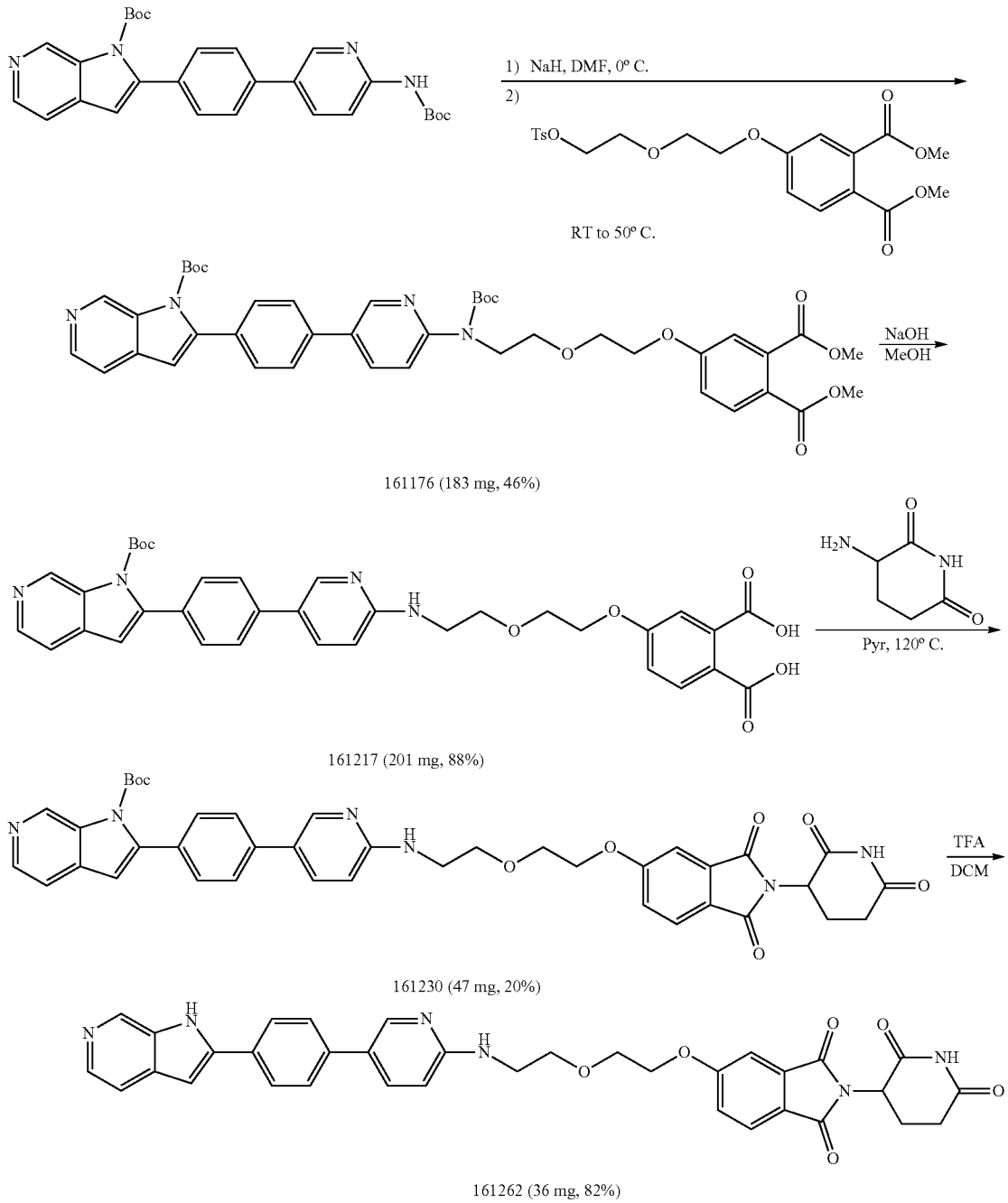

Compound 161176: To a solution of tert-butyl 2-[4-[6-[(2-methylpropan-2-yl)oxycarbonylamino]pyridin-3-yl]phenyl]pyrrolo[2,3-c]pyridine-1-carboxylate (250 mg, 0.51 mmol) in DMF (5 mL) was cooled to 0° C., added NaH (37 mg, 0.92 mmol) and stirred at the same temperature for 30 min. Dimethyl 4-[2-[2-(4-methylphenyl)sulfonyloxyethoxy]

phy on silica gel (EtOAc:DCM=1:2.3, Rf=0.375) to afford dimethyl 4-[2-[2-[(2-methylpropan-2-yl)oxycarbonyl-[5-[4-[1-[(2-methylpropan-2-yl)oxycarbonyl]pyrrolo[2,3-c]pyridin-2-yl]phenyl]pyridin-2-yl]amino]ethoxy]ethoxy]benzene-1,2-dicarboxylate (183 mg, 0.24 mmol, 46% yield) as a yellow oil.

Compound 161217: To a solution of dimethyl 4-[2-[2-[(2-methylpropan-2-yl)oxycarbonyl-[5-[4-[1-[(2-methyl-propan-2-yl)oxycarbonyl]pyrrolo[2,3-c]pyridin-2-yl]phenyl]pyridin-2-yl]amino]ethoxy]ethoxy]benzene-1,2-dicarboxylate (273 mg, 0.36 mmol) in EtOH (3 mL) was added NaOH (228 mg, 5.70 mmol) in water (3 mL) and stirred at room temperature for 4 days. The reaction was neutralized with 1N HCl solution to pH 1. The resulting precipitate was collected, washed with water (10 mL) and dried over vacuo to give 4-[2-[2-[[5-[4-[1-[(2-methylpropan-2-yl)oxycarbonyl]pyrrolo[2,3-c]pyridin-2-yl]phenyl]pyridin-2-yl]amino]ethoxy]ethoxy]phthalic acid (201 mg, 0.31 mmol, 88% yield) as a white solid.

Compound 161230: A mixture of 4-[2-[2-[[5-[4-[1-[(2-methylpropan-2-yl)oxycarbonyl]pyrrolo[2,3-c]pyridin-2-yl]phenyl]pyridin-2-yl]amino]ethoxy]ethoxy]phthalic acid (201 mg, 0.31 mmol) and 3-azanylpiperidine-2,6-dione hydrochloride (78 mg, 0.47 mmol) in pyridine (3 mL) was heated at 120° C. for 19 h. The solvent was removed by vacuum and the resulting residue was triturated with water. The precipitate was collected and purified by column chromatography on NH silica gel (MeOH:DCM=3:100, Rf=0.25) to give tert-butyl 2-[4-[6-[2-[2-[2-[2,6-bis(oxidanylidene)piperidin-3-yl]-1,3-bis(oxidanylidene)isoindol-5-yl]oxyethoxy]ethylamino]pyridin-3-yl]phenyl]pyrrolo[2,3-c]pyridine-1-carboxylate (47 mg, 0.06 mmol, 20% yield) as a yellow solid.

Compound 161262: A solution of tert-butyl 2-[4-[6-[2-[2-[2-[2,6-bis(oxidanylidene)piperidin-3-yl]-1,3-bis(oxidanylidene)isoindol-5-yl]oxyethoxy]ethylamino]pyridin-3-yl] phenyl]pyrrolo[2,3-c]pyridine-1-carboxylate (47 mg, 0.06 mmol) in DCM (3 mL) was added TFA (0.07 mL, 0.96 mmol) and stirred at room temperature for 23 h. The mixture was neutralized with sat. NaHCO₃ solution to pH 8. The resulting precipitate was collected, washed with water and dried over vacuum to give 2-[2,6-bis(oxidanylidene)piperidin-3-yl]-5-[2-[2-[[5-[4-(1H-pyrrolo[2,3-c]pyridin-2-yl)phenyl]pyridin-2-yl]amino]ethoxy]ethoxy]isoindole-1,3-dione (36 mg, 0.05 mmol, 82% yield) as a yellow solid.

Example 27: Synthesis of Compound 164625

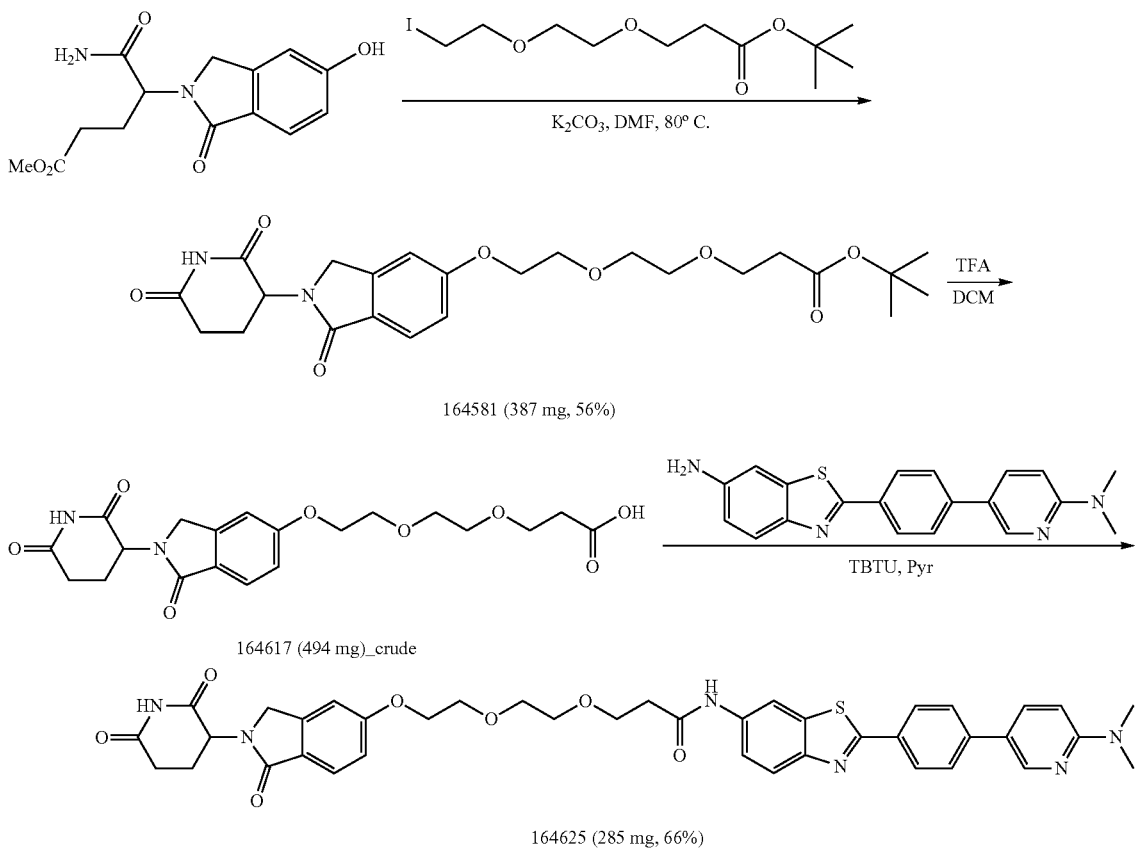

164581 (387 mg, 56%)

164617 (494 mg)_crude 164625 (285 mg, 66%)

Compound 164581: A mixture of tert-butyl 3-[2-(2-iodanylethoxy)ethoxy]propanoate (500 mg, 1.45 mmol), K₂CO₃ (602 mg, 4.36 mmol) and methyl 5-azanyl-5-oxidanylidene-4-(6-oxidanyl-3-oxidanylidene-1H-isoindol-2-yl)pentanoate (467 mg, 1.60 mmol) in DMF (15 mL) was heated at 80° C. for 7 h. The mixture was diluted with EtOAc, extracted with brine, dried over MgSO₄, concentrated and purified by column chromatography (MeOH:DCM=1:20, Rf=0.48) to give tert-butyl 3-[2-[2-[[2-[2,6-bis(oxidanylidene)piperidin-3-yl]-1-oxidanylidene-3H-isoindol-5-yl]oxy]ethoxy]ethoxy]propanoate (387 mg, 0.81 mmol, 56% yield) as a white solid.

Compound 164617: To a solution of tert-butyl 3-[2-[2-[[2-[2,6-bis(oxidanylidene)piperidin-3-yl]-1-oxidanylidene-3H-isoindol-5-yl]oxy]ethoxy]ethoxy]propanoate (387 mg, 0.81 mmol) in DCM (10 mL) was added TFA (0.62 mL, 8.12 mmol) and stirred at room temperature for 15 h. The mixture was concentrated to dryness to give 3-[2-[2-[[2-[2,6-bis(oxidanylidene)piperidin-3-yl]-1-oxidanylidene-3H-isoindol-5-yl]oxy]ethoxy]ethoxy]propanoic acid TFA salt (494 mg, 1.18 mmol) as a white oil.

Compound 164625: A mixture of 3-[2-[2-[[2-[2,6-bis(oxidanylidene)piperidin-3-yl]-1-oxidanylidene-3H-isoindol-5-yl]oxy]ethoxy]ethoxy]propanoic acid (346 mg, 0.82 mmol), TBTU (352 mg, 1.10 mmol) and 2-[4-[6-(dimethylamino)pyridin-3-yl]phenyl]-1,3-benzothiazol-6-amine (190 mg, 0.55 mmol) in pyridine (3 mL) was stirred at room temperature for 17 h. The mixture was added with water and the resulting precipitate was collected by filtration and purified by column chromatography (MeOH:DCM=1:19, Rf=0.3) to give 3-[2-[2-[[2-[2,6-bis(oxidanylidene)piperidin-3-yl]-1-oxidanylidene-3H-isoindol-5-yl]oxy]ethoxy]ethoxy]-N-[2-[4-[6-(dimethylamino)pyridin-3-yl]phenyl]-1,3-benzothiazol-6-yl]propanamide (285 mg, 0.36 mmol, 66% yield) as a yellow solid.

Example 28: Synthesis of Compound 164657

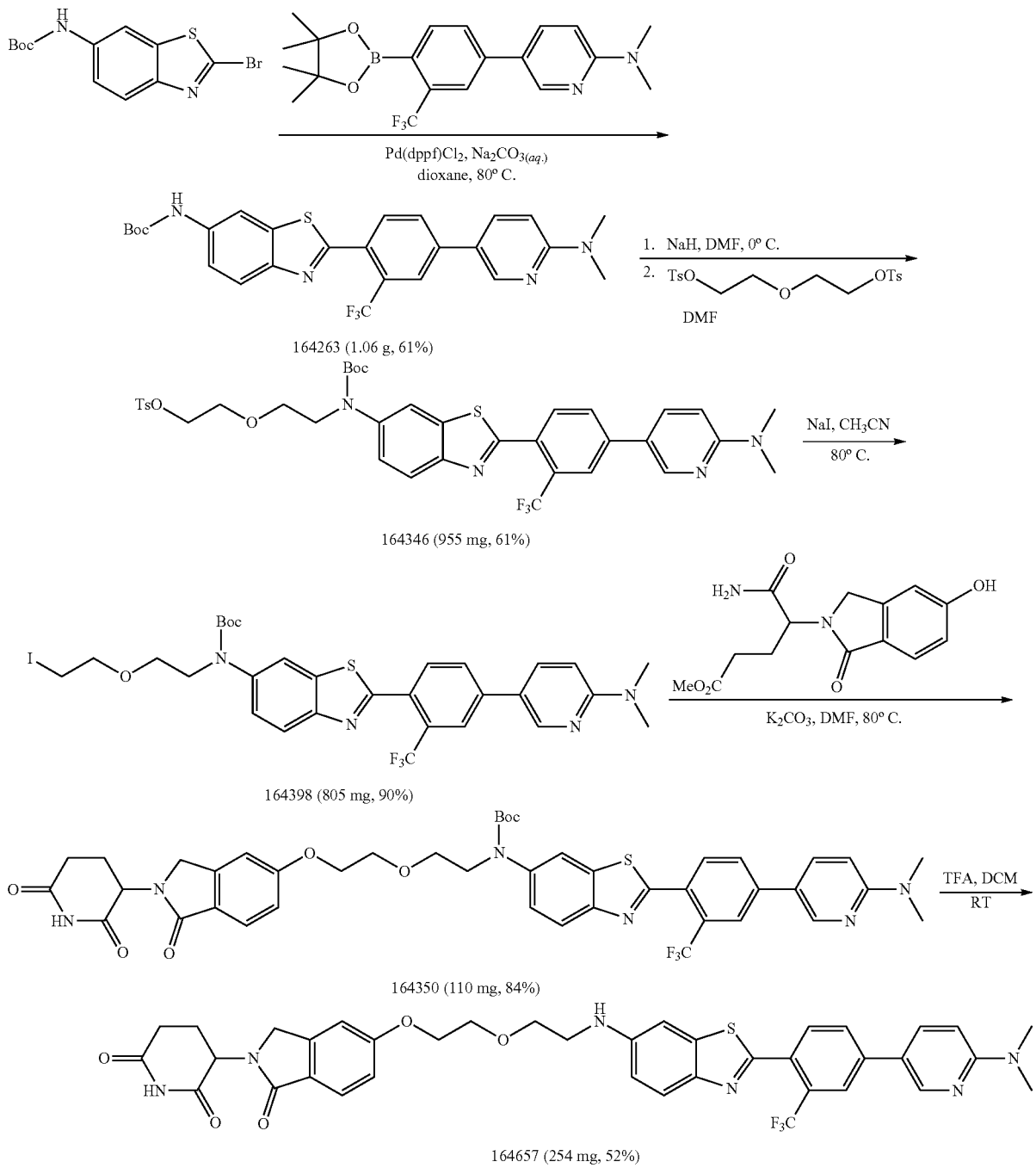

Compound 164263: A mixture of tert-butyl N-(2-bromanyl-1,3-benzothiazol-6-yl)carbamate (1100 mg, 3.34 mmol), N,N-dimethyl-5-[4-(4,4,5,5-tetramethyl-1,3,2-dioxaborolan-2-yl)-3-(trifluoromethyl)phenyl]pyridin-2-amine (1704 mg, 4.34 mmol), Pd(dppf)Cl$_2$ (247 mg, 0.33 mmol) and 2M Na₂CO₃ (aq) solution (5 mL, 10.02 mmol) in dioxane (35 mL) was heated at 80° C. for 16 h under argon. The mixture was filtered through a Celite pad and the residue was taken up in EtOAc (100 mL) and water (50 mL). The organic layer was washed with water (50 mL), brine (50 mL), dried over Na₂SO₄ and concentrated to dryness. The residue was purified by column chromatography (EtOAc:Hex=1:4, Rf=0.15) to give tert-butyl N-[2-[4-[6-(dimethylamino)pyridin-3-yl]-2-(trifluoromethyl)phenyl]-1,3-benzothiazol-6-yl]carbamate (1.06 g, 2.05 mmol, 61% yield) as a yellow oil.

Compound 164346: To a solution of tert-butyl N-[2-[4-[6-(dimethylamino)pyridin-3-yl]-2-(trifluoromethyl)phenyl]-1,3-benzothiazol-6-yl]carbamate (1056 mg, 2.05 mmol) in DMF (20 mL) was added NaH (148 mg, 6.16 mmol) at 0° C. and stirred at 25° C. for 1 h. 2-[2-(4-methylphenyl)sulfonyloxyethoxy]ethyl 4-methylbenzenesulfonate (2.55 g, 6.16 mmol) in DMF (20 mL) was added to the reaction mixture and stirred at room temperature for 14 h. The mixture was quenched with water at 0° C. The residue was taken up in EtOAc (50 mL) and water (50 mL). The organic layer was washed with water (50 mL), brine (50 mL), dried over Na₂SO₄ and concentrated to dryness. The residue was purified by column chromatography (EtOAc:Hex=1:1, Rf=0.4) to give 2-[2-[[2-[4-[6-(dimethylamino)pyridin-3-yl]-2-(trifluoromethyl)phenyl]-1,3-benzothiazol-6-yl]-[(2-methylpropan-2-yl)oxycarbonyl]amino]ethoxy]ethyl 4-methylbenzenesulfonate (955 mg, 1.26 mmol, 61% yield) as a yellow oil.

Compound 164398: A mixture of 2-[2-[[2-[4-[6-(dimethylamino)pyridin-3-yl]-2-(trifluoromethyl)phenyl]-1,3-benzothiazol-6-yl]-[(2-methylpropan-2-yl)oxycarbonyl]amino]ethoxy]ethyl 4-methylbenzenesulfonate (955 mg, 1.26 mmol), NaI (378 mg, 2.52 mmol) in MeCN (20 mL) was heated at 80° C. for 17 h. The residue was taken up in EtOAc (50 mL) and water (50 mL). The organic layer was washed with water (50 mL), brine (50 mL), dried over Na₂SO₄ and concentrated. The residue was purified by column chromatography (EtOAc:Hex=1:1, Rf=0.7) to give tert-butyl N-[2-[4-[6-(dimethylamino)pyridin-3-yl]-2-(trifluoromethyl)phenyl]-1,3-benzothiazol-6-yl]-N-[2-(2-iodanylethoxy)ethyl]carbamate (805 mg, 1.13 mmol, 90% yield) as a yellow oil.

Compound 164350: A mixture of tert-butyl N-[2-[4-[6-(dimethylamino)pyridin-3-yl]-2-(trifluoromethyl)phenyl]-1,3-benzothiazol-6-yl]-N-[2-(2-iodanylethoxy)ethyl]carbamate (110 mg, 0.15 mmol), K₂CO₃ (64 mg, 0.46 mmol), and methyl 5-azanyl-5-oxidanylidene-4-(6-oxidanyl-3-oxidanylidene-1H-isoindol-2-yl)pentanoate (50 mg, 0.17 mmol) in DMF (2.5 mL) was heated at 80° C. for 8 h. The mixture was added water, extracted with DCM, dried over MgSO₄ and concentrated to dryness. The residue was purified by column chromatography (MeOH:DCM=1:20, Rf=0.4) to give tert-butyl N-[2-[[2-[2,6-bis(oxidanylidene)piperidin-3-yl]-1-oxidanylidene-3H-isoindol-5-yl]oxy]ethoxy]ethyl]-N-[2-[4-[6-(dimethylamino)pyridin-3-yl]-2-(trifluoromethyl)phenyl]-1,3-benzothiazol-6-yl]carbamate (110 mg, 0.13 mmol, 84% yield) as a yellow solid.

Compound 164657: To a solution of tert-butyl N-[2-[2-[[2-[2,6-bis(oxidanylidene)piperidin-3-yl]-1-oxidanylidene-3H-isoindol-5-yl]oxy]ethoxy]ethyl]-N-[2-[4-[6-(dimethylamino)pyridin-3-yl]-2-(trifluoromethyl)phenyl]-1,3-benzothiazol-6-yl]carbamate (550 mg, 0.65 mmol) in DCM (10 mL) was added TFA (0.75 mL, 9.76 mmol) at 25° C. and stirred for 15 h. The mixture was poured into ice water and neutralized with sat. NaHCO₃ solution to pH 8. The residue was taken up in DCM (20 mL) and water (10 mL). The organic layer was washed with water (10 mL), brine (10 mL), dried over Na₂SO₄ and concentrated to dryness. The residue was purified by column chromatography (DCM:MeOH=10:1, Rf=0.58) to give 3-[6-[2-[2-[[2-[4-[6-(dimethylamino)pyridin-3-yl]-2-(trifluoromethyl)phenyl]-1,3-benzothiazol-6-yl]amino]ethoxy]ethoxy]-3-oxidanylidene-1H-isoindol-2-yl]piperidine-2,6-dione (254 mg, 0.34 mmol, 52% yield) as a yellow solid.

Example 29: Synthesis of Compound 162640

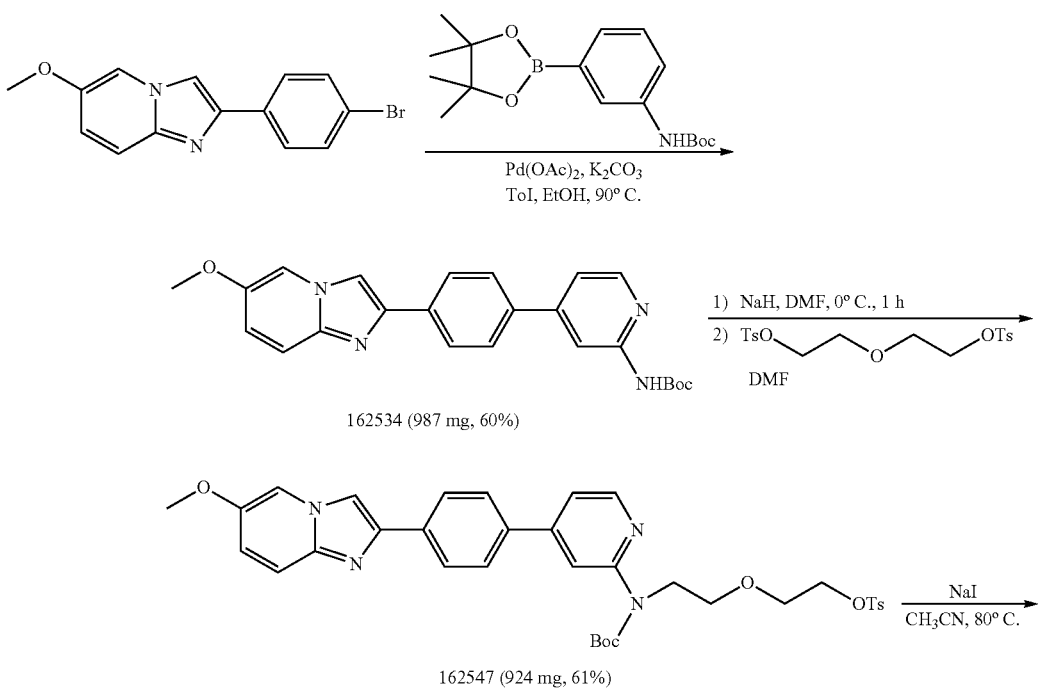

162534 (987 mg, 60%)

162547 (924 mg, 61%)

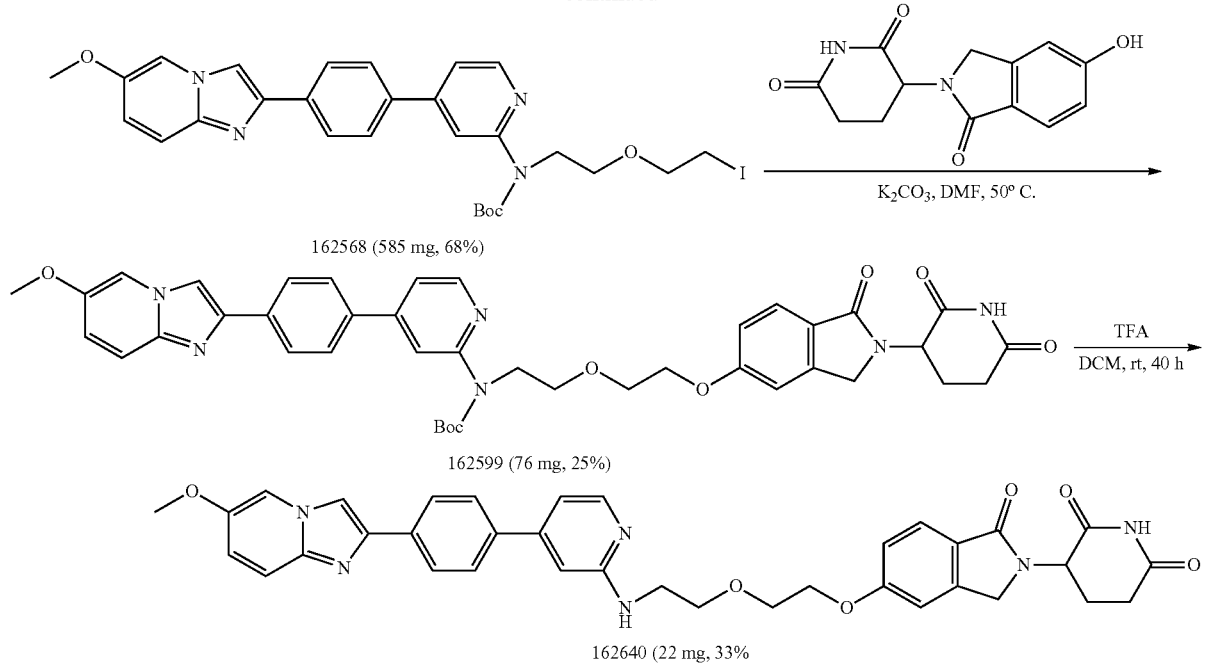

Compound 162534: A solution of tert-butyl N-[4-(4,4,5,5-tetramethyl-1,3,2-dioxaborolan-2-yl)pyridin-2-yl]carbamate (1.52 g, 4.75 mmol), 2-(4-bromophenyl)-6-methoxyimidazo[1,2-a]pyridine (1.2 g, 3.96 mmol), and triphenylphosphine (34.6 mg, 0.13 mmol) in EtOH (4 mL) and toluene (2.8 mL) was purged with argon and then added with $K_2CO_3$ solution (1.75M, 7.92 mL, 13.85 mmol) dropwise. The mixture was added with $Pd(OAc)_2$ (87 mg, 0.40 mmol) under argon and heated at 90° C. for 4 h. The mixture was filtered through celite pad, poured into saturated $NaHCO_3$ solution, and extracted with EtOAc. The organic layer was dried over $MgSO_4$, concentrated and purified by column chromatography (EtOAc:DCM=1:4, Rf=0.3) to give tert-butyl N-[4-[4-(6-methoxyimidazo[1,2-a]pyridin-2-yl)phenyl]pyridin-2-yl]carbamate (987 mg, 2.37 mmol, 60% yield) as a pale-brown solid.

Compound 162547: A solution of 2-[2-(4-methylphenyl)sulfonyloxyethoxy]ethyl 4-methylbenzenesulfonate (2.86 g, 6.90 mmol) in DMF (10 mL) was added NaH (368 mg, 9.20 mmol) at 0° C. and stirred at room temperature for 1 h. The mixture was added with 2-[2-(4-methylphenyl)sulfonyloxyethoxy]ethyl 4-methylbenzenesulfonate (2.86 g, 6.90 mmol) in DMF (10 mL) and stirred at room temperature for 19 h. The mixture was cooled to 0° C., quenched by adding water and diluted with DCM. The resulting mixture was washed with water and brine, dried over $Na_2SO_4$, concentrated and purified by column chromatography (EtOAc:DCM=4:1, Rf=0.4) to give 2-[2-[[4-[4-(6-methoxyimidazo[1,2-a]pyridin-2-yl)phenyl]pyridin-2-yl]-[(2-methylpropan-2-yl)oxycarbonyl]amino]ethoxy]ethyl 4-methylbenzenesulfonate (924 mg, 1.40 mmol, 61% yield) as an orange oil.

Compound 162568: A mixture of 2-[2-[[4-[4-(6-methoxyimidazo[1,2-a]pyridin-2-yl)phenyl]pyridin-2-yl]-[(2-methylpropan-2-yl)oxycarbonyl]amino]ethoxy]ethyl 4-methylbenzenesulfonate (924 mg, 1.40 mmol) and NaI (421 mg, 2.81 mmol) in $CH_3CN$ (20 mL) was heated at 80° C. for 17 h. The mixture was diluted with DCM, washed with water (50 mL) and brine (50 mL), dried over $Na_2SO_4$, concentrated and purified by column chromatography (MeOH:DCM=1:100, Rf=0.19) to give tert-butyl N-[2-(2-iodanylethoxy)ethyl]-N-[4-[4-(6-methoxyimidazo[1,2-a]pyridin-2-yl)phenyl]pyridin-2-yl]carbamate (585 mg, 0.95 mmol, 68% yield) as an orange solid.

Compound 162599: A solution of tert-butyl N-[2-(2-iodanylethoxy)ethyl]-N-[4-[4-(6-methoxyimidazo[1,2-a]pyridin-2-yl)phenyl]pyridin-2-yl]carbamate (250 mg, 0.41 mmol), 3-(6-oxidanyl-3-oxidanylidene-1H-isoindol-2-yl)piperidine-2,6-dione (212 mg, 0.81 mmol) and $K_2CO_3$ (169 mg, 1.22 mmol) in DMF (4 mL) was heated at 50° C. for 3 h. The mixture was quenched with water and the resulting solid was collected by filtration. The solid was washed with water and the residue was purified by NH gel column chromatography (MeOH:DCM=3:100, Rf=0.33) to give tert-butyl N-[2-[2-[[2-[2,6-bis(oxidanylidene)piperidin-3-yl]-1-oxidanylidene-3H-isoindol-5-yl]oxy]ethoxy]ethyl]-N-[4-[4-(6-methoxyimidazo[1,2-a]pyridin-2-yl)phenyl]pyridin-2-yl]carbamate (76 mg, 0.10 mmol, 25% yield) as a white solid.

Compound 162640: To a solution of tert-butyl N-[2-[2-[[2-[2,6-bis(oxidanylidene)piperidin-3-yl]-1-oxidanylidene-3H-isoindol-5-yl]oxy]ethoxy]ethyl]-N-[4-[4-(6-methoxyimidazo[1,2-a]pyridin-2-yl)phenyl]pyridin-2-yl]carbamate (76 mg, 0.10 mmol) in DCM (2 mL) was added TFA (0.12 mL, 1.53 mmol) and stirred for 38 h. The mixture was poured into iced water and neutralized with sat. $NaHCO_3$ solution to pH 8. The residue was taken up in DCM (20 mL) and water (10 mL). The organic layer was washed with water (10 mL), brine (10 mL), dried over $Na_2SO_4$, concentrated and purified by column chromatography (DCM:MeOH=100:3, Rf=0.35) to give 3-[6-[2-[2-[[4-[4-(6-methoxyimidazo[1,2-a]pyridin-2-yl)phenyl]pyridin-2-yl]amino]ethoxy]ethoxy]-3-oxidanylidene-1H-isoindol-2-yl]piperidine-2,6-dione (22 mg, 0.03 mmol, 33% yield) as a pale-brown solid.

Example 30: Synthesis of Compound 162843

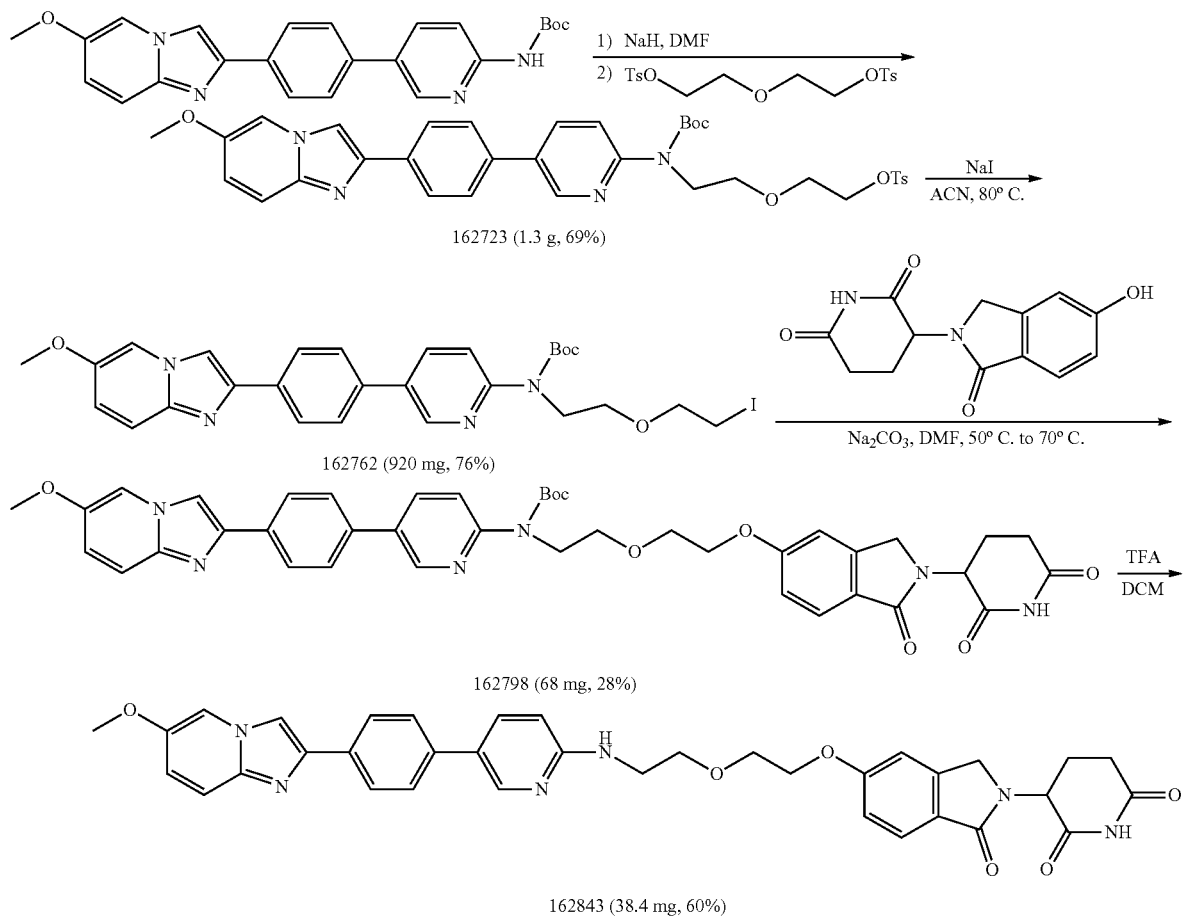

Compound 162723: To a solution of 2-[2-(4-methylphenyl)sulfonyloxyethoxy]ethyl 4-methylbenzenesulfonate (4.72 g, 11.38 mmol) in DMF (30 mL) was added NaH (455 mg, 11.38 mmol) at 0° C. and stirred at room temperature for 1 h. 2-[2-(4-methylphenyl)sulfonyloxyethoxy]ethyl 4-methylbenzenesulfonate (4.72 g, 11.38 mmol) in DMF (30 mL) was added to the reaction mixture and stirred at room temperature for another 16 h. The mixture was cooled to 0° C. and quenched with water. The mixture was diluted with DCM, washed with water and brine, dried over $Na_2SO_4$, concentrated and purified by column chromatography (EtOAc:Hex=1:1, Rf=0.23) to give 2-[2-[[5-[4-(6-methoxyimidazo[1,2-a]pyridin-2-yl)phenyl]pyridin-2-yl]-[(2-methylpropan-2-yl)oxycarbonyl]amino]ethoxy]ethyl 4-methylbenzenesulfonate (1.3 g, 1.97 mmol, 69% yield) as an orange solid.

Compound 162762: A mixture of 2-[2-[[5-[4-(6-methoxyimidazo[1,2-a]pyridin-2-yl)phenyl]pyridin-2-yl]-[(2-methylpropan-2-yl)oxycarbonyl]amino]ethoxy]ethyl 4-methylbenzenesulfonate (1.3 g, 1.97 mmol) and NaI (592 mg, 3.95 mmol) in ACN (10 mL) was heated at 80° C. for 15 h. The mixture was added water and extracted with DCM. The organic layer was washed with water (50 mL), brine (50 mL), dried over $Na_2SO_4$, concentrated to dryness and purified by chromatography (MeOH:DCM=1:100, Rf=0.19) to give tert-butyl N-[2-(2-iodanylethoxy)ethyl]-N-[5-[4-(6-methoxyimidazo[1,2-a]pyridin-2-yl)phenyl]pyridin-2-yl]carbamate (920 mg, 1.50 mmol, 76% yield) as a yellow solid.

Compound 162798: A mixture of tert-butyl N-[2-(2-iodanylethoxy)ethyl]-N-[5-[4-(6-methoxyimidazo[1,2-a]pyridin-2-yl)phenyl]pyridin-2-yl]carbamate (200 mg, 0.33 mmol), 3-(6-oxidanyl-3-oxidanylidene-1H-isoindol-2-yl)piperidine-2,6-dione (169 mg, 0.65 mmol) and $Na_2CO_3$ (103 mg, 0.98 mmol) in DMF (4 mL) was heated at 50° C. for 37 h. The mixture was added with water and the resulting precipitate was collected by filtration, washed with water and purified by column chromatography on NH gel (MeOH:DCM=1:100, Rf=0.21) to give tert-butyl N-[2-[2-[[2-[2,6-bis(oxidanylidene)piperidin-3-yl]-1-oxidanylidene-3H-isoindol-5-yl]oxy]ethoxy]ethyl]-N-[5-[4-(6-methoxyimidazo[1,2-a]pyridin-2-yl)phenyl]pyridin-2-yl]carbamate (68 mg, 0.09 mmol, 28% yield) as a yellow solid.

Compound 162843: To a solution of tert-butyl N-[2-[2-[[2-[2,6-bis(oxidanylidene)piperidin-3-yl]-1-oxidanylidene-3H-isoindol-5-yl]oxy]ethoxy]ethyl]-N-[5-[4-(6-methoxyimidazo[1,2-a]pyridin-2-yl)phenyl]pyridin-2-yl]carbamate (68 mg, 0.09 mmol) in DCM (2 mL) was added TFA (0.07 mL, 0.9100 mmol) and stirred at room temperature for 48 h. The mixture was diluted with DCM (3 mL) and neutralized with sat. $NaHCO_3$ (aq.) solution to pH 8. The precipitate was collected and washed with DCM to give 3-[6-[2-[2-[[5-[4-

(6-methoxyimidazo[1,2-a]pyridin-2-yl)phenyl]pyridin-2-yl]amino]ethoxy]ethoxy]-3-oxidanylidene-1H-isoindol-2-yl]piperidine-2,6-dione (38 mg, 0.05 mmol, 59% yield) as a yellow solid.

Example 31: Synthesis of Compound 165559

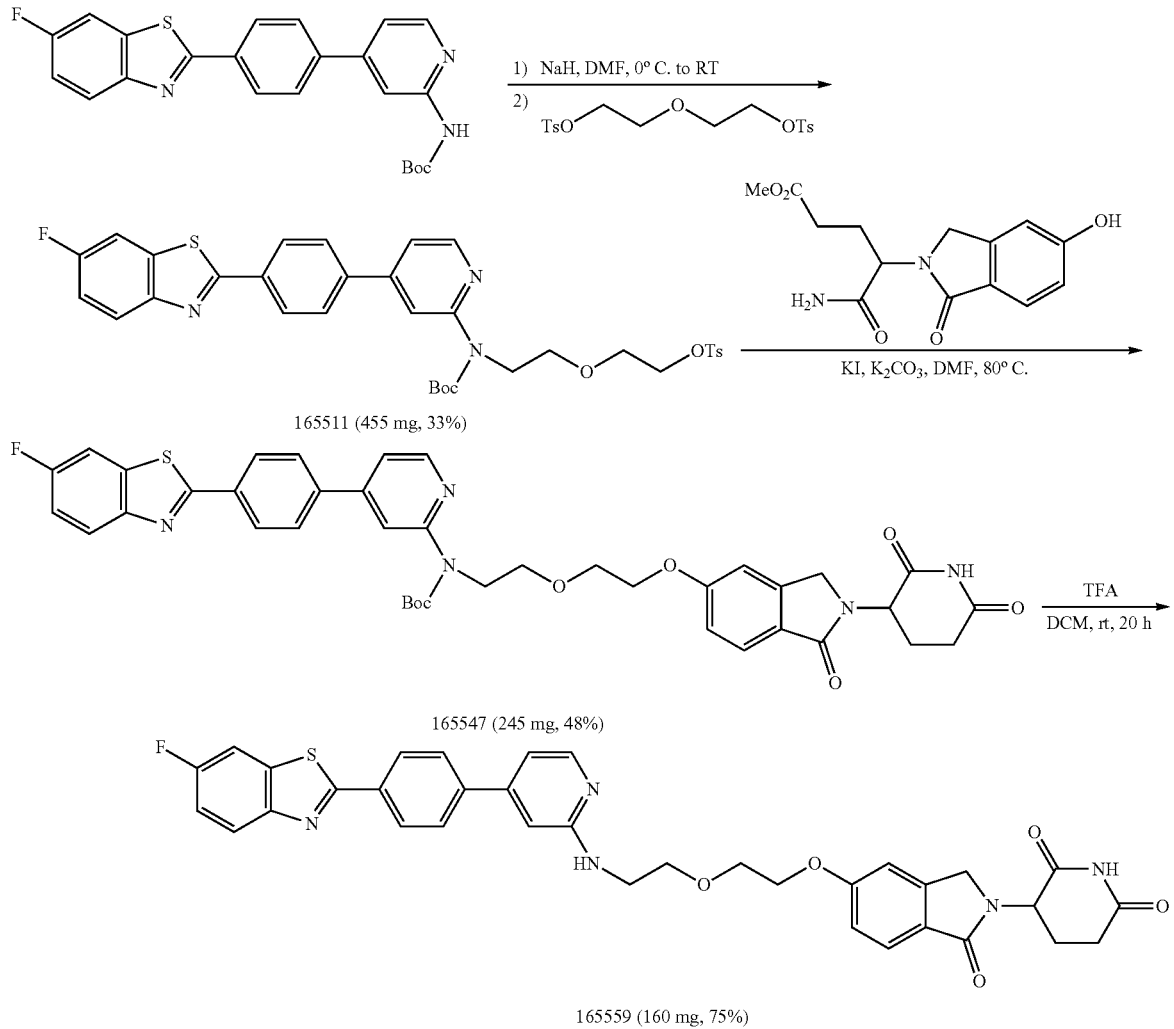

Compound 165511: A solution of 2-[2-(4-methylphenyl)sulfonyloxyethoxy]ethyl 4-methylbenzenesulfonate (2567 mg, 6.19 mmol) in DMF (10 mL) was cooled to 0° C., added NaH (248 mg, 6.19 mmol) and then stirred at room temperature for 1 h. 2-[2-(4-methylphenyl)sulfonyloxyethoxy]ethyl 4-methylbenzenesulfonate (2567 mg, 6.19 mmol) was added to the reaction mixture and stirred at room temperature for 17 h. The reaction was cooled to 0° C. and quenched by adding water. The mixture was diluted with DCM, washed with water and brine, dried over $Na_2SO_4$, concentrated and purified by column chromatography (DCM:EtOAc=10:1, Rf=0.3) to give 2-[2-[[4-[4-(6-fluoranyl-1,3-benzothiazol-2-yl)phenyl]pyridin-2-yl]-[(2-methylpropan-2-yl)oxycarbonyl]amino]ethoxy]ethyl 4-methylbenzenesulfonate (455 mg, 0.68 mmol, 33% yield) as a white solid.

Compound 165547: A mixture of methyl 5-azanyl-5-oxidanylidene-4-(6-oxidanyl-3-oxidanylidene-1H-isoindol-2-yl)pentanoate (220 mg, 0.75 mmol), $K_2CO_3$ (284 mg, 2.06 mmol), KI (11 mg, 0.07 mmol) and 2-[2-[[4-[4-(6-fluoranyl-1,3-benzothiazol-2-yl)phenyl]pyridin-2-yl]-[(2-methylpropan-2-yl)oxycarbonyl]amino]ethoxy]ethyl 4-methylbenzenesulfonate (455 mg, 0.69 mmol) in DMF (6 mL) was heated at 80° C. for 7 h. The mixture was diluted with EtOAc (20 mL), extracted with water (10 mL) and brine (10 mL), dried over $Na_2SO_4$, concentrated and purified by column chromatography (MeOH:DCM=1:20, Rf=0.4) to give tert-butyl N-[2-[2-[[2-[2,6-bis(oxidanylidene)piperidin-3-yl]-1-oxidanylidene-3H-isoindol-5-yl]oxy]ethoxy]ethyl]-N-[4-[4-(6-fluoranyl-1,3-benzothiazol-2-yl)phenyl]pyridin-2-yl]carbamate (245 mg, 0.33 mmol, 48% yield) as white solid.

Compound 165559: A solution of tert-butyl N-[2-[2-[[2-[2,6-bis(oxidanylidene)piperidin-3-yl]-1-oxidanylidene-3H-isoindol-5-yl]oxy]ethoxy]ethyl]-N-[4-[4-(6-fluoranyl-1,3-benzothiazol-2-yl)phenyl]pyridin-2-yl]carbamate (245 mg, 0.33 mmol) in DCM (5 mL) was added TFA (0.38 mL, 4.89 mmol) and stirred at room temperature for 20 h. The mixture was diluted with DCM (20 mL) and neutralized with sat. $NaHCO_3$ solution to pH 8. The mixture extracted with water, dried over $MgSO_4$, concentrated and purified by column chromatography (DCM:MeOH=20:1, Rf=0.3) to give 3-[6-[2-[2-[[4-[4-(6-fluoranyl-1,3-benzothiazol-2-yl)

phenyl]pyridin-2-yl]amino]ethoxy]ethoxy]-3-oxida-nylidene-1H-isoindol-2-yl]piperidine-2,6-dione (160 mg, 0.24 mmol, 75% yield) as a white solid.

Example 32: Synthesis of Compound 163685 zothiazol-6-yl]oxy]ethoxy]ethyl 4-methylbenzenesulfonate (627 mg, 0.95 mmol) and NaI (286 mg, 1.91 mmol) in ACN (10 mL) was heated at 80° C. for 17 h. The mixture was added water (20 mL) and extracted with EtOAc. The organic layer was washed with brine, dried over MgSO₄ and concentrated to dryness to give 5-[4-[6-[2-(2-iodanylethoxy)

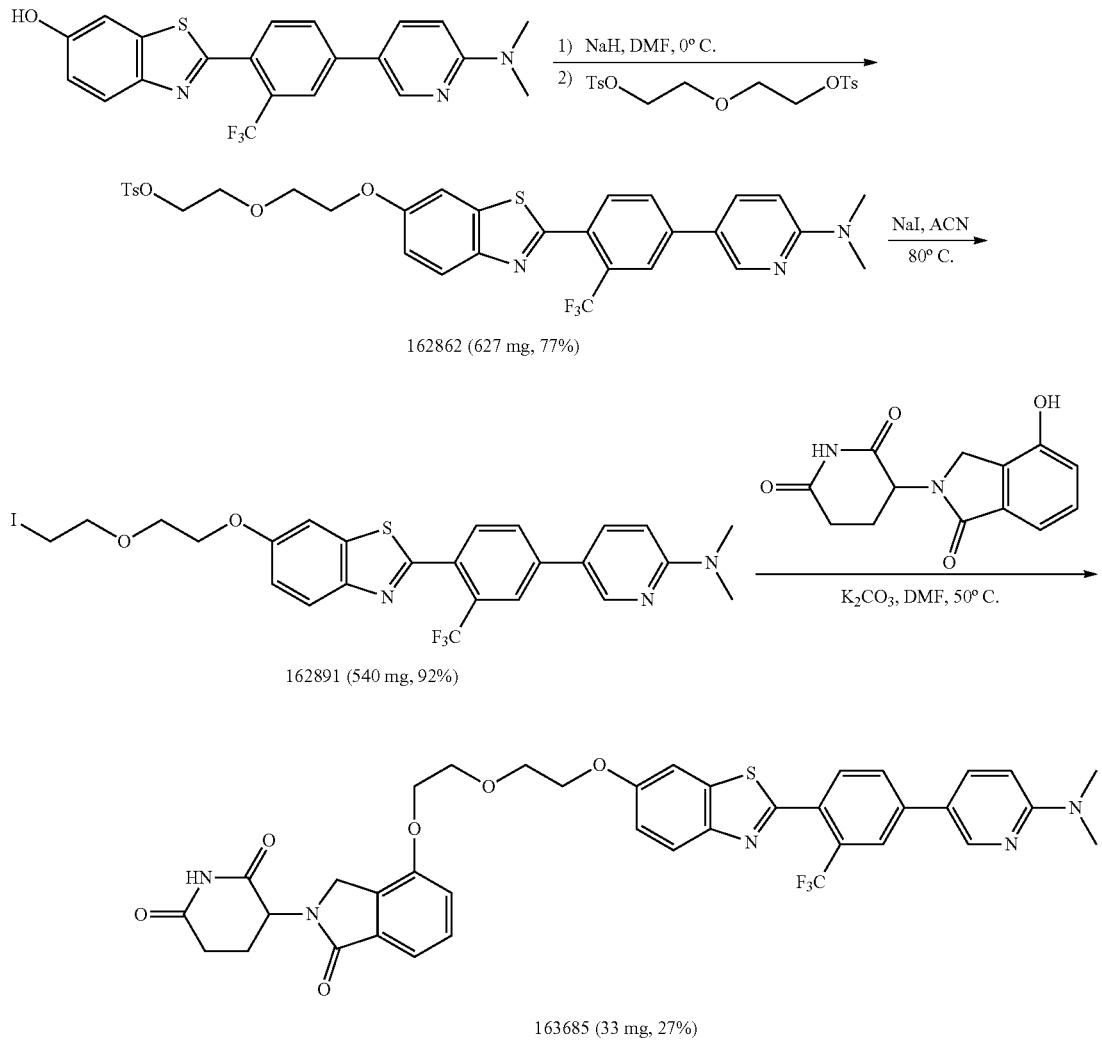

Compound 162862: To a solution of 2-[4-[6-(dimethylamino)pyridin-3-yl]-2-(trifluoromethyl)phenyl]-1,3-benzothiazol-6-ol (516 mg, 1.24 mmol) in dry DMF (12 mL) was added NaH (149 mg, 3.72 mmol) at 0° C. and stirred at room temperature for 1 h. 2-[2-(4-methylphenyl)sulfonyloxyethoxy]ethyl 4-methylbenzenesulfonate (1543 mg, 3.72 mmol) in dry DMF (12 mL) was added to the reaction mixture and stirred at the same temperature for 18 h. The mixture was poured into water (50 mL) and extracted with DCM (50 mL). The organic layer was washed with water (50 mL) and brine (50 mL), dried over anhydrous Na₂SO₄, concentrated and purified by column chromatography (Rf=0.51, EtOAc:DCM=1:9) to give 2-[2-[[2-[4-[6-(dimethylamino)pyridin-3-yl]-2-(trifluoromethyl)phenyl]-1,3-benzothiazol-6-yl]oxy]ethoxy]ethyl 4-methylbenzenesulfonate (627 mg, 0.95 mmol, 77% yield) as a pale yellow solid.

Compound 162891: A mixture of 2-[2-[[2-[4-[6-(dimethylamino)pyridin-3-yl]-2-(trifluoromethyl)phenyl]-1,3-ben-zothiazol-6-yl]oxy]ethoxy]ethyl 4-methylbenzenesulfonate (627 mg, 0.95 mmol) and NaI (286 mg, 1.91 mmol) in ACN (10 mL) was heated at 80° C. for 17 h. The mixture was added water (20 mL) and extracted with EtOAc. The organic layer was washed with brine, dried over MgSO₄ and concentrated to dryness to give 5-[4-[6-[2-(2-iodanylethoxy)ethoxy]-1,3-benzothiazol-2-yl]-3-(trifluoromethyl)phenyl]-N,N-dimethyl-pyridin-2-amine (540 mg, 0.88 mmol, 92% yield) as a yellow solid.

Compound 163685: A mixture of 5-[4-[6-[2-(2-iodanylethoxy)ethoxy]-1,3-benzothiazol-2-yl]-3-(trifluoromethyl)phenyl]-N,N-dimethyl-pyridin-2-amine (100 mg, 0.16 mmol), 3-(7-oxidanyl-3-oxidanylidene-1H-isoindol-2-yl)piperidine-2,6-dione (85 mg, 0.33 mmol) and K₂CO₃ (68 mg, 0.49 mmol) in DMF (5 mL) was heated at 50° C. for 18 h. The mixture was added water and extracted with DCM. The organic layer was washed with brine, dried over MgSO₄, concentrated and purified by column chromatography (MeOH:DCM=1:20, Rf=0.45) to give 3-[7-[2-[2-[[2-[4-[6-(dimethylamino)pyridin-3-yl]-2-(trifluoromethyl)phenyl]-1,3-benzothiazol-6-yl]oxy]ethoxy]ethoxy]-3-oxidanylidene-1H-isoindol-2-yl]piperidine-2,6-dione (33 mg, 0.04 mmol, 25% yield) as a yellow solid.

Example 33: Synthesis of Compound 163863

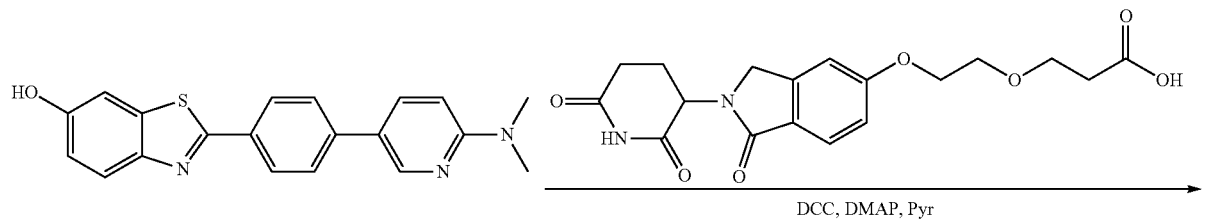

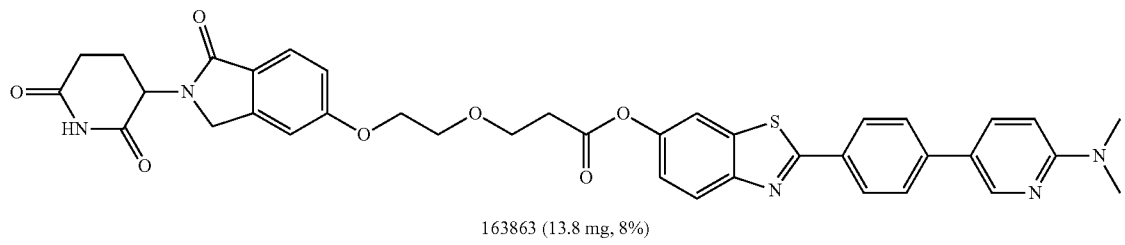

163863 (13.8 mg, 8%)

Compound 163863: A mixture of 2-[4-[6-(dimethylamino)pyridin-3-yl]phenyl]-1,3-benzothiazol-6-ol (166 mg, 0.48 mmol), 3-[2-[[2-[2,6-bis(oxidanylidene)piperidin-3-yl]-1-oxidanylidene-3H-isoindol-5-yl]oxy]ethoxy]propanoic acid (90 mg, 0.24 mmol), DMAP (3 mg, 0.02 mmol) and DCC (52 mg, 0.25 mmol) in pyridine (2 mL) was stirred at room temperature for 15 h. The solvent was removed by reduced pressure. The residue was redissolved in DCM (10 mL), washed with water (5 mL) and brine (5 mL), dried over MgSO$_4$, concentrated and purified by column chromatography (MeOH:DCM=5:100, Rf=0.14) to give [2-[4-[6-(dimethylamino)pyridin-3-yl]phenyl]-1,3-benzothiazol-6-yl] 3-[2-[[2-[2,6-bis(oxidanylidene)piperidin-3-yl]-1-oxidanylidene-3H-isoindol-5-yl]oxy]ethoxy]propanoate (14 mg, 0.02 mmol, 8% yield) as a yellow solid.

Example 34: Synthesis of Compound 164484

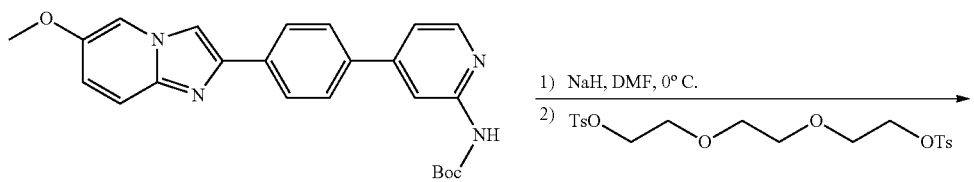

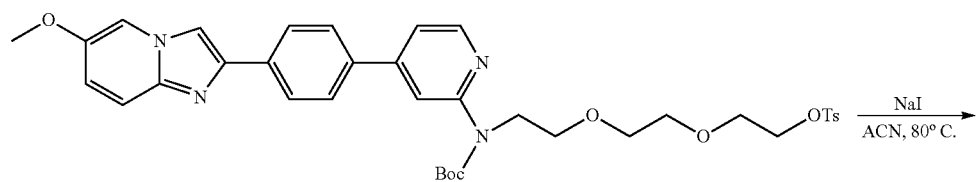

164431 (351 mg, 52%)

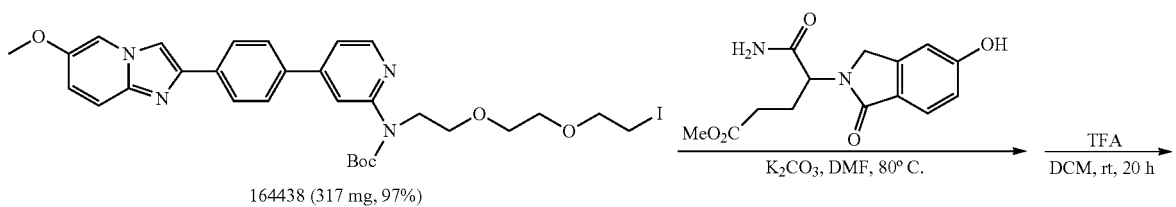

164438 (317 mg, 97%)

-continued

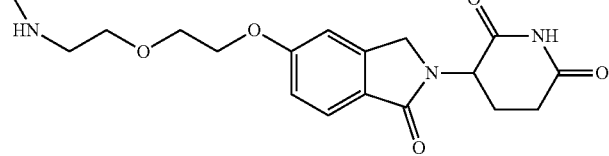

165559 (160 mg, 75%)

Compound 164431: A solution of tert-butyl N-[4-[4-(6-methoxyimidazo[1,2-a]pyridin-2-yl)phenyl]pyridin-2-yl] carbamate (400 mg, 0.96 mmol) in dry DMF (10 mL) was cooled to 0° C. and added NaH (115 mg, 2.88 mmol). The resulting mixture was stirred at room temperature for 1 h. 2-[2-[2-[2-(4-methylphenyl)sulfonyloxyethoxy]ethoxy]ethyl 4-methylbenzenesulfonate (1321 mg, 2.88 mmol) in dry DMF (10 mL) was added to the reaction mixture and stirred at the same temperature for 17 h. The mixture was quenched with water (30 mL) and extracted with DCM (30 mL). The organic layer was washed with brine (30 mL), dried over anhydrous Na₂SO₄, concentrated and purified by column chromatography (EtOAc:DCM=1:4, Rf=0.4) to give 2-[2-[2-[[4-[4-(6-methoxyimidazo[1,2-a]pyridin-2-yl)phenyl]pyridin-2-yl]-[(2-methylpropan-2-yl)oxycarbonyl]amino]ethoxy]ethoxy]ethyl 4-methylbenzenesulfonate (350 mg, 0.50 mmol, 52% yield) as a yellow solid.

Compound 164438: A mixture of 2-[2-[2-[[4-[4-(6-methoxyimidazo[1,2-a]pyridin-2-yl)phenyl]pyridin-2-yl]-[(2-methylpropan-2-yl)oxycarbonyl]amino]ethoxy]ethoxy]ethyl 4-methylbenzenesulfonate (350 mg, 0.50 mmol) and NaI (149 mg, 1.00 mmol) in ACN (10 mL) was heated at 80° C. for 6 h. The mixture was added water and extracted with DCM. The organic layer was washed with water (50 mL) and brine (50 mL), dried over Na₂SO₄ and concentrated to dryness to give tert-butyl N-[2-[2-(2-iodanylethoxy)ethoxy]ethyl]-N-[4-[4-(6-methoxyimidazo[1,2-a]pyridin-2-yl)phenyl]pyridin-2-yl]carbamate (317 mg, 0.48 mmol, 97% yield) as a yellow solid.

Compound 164465: A mixture of tert-butyl N-[2-[2-(2-iodanylethoxy)ethoxy]ethyl]-N-[4-[4-(6-methoxyimidazo[1,2-a]pyridin-2-yl)phenyl]pyridin-2-yl]carbamate (100 mg, 0.15 mmol), K₂CO₃ (63 mg, 0.46 mmol) and methyl 5-aza-nyl-5-oxidanyl-4-(6-oxidanyl-3-oxidanylidene-1H-isoindol-2-yl)pentanoate (49 mg, 0.17 mmol) in DMF (5 mL) was heated at 80° C. for 6 h. The mixture was added water and extracted with DCM. The organic layer was dried over MgSO₄, concentrated and purified by column chromatography (MeOH:DCM=3:100, Rf=0.3) to give tert-butyl N-[2-[2-[2-[[2-[2,6-bis(oxidanylidene)piperidin-3-yl]-1-oxidanylidene-3H-isoindol-5-yl]oxy]ethoxy]ethoxy]ethyl]-N-[4-[4-(6-methoxyimidazo[1,2-a]pyridin-2-yl)phenyl]pyridin-2-yl]carbamate (63 mg, 0.08 mmol, 52% yield) as a white solid.

Compound 164484: To a solution of tert-butyl N-[2-[2-[2-[[2-[2,6-bis(oxidanylidene)piperidin-3-yl]-1-oxidanylidene-3H-isoindol-5-yl]oxy]ethoxy]ethoxy]ethyl]-N-[4-[4-(6-methoxyimidazo[1,2-a]pyridin-2-yl)phenyl]pyridin-2-yl]carbamate (63 mg, 0.08 mmol) in DCM (5 mL) was added TFA (0.09 mL, 1.19 mmol) and stirred at room temperature for 14 h. The mixture was poured into iced water and neutralized with sat. NaHCO₃ solution to pH 8. The mixture was diluted with DCM (20 mL) and extracted with water (10 mL) and brine (10 mL), dried over Na2SO4 and concentrated to dryness to give 3-[6-[2-[2-[2-[[4-[4-(6-methoxyimidazo[1,2-a]pyridin-2-yl)phenyl]pyridin-2-yl]amino]ethoxy]ethoxy]ethoxy]-3-oxidanylidene-1H-isoindol-2-yl]piperidine-2,6-dione (52 mg, 0.07 mmol, 89% yield) as a pale-brown solid.

Example 35: Synthesis of Compound 165013

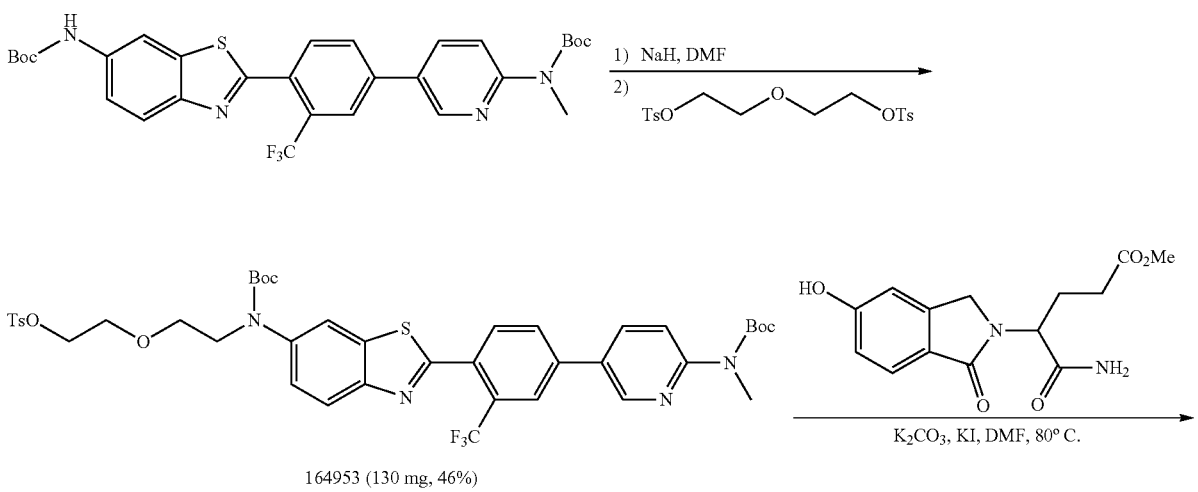

164953 (130 mg, 46%)

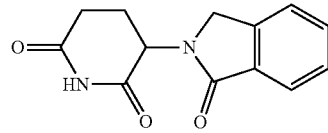
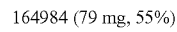
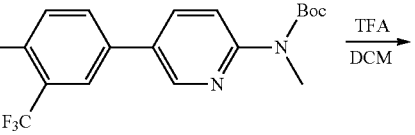

164984 (79 mg, 55%)

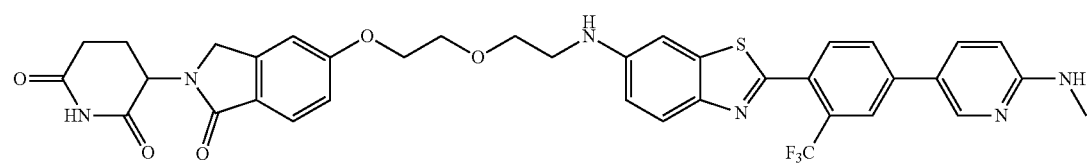

165013 (28.5 mg, 45%)

Compound 164953: To a solution of tert-butyl N-methyl-N-[5-[4-[6-[(2-methylpropan-2-yl)oxycarbonylamino]-1,3-benzothiazol-2-yl]-3-(trifluoromethyl)phenyl]pyridin-2-yl] carbamate (200 mg, 0.33 mmol) in dry DMF (5 mL) was added NaH (40 mg, 1.00 mmol) at 0° C. and stirred at room temperature for 1 h. 2-[2-(4-methylphenyl)sulfonyloxy-ethoxy]ethyl 4-methylbenzenesulfonate (414 mg, 1.00 mmol) in dry DMF (5 mL) was added to the reaction mixture and stirred at the same temperature for 14 h. The mixture was quenched with water (30 mL) and extracted with DCM (30 mL). The organic layer was washed with water (30 mL) and brine (30 mL), dried over anhydrous Na$_2$SO$_4$, concentrated and purified by column chromatography (EtOAc:DCM=1:9, Rf=0.4) to give 2-[2-[[2-[4-[6-[methyl-[(2-methylpropan-2-yl)oxycarbonyl]amino]pyridin-3-yl]-2-(trifluoromethyl)phenyl]-1,3-benzothiazol-6-yl]-[(2-methylpropan-2-yl)oxycarbonyl]amino]ethoxy]ethyl 4-methylbenzenesulfonate (130 mg, 0.15 mmol, 46% yield) as a yellow solid.

Compound 164984: A mixture of methyl 5-azanyl-5-oxidanylidene-4-(6-oxidanyl-3-oxidanylidene-1H-isoindol-2-yl)pentanoate (50 mg, 0.17 mmol), K$_2$CO$_3$ (64 mg, 0.46 mmol), KI (2.56 mg, 0.02 mmol) and 2-[2-[[2-[4-[6-[methyl-[(2-methylpropan-2-yl)oxycarbonyl]amino]pyridin-3-yl]-2-(trifluoromethyl)phenyl]-1,3-benzothiazol-6-yl]-[(2-methylpropan-2-yl)oxycarbonyl]amino]ethoxy]ethyl 4-methylbenzenesulfonate (130 mg, 0.15 mmol) in DMF (5 mL) was heated at 80° C. for 6 h. The mixture was diluted with DCM (5 mL), cooled to 0° C. and added water (5 mL) dropwise. The mixture was extracted with water (10 mL) and brine (10 mL), dried over Na$_2$SO$_4$, concentrated and purified by column chromatography (MeOH:DCM=3:100, Rf=0.3) to give tert-butyl N-[2-[2-[[2-[2,6-bis(oxidanylidene)piperidin-3-yl]-1-oxidanylidene-3H-isoindol-5-yl]oxy]ethoxy]ethyl]-N-[2-[4-[6-[methyl-[(2-methylpropan-2-yl)oxycarbonyl]amino]pyridin-3-yl]-2-(trifluoromethyl)phenyl]-1,3-benzothiazol-6-yl]carbamate (79 mg, 0.08 mmol, 55% yield) as colorless oil.

Compound 165013: To a solution of tert-butyl N-[2-[2-[[2-[2,6-bis(oxidanylidene)piperidin-3-yl]-1-oxidanylidene-3H-isoindol-5-yl]oxy]ethoxy]ethyl]-N-[2-[4-[6-[methyl-[(2-methylpropan-2-yl)oxycarbonyl]amino]pyridin-3-yl]-2-(trifluoromethyl)phenyl]-1,3-benzothiazol-6-yl]carbamate (79 mg, 0.08 mmol) in DCM (3 mL) was added TFA (0.1 mL, 1.27 mmol) and stirred at room temperature for 14 h. The mixture was poured into ice water and neutralized with sat. NaHCO$_3$ solution to pH 8. The mixture was diluted with DCM (20 mL) and extracted with water (10 mL) and brine (10 mL). The organic layer was collected, dried over Na$_2$SO$_4$, concentrated and purified by column chromatography on silica gel (MeOH:DCM=3:100, Rf=0.2) to give 3-[6-[2-[2-[[2-[4-[6-(methylamino)pyridin-3-yl]-2-(trifluoromethyl)phenyl]-1,3-benzothiazol-6-yl]amino]ethoxy]ethoxy]-3-oxidanylidene-1H-isoindol-2-yl]piperidine-2,6-dione (29 mg, 0.04 mmol, 45% yield) as a yellow solid.

Example 36: Synthesis of Compound 166288

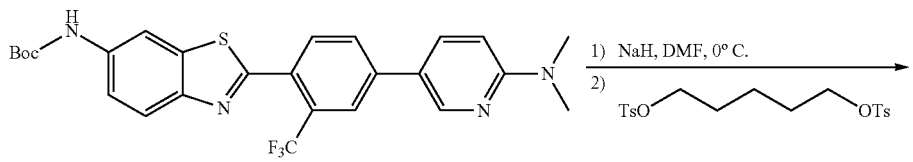

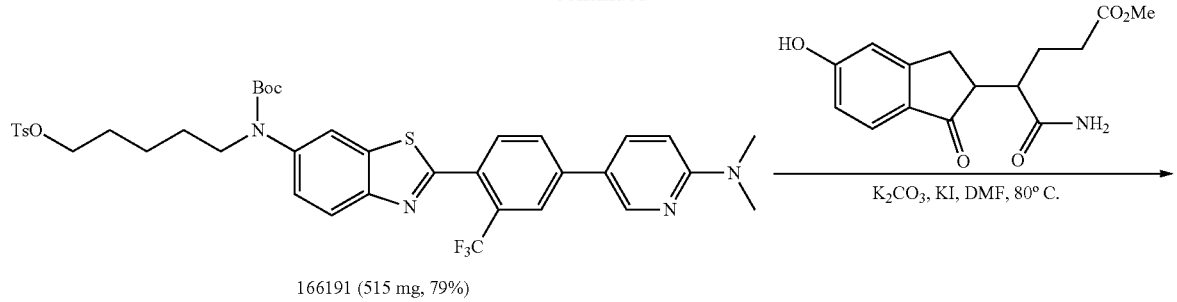

166191 (515 mg, 79%)

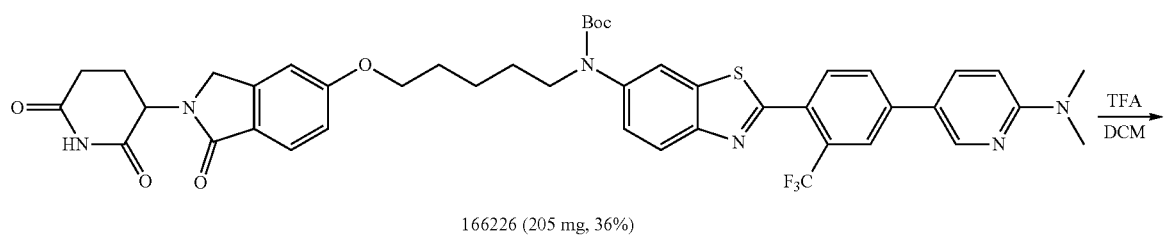

166226 (205 mg, 36%)

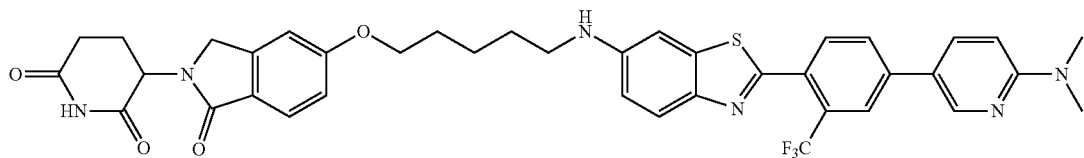

166288 (132 mg, 71%)

Compound 166191: A solution of tert-butyl N-[2-[4-[6-(dimethylamino)pyridin-3-yl]-2-(trifluoromethyl)phenyl]-1,3-benzothiazol-6-yl]carbamate (447 mg, 0.87 mmol) in DMF (8 mL) was added NaH (63 mg, 2.61 mmol) at 0° C., stirred at room temperature for 1 h and then added 5-(4-methylphenyl)sulfonyloxypentyl 4-methylbenzenesulfonate (1075 mg, 2.61 mmol) in DMF (8 mL). The resulting mixture was stirred at room temperature for another 16 h, cooled to 0° C. and quenched by adding water. The residue was taken up in DCM (50 mL) and water (50 mL). The organic layer was washed with water (50 mL), brine (50 mL), dried over Na$_2$SO$_4$, and purified by column chromatography on silica gel (DCM:EtOAc=9:1, Rf=0.52) to give 5-[[2-[4-[6-(dimethylamino)pyridin-3-yl]-2-(trifluoromethyl)phenyl]-1,3-benzothiazol-6-yl]-[(2-methylpropan-2-yl)oxycarbonyl]amino]pentyl 4-methylbenzenesulfonate (515 mg, 0.68 mmol, 79% yield) as a yellow solid.

Compound 166226: A mixture of 5-[[2-[4-[6-(dimethylamino)pyridin-3-yl]-2-(trifluoromethyl)phenyl]-1,3-benzothiazol-6-yl]-[(2-methylpropan-2-yl)oxycarbonyl]amino]pentyl 4-methylbenzenesulfonate (514 mg, 0.68 mmol), K$_2$CO$_3$ (282 mg, 2.04 mmol), KI (11 mg, 0.07 mmol) and methyl 5-azanyl-5-oxidanylidene-4-(6-oxidanyl-3-oxidanylidene-1H-isoindol-2-yl)pentanoate (219 mg, 0.75 mmol) in DMF (8 mL) was stirred at room temperature for 22 h and then heated to 80° C. for 6 h. The mixture was diluted with DCM (5 mL), cooled to 0° C. and added water (5 mL) dropwise. The mixture was washed with water (10 mL) and brine (10 mL), dried over Na$_2$SO$_4$, concentrated and purified by column chromatography on silica gel (MeOH:DCM=1:20, Rf=0.55) to give tert-butyl N-[5-[[2-[2,6-bis(oxidanylidene)piperidin-3-yl]-1-oxidanylidene-3H-isoindol-5-yl]oxy]pentyl]-N-[2-[4-[6-(dimethylamino)pyridin-3-yl]-2-(trifluoromethyl)phenyl]-1,3-benzothiazol-6-yl]carbamate (205 mg, 0.24 mmol, 36% yield) as yellow solid.

Compound 166288: To a solution of tert-butyl N-[5-[[2-[2,6-bis(oxidanylidene)piperidin-3-yl]-1-oxidanylidene-3H-isoindol-5-yl]oxy]pentyl]-N-[2-[4-[6-(dimethylamino)pyridin-3-yl]-2-(trifluoromethyl)phenyl]-1,3-benzothiazol-6-yl]carbamate (205 mg, 0.24 mmol) in DCM (3 mL) was added TFA (0.28 mL, 3.65 mmol) and stirred at room temperature for 16 h. The mixture was poured into iced water and neutralized with sat. NaHCO$_3$ solution to pH 8. The residue was taken up in DCM (20 mL) and water (10 mL). The organic layer was washed with water (10 mL) and brine (10 mL), dried over Na$_2$SO$_4$ and concentrated to dryness to give 3-[6-[5-[[2-[4-[6-(dimethylamino)pyridin-3-yl]-2-(trifluoromethyl)phenyl]-1,3-benzothiazol-6-yl]amino]pentoxy]-3-oxidanylidene-1H-isoindol-2-yl]piperidine-2,6-dione (132 mg, 0.17 mmol, 71% yield) as a yellow solid.

Example 37: Synthesis of Compound 166399

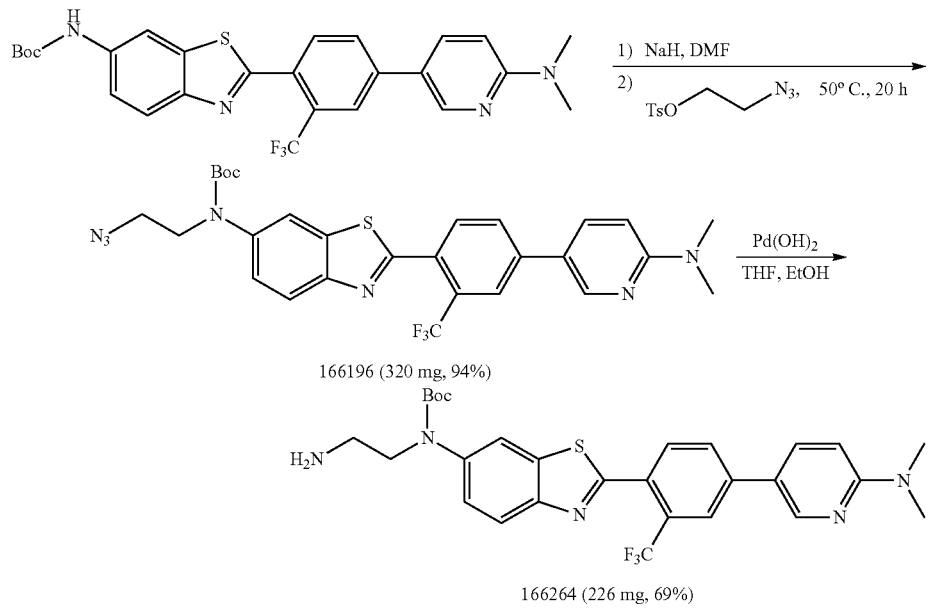

Compound 166196: A solution of tert-butyl N-[2-[4-[6-(dimethylamino)pyridin-3-yl]-2-(trifluoromethyl)phenyl]-1,3-benzothiazol-6-yl]carbamate (300 mg, 0.58 mmol) in DMF (5 mL) was cooled to 0° C. and added NaH (56 mg, 2.33 mmol). The mixture was stirred at room temperature for 1 h, added 2-azidoethyl 4-methylbenzenesulfonate (281 mg, 1.17 mmol) in DMF (5 mL) and heated at 50° C. for 20 h. The mixture was cooled to 0° C. and added water (5 mL). The resulting precipitation was collected by filtration, washed with water and dried over vacuum. The residue was purified by column chromatography on silica gel (EtOAc: DCM=1:20, Rf=0.6) to give tert-butyl N-(2-azidoethyl)-N-[2-[4-[6-(dimethylamino)pyridin-3-yl]-2-(trifluoromethyl) phenyl]-1,3-benzothiazol-6-yl]carbamate (320 mg, 0.55 mmol, 94% yield) as a yellow solid.

Compound 166264: A solution of tert-butyl N-(2-azidoethyl)-N-[2-[4-[6-(dimethylamino)pyridin-3-yl]-2-(trifluoromethyl)phenyl]-1,3-benzothiazol-6-yl]carbamate (341 mg, 0.58 mmol) in THF (5 mL)/EtOH (5 mL) was added Pd(OH)$_2$ (1701 mg, 1.61 mmol) and stirred under 1 atmosphere of H2 for 4 h. The mixture was filtered through a Celite pad and the filtrate was concentrated to dryness. The residue was purified by column chromatography (DCM: EtOAc=20:1, Rf=0.15) to give tert-butyl N-(2-azanylethyl)-N-[2-[4-[6-(dimethylamino)pyridin-3-yl]-2-(trifluoromethyl)phenyl]-1,3-benzothiazol-6-yl]carbamate (226 mg, 0.41 mmol, 69% yield) as pale-yellow solid.

Compound 166306: A mixture of tert-butyl N-(2-azanylethyl)-N-[2-[4-[6-(dimethylamino)pyridin-3-yl]-2-(trifluoromethyl)phenyl]-1,3-benzothiazol-6-yl]carbamate (326 mg, 0.59 mmol), 2-[[2-[2,6-bis(oxidanylidene)piperidin-3-yl]-1-oxidanylidene-3H-isoindol-5-yl]oxy]ethanoic acid (372 mg, 1.17 mmol), EDC (280 mg, 1.46 mmol) and HOBt (198 mg, 1.46 mmol) in pyridine (6 mL) was stirred at room temperature for 16 h. The solvent was removed by vacuum and the resulting residue was redissolved in EtOAc (100 mL) and washed with water (50 mL) and brine (50 mL). The organic layer was dried over Na$_2$SO$_4$, concentrated and purified by column chromatography on silica gel (MeOH: DCM=1:20, Rf=0.3) to give tert-butyl N-[2-[2-[[2-[2,6-bis(oxidanylidene)piperidin-3-yl]-1-oxidanylidene-3H-isoindol-5-yl]oxy]ethanoylamino]ethyl]-N-[2-[4-[6-(dimethylamino)pyridin-3-yl]-2-(trifluoromethyl)phenyl]-1,3-benzothiazol-6-yl]carbamate (277 mg, 0.32 mmol, 55% yield) as a yellow solid.

Compound 166399: A solution of tert-butyl N-[2-[2-[[2-[2,6-bis(oxidanylidene)piperidin-3-yl]-1-oxidanylidene-3H-isoindol-5-yl]oxy]ethanoylamino]ethyl]-N-[2-[4-[6-(dimethylamino)pyridin-3-yl]-2-(trifluoromethyl)phenyl]-1,3-benzothiazol-6-yl]carbamate (277 mg, 0.32 mmol) in DCM (3 mL) was added TFA (0.37 mL, 4.85 mmol) and stirred at room temperature for 23 h. The mixture was poured into iced water and neutralized with sat. NaHCO$_3$ solution to pH 8. The residue was taken up in DCM (20 mL) and water (10 mL). The organic layer was washed with water (10 mL) and brine (10 mL), dried over Na$_2$SO$_4$ and concentrated to give 2-[[2-[2,6-bis(oxidanylidene)piperidin-3-yl]-1-oxidanylidene-3H-isoindol-5-yl]oxy]-N-[2-[[2-[4-[6-(dimethylamino)pyridin-3-yl]-2-(trifluoromethyl)phenyl]-1,3-benzothiazol-6-yl]amino]ethyl]ethanamide (239 mg, 0.30 mmol, 93% yield) as a yellow solid.

Example 38: Alpha-synuclein Competitive Binding Assay (A) Expression and purification of recombinant wild-type human α-synuclein: 0.5 mM IPTG was used to induce production of wild type human α-synuclein by bacteria transformed with a full-length α-synuclein expression plasmid. After shaking at 16° C. for 20 hours, cell pellet was resuspended in lysis buffer (10 mM Tris, 1 mM EGTA, 0.75 mM NaCl, 1 mM PMSF, pH 7.5) and lysed by sonication followed by centrifugation (6000 g, 30 min, 4° C.). The supernatant was then boiled at 95° C. for 15 min with manual agitation by every 5 minutes, followed by centrifugation (6000 g, 30 min, 4° C.). Supernatant was dialyzed with (10 mM Tris, 1 mM EGTA, 50 mM NaCl, pH 7.5) buffer and concentrated with concentrator. The collected sample was loaded onto a Superdex200 column, the flow-through fraction was then loaded onto a Q-HP column. Collected fractions with α-synuclein eluates were pooled, concentrated and stored at −80° C.

(B) Preparation of aggregated α-synuclein: 5 mg/mL of α-synuclein in PBS buffer (pH 7.4) was incubated in tube with at 37° C. with shaking (700 rpm) for 5-10 days.

(C) In vitro fluorometric α-synuclein binding assays: 2 μM α-synuclein was incubated with serially diluted compound (three-fold serial dilutions, from 10 to 0.001 μM) in a 96-well plate at 37° C. for 1 hour. Fluorescence intensity was read by microplate spectrometer. Compound Kd values were calculated using the following equation: $Y=B_{max}*X/(Kd+X)$, where X is the concentration of compound; Y is the fluorescence signal of (compound+α-synuclein)−(compound+DMSO); and $B_{max}$ is the maximum signal.

(D) PBB5 competition assay: 2 μM of α-synuclein was incubated with 0.26 μM 2-(4-(2-(methylamino)pyridine-5-yl)-1,3-butadiene-1-yl)benzothiazole-6-ol (PBB5) and serially diluted compound (three-fold serial dilution, from 10 to 0.001 μM) in a 96-well plate at 37° C. for 1 hour. Fluorescence intensity (excitation/emission=530/690 nm) of PBB5 was read by microplate spectrometer. Percentage of competition was calculated using the following equation: (Max−well of compound alone)/(Max−Min)*100%, where Max=(α-synuclein+PBB5) signals−(buffer+PBB5) signals; and Min=(buffer+PBB5) signals−(buffer+PBB5) signals. The $IC_{50}$ value of each compound was calculated with GraphPad Prism software using the "4 Parameter Logistic Model or Sigmoidal Dose-Response Model": $Y=Bottom+(Top-Bottom)/(1+(IC50/X)^{HillSlope})$

TABLE 2

Competition Assay with PBB5

| Compound | Ex/Em (nm) | Kd (μM) | PBB5 (μM) |
|---|---|---|---|
| 165825 | 340/480 | ND | >10 |
| 166099 | 350/500 | 5.63 | 0.04 |
| 165802 | 335/435 | 2.44 | >10 |
| 166124 | 345/545 | 0.34 | 0.03 |
| 166330 | 370/500 | 0.59 | 2.6 |
| 177032 | 350/480 | 0.06 | ND |
| 177033 | 350/480 | 0.65 | 0.63 |
| 180944 | 345/475 | 0.43 | 0.61 |
| 163123 | 340/480 | 0.26 | >10 |
| 166965 | 305/485 | 0.22 | 10 |
| 166123 | 340/480 | 0.48 | 0.41 |

Example 39: In Vitro Assay For Degradinh α-Synuclein Aggregates

The ReNcell VM α-synuclein aggregation assay was conducted at Charles River Laboratories (CRL). ReNcell VM is an immortalized human neural progenitor cell line derived from the ventral mesencephalon region of the brain. ReNcell VM cells were selected as in vitro cellular model for the α-synuclein aggregation assay, based on their growth features, differentiation potential into terminally differentiated neurons and amenability to adenoviral transduction. Aggregated human wild type α-synuclein was overexpressed through adenoviral delivery. Aggregated α-synuclein was detected with the aggregate-selective anti-α-synuclein antibody MJFR14 using immunocytochemistry; total α-synuclein levels were detected with Syn205 (α/β-synuclein-specific antibody).

The ReNcell VM α-synuclein aggregation assay was applied for compound screening to identify compounds capable of degrading α-synuclein aggregates. Specifically, adenovirally transduced ReNcell VM cells were treated with test compounds (serially diluted) for 24 hours, followed by fixation, and then processed for ReNcell immunocytochemistry by staining with Syn205 and MJFR14. Immunoreactivity toward aggregated (MJFR14) and total α-synuclein (Syn205) was quantified using high content-based segmentation of immunoactive areas in immunocytochemical images (performed with the IN Cell 2200 (GE Healthcare)), followed by quantification of immunofluorescent intensity (performed by CRL's developed algorithm using IN Cell Developer Toolbox software).

A set of more than 100 compounds was tested for inhibition of MJFR14 immunoreactivity. FIG. 1 shows the high content-based quantifications of aggregated α-synuclein species in combination with determination of nuclei count (% remaining cells) in differentiated ReNcell VM cells. Results showed that 24 hour treatment with test compounds 166362, 170357, 162640 and 180948, respectively, induced a concentration-dependent inhibition of MJFR14 immunoreactivity, indicative of decreased α-synuclein aggregation. Each panel of graph displays normalized data for percentage effect (PE) and remaining cells (%).

Percentage effect (PE): Inhibition in comparison to BLANK (0.1% DMSO).

PE=100−(signal of compound/average signal BLANK)×100

Compound-induced cytotoxicity (% remaining cells)

% remaining cells=(nuclei count of compound/average nuclei count of BLANK)×100

FIGS. 2A-2D show the representative immunocytochemical images of cells treated with vehicle (0.1% DMSO) and test compounds 132168, 166362, and 170357, and immunostained with MJFR14, illustrating the reduction in α-synuclein expression following treatment with compounds 132168 and 166362. The results demonstrated that 6-day treatment with compound 132168 and 166362, respectively, induced a clear inhibition of MJFR14 immunoreactivity, indicating compounds 132168 and 166362 effectively reduce α-synuclein aggregation.

Some embodiments of compounds were evaluated in the ReNcell VM α-synuclein aggregation assay. Results are summarized in Table 3.

TABLE 3

| Compound | Activity |
|---|---|
| 159985 | A |
| 160273 | C |
| 160313 | A |
| 170350 | B |
| 161177 | A |
| 160219 | A |
| 170351 | B |
| 170352 | A |
| 161103 | A |
| 161111 | A |
| 170353 | A |
| 170354 | C |
| 170355 | A |
| 170356 | A |
| 170357 | C |
| 160624 | A |
| 170358 | A |
| 170450 | A |
| 170451 | A |

TABLE 3-continued

| Compound | Activity |
|---|---|
| 162641 | A |
| 162640 | C |
| 177031 | A |
| 177032 | A |
| 177033 | A |
| 177036 | A |
| 177037 | B |
| 177038 | A |
| 177039 | A |
| 170742 | A |
| 163123 | A |
| 184605 | A |
| 163365 | C |
| 180948 | D |
| 189149 | A |
| 180950 | A |
| 174251 | A |
| 175552 | A |
| 190753 | A |
| 137955 | A |
| 132560 | A |
| 185563 | A |
| 133065 | A |
| 138266 | A |
| 132168 | C |
| 129071 | A |
| 127973 | C |
| 123374 | A |
| 129975 | A |
| 138876 | B |
| 130177 | A |
| 133678 | A |
| 161247 | A |
| 161598 | A |
| 178884 | A |
| 177685 | A |
| 180187 | A |
| 165554 | A |
| 165802 | A |
| 165824 | A |
| 165810 | A |
| 165950 | A |
| 165954 | A |
| 165952 | A |
| 166099 | A |
| 166330 | A |
| 166362 | B |

Notes:
A indicates $DC_{50}$ >10 μM
B indicates $DC_{50}$ between 0.9 and 10 μM
C indicates $DC_{50}$ between 0.01 and 0.9 μM
D indicates $DC_{50}$ <0.01 μM
$DC_{50}$ indicates the concentration at which 50% of α-synuclein aggregates has been degraded.

Example 40: In Vivo Assay For Degrading α-Synuclein Aggregates

Figure 3:
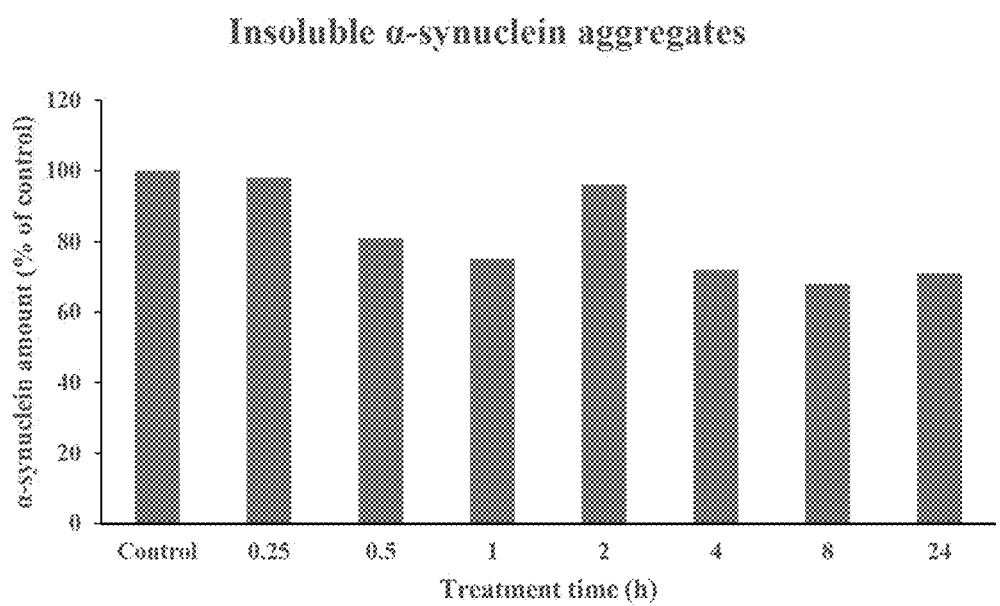
FIG. 3 shows the result of an in vivo α-synuclein degradation study. Upon treatment of compound 132168, insoluble α-synuclein fraction decreases 30% compared to DMSO vehicle control, indicating the reduction of insoluble α-synuclein aggregates.

Male transgenic Line61 mice at age of three-month-old were used for the study. Mice were treated once via intravenous injection with the compound 132168 (25 mpk). Plasma and brain samples were collected at 0.25, 0.5, 1, 2, 4, 8 and 24 h post treatment. Blood samples were collected via cardiac puncture into MiniCollect® 0.5 mL K₂EDTA (Potassium ethylenediaminetetraacetic acid) tubes. The blood samples were centrifuged at 3000×g for 10 minutes at room temperature (22° C.). Plasma was transferred to a pre-labeled 1.5 ml LoBind Eppendorf tube (2 aliquot, each ~75 μl), frozen on dry ice and stored at −80° C. until analysis. For brain samples, a perfusion with 0.9% saline was performed before collection. Brain was weighed, hemisected on a cooled surface, weighed and snap frozen. The hemibrain was used for WES System analysis of human α-synuclein in soluble and insoluble fraction. Upon treatment of compound 132168, insoluble α-synuclein fraction decreases 30% compared to DMSO vehicle control, reflecting the reduction of insoluble α-synuclein aggregates. Results are shown in FIG. 3.

Example 41: In Vivo Pharmacokinetic Study

To determine whether the compounds of the present disclosure are capable of crossing the blood brain barrier (BBB), example compound 132168 was administered to mice in a pharmacokinetic study (10 and 25 mg/kg, intravenous).

Animal Husbandry: Mice were housed at animal room environment with ventilation 15 times/hour, lighting 12 hours/day, temperature 20° C. to 24° C. and humidity 40% to 70%. The study rooms were disinfected and cleaned prior to the start of the study and the operation area was cleaned after each dosing or sampling during the study conduct. All animals had free access to food and water during the study. The animals had access to Certified Rodent Diet and water ad libitum. The nutritional composition and levels of contaminants of the diet and impurities and contaminants of the water were monitored by third organization. The health status of the animals was evaluated in accordance with accepted animal husbandry procedures and deemed suitable for experimental use.

Sample Collection & Processing: Approximately 110 μL of whole blood were collected from all animals via facial or cardiac puncture under anesthesia with Isoflurane into test tubes containing potassium ethylenediaminetetraacetate (K₂EDTA) at 0.25, 0.5, 1, 2, 4, 8 and 24 hr post dose. Brian samples were collected at 0.25, 0.5, 1, 2, 4, 8 and 24 hours post dose. A perfusion with pre-cold saline will be conducted via cardiac puncture before brain collection. Blood samples were centrifuged at 2000 g at 4° C. for 5 minutes to obtain plasma samples by transferring the supernatants into new tubes. All plasma and brain samples were stored at approximately −70° C. until analysis.

Bioanalytical Method Development: The concentrations of compound in plasma and brain samples were determined using a liquid chromatography with tandem mass spectrometry (LC-MS/MS) based method. Results: The PK parameters were summarized in Table 4. Compound 132168 was able to penetrate BBB in short period of time.

TABLE 4

In vivo pharmacokinetic profile of Compound 132168

| | Plasma | | Brain | |
|---|---|---|---|---|
| Dosage (mg/kg) | 10 | 25 | 10 | 25 |
| $AUC_{last}$ (hr*ng/mL) | 17780 | 48660 | 1330 | 4069 |
| $T_{1/2}$ (h) | 2.87 | 2.12 | 5.88 | NA |
| $C_{max}$ (ng/mL) | — | — | 319 | 581 |
| $T_{max}$ (h) | — | — | 0.5 | 4 |

Certain embodiments are as follows:

Embodiment 1. A method to treat synucleinopathy in a subject in need thereof, the method comprising administering to the subject an effective amount of a compound of Formula A, EBM-L-SBM (Formula A)

wherein
 EBM is an E3 ubiquitin ligase binding moiety;
 L is a linker covalently attached to EBM and SBM; and
 SBM is an α-synuclein protein binding moiety of the formula:

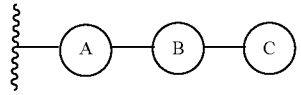

or a pharmaceutical acceptable salt, an enantiomer, a non-enantiomer, a tautomer, a racemate, a solvate, a metabolic precursor, a prodrug thereof,
wherein

is covalently linked to L; and
 (i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
 (ii)

is a substituted or unsubstituted monocyclic aromatic ring containing 0 to 2 ring heteroatoms selected from O, S, and N;

is a substituted or unsubstituted monocyclic aromatic ring containing 0 to 2 ring heteroatoms selected from O, S, and N; and

is a substituted or unsubstituted bicyclic fused aromatic ring containing at least 1 ring heteroatom selected from O, S, and N.

Embodiment 2. A method to reduce α-synuclein aggregation in a subject in need thereof, the method comprising administering to the subject an effective amount of a compound of Formula A, EBM-L-SBM  (Formula A)

wherein
 EBM is an E3 ubiquitin ligase binding moiety;
 L is a linker covalently attached to EBM and SBM; and
 SBM is an α-synuclein protein binding moiety of the formula:

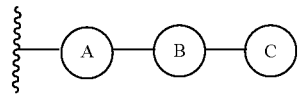

or a pharmaceutical acceptable salt, an enantiomer, a non-enantiomer, a tautomer, a racemate, a solvate, a metabolic precursor, a prodrug thereof, wherein

is covalently linked to L; and
 (i)

is a substituted or unsubstituted bicyclic fused aromatic ring containing at least 1 ring heteroatom selected from O, S, and N

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
  (ii)

(A)

is a substituted or unsubstituted monocyclic aromatic ring containing 0 to 2 ring heteroatoms selected from O, S, and N;

(B)

is a substituted or unsubstituted monocyclic aromatic ring containing 0 to 2 ring heteroatoms selected from O, S, and N; and (C)

is a substituted or unsubstituted bicyclic fused aromatic ring containing at least 1 ring heteroatom selected from O, S, and N.

Embodiment 3. A method to reduce Lewy bodies in a subject in need thereof, the method comprising administering to the subject an effective amount of a compound of Formula A, EBM-L-SBM  (Formula A)

wherein
  EBM is an E3 ubiquitin ligase binding moiety;
  L is a linker covalently attached to EBM and SBM; and
  SBM is an α-synuclein protein binding moiety of the formula:

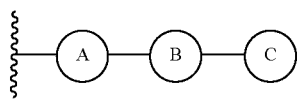

or a pharmaceutical acceptable salt, an enantiomer, a non-enantiomer, a tautomer, a racemate, a solvate, a metabolic precursor, a prodrug thereof,
wherein (A)

is covalently linked to L; and
  (i)

(A)

is a substituted or unsubstituted bicyclic fused aromatic ring containing at least 1 ring heteroatom selected from O, S, and N;

(B)

is a substituted or unsubstituted monocyclic aromatic ring containing 0 to 2 ring heteroatoms selected from O, S, and N; and (C)

is a substituted or unsubstituted monocyclic aromatic ring containing 0 to 2 ring heteroatoms selected from O, S, and N; or
  (ii)

(A)

is a substituted or unsubstituted monocyclic aromatic ring containing 0 to 2 ring heteroatoms selected from O, S, and N;

(B)

is a substituted or unsubstituted monocyclic aromatic ring containing 0 to 2 ring heteroatoms selected from O, S, and N; and (C)

is a substituted or unsubstituted bicyclic fused aromatic ring containing at least 1 ring heteroatom selected from O, S, and N.

Embodiment 4. Use of a compound of Formula A:

EBM-L-SBM  (Formula A)

or a pharmaceutical acceptable salt, a enantiomer, a non-enantiomer, a tautomer, a racemate, a solvate, a metabolic precursor, or a prodrug thereof, in the manufacture of a medicament for treating synucleinopathy, wherein
  EBM is an E3 ubiquitin ligase binding moiety;
  L is a linker covalently attached to EBM and SBM; and
  SBM is an α-synuclein protein binding moiety of the formula:

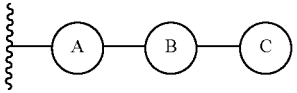

wherein

is covalently linked to L; and
  (i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
  (ii)

is a substituted or unsubstituted monocyclic aromatic ring containing 0 to 2 ring heteroatoms selected from O, S, and N;

is a substituted or unsubstituted monocyclic aromatic ring containing 0 to 2 ring heteroatoms selected from O, S, and N; and

is a substituted or unsubstituted bicyclic fused aromatic ring containing at least 1 ring heteroatom selected from O, S, and N.

Embodiment 5. Use of a compound of Formula A:

EBM-L-SBM  (Formula A)

or a pharmaceutical acceptable salt, a enantiomer, a non-enantiomer, a tautomer, a racemate, a solvate, a metabolic precursor, or a prodrug thereof, in the manufacture of a medicament for reducing α-synuclein aggregation, wherein
  EBM is an E3 ubiquitin ligase binding moiety;
  L is a linker covalently attached to EBM and SBM; and
  SBM is an α-synuclein protein binding moiety of the formula:

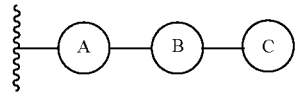

wherein

is covalently linked to L; and
  (i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
  (ii)

is a substituted or unsubstituted monocyclic aromatic ring containing 0 to 2 ring heteroatoms selected from O, S, and N;

is a substituted or unsubstituted monocyclic aromatic ring containing 0 to 2 ring heteroatoms selected from O, S, and N; and

is a substituted or unsubstituted bicyclic fused aromatic ring containing at least 1 ring heteroatom selected from O, S, and N.

Embodiment 6. Use of a compound of Formula A:

EBM-L-SBM  (Formula A)

or a pharmaceutical acceptable salt, a enantiomer, a non-enantiomer, a tautomer, a racemate, a solvate, a metabolic precursor, or a prodrug thereof, in the manufacture of a medicament for reducing Lewy bodies, wherein
EBM is an E3 ubiquitin ligase binding moiety;
L is a linker covalently attached to EBM and SBM; and
SBM is an α-synuclein protein binding moiety of the formula:

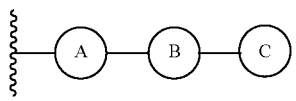

wherein

is covalently linked to L; and
(i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
(ii)

is a substituted or unsubstituted monocyclic aromatic ring containing 0 to 2 ring heteroatoms selected from O, S, and N;

is a substituted or unsubstituted monocyclic aromatic ring containing 0 to 2 ring heteroatoms selected from O, S, and N; and

is a substituted or unsubstituted bicyclic fused aromatic ring containing at least 1 ring heteroatom selected from O, S, and N.

Embodiment 7. The method of Embodiment 1 or the use of Embodiment 4, wherein the synucleinopathy is Parkinson's Disease (PD), dementia with Lewy bodies (DLB), multiple system atrophy (MSA), or a combination of two or more thereof.

Embodiment 8. The method or use of any one of Embodiments 1-7, wherein the substituted or unsubstituted bicyclic fused aromatic ring is a substituted or unsubstituted bicyclic 5-6 system.

Embodiment 9. The method or use of any one of Embodiments 1-8, wherein SBM is of Formula B or Formula C

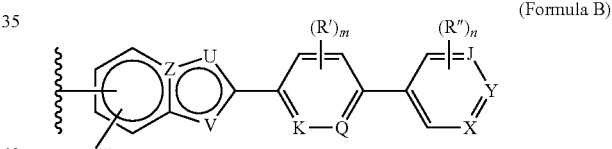

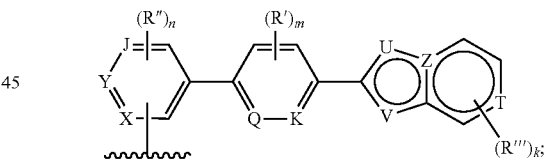

wherein
Z is C or N; U is O, S or CH; V is N or NH;
K is CH or N; Q is CH or N; where K and Q are not N at the same time;
each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3;
each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;
each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;
J is $CR^6$ or N; X is $CR^6$ or N; Y is $CR^6$ or N; where at least one of J, X and Y is N, but J and Y are not N at the same time, X and Y are not N at the same time;

$R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo; and in Formula B, V is N, where Z and U are not heteroatoms at the same time; and in Formula C, V is N or NH; T is CH or N; where up to two of U, Z, V and T contain heteroatoms.

Embodiment 10. The method or use of any one of Embodiments 1-9, wherein EBM is

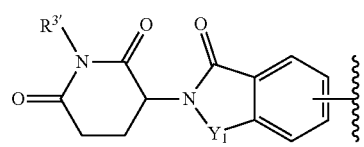

,

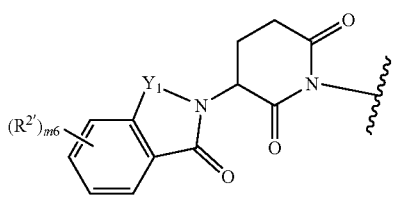

, or

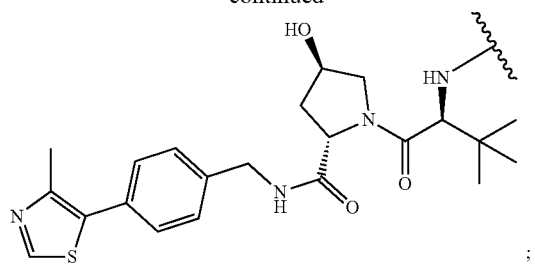

;

wherein
$R^{3'}$ is H or $C_{1-6}$ alkyl;
each occurrence of $R^{2'}$ is independently selected from the group consisting of H, OH, $C_{1-6}$ alkyl, $C_{1-6}$ alkoxy, $C_{1-6}$ alkylamino and $NH_2$;
m6 is 0, 1, 2, 3 or 4; and
$Y_1$ is $CH_2$ or

.

Embodiment 11. The method or use of any one of Embodiments 1-10, wherein the compound is of any one of Formula I to Formula VI,

I

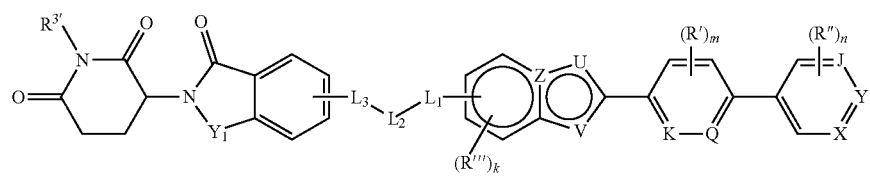

II

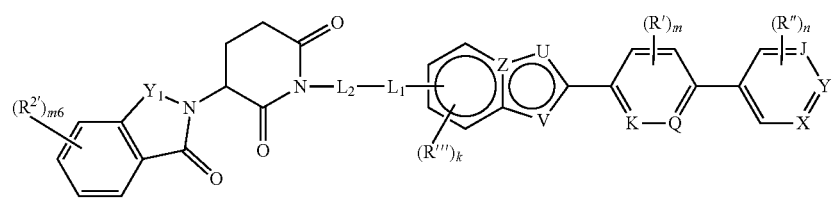

III

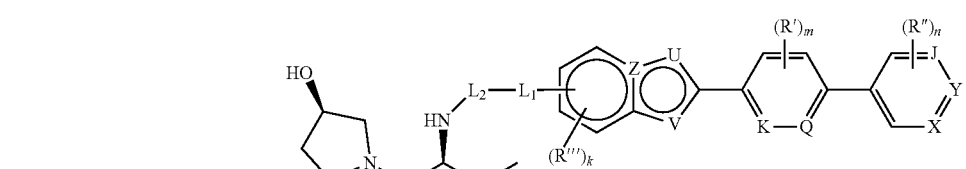

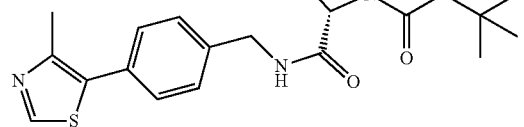

IV

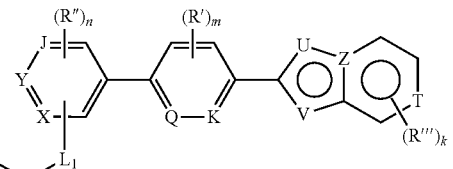

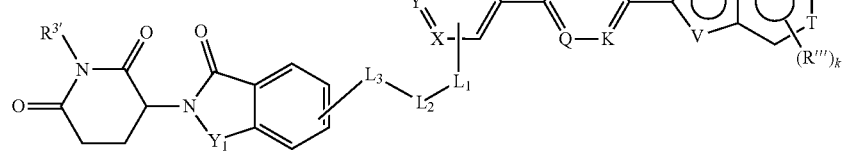

V

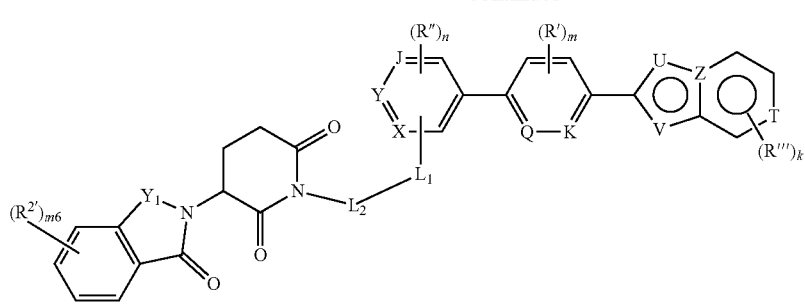

VI

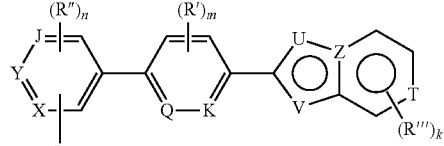

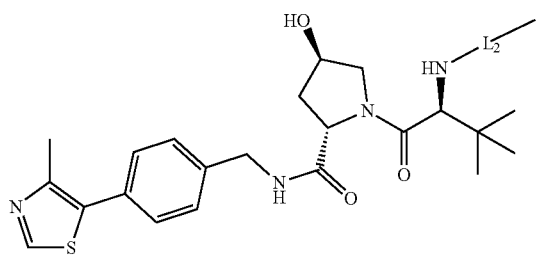

or the pharmaceutical acceptable salt, the enantiomer, the non-enantiomer, the tautomer, the racemate, the solvate, the metabolic precursor, or the prodrug thereof; wherein, $L_1$ is a bond, —C(=O)—, —NR—, —O—, or —S—, wherein R is hydrogen, optionally substituted acyl, optionally substituted alkyl or a nitrogen protecting group;

$L_2$ is a substituted or unsubstituted $C_{1-50}$ hydrocarbon chain, optionally wherein one or more chain atoms of the hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group;

Z is C or N; U is O, S or CH;

K is CH or N; Q is CH or N; where K and Q are not N at the same time;

each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3;

each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;

each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;

J is $CR^6$ or N; X is $CR^6$ or N; Y is $CR^6$ or N; where at least one of J, X and Y is N, but J and Y are not N at the same time, X and Y are not N at the same time;

$R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula I, $L_3$ is a bond, —NR—, —O—, or —S—, wherein R is hydrogen, optionally substituted acyl, optionally substituted alkyl or a nitrogen protecting group; $R^{3'}$ is H or $C_{1-6}$ alkyl; $Y_1$ is $CH_2$ or

V is N, where Z and U are not heteroatoms at the same time;
in Formula II, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

V is N, where Z and U are not heteroatoms at the same time;
in Formula III, V is N, where Z and U are not heteroatoms at the same time;
in Formula IV, $L_3$ is a bond, —NR—, —O—, or —S—, wherein R is hydrogen, optionally substituted acyl, optionally substituted alkyl or a nitrogen protecting group; $R^{3'}$ is H or $C_{1-6}$ alkyl; $Y_1$ is $CH_2$ or

V is N or NH; T is CH or N; where up to two of U, Z, V and T contain heteroatoms;
in Formula V, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

V is N or NH; T is CH or N; where up to two of U, Z, V and T contain heteroatoms;

in Formula VI, V is N; T is CH or N; where up to two of U, Z, V and T contain heteroatoms.

Embodiment 12. The method or use of Embodiment 11, wherein $L_2$ is an optionally substituted $C_{1-45}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group;

preferably, $L_2$ is a substituted or unsubstituted $C_{5-40}$ hydrocarbon chain;

preferably, $L_2$ is a substituted or unsubstituted $C_{1-30}$, $C_{1-24}$, or $C_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group;

preferably, $L_2$ is an unsubstituted $C_{1-26}$, $C_{5-26}$, $C_{5-20}$, $C_{5-15}$, $C_{15-20}$, or $C_{20-25}$ hydrocarbon chain, wherein one or more chain atoms of the hydrocarbon chain are independently replaced with —C(=O)—, —O— or —NR$^{a1}$—, wherein R$^{a1}$ is independently hydrogen, substituted or unsubstituted $C_{1-6}$ alkyl or a nitrogen protecting group.

Embodiment 13. The method or use of Embodiment 11, wherein $L_2$ is an optionally substituted $C_{1-30}$ hydrocarbon chain, wherein one or more chain atoms of the hydrocarbon chain are independently replaced with —O— or —NR$^{a1}$—, wherein R$^{a1}$ is independently hydrogen, substituted or unsubstituted $C_{1-6}$ alkyl or a nitrogen protecting group;

preferably, at least one chain atom of the hydrocarbon chain of $L_2$ is independently replaced with —C(=O)—, —O—, —S—, —NR$^{a1}$—, —N= or =N—, wherein R$^{a1}$ is independently hydrogen, substituted or unsubstituted $C_{1-6}$ alkyl or a nitrogen protecting group; preferably replaced with —O—.

Embodiment 14. The method or use of Embodiment 11, wherein $L_2$ is selected from the group consisting of substituted or unsubstituted carbocyclylene, substituted or unsubstituted heterocyclylene, substituted or unsubstituted arylene, substituted or unsubstituted heteroarylene, or substituted or unsubstituted heteroalkylene, and combinations thereof;

preferably, $L_2$ is selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof.

Embodiment 15. The method or use of Embodiment 14, wherein the carbocyclylene or the heterocyclylene is

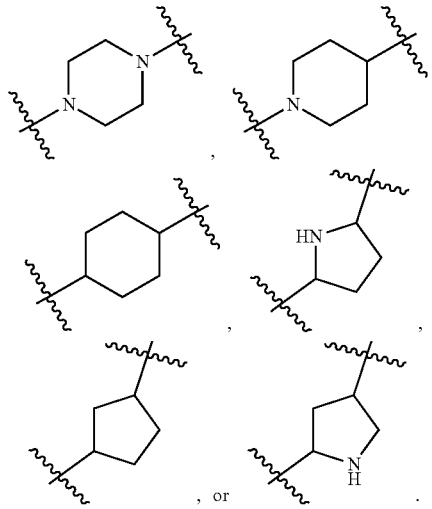

Embodiment 16. The method or use of Embodiment 14, wherein $L_2$ comprises at least one instance selected from the group consisting of substituted or unsubstituted $C_{1-6}$ alkylene, substituted or unsubstituted $C_{2-6}$ alkenylene, substituted or unsubstituted $C_{2-6}$ alkynylene, substituted or unsubstituted heteroC$_{1-6}$alkylene, substituted or unsubstituted heteroC$_{2-6}$alkenylene, substituted or unsubstituted heteroC$_{2-6}$alkynylene, substituted or unsubstituted $C_{3-6}$carbocyclylene, substituted or unsubstituted 3-6 membered heterocyclylene, substituted or unsubstituted phenylene, and substituted or unsubstituted 5- to 6-membered heteroarylene.

Embodiment 17. The method or use of Embodiment 14, wherein $L_2$ comprises at least one instance selected from the group consisting of substituted or unsubstituted methylene, ethylene, n-propylene, n-butylene, n-pentylene, n-hexylene, —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$O—, —O(CH$_2$)$_5$—, —(CH$_2$)$_5$O—, —O(CH$_2$)$_6$—, —O(CH$_2$)$_6$O—, —C(=O)O—, —O—C(=O)—, —NH—C(=O)— and —C(=O)NH—.

Embodiment 18. The method or use of Embodiment 14, wherein at least one chain atom of the hydrocarbon chain of $L_2$ is independently replaced with a 6-membered heterocyclyl group with 1-3 ring heteroatoms selected from the group consisting of nitrogen and oxygen;

preferably, at least one chain atom of the hydrocarbon chain of $L_2$ is independently replaced with piperidine, piperazine or morpholine;

preferably, at least one chain atom of the hydrocarbon chain of $L_2$ is independently replaced with an optionally substituted phenyl group.

Embodiment 19. The method or use of Embodiment 14, wherein $L_2$ is an unsubstituted hydrocarbon chain, optionally wherein one or more chain atoms of the hydrocarbon chain are independently replaced with —NR$^{a1}$—, and each instance of R$^{a1}$ is independently hydrogen, substituted or unsubstituted $C_{1-6}$ alkyl or a nitrogen protecting group, or optionally two instances of R$^a$ are taken together with their intervening atoms to form a substituted or unsubstituted heterocyclic or substituted or unsubstituted heteroaryl ring.

Embodiment 20. The method or use of Embodiment 19, wherein at least one instance of $R^{a1}$ is hydrogen, substituted or unsubstituted $C_{1-6}$ alkyl (e.g., substituted or unsubstituted methyl or ethyl), or a nitrogen protecting group (e.g., benzyl, t-butyl carbonate, benzyl carbamate, 9-fluorenylmethyl carbonate, trifluoroacetyl, triphenylmethyl, acetyl or p-toluenesulfonamide).

Embodiment 21. The method or use of Embodiment 11, wherein $L_2$ is

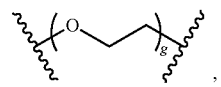

wherein g is 1, 2, 3, 4, 5, or 6.

Embodiment 22. The method or use of Embodiment 11, wherein $L_2$ includes the moiety —O—,

—NHC(=O)— or —NH—.

Embodiment 23. The method or use of Embodiment 11, wherein $L_2$ is selected from the group consisting of

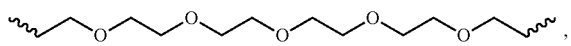

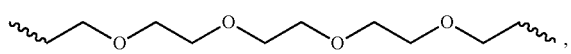

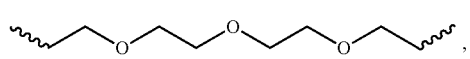

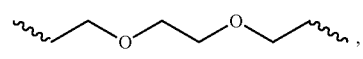

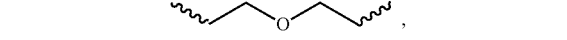

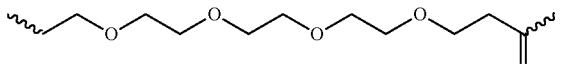

-continued

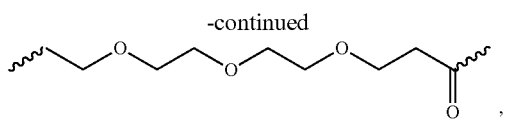

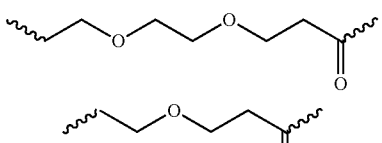

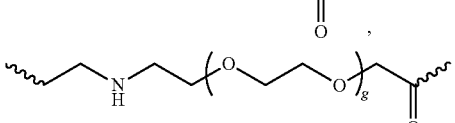

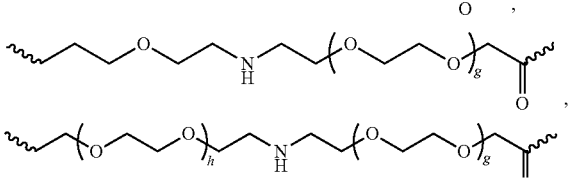

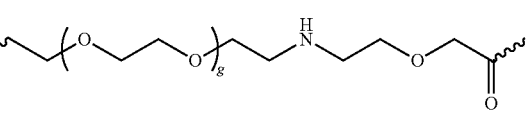

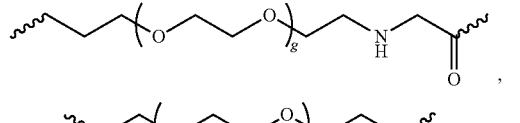

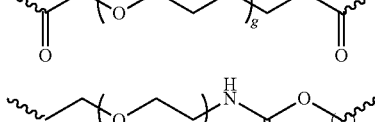

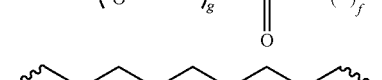

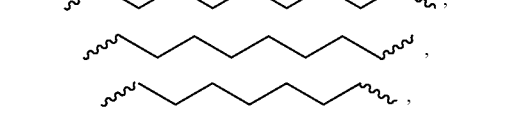

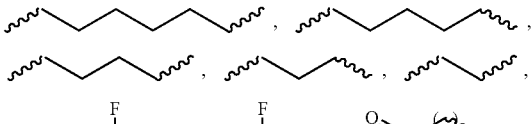

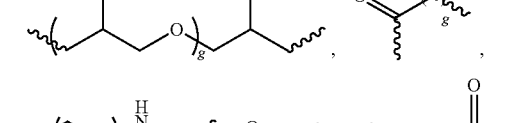

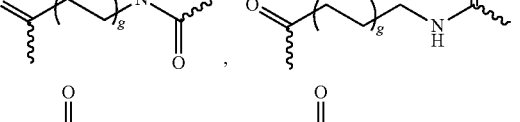

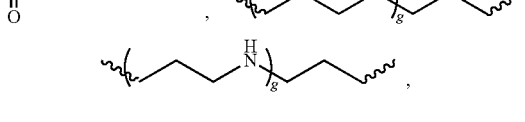

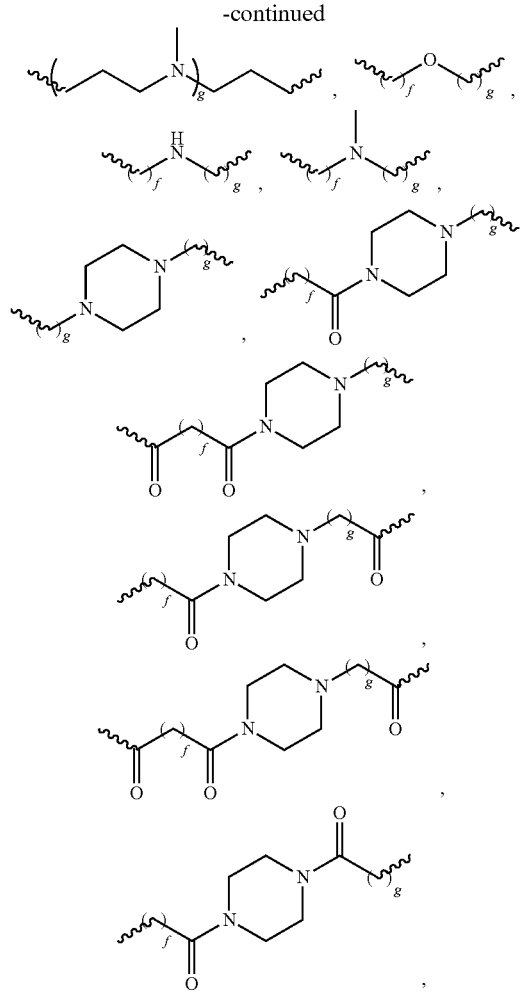

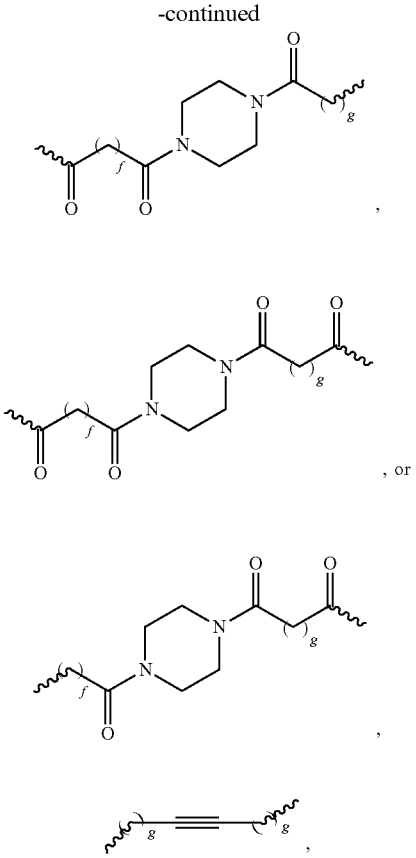

wherein each g is independently 1, 2, 3, 4, 5, or 6; f is 1, 2, 3, 4, 5, or 6, and h is 1, 2, 3, 4, 5, or 6.

Embodiment 24. The method or use of Embodiment 11, wherein the compound of Formula I is of Formula I-1;

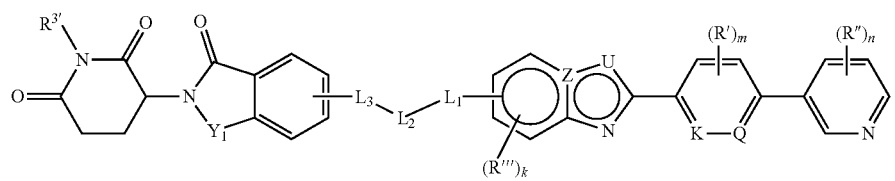

I-1 or the pharmaceutical acceptable salt, the enantiomer, the non-enantiomer, the tautomer, the racemate, the solvate, the metabolic precursor, or the prodrug thereof.

Embodiment 25. The method or use of Embodiment 11, wherein the compound of Formula II is of Formula II-1;

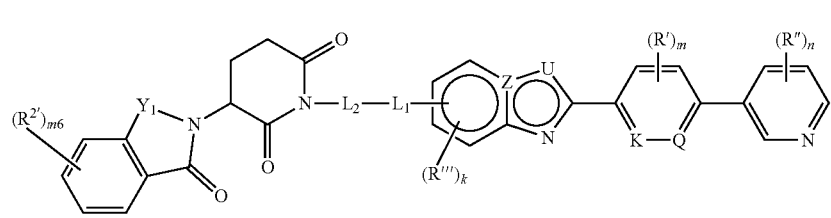

II-1 or the pharmaceutical acceptable salt, the enantiomer, the non-enantiomer, the tautomer, the racemate, the solvate, the metabolic precursor, or the prodrug thereof.

Embodiment 26. The method or use of Embodiment 11, wherein the compound of Formula III is of Formula III-1;

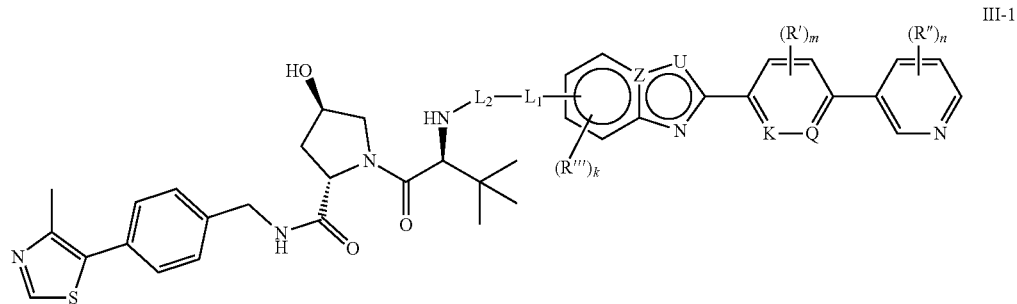

III-1 or the pharmaceutical acceptable salt, the enantiomer, the non-enantiomer, the tautomer, the racemate, the solvate, the metabolic precursor, or the prodrug thereof.

Embodiment 27. The method or use of Embodiment 11, wherein the compound of Formula IV is of Formula IV-1;

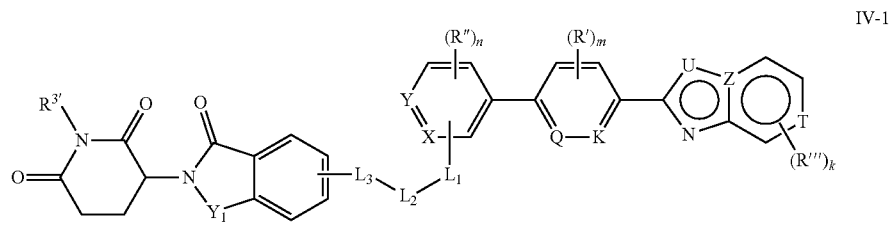

IV-1 or the pharmaceutical acceptable salt, the enantiomer, the non-enantiomer, the tautomer, the racemate, the solvate, the metabolic precursor, or the prodrug thereof.

Embodiment 28. The method or use of Embodiment 11, wherein the compound of Formula V is of Formula V-1;

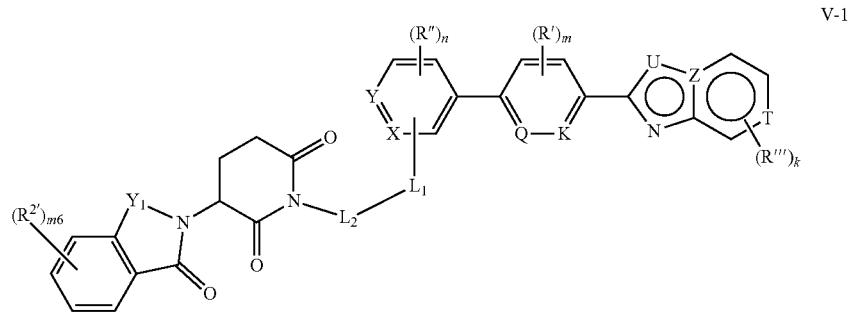

V-1 or the pharmaceutical acceptable salt, the enantiomer, the non-enantiomer, the tautomer, the racemate, the solvate, the metabolic precursor, or the prodrug thereof.

Embodiment 29. The method or use of Embodiment 11, wherein the compound of Formula VI is of Formula VI-1;

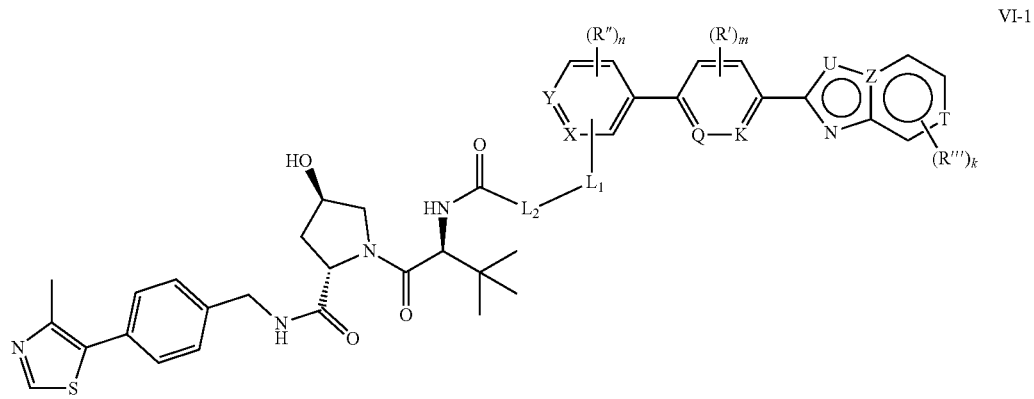

VI-1 or the pharmaceutical acceptable salt, the enantiomer, the non-enantiomer, the tautomer, the racemate, the solvate, the metabolic precursor, or the prodrug thereof.

Embodiment 30. The method or use of Embodiment 24, wherein the compound of Formula I-1 is of Formula 1, 5, 6, 8, 10 or 13;

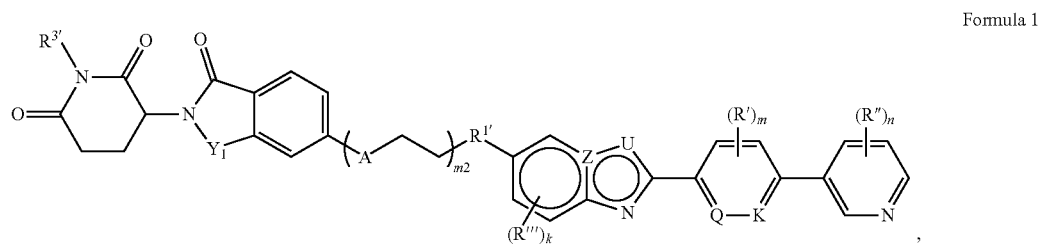

Formula 1

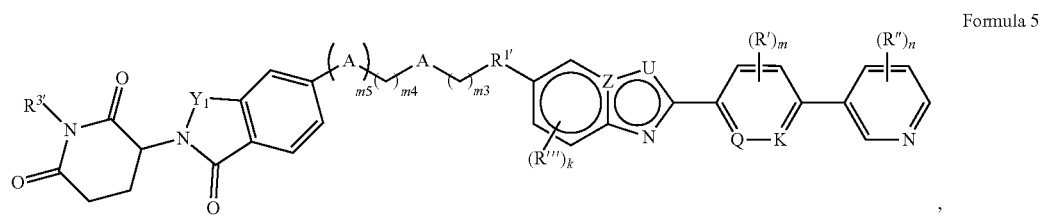

Formula 5

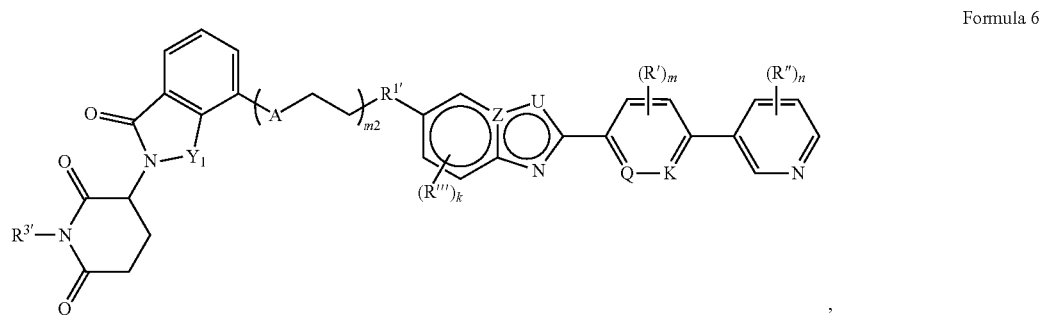

Formula 6

-continued

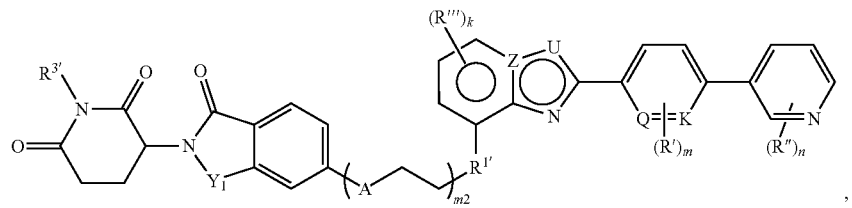

Formula 8

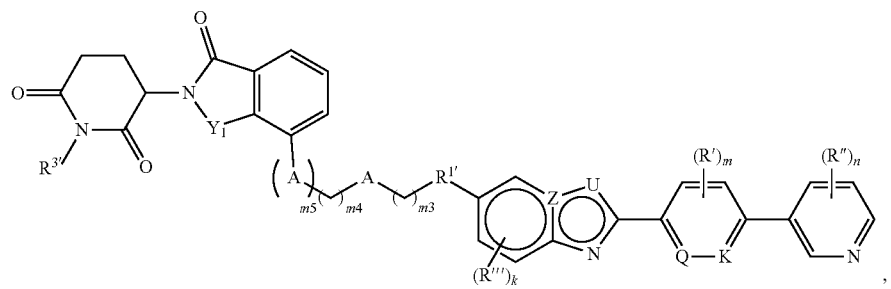

Formula 10

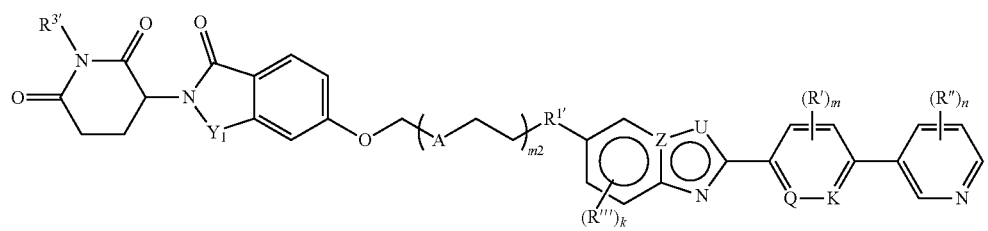

Formula 13 or the pharmaceutical acceptable salt, the enantiomer, the non-enantiomer, the tautomer, the racemate, the solvate, the metabolic precursor, or the prodrug thereof; wherein each A is independently O, NH,

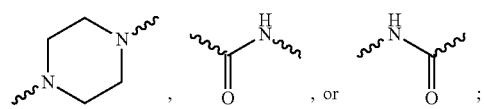

m2 is 1, 2, 3, 4, 5, 6, or 7;
m3 is 1, 2, 3, 4, 5, or 6;
m4 is 0, 1, 2, or 3;
m5 is 0, 1, 2, or 3; and
$R^{1'}$ is O, NH,

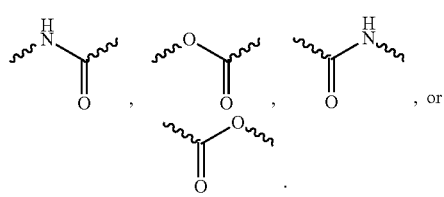

Embodiment 31. The method or use of Embodiment 30, wherein the compound is of Formula 1, and wherein R' is H, $C_{1-3}$ haloalkyl or $C_{1-3}$ alkoxy; and/or, R'' is H, halo, OH, $NH_2$, $C_{1-3}$ alkoxy, $C_{1-3}$ alkylamino, $C_{3-5}$ cycloalkyl, $C_{3-5}$ cycloalkylamino and $C_{3-5}$ heterocycloalkyl; and/or, R''' is H, OH or halogen; and/or, R'' is O, NH,

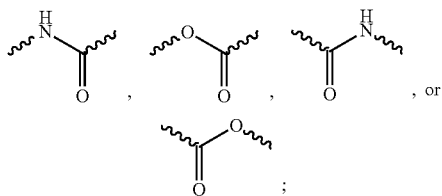

and/or, A is O, NH,

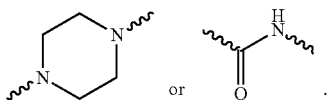

and/or, m2 is 2, 3, 4 or 6; and/or, $R^{3'}$ is H or $C_{1-3}$ alkyl; or the pharmaceutical acceptable salt, the enantiomer, the non-enantiomer, the tautomer, the racemate, the solvate, the metabolic precursor, or the prodrug thereof.

Embodiment 32. The method or use of Embodiment 30, wherein the compound is of Formula 5, and wherein $R^{3'}$ is H or $C_{1-3}$ alkyl; and/or, each A is independently O, NH,

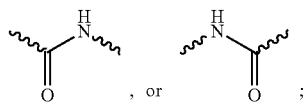

and/or, m4 is 0, 1, 2, or 3; and/or, m5 is 0, 1, 2 or 3; and/or, m3 is 1, 2, 3, 4, 5 or 6; and/or, $R^{1'}$ is O, NH or

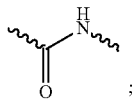

and/or, R''' is H, OH, $C_{1-3}$ alkyl, $C_{1-3}$ alkoxy or halogen; and/or, R' is H, halogen, OH, $C_{1-3}$ alkyl, $C_{1-3}$ haloalkyl or $C_{1-3}$ alkoxy; and/or, m is 0, 1, 2 or 3; and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; or the pharmaceutical acceptable salt, the enantiomer, the non-enantiomer, the tautomer, the racemate, the solvate, the metabolic precursor, or the prodrug thereof.

Embodiment 33. The method or use of Embodiment 30, wherein the compound is of Formula 6, and wherein $R^{3'}$ is H or $C_{1-3}$ alkyl; and/or, A is O, NH or

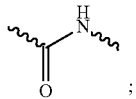

and/or, m2 is 1, 2, 3, 4, 5, 6 or 7; and/or, $R^{1'}$ is O, NH or

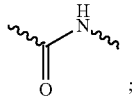

and/or, R''' is H, OH, $C_{1-3}$ alkyl, $C_{1-3}$ alkoxy or halogen; and/or, R' is H, halogen, OH, $C_{1-3}$ alkyl, $C_{1-3}$ haloalkyl or $C_{1-3}$ alkoxy; and/or, m is 0, 1, 2 or 3; and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, n is 0 or 1; or the pharmaceutical acceptable salt, the enantiomer, the non-enantiomer, the tautomer, the racemate, the solvate, the metabolic precursor, or the prodrug thereof.

Embodiment 34. The method or use of Embodiment 30, wherein the compound is of Formula 8, and wherein $R^{3'}$ is H or $C_{1-3}$ alkyl; and/or, A is O, NH,

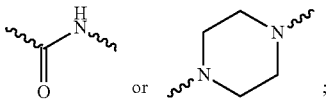

and/or, m2 is 1, 2, 3 or 4; and/or, $R^{1'}$ is O, NH,

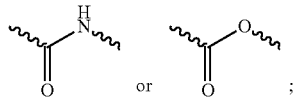

and/or, R''' is H, OH, $C_{1-3}$ alkyl, $C_{1-3}$ alkoxy or halogen; and/or, k is 0 or 1; and/or, R' is H, halogen, OH, $C_{1-3}$ alkyl, $C_{1-3}$ haloalkyl or $C_{1-3}$ alkoxy; and/or, m is 0, 1 or 2; and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, n is 0, 1 or 2; or the pharmaceutical acceptable salt, the enantiomer, the non-enantiomer, the tautomer, the racemate, the solvate, the metabolic precursor, or the prodrug thereof.

Embodiment 35. The method or use of Embodiment 30, wherein the compound is of Formula 10, and wherein $R^{3'}$ is H or $C_{1-3}$ alkyl; and/or, each A is independently O, NH,

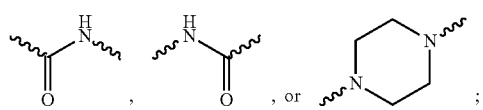

and/or, m5 is 0 or 1; and/or, m4 is 0 or 1; and/or, m3 is 1, 2, 3, 4 or 5; and/or, $R^{1'}$ is O, NH,

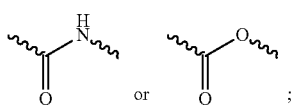

and/or, R''' is H, OH, $C_{1-3}$ alkyl, $C_{1-3}$ alkoxy or halogen; and/or, k is 0 or 1; and/or, R' is H, halogen, OH, $C_{1-3}$ alkyl, $C_{1-3}$ haloalkyl or $C_{1-3}$ alkoxy; and/or, m is 0 or 1; and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, n is 0 or 1; or the pharmaceutical acceptable salt, the enantiomer, the non-enantiomer, the tautomer, the racemate, the solvate, the metabolic precursor, or the prodrug thereof.

Embodiment 36. The method or use of Embodiment 30, wherein the compound is of Formula 13, and wherein $R^{3'}$ is H or $C_{1-3}$ alkyl; and/or, A is O, NH,

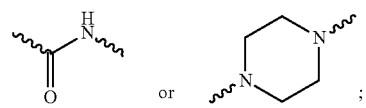

and/or, m2 is 1, 2, 3 or 4; and/or, $R^{1'}$ is O, NH,

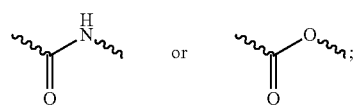

and/or, R''' is H, OH, $C_{1-3}$ alkyl, $C_{1-3}$ alkoxy or halogen; and/or, R' is H, halogen, OH, $C_{1-3}$ alkyl, $C_{1-3}$ haloalkyl or $C_{1-3}$ alkoxy; and/or, m is 0, 1, 2 or 3; and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; or the pharmaceutical acceptable salt, the enantiomer, the non-enantiomer, the tautomer, the racemate, the solvate, the metabolic precursor, or the prodrug thereof.

Embodiment 37. The method or use of Embodiment 30, wherein the compound of Formula 1 is of Formula 1-1;

Formula 1-1

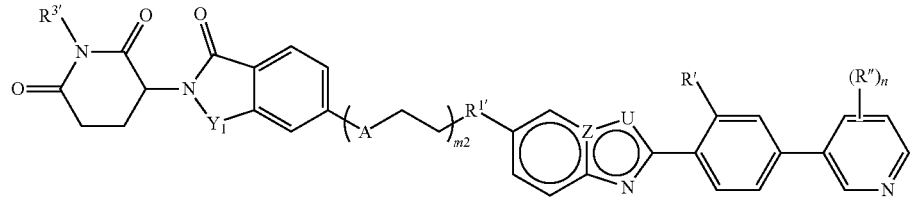

or the pharmaceutical acceptable salt, the enantiomer, the non-enantiomer, the tautomer, the racemate, the solvate, the metabolic precursor, or the prodrug thereof.

Embodiment 38. The method or use of Embodiment 30, wherein the compound of Formula 5 is of Formula 5-1;

Formula 5-1

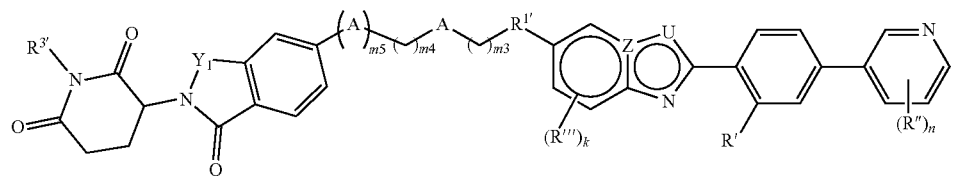

or the pharmaceutical acceptable salt, the enantiomer, the non-enantiomer, the tautomer, the racemate, the solvate, the metabolic precursor, or the prodrug thereof.

Embodiment 39. The method or use of Embodiment 30, wherein the compound of Formula 6 is of Formula 6-1;

Formula 6-1

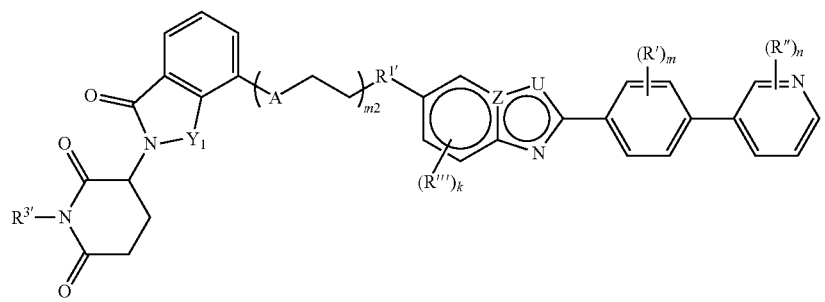

or the pharmaceutical acceptable salt, the enantiomer, the non-enantiomer, the tautomer, the racemate, the solvate, the metabolic precursor, or the prodrug thereof.

Embodiment 40. The method or use of Embodiment 37, wherein $R^{3'}$ is H or $C_{1-3}$ alkyl; A is O, NH,

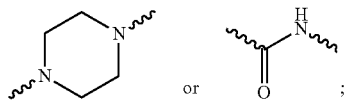

m2 is 1, 2, 3, 4, 5, 6 and 7; $R^{1'}$ is O, NH,

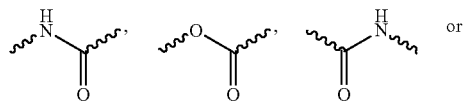

R' is H, $C_{1-3}$ haloalkyl or $C_{1-3}$ alkoxy; R" is H, F, Cl, OH, $NH_2$, $C_{1-3}$ alkoxy, methylamino, dimethylamino, diethylamino or cyclopropylamino.

Embodiment 41. The method or use of Embodiment 38, wherein $R^{3'}$ is H or $C_{1-3}$ alkyl; A is O, NH,

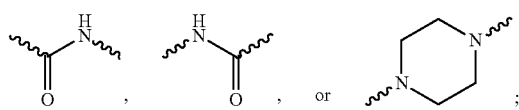

m5 is 0 or 1; m4 is 0, 1, 2, 3 or 4; m3 is 1, 2, 3, 4, 5 or 6; $R^{1'}$ is O, NH,

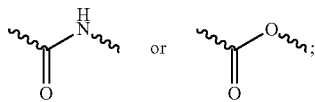

R''' is H, OH, $C_{1-3}$ alkyl, $C_{1-3}$ alkoxy or halogen; R' is H, halogen, OH, $C_{1-3}$ alkyl, $C_{1-3}$ haloalkyl or $C_{1-3}$ alkoxy; R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino and $C_{3-5}$ heterocycloalkyl.

Embodiment 42. The method or use of Embodiment 39, wherein $R^{3'}$ is H or $C_{1-3}$ alkyl; A is O, NH,

m2 is 1, 2, 3, 4, 5, 6 or 7; $R^{1'}$ is O, NH,

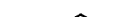

R''' is H, OH, $C_{1-3}$ alkyl, $C_{1-3}$ alkoxy or halogen; R' is H, halogen, OH, $C_{1-3}$ alkyl, $C_{1-3}$ haloalkyl or $C_{1-3}$ alkoxy; m is 0, 1, 2 or 3; R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl.

Embodiment 43. The method or use of Embodiment 30, wherein the compound is of Formula 1, 5, 6, 8, 10 or 13, and wherein K is CH and Q is N, or K is N and Q is CH, or both of K and Q are CH; or the pharmaceutical acceptable salt, the enantiomer, the non-enantiomer, the tautomer, the racemate, the solvate, the metabolic precursor, or the prodrug thereof.

Embodiment 44. The method or use of Embodiment 25, wherein the compound is of Formula 3;

Formula 3

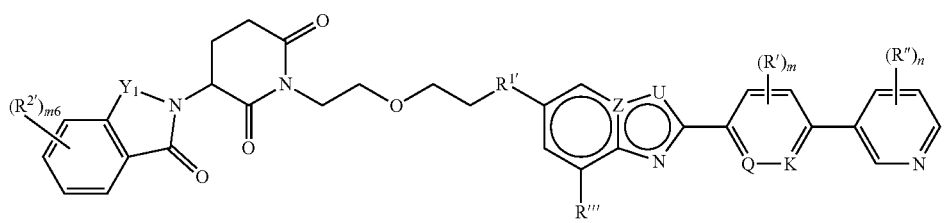

wherein $R^{1'}$ is O, NH,

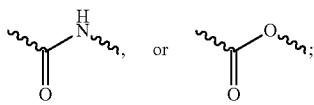

or the pharmaceutical acceptable salt, the enantiomer, the non-enantiomer, the tautomer, the racemate, the solvate, the metabolic precursor, or the prodrug thereof.

Embodiment 45. The method or use of Embodiment 44, wherein $R^2$, is H, OH, $C_{1-3}$ alkyl, $C_{1-3}$ alkoxy, $C_{1-3}$ alkylamino or $NH_2$; and/or, m6 is 0, 1, 2 or 3; and/or, $R^{1'}$ is O or NH; and/or, R' is H, halogen, OH, $C_{1-3}$ alkyl, $C_{1-3}$ haloalkyl or $C_{1-3}$ alkoxy; and/or, R" is H, halo, OH, $NH_2$, $C_{1-3}$ alkoxy, $C_{3-5}$ cycloalkyl, $C_{3-5}$ cycloalkylamino or $C_{1-3}$ alkylamino; and/or, R''' is H, OH, $C_{1-3}$ alkyl, $C_{1-3}$ alkoxy or halogen.

Embodiment 46. The method or use of Embodiment 44, wherein Z is C and U is O or S; or Z is N and U is CH; and/or, K is CH and Q is N, or K is N and Q is CH, or both of K and Q are CH.

Embodiment 47. The method or use of Embodiment 44, wherein the compound is of Formula 3-1;

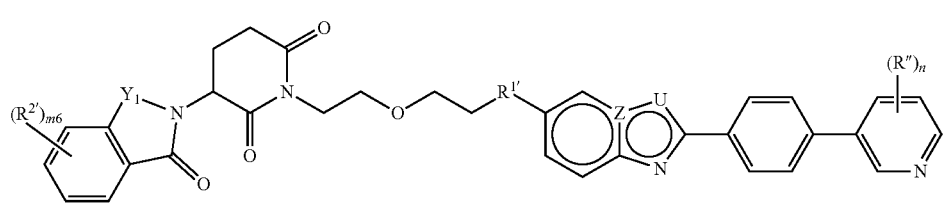

Formula 3-1 or the pharmaceutical acceptable salt, the enantiomer, the non-enantiomer, the tautomer, the racemate, the solvate, the metabolic precursor, or the prodrug thereof.

Embodiment 48. The method or use of Embodiment 47, wherein $R^{2'}$ is H, OH, $C_{1-3}$ alkyl, $C_{1-3}$ alkoxy, $C_{1-3}$ alkylamino or $NH_2$; m6 is 0, 1, 2 or 3; $R^{1'}$ is O, NH,

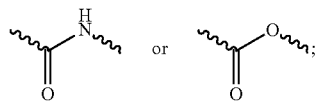

R" is H, halo, OH, $NH_2$, $C_{1-3}$ alkoxy, $C_{1-3}$ haloalkyl, $C_{3-5}$ cycloalkyl, $C_{3-5}$ cycloalkylamino or $C_{1-3}$ alkylamino.

Embodiment 49. The method or use of Embodiment 26, wherein the compound is of Formula 15;

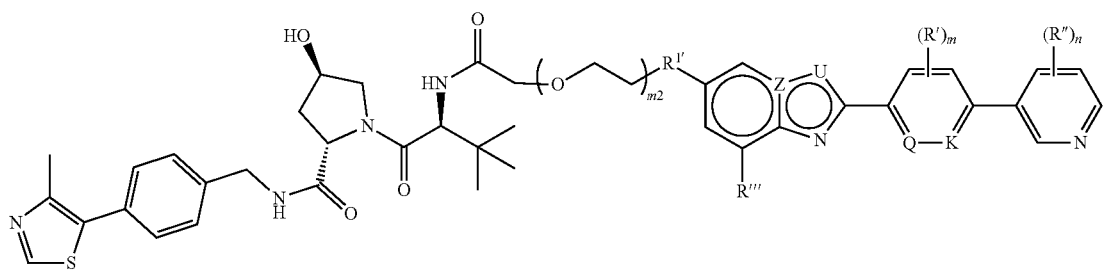

Formula 15 wherein m2 is 1, 2, 3, 4, 5, 6, or 7; and R$^{1'}$ is O, NH,

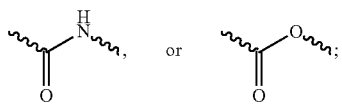

or the pharmaceutical acceptable salt, the enantiomer, the non-enantiomer, the tautomer, the racemate, the solvate, the metabolic precursor, or the prodrug thereof.

Embodiment 50. The method or use of Embodiment 49, wherein m2 is 1, 2, 3, 4, 5, 6 or 7; and/or, R$^{1'}$ is O, NH,

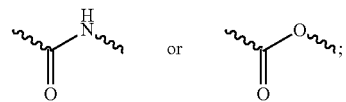

and/or, R''' is H, OH, C$_{1-3}$ alkyl, C$_{1-3}$ alkoxy or halogen; and/or, R' is H, halogen, OH, C$_{1-3}$ alkyl, C$_{1-3}$ haloalkyl or C$_{1-3}$ alkoxy; m is 0, 1, 2 or 3; and/or, R'' is H, halo, OH, NH$_2$, C$_{1-3}$ alkoxy, C$_{3-5}$ cycloalkyl, C$_{3-5}$ cycloalkylamino or C$_{1-3}$ alkylamino.

Embodiment 51. The method or use of Embodiment 27, wherein the compound is of Formula 2, 7, 9, 11, 12 or 14;

Formula 2

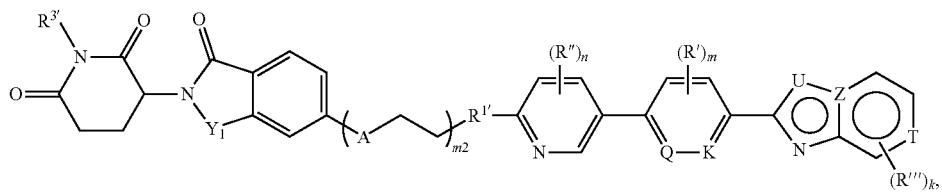

Formula 7

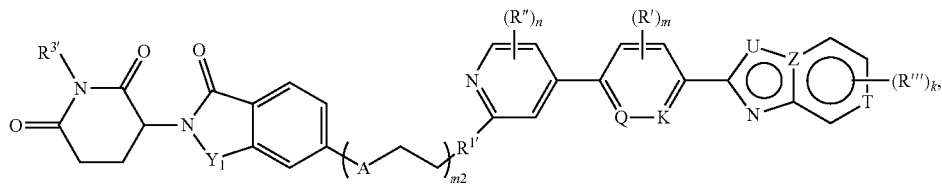

Formula 9

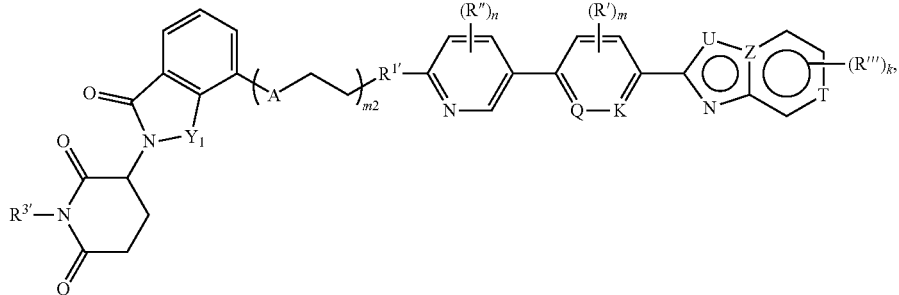

Formula 11

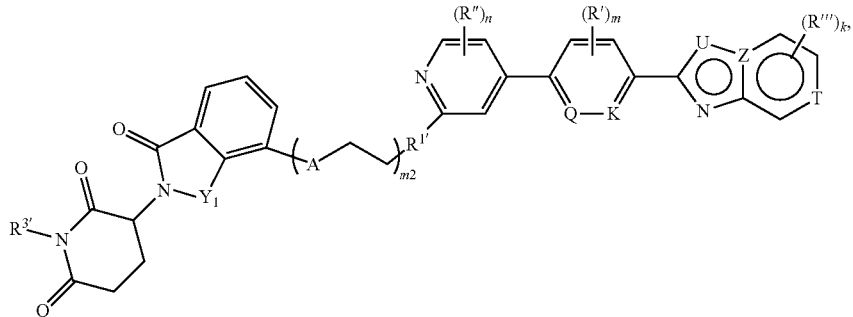

Formula 12

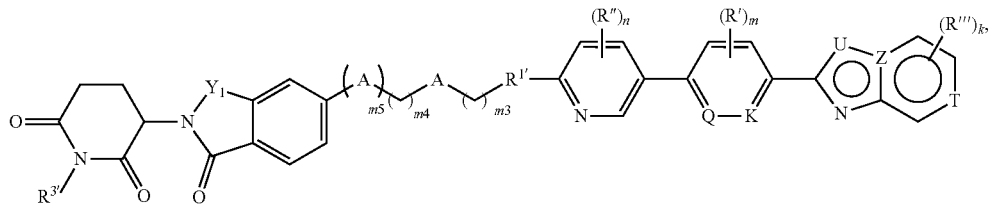

Formula 14

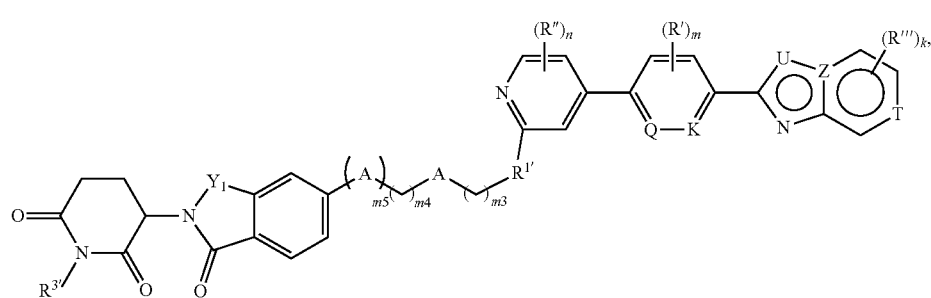

or the pharmaceutical acceptable salt, the enantiomer, the non-enantiomer, the tautomer, the racemate, the solvate, the metabolic precursor, or the prodrug thereof;
wherein
each A is independently O, NH,

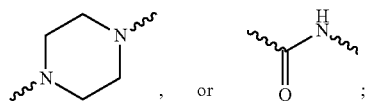

m2 is 2, 3, 4, 5, or 6;
m3 is 1, 2, 3, 4, 5, or 6;
m4 is 0, 1, 2, 3, or 4;
m5 is 0, 1, 2, or 3; and
$R^{1'}$ is O, NH,

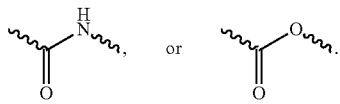

Embodiment 52. The method or use of Embodiment 51, wherein the compound is of Formula 2, and wherein $R^{3'}$ is H or $C_{1-3}$ alkyl; and/or, A is O, NH,

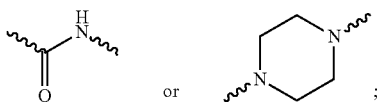

and/or, m2 is 2, 3, 4, 5 or 6; and/or, $R^{1'}$ is O, NH,

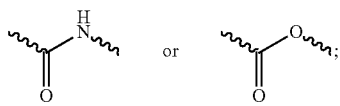

and/or, R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; and/or, R'" is H, OH, $NH_2$, $C_{1-3}$ alkyl, $C_{1-3}$ alkylamino, $C_{1-3}$ alkoxy or halogen; or the pharmaceutical acceptable salt, the enantiomer, the non-enantiomer, the tautomer, the racemate, the solvate, the metabolic precursor, or the prodrug thereof.

Embodiment 53. The method or use of Embodiment 51, wherein the compound is of Formula 7, and wherein $R^{3'}$ is H or $C_{1-3}$ alkyl; and/or, A is O, NH,

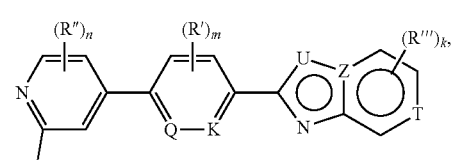

and/or, m2 is 2, 3, 4, 5 or 6; and/or, $R^{1'}$ is O, NH,

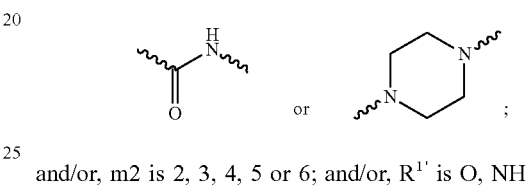

and/or, R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; or the pharmaceutical acceptable salt, the enantiomer, the non-enantiomer, the tautomer, the racemate, the solvate, the metabolic precursor, or the prodrug thereof.

Embodiment 54. The method or use of Embodiment 51, wherein the compound is of Formula 9, and wherein $R^{3'}$ is H or $C_{1-3}$ alkyl; and/or, A is O, NH,

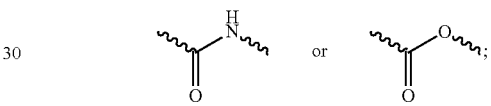

and/or, m2 is 2, 3, 4, 5 or 6; and/or, $R^{1'}$ is O, NH,

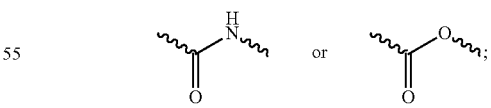

and/or, R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; and/or, R'" is H, OH, $NH_2$, $C_{1-3}$ alkyl, $C_{1-3}$ alkylamino, $C_{1-3}$ alkoxy or halogen; or the pharmaceutical acceptable salt, the enantiomer, the non-enantiomer, the tautomer, the racemate, the solvate, the metabolic precursor, or the prodrug thereof.

Embodiment 55. The method or use of Embodiment 51, wherein the compound is of Formula 11, and wherein $R^{3'}$ is H or $C_{1-3}$ alkyl; and/or, A is O, NH,

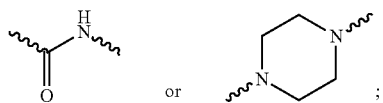

and/or, m2 is 2, 3, 4, 5 or 6; and/or, $R^{1'}$ is O, NH,

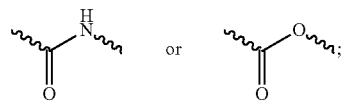

and/or, R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; and/or, R'" is H, OH, $NH_2$, $C_{1-3}$ alkyl, $C_{1-3}$ alkylamino, $C_{1-3}$ alkoxy or halogen; or the pharmaceutical acceptable salt, the enantiomer, the non-enantiomer, the tautomer, the racemate, the solvate, the metabolic precursor, or the prodrug thereof.

Embodiment 56. The method or use of Embodiment 51, wherein the compound is of Formula 12, and wherein $R^{3'}$ is H or $C_{1-3}$ alkyl; each A is independently O, NH,

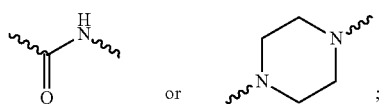

m3 is 1, 2, 3, 4, 5 or 6; m4 is 0 or 1, 2 or 3; m5 is 0 or 1, 2 or 3; $R^{1'}$ is O, NH,

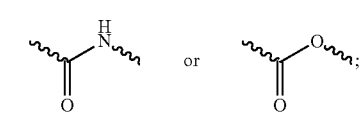

R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; R' is H, halogen, OH, $C_{1-3}$ alkyl, $C_{1-3}$ haloalkyl or $C_{1-3}$ alkoxy; m is 0, 1, 2 or 3; R'" is H, OH, $NH_2$, $C_{1-3}$ alkyl, $C_{1-3}$ alkylamino, $C_{1-3}$ alkoxy or halogen; or the pharmaceutical acceptable salt, the enantiomer, the non-enantiomer, the tautomer, the racemate, the solvate, the metabolic precursor, or the prodrug thereof.

Embodiment 57. The method or use of Embodiment 51, wherein the compound is of Formula 14, and wherein $R^{3'}$ is H or $C_{1-3}$ alkyl; and/or, each A is independently O, NH,

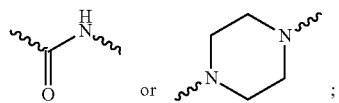

and/or, m3 is 1, 2, 3, 4, 5 or 6; and/or, m4 is 0, 1, 2, 3 or 4; and/or, m5 is 0 or 1, 2 or 3; and/or, $R^{1'}$ is O, NH,

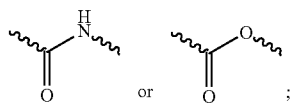

and/or, R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; m is 0, 1, 2 or 3; and/or, R'" is H, OH, $NH_2$, $C_{1-3}$ alkyl, $C_{1-3}$ alkylamino, $C_{1-3}$ alkoxy or halogen; or the pharmaceutical acceptable salt, the enantiomer, the non-enantiomer, the tautomer, the racemate, the solvate, the metabolic precursor, or the prodrug thereof.

Embodiment 58. The method or use of Embodiment 28, wherein the compound is of Formula 4;

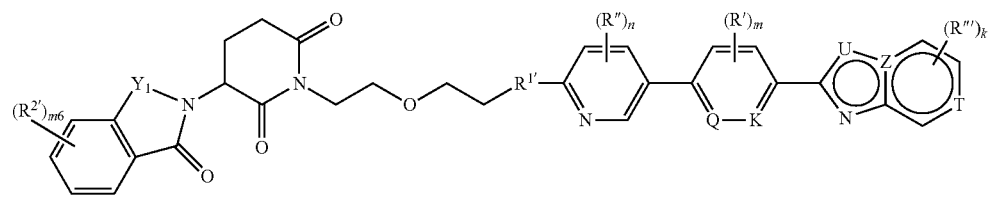

Formula 4 wherein $R^{1'}$ is O, NH,

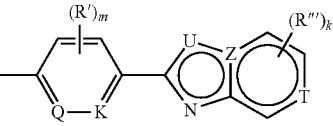

or the pharmaceutical acceptable salt, the enantiomer, the non-enantiomer, the tautomer, the racemate, the solvate, the metabolic precursor, or the prodrug thereof.

Embodiment 59. The method or use of Embodiment 58, wherein $R^{2'}$ is H, OH, $C_{1-3}$ alkyl, $C_{1-3}$ alkoxy, $C_{1-3}$ alkylamino or $NH_2$; and/or, m6 is 0, 1, 2 or 3; and/or, $R^{1'}$ is O, NH,

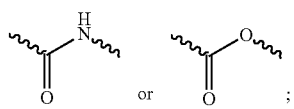

and/or, R' is H, halogen, OH, $C_{1-3}$ alkyl, $C_{1-3}$ haloalkyl or $C_{1-3}$ alkoxy; R" is H, halo, OH, $NH_2$, $C_{1-3}$ alkoxy, $C_{3-5}$ cycloalkyl, $C_{3-5}$ cycloalkylamino or $C_{1-3}$ alkylamino; and/or, R''' is H, OH, $NH_2$, $C_{1-3}$ alkyl, $C_{1-3}$ alkylamino, $C_{1-3}$ alkoxy or halogen.

Embodiment 60. The method or use of Embodiment 58, wherein the compound is of Formula 4-1;

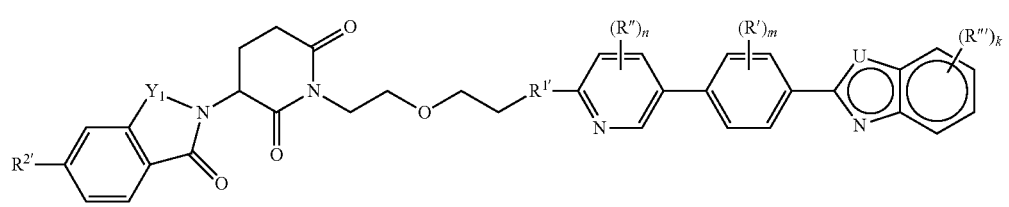

Formula 4-1 or the pharmaceutical acceptable salt, the enantiomer, the non-enantiomer, the tautomer, the racemate, the solvate, the metabolic precursor, or the prodrug thereof.

Embodiment 61. The method or use of Embodiment 29, wherein the compound is of Formula 16 or 17;

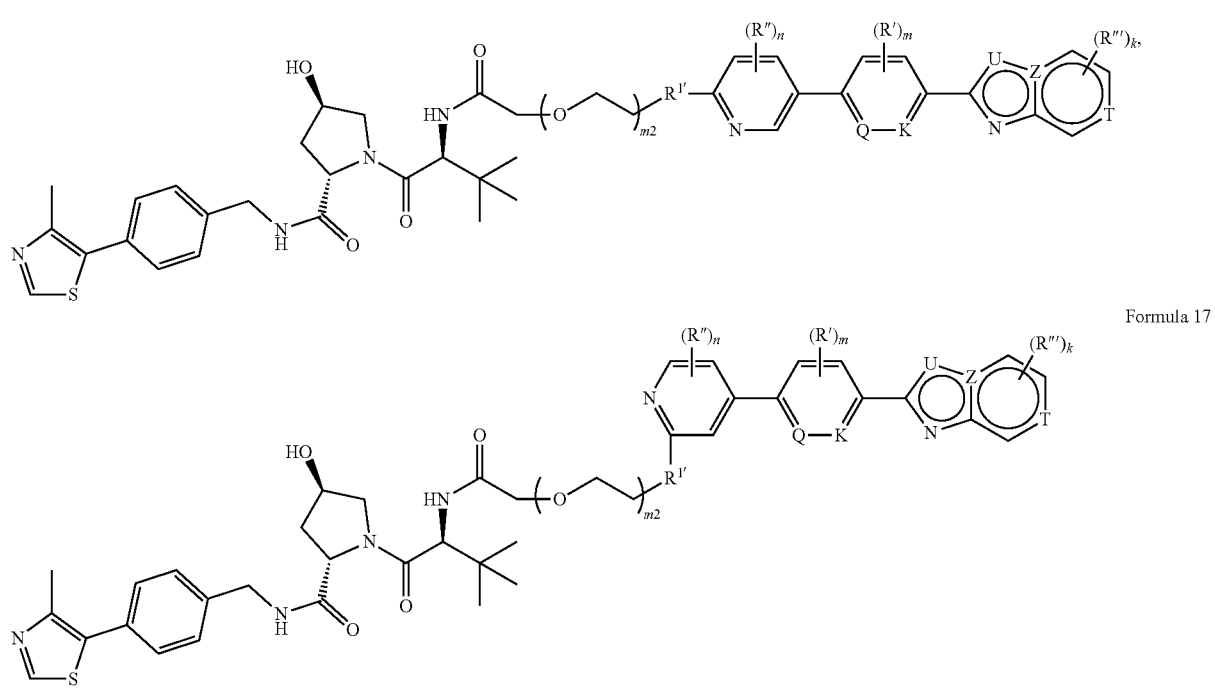

wherein m2 is 1, 2, 3, 4, 5, 6, or 7; and $R^{1'}$ is O, NH,

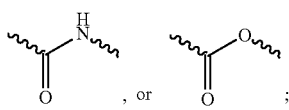, or or the pharmaceutical acceptable salt, the enantiomer, the non-enantiomer, the tautomer, the racemate, the solvate, the metabolic precursor, or the prodrug thereof.

Embodiment 62. The method or use of Embodiment 61, wherein the compound is of Formula 16, and wherein Z is C, U is O or S and T is CH; or, Z is N, U is CH and T is CH; Z is C, T is N and U is CH; or the pharmaceutical acceptable salt, the enantiomer, the non-enantiomer, the tautomer, the racemate, the solvate, the metabolic precursor, or the prodrug thereof.

Embodiment 63. The method or use of Embodiment 61, wherein the compound is of Formula 17, and wherein Z is C, U is O or S and T is CH; or, Z is N, U is CH and T is CH; Z is C, T is N and U is CH; or the pharmaceutical acceptable salt, the enantiomer, the non-enantiomer, the tautomer, the racemate, the solvate, the metabolic precursor, or the prodrug thereof.

Embodiment 64. The method or use of any one of Embodiments 1-7, wherein the compound is selected from the compounds listed in Table 2, or the pharmaceutical acceptable salt, the enantiomer, the non-enantiomer, the tautomer, the racemate, the solvate, the metabolic precursor, or the prodrug thereof.

Embodiment 65. A compound of Formula A:

EBM-L-SBM (Formula A)

or the pharmaceutical acceptable salt, the enantiomer, the non-enantiomer, the tautomer, the racemate, the solvate, the metabolic precursor, or the prodrug thereof, for treating synucleinopathy, wherein EBM is an E3 ubiquitin ligase binding moiety;

L is a linker covalently attached to EBM and SBM; and

SBM is an α-synuclein protein binding moiety of the formula:

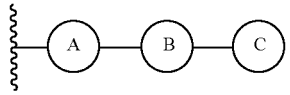

or a pharmaceutical acceptable salt, an enantiomer, a non-enantiomer, a tautomer, a racemate, a solvate, a metabolic precursor, a prodrug thereof,
wherein

is covalently linked to L; and
(i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
(ii)

is a substituted or unsubstituted monocyclic aromatic ring containing 0 to 2 ring heteroatoms selected from O, S, and N;

is a substituted or unsubstituted monocyclic aromatic ring containing 0 to 2 ring heteroatoms selected from O, S, and N; and

is a substituted or unsubstituted bicyclic fused aromatic ring containing at least 1 ring heteroatom selected from O, S, and N.

Embodiment 66. A compound of Formula A:

EBM-L-SBM   (Formula A)

or the pharmaceutical acceptable salt, the enantiomer, the non-enantiomer, the tautomer, the racemate, the solvate, the metabolic precursor, or the prodrug thereof, for reducing α-synuclein aggregation, wherein EBM is an E3 ubiquitin ligase binding moiety;

L is a linker covalently attached to EBM and SBM; and

SBM is an α-synuclein protein binding moiety of the formula:

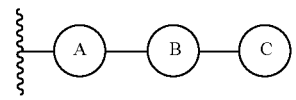

or a pharmaceutical acceptable salt, an enantiomer, a non-enantiomer, a tautomer, a racemate, a solvate, a metabolic precursor, a prodrug thereof,
wherein

is covalently linked to L; and
(i)

is a substituted or unsubstituted bicyclic fused aromatic ring containing at least 1 ring heteroatom selected from O, S, and N;

is a substituted or unsubstituted monocyclic aromatic ring containing 0 to 2 ring heteroatoms selected from O, S, and N; and

is a substituted or unsubstituted monocyclic aromatic ring containing 0 to 2 ring heteroatoms selected from O, S, and N; or
(ii)

(A)

is a substituted or unsubstituted monocyclic aromatic ring containing 0 to 2 ring heteroatoms selected from O, S, and N;

(B)

is a substituted or unsubstituted monocyclic aromatic ring containing 0 to 2 ring heteroatoms selected from O, S, and N; and (C)

is a substituted or unsubstituted bicyclic fused aromatic ring containing at least 1 ring heteroatom selected from O, S, and N.

Embodiment 67. A compound of Formula A:

EBM-L-SBM    (Formula A)

or the pharmaceutical acceptable salt, the enantiomer, the non-enantiomer, the tautomer, the racemate, the solvate, the metabolic precursor, or the prodrug thereof, for reducing Lewy bodies, wherein EBM is an E3 ubiquitin ligase binding moiety;
L is a linker covalently attached to EBM and SBM; and
SBM is an α-synuclein protein binding moiety of the formula:

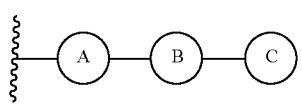

or a pharmaceutical acceptable salt, an enantiomer, a non-enantiomer, a tautomer, a racemate, a solvate, a metabolic precursor, a prodrug thereof,
wherein (A)

is covalently linked to L; and
(i)

(A)

is a substituted or unsubstituted bicyclic fused aromatic ring containing at least 1 ring heteroatom selected from O, S, and N;

(B)

is a substituted or unsubstituted monocyclic aromatic ring containing 0 to 2 ring heteroatoms selected from O, S, and N; and (C)

is a substituted or unsubstituted monocyclic aromatic ring containing 0 to 2 ring heteroatoms selected from O, S, and N; or
(ii)

(A)

is a substituted or unsubstituted monocyclic aromatic ring containing 0 to 2 ring heteroatoms selected from O, S, and N;

(B)

is a substituted or unsubstituted monocyclic aromatic ring containing 0 to 2 ring heteroatoms selected from O, S, and N; and (C)

is a substituted or unsubstituted bicyclic fused aromatic ring containing at least 1 ring heteroatom selected from O, S, and N.

What is claimed is:

1. A method to treat synucleinopathy in a subject in need thereof, the method comprising administering to the subject an effective amount of a compound of Formula A, EBM-L-SBM                                           (Formula A)

wherein
EBM is an E3 ubiquitin ligase binding moiety having a chemical structure of:

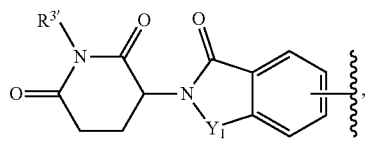

wherein $R^{3'}$ is H and $Y_1$ is $CH_2$;
L is a linker covalently attached to EBM and SBM; and
SBM is an α-synuclein protein binding moiety of Formula B or Formula C:

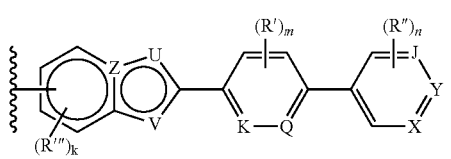
(Formula B)

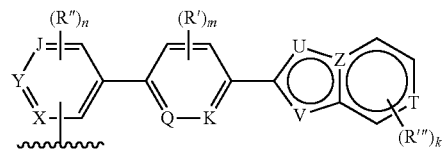
(Formula C)

or a pharmaceutical acceptable salt, an enantiomer, a tautomer, a racemate, or a solvate thereof, wherein
Z is C or N; U is O, S or CH; V is N; T is CH; Z and U are not heteroatoms at the same time;

K is CH or N; Q is CH or N: where K and Q are not N at the same time;

each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3;

each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;

each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;

J is $CR^6$ or N; X is $CR^6$ or N; Y is $CR^6$ or N; where at least one of J, X and Y is N, but J and Y are not N at the same time, X and Y are not N at the same time; and $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo.

2. The method of claim 1, wherein the synucleinopathy is Parkinson's Disease (PD), dementia with Lewy bodies (DLB), multiple system atrophy (MSA), or a combination of two or more thereof.

3. The method of claim 1, wherein the compound is of Formula I or Formula IV,

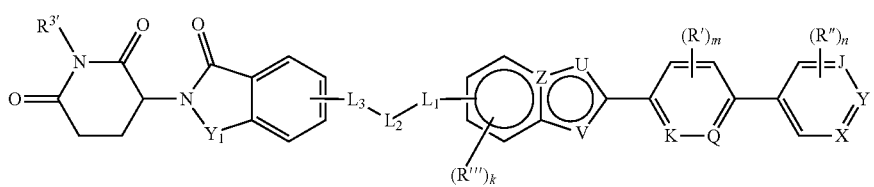
I

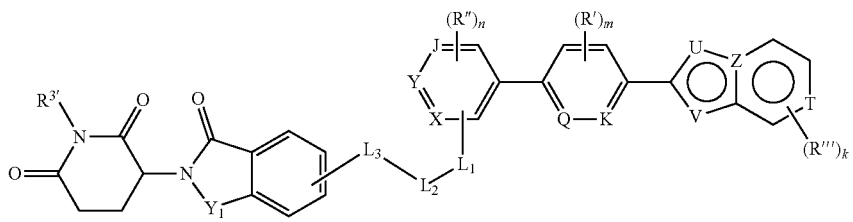
IV or the pharmaceutical acceptable salt, the enantiomer, the tautomer, the racemate, or the solvate thereof;
wherein,
- $L_1$ is a bond, —NR—, —O—, or —S—, wherein R is hydrogen, optionally substituted acyl, optionally substituted alkyl or a nitrogen protecting group;
- $L_2$ is a substituted or unsubstituted $C_{1-50}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group;
- Z is C or N; U is O, S or CH;
- K is CH or N; Q is CH or N; where K and Q are not N at the same time;
- each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3;
- each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;
- each occurrence of R'' is independently selected from the group consisting of H, halo, OH, NH$_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;
- J is CR$^6$ or N; X is CR$^6$ or N; Y is CR$^6$ or N; where at least one of J, X and Y is N, but J and Y are not N at the same time, X and Y are not N at the same time;
- R$^6$ is independently selected from the group consisting of H, NH$_2$, $C_{1-6}$ alkyl and $C_{1-6}$ alkoxy, wherein NH$_2$, $C_{1-6}$ alkyl or $C_{1-6}$ alkoxy is optionally substituted by 1 to 3 of $C_{1-3}$ alkyl, $C_{3-6}$ cycloalkyl and/or halo; and
- $L_3$ is a bond, —NR—, —O—, or —S—, wherein R is hydrogen, optionally substituted acyl, optionally substituted alkyl or a nitrogen protecting group.

4. The method of claim 3, wherein $L_2$ is an optionally substituted $C_{1-45}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

5. The method of claim 3, wherein $L_2$ is selected from the group consisting of substituted or unsubstituted carbocyclylene, substituted or unsubstituted heterocyclylene, substituted or unsubstituted arylene, substituted or unsubstituted heteroarylene, or substituted or unsubstituted heteroalkylene, and combinations thereof.

6. The method of claim 4, wherein $L_2$ comprises at least one instance selected from the group consisting of substituted or unsubstituted methylene, ethylene, n-propylene, n-butylene, n-pentylene, n-hexylene, —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$O—, —O(CH$_2$)$_5$—, —(CH$_2$)$_5$O—, —O(CH$_2$)$_6$—, —O(CH$_2$)$_6$O—, —C(=O)O—, —O—C(=O)—, —NHC(=O)— and —C(=O)NH—.

7. The method of claim 4, wherein at least one chain atom of the hydrocarbon chain of $L_2$ is independently replaced with a 6-membered heterocyclyl group with 1-3 ring heteroatoms selected from the group consisting of nitrogen and oxygen.

8. The method of claim 4, wherein $L_2$ is an unsubstituted hydrocarbon chain, optionally wherein one or more chain atoms of the hydrocarbon chain are independently replaced with —NR$^a$—, and each instance of R$^{a1}$ is independently hydrogen, substituted or unsubstituted $C_{1-6}$ alkyl or a nitrogen protecting group, or optionally two instances of R$^{a1}$ are taken together with their intervening atoms to form a substituted or unsubstituted heterocyclic or substituted or unsubstituted heteroaryl ring.

9. The method of claim 3, wherein $L_2$ is

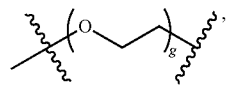

wherein g is 1, 2, 3, 4, 5, or 6.

10. The method of claim 3, wherein $L_2$ includes the moiety —O—,

—NHC(=O)— or —NH—.

11. The method of claim 3, wherein $L_2$ is selected from the group consisting of

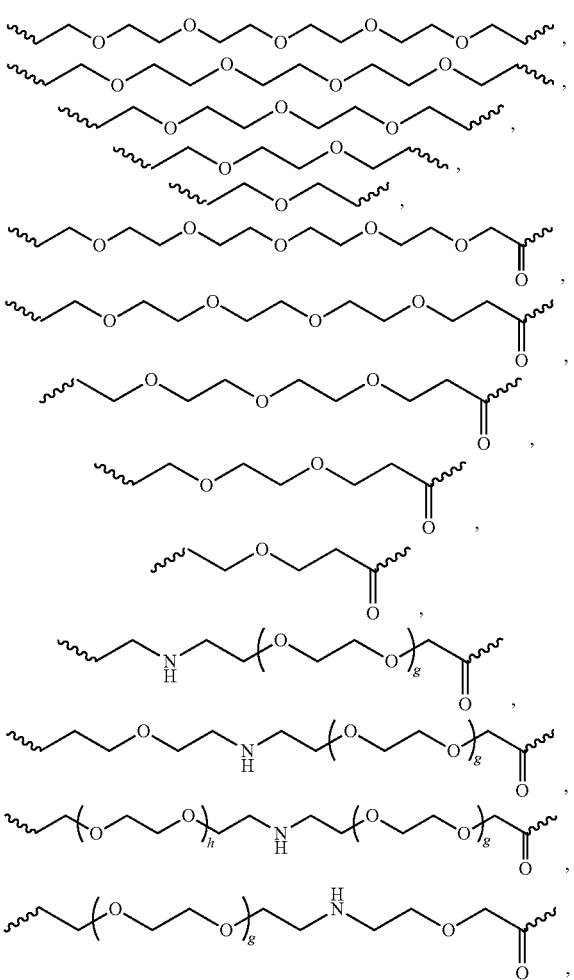

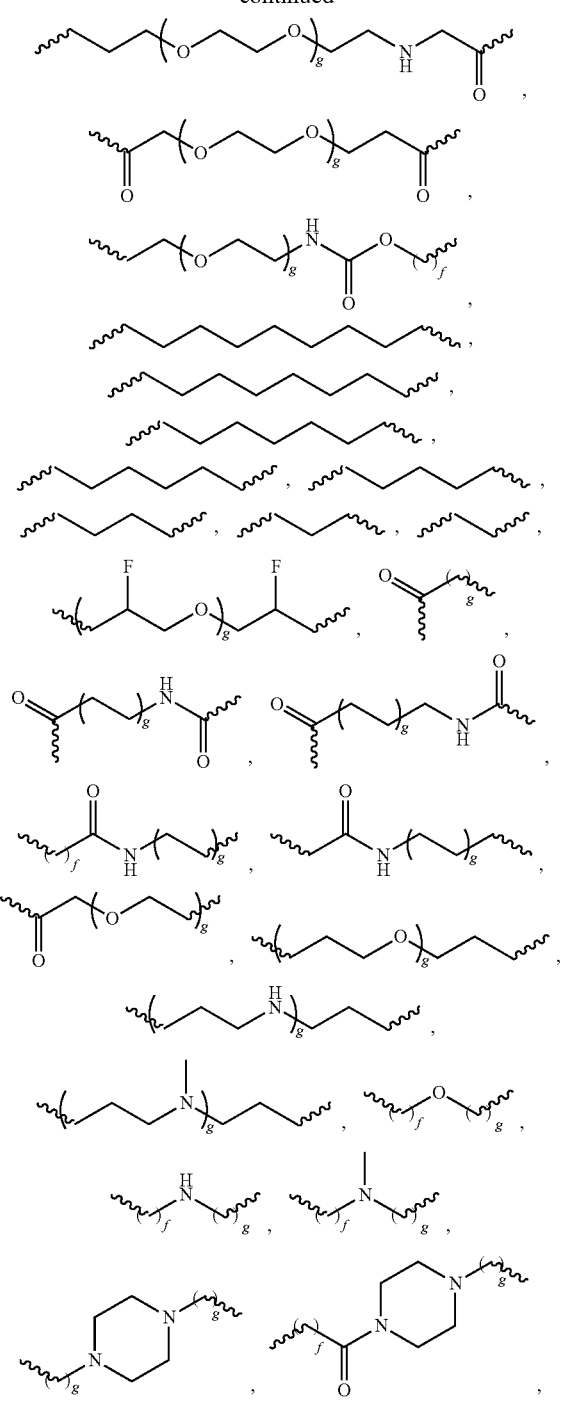
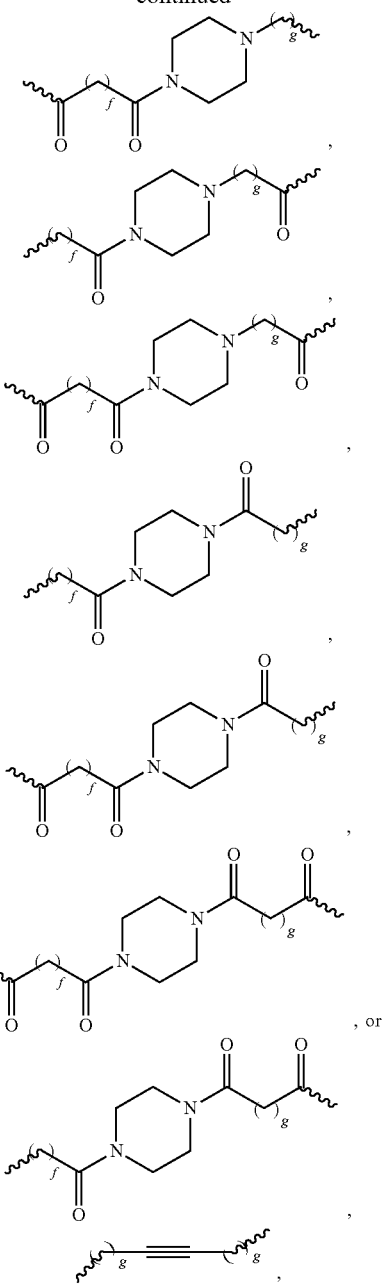
wherein each g is independently 1, 2, 3, 4, 5, or 6; f is 1, 2, 3, 4, 5, or 6, and h is 1, 2, 3, 4, 5, or 6.
12. The method of claim 3, wherein the compound of Formula I is of Formula I-1;
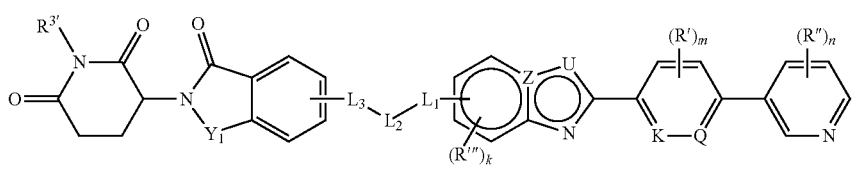

or the pharmaceutical acceptable salt, the entantiomer, the tautomer, the racemate, or the solvate thereof.
13. The method of claim 3, wherein the compound of Formula IV is of Formula IV-1;
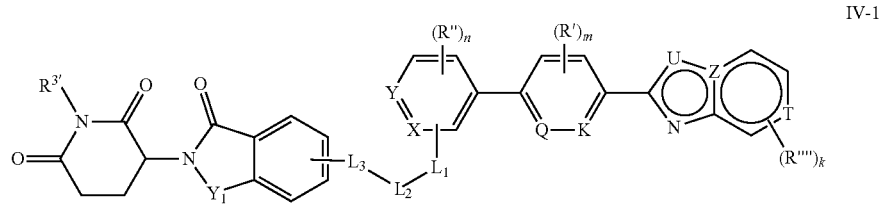
IV-1
or the pharmaceutical acceptable salt, the enantiomer, the tautomer, the racemate, or the solvate thereof.
14. The method of claim 1, wherein the compound is selected from:
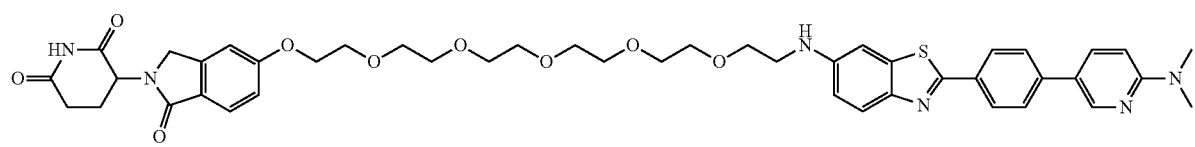
160273
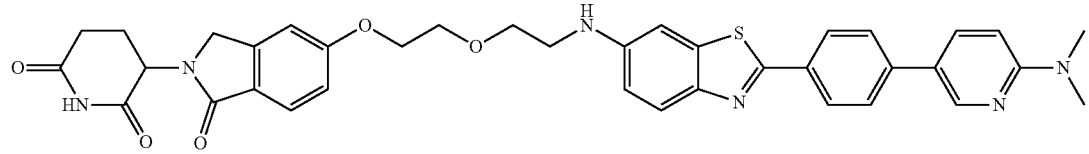
160313
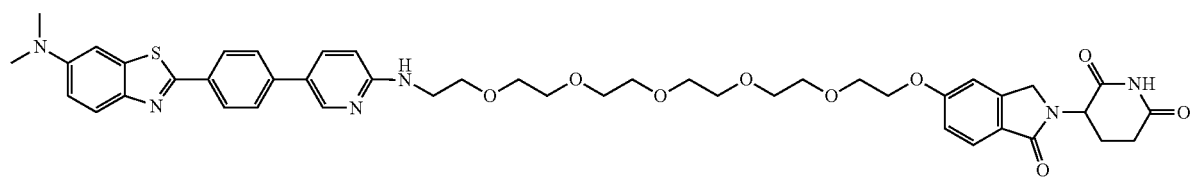
160383
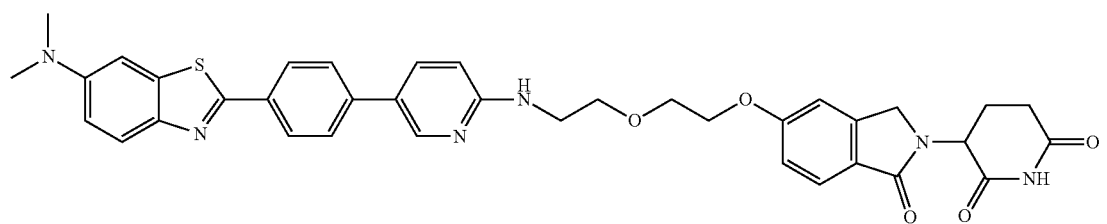
170352
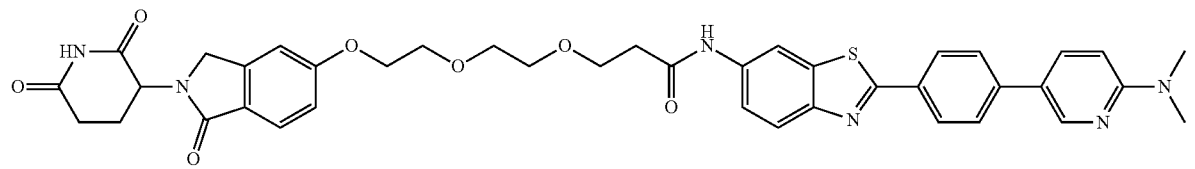
170357

-continued
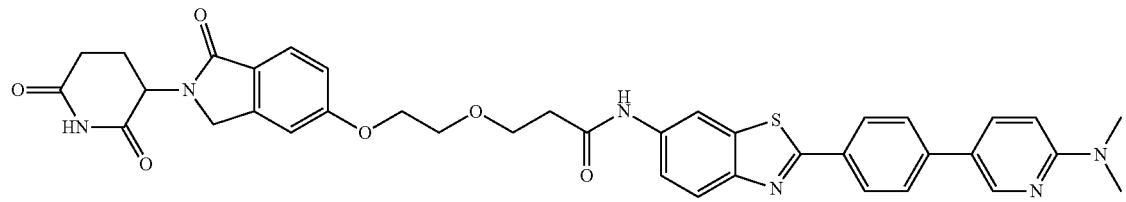
170358
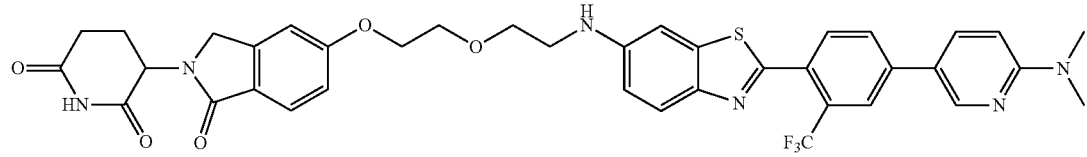
170359
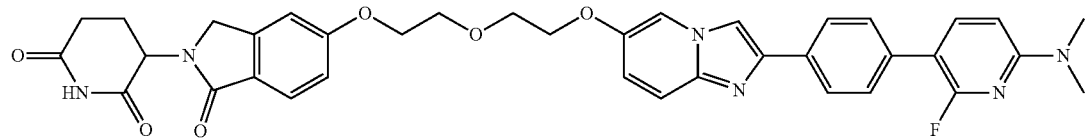
170450
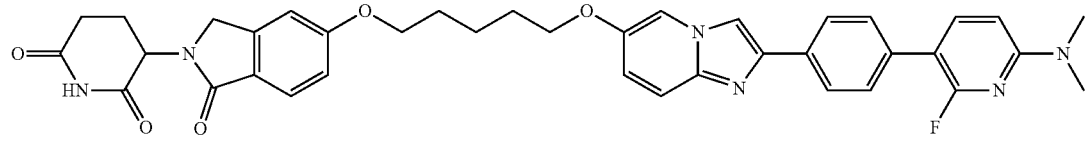
170451
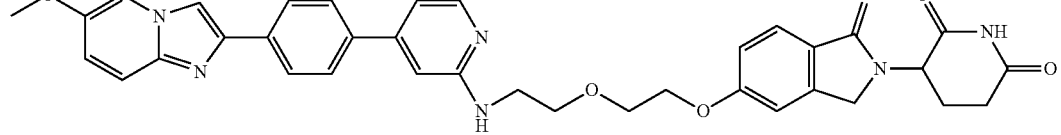
162640
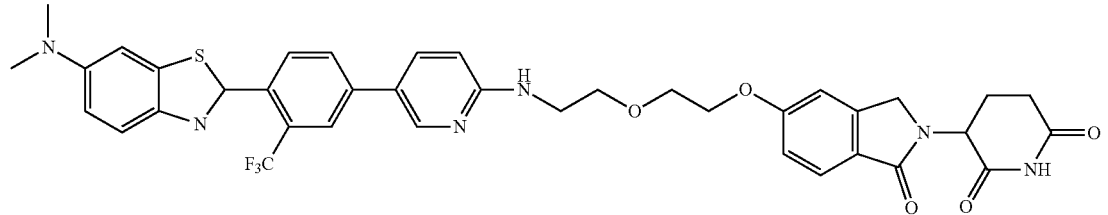
177031
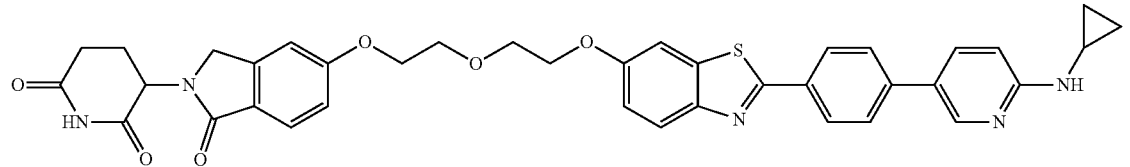
177032
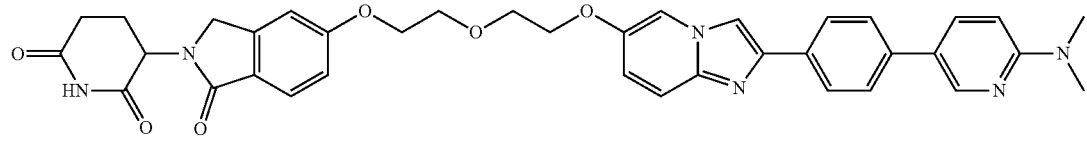
177033
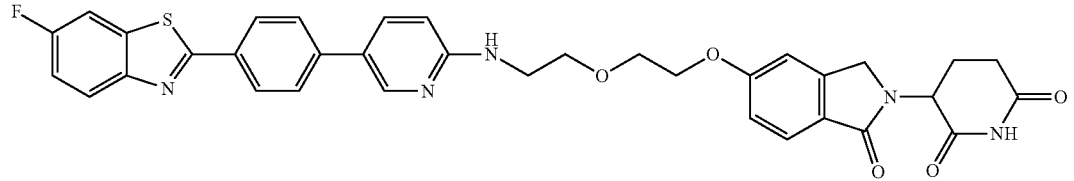
177035

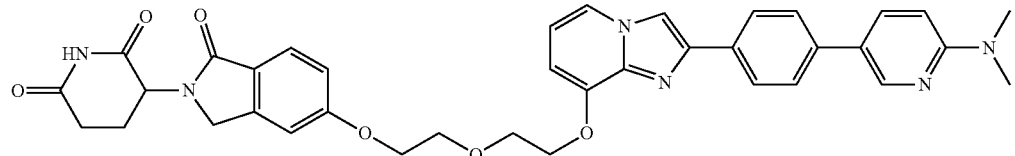
162842
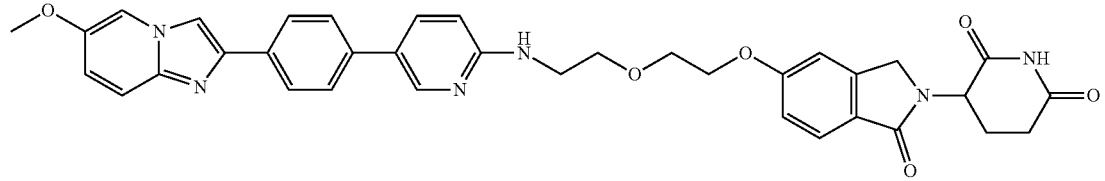
177037
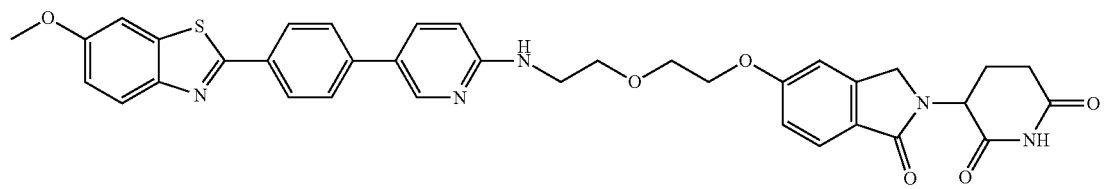
177039
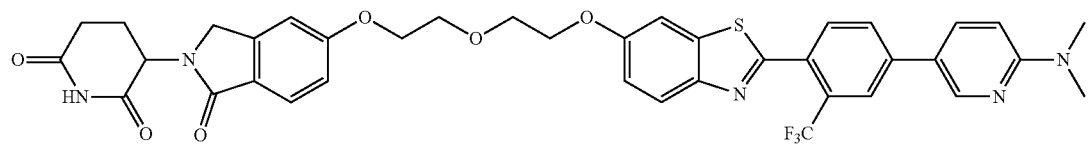
162903
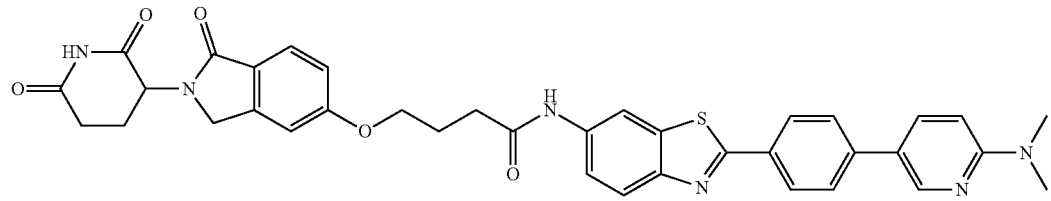
170742
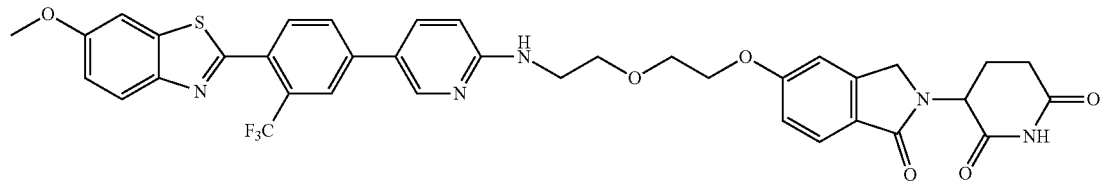
179143
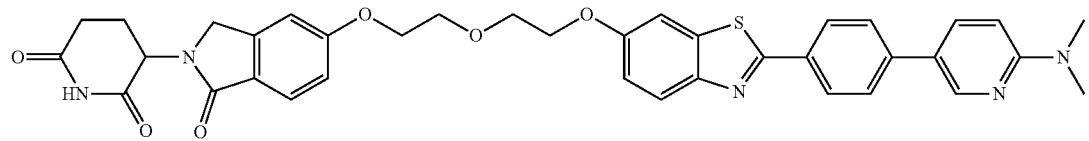
163123
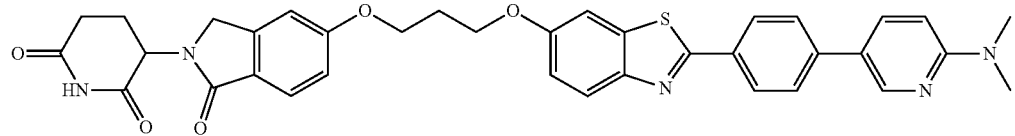
184605
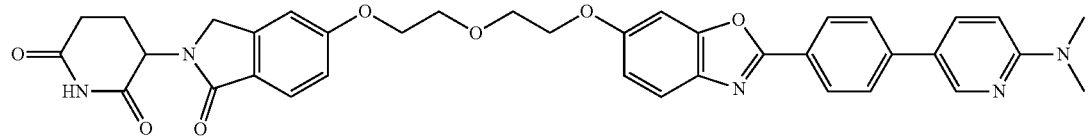
163365

321 322
-continued
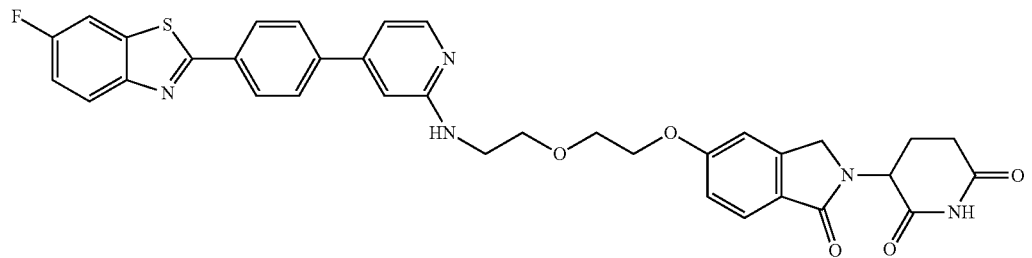
180948
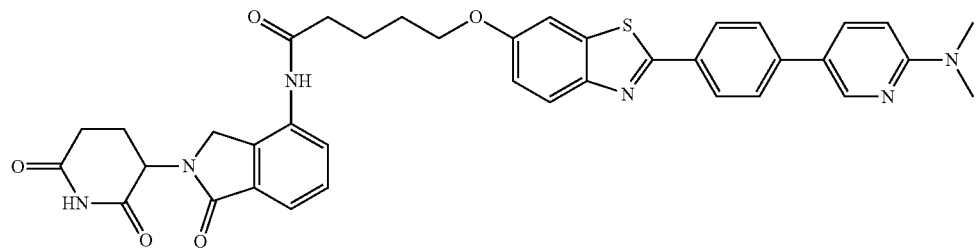
189149
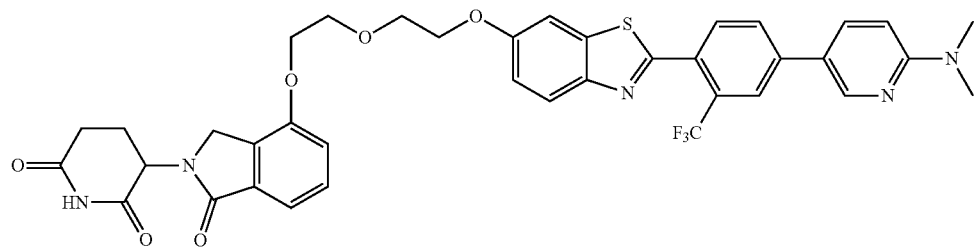
180950
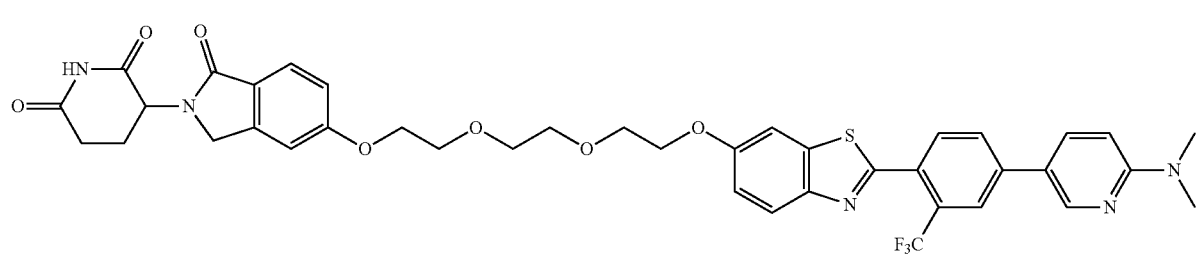
174251
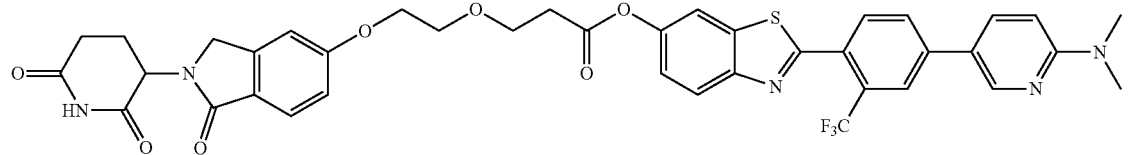
175552
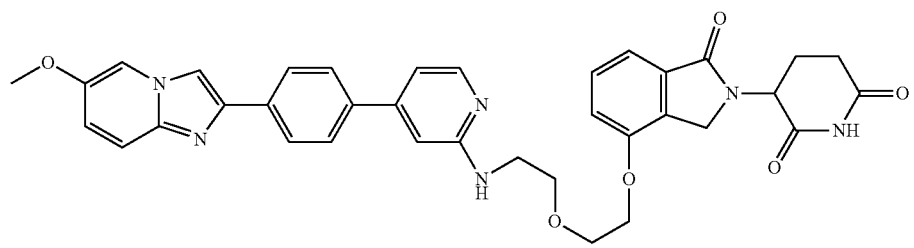
190753

139854
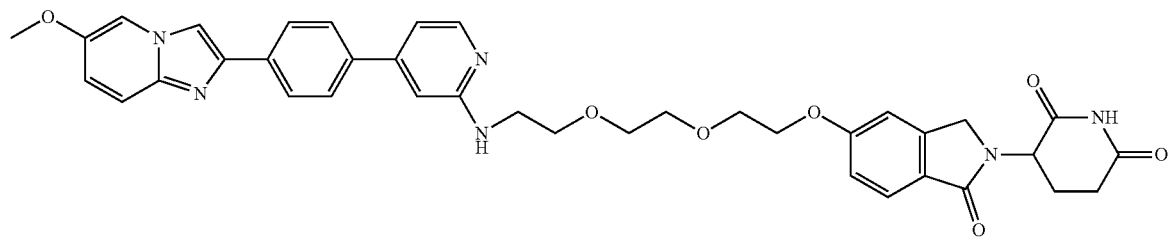
137955
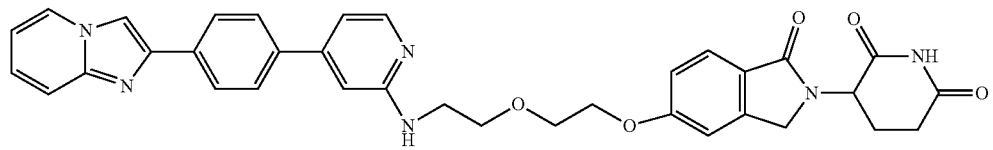
186756
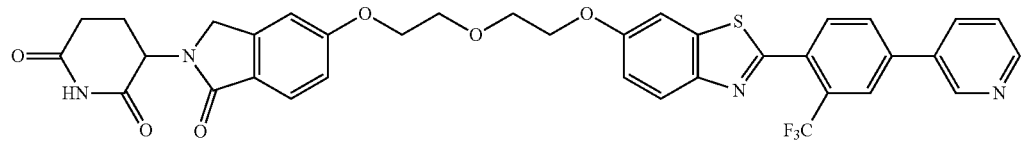
170257
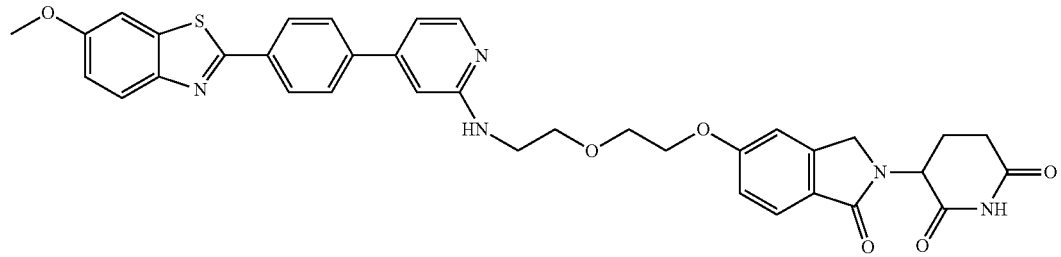
185458
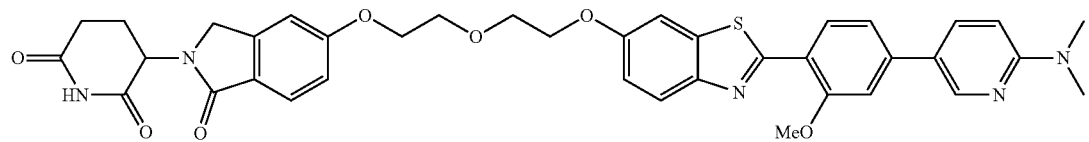
132159
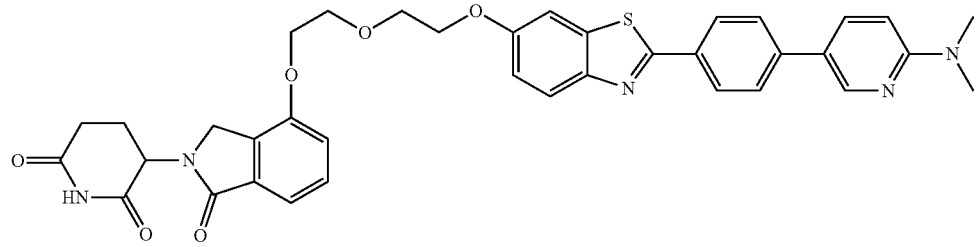
132560
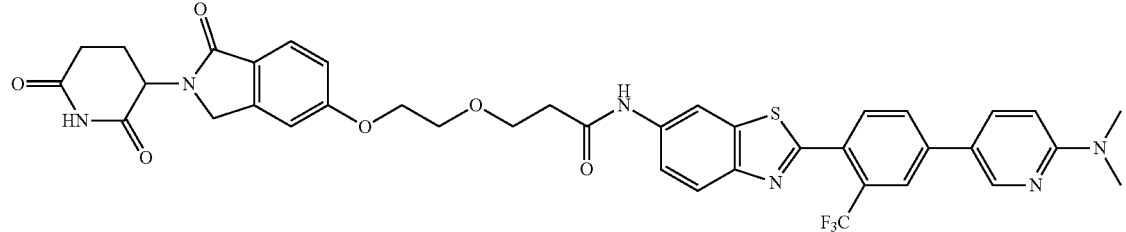

-continued
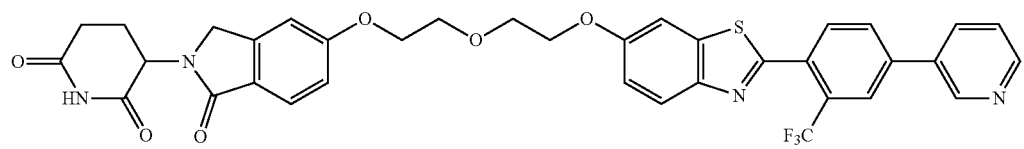
137361
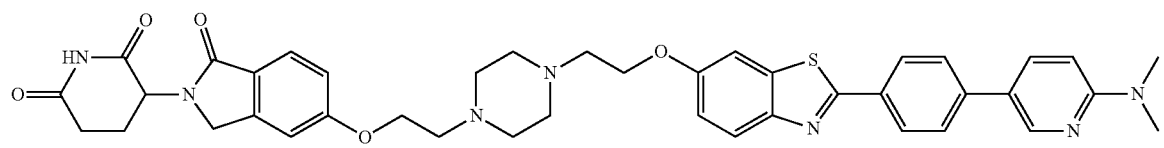
180262
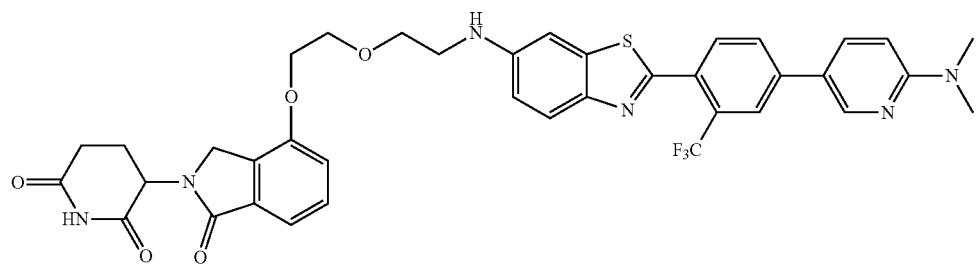
185563
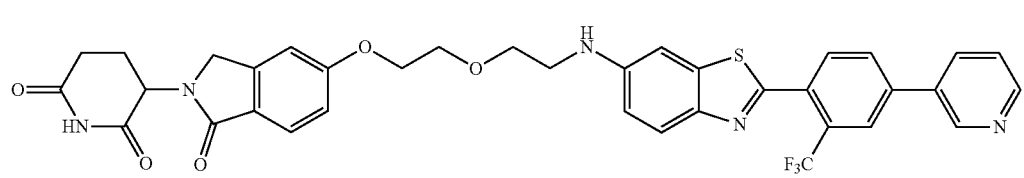
181964
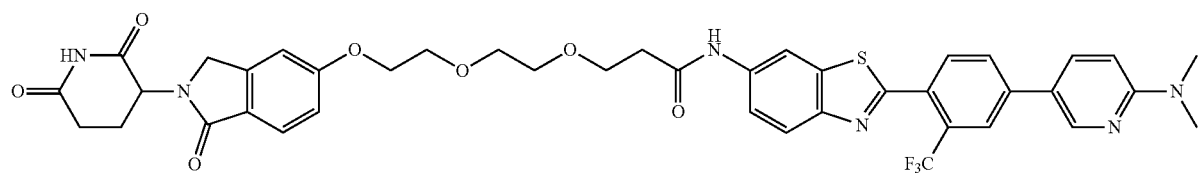
138266
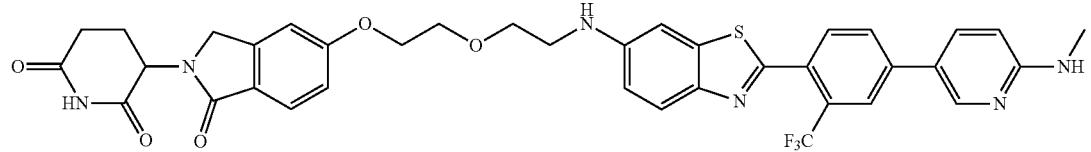
136767
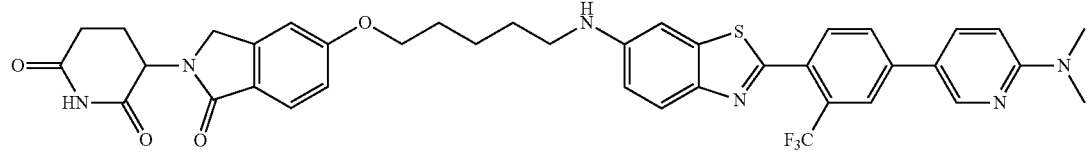
132168
139269
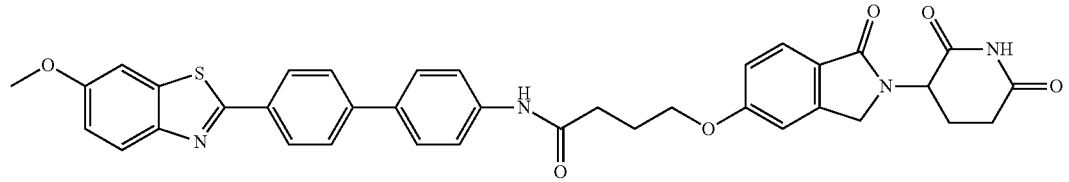

-continued
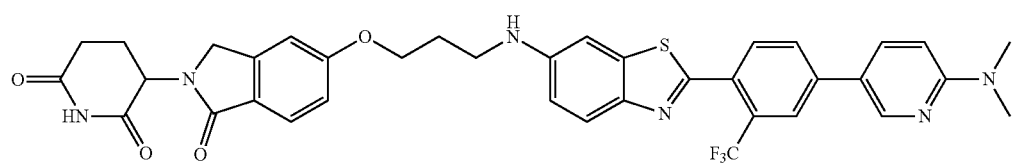
113070
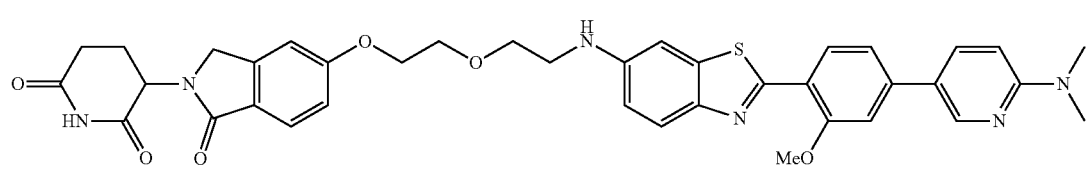
129071
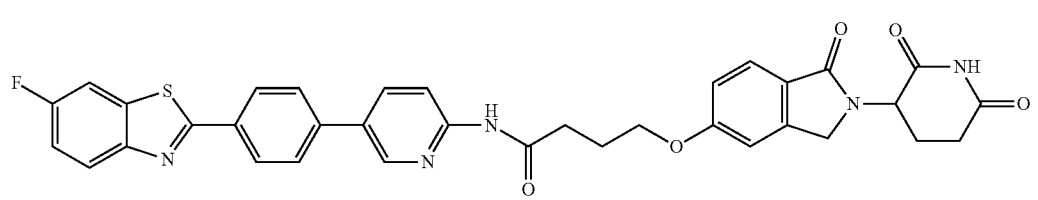
112772
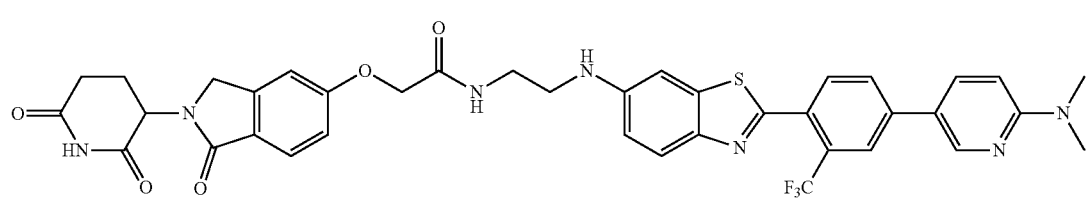
127913
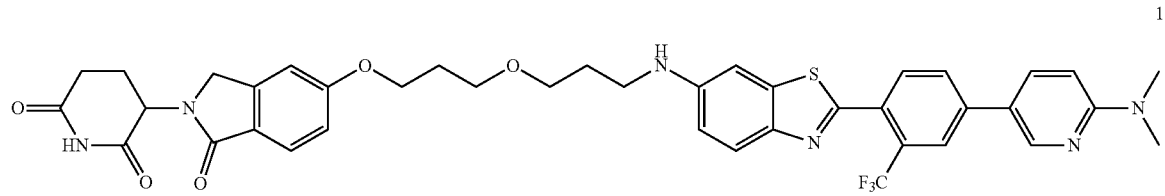
123374
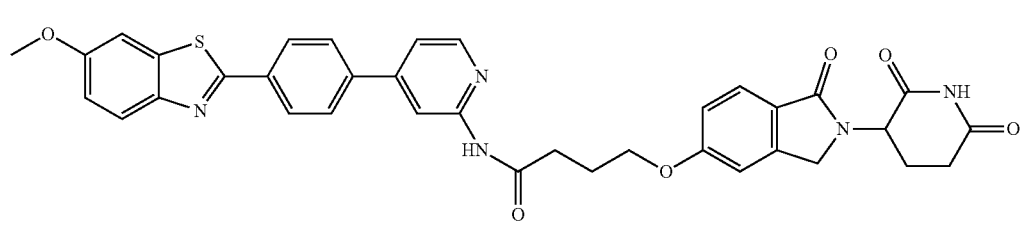
138876
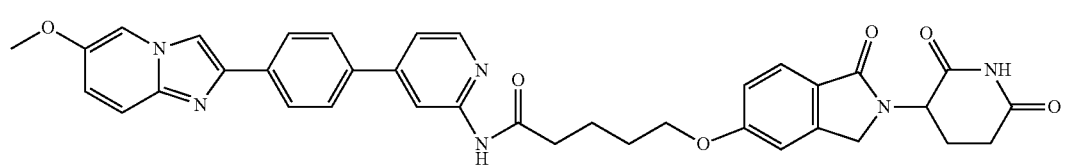
130177
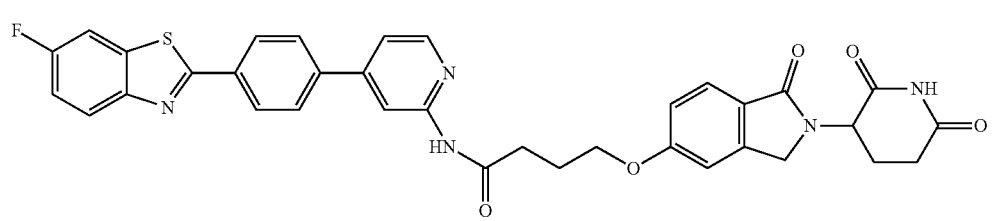
133678

190279
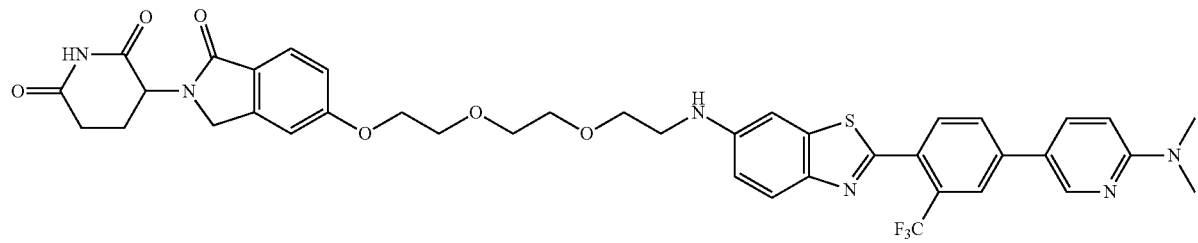
133380
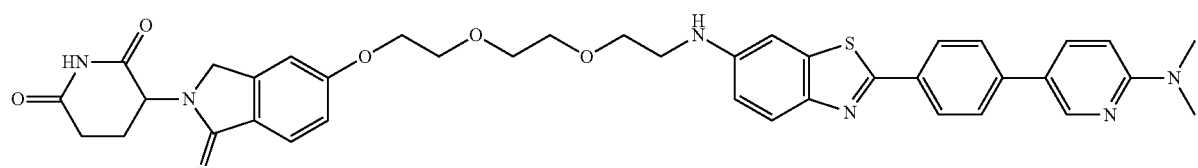
120581
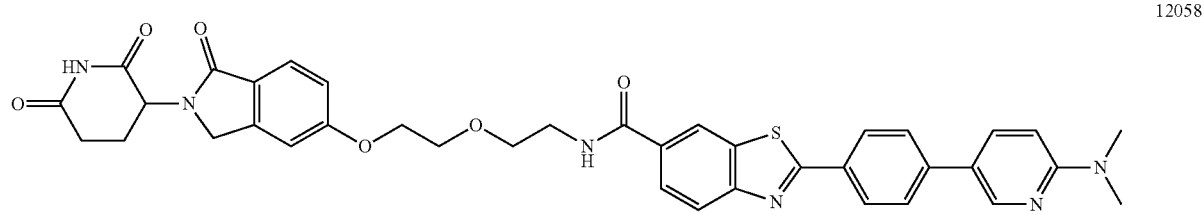
190222
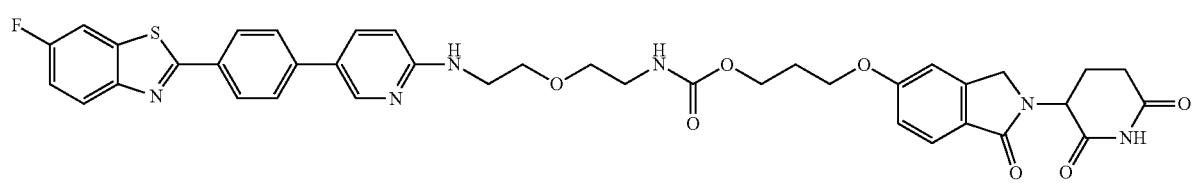
190083
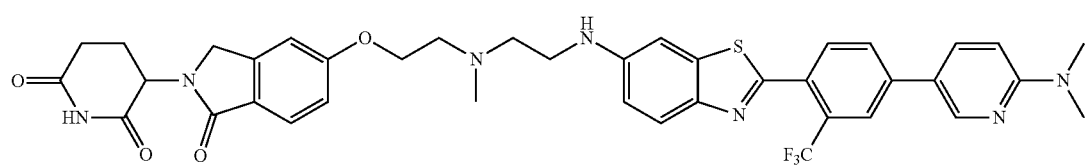
129804
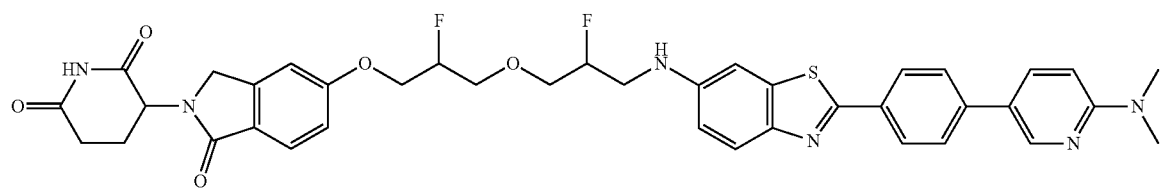
134555
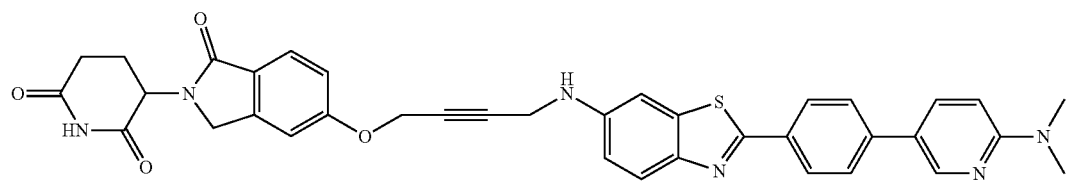

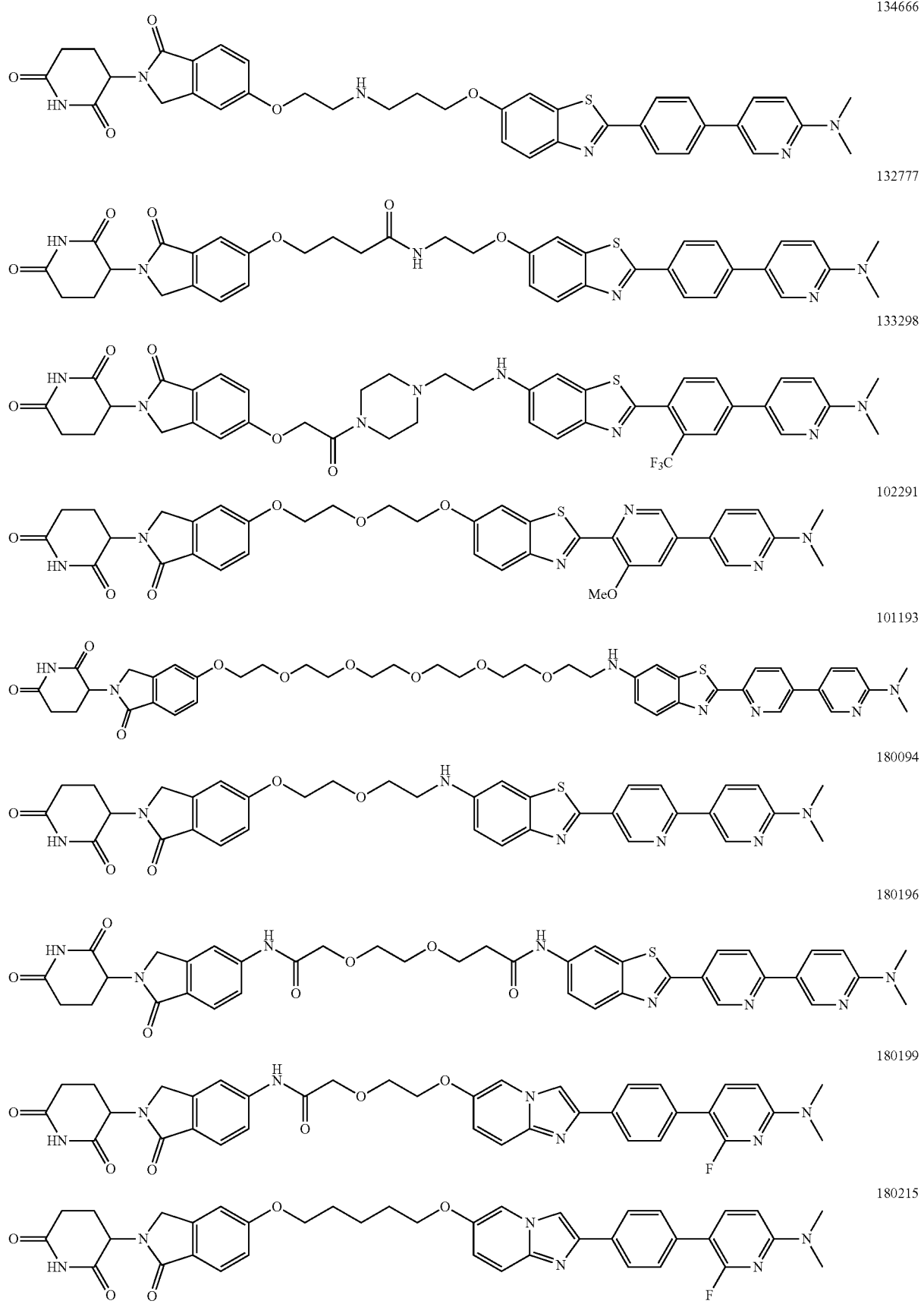

-continued
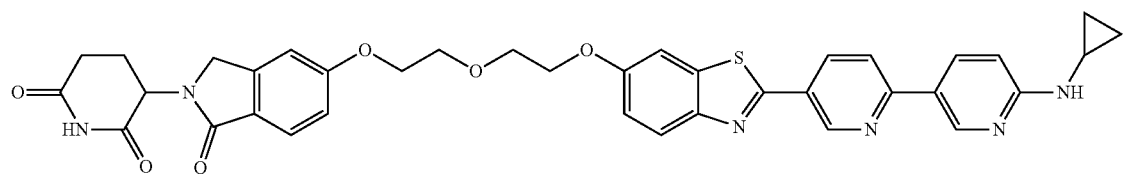
180216
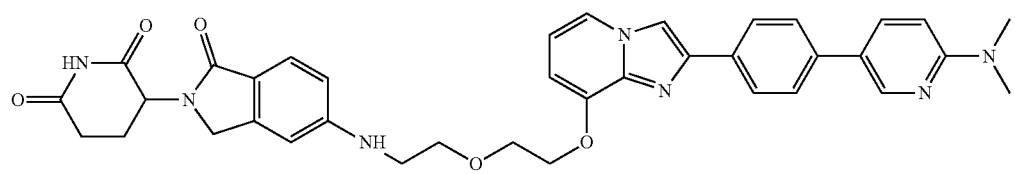
180218
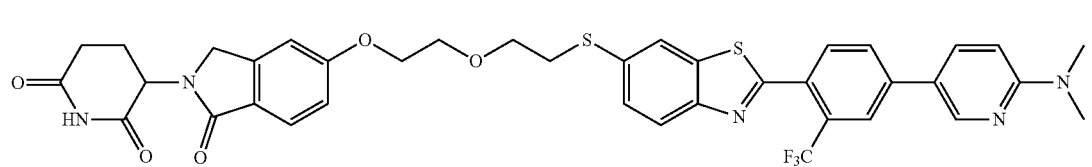
180310
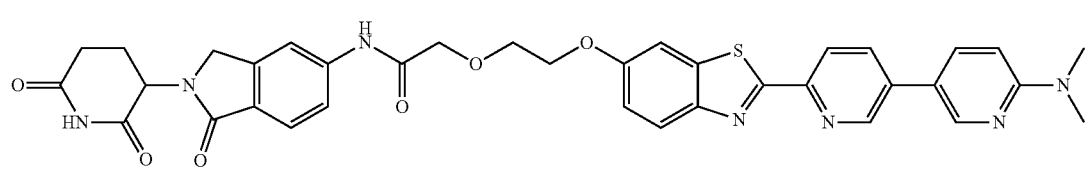
180313
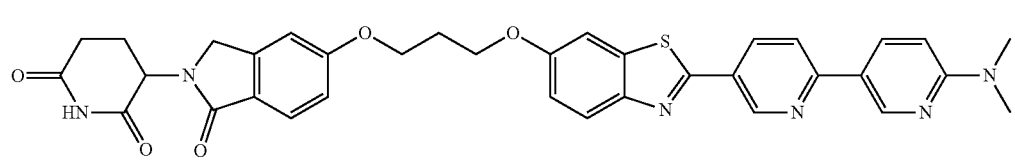
180314
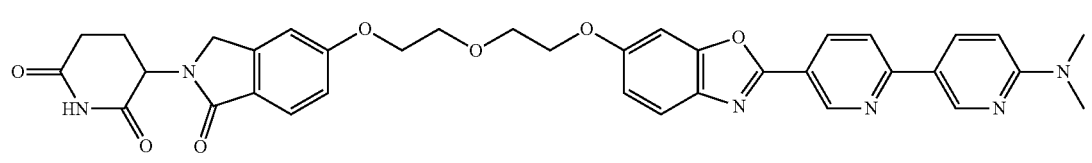
180315
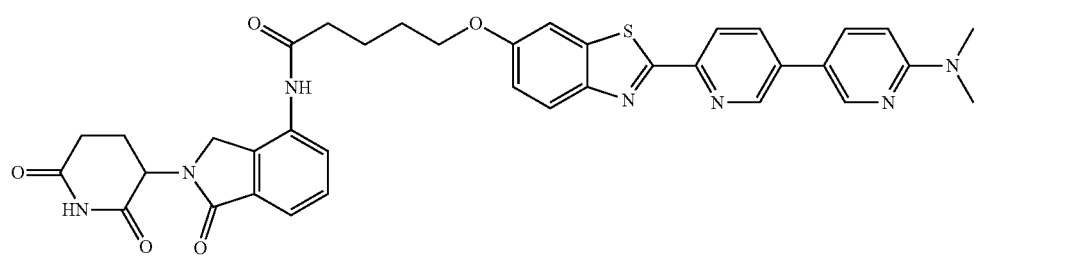
180316
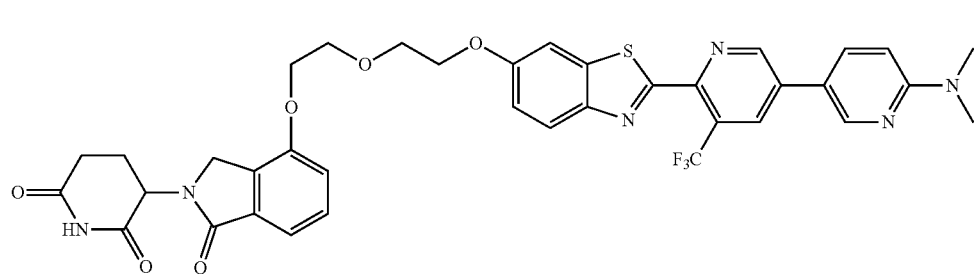
180317

-continued
180318
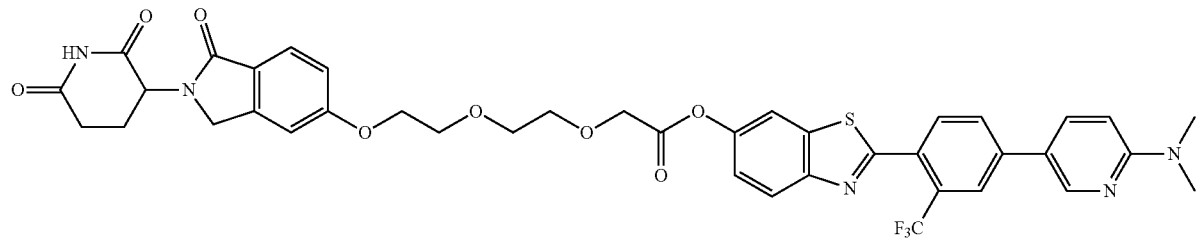
120010
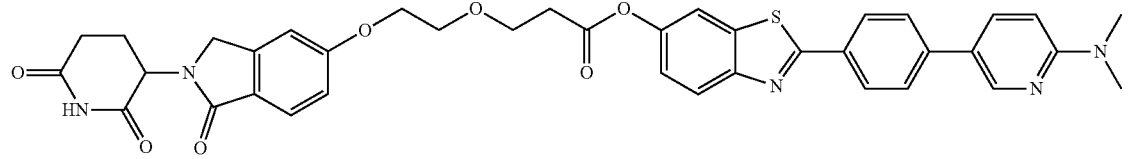
120011
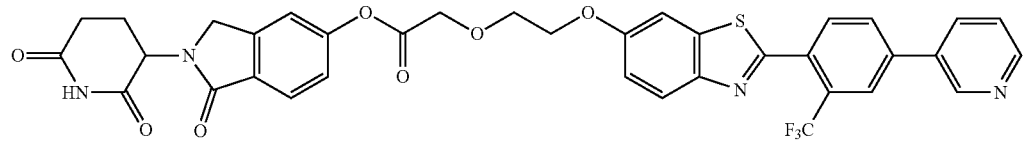
120012
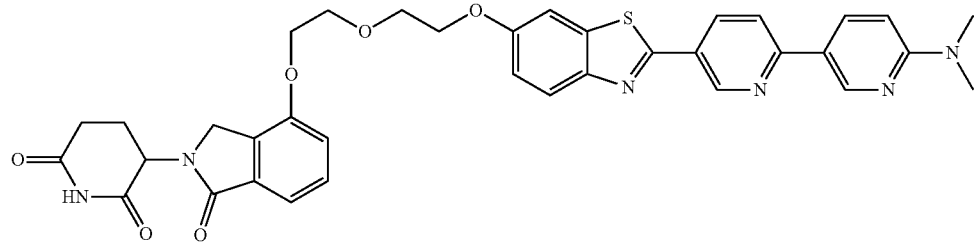
120013
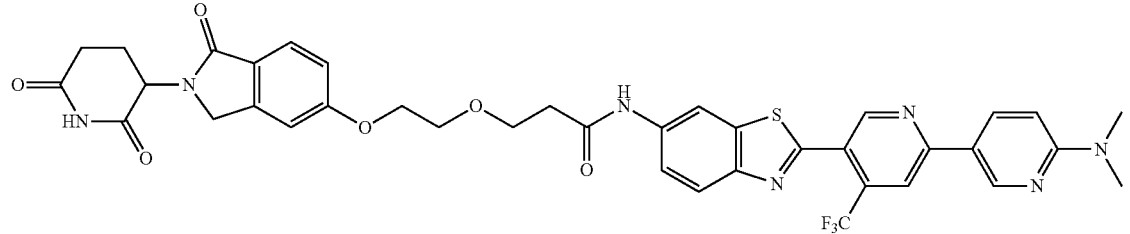
120014
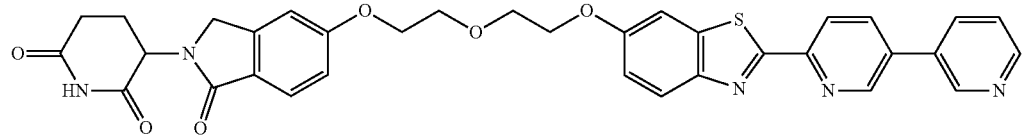
120015
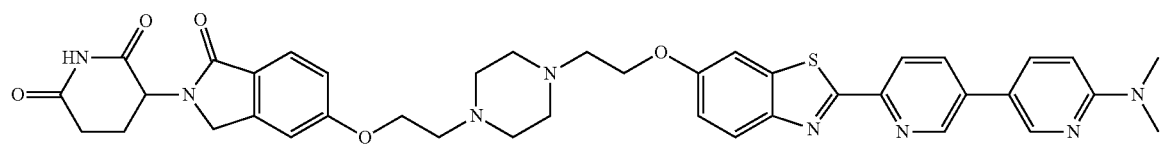

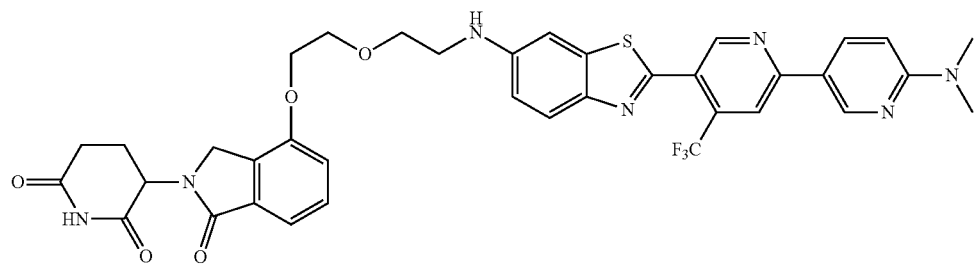
120016
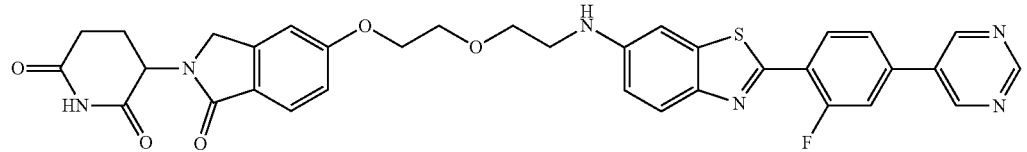
120017
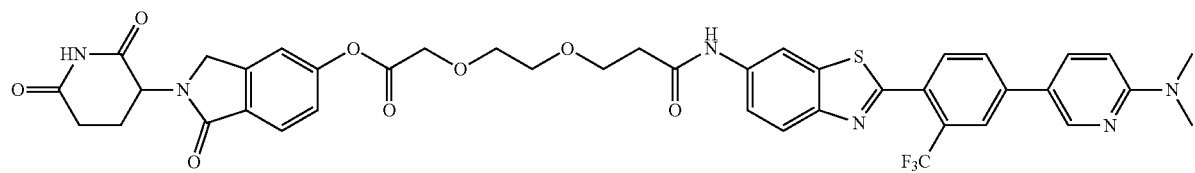
120019
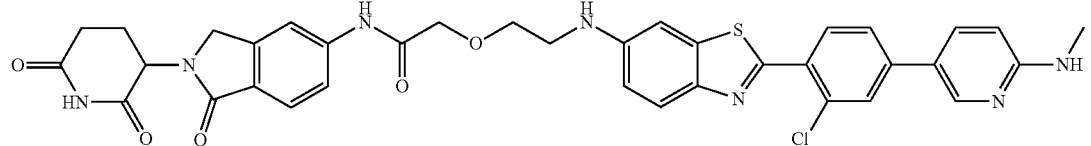
123013
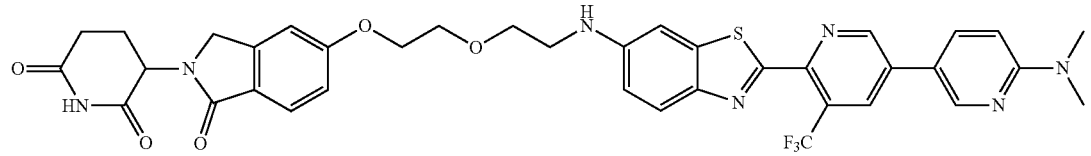
123014
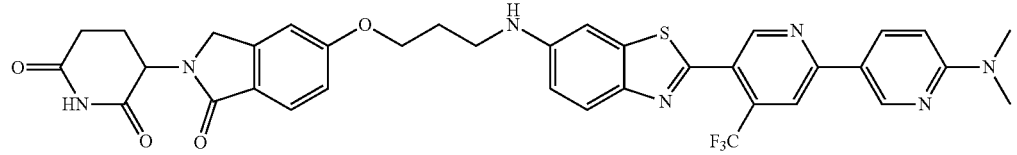
123015
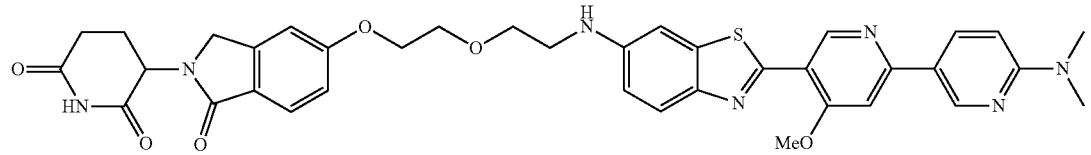
123016
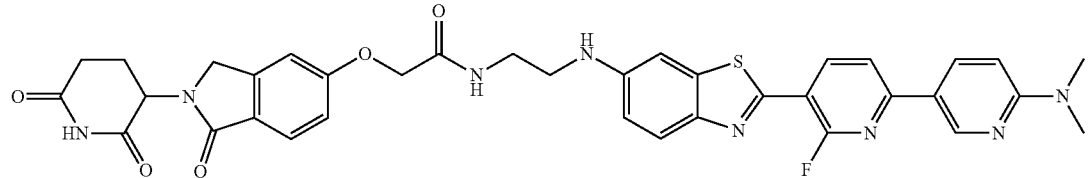
123017

339 340
-continued
123018
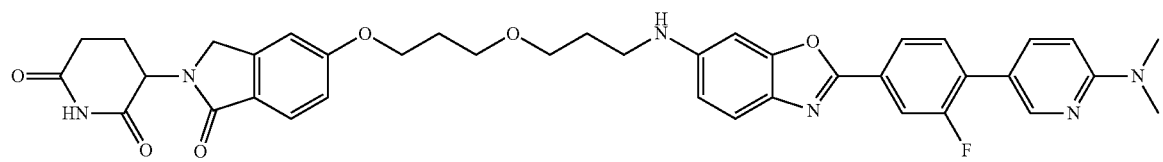
123019
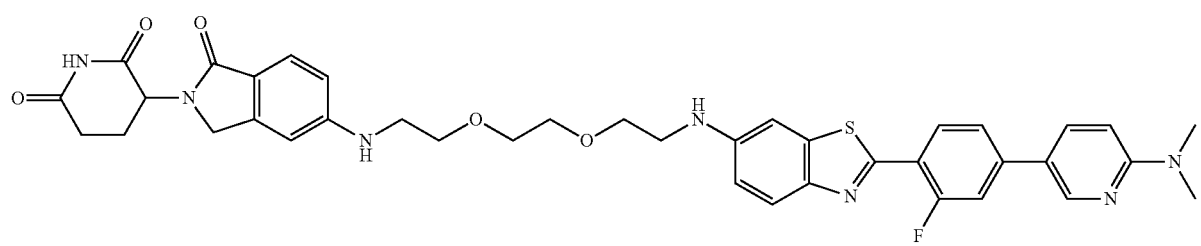
123418
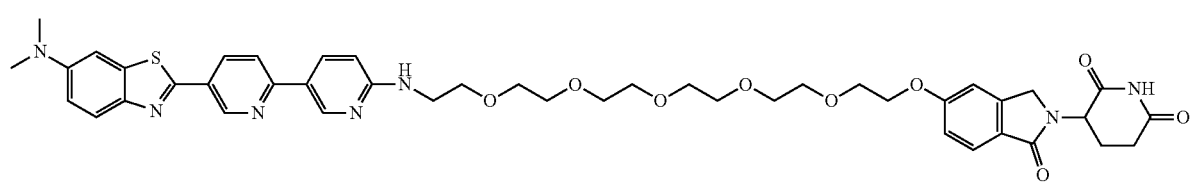
123419
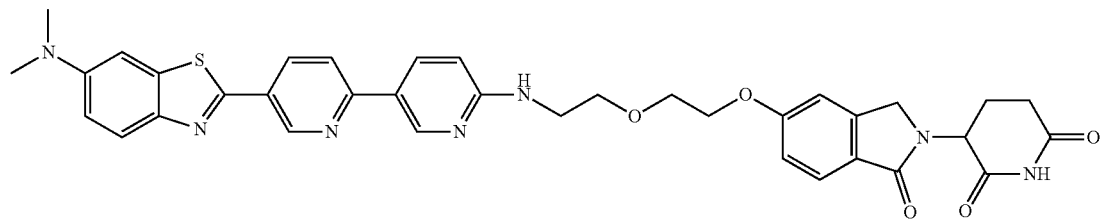
136176
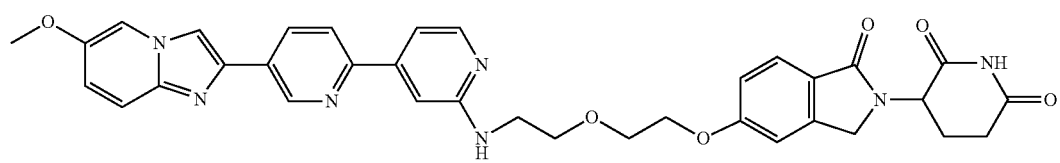
136177
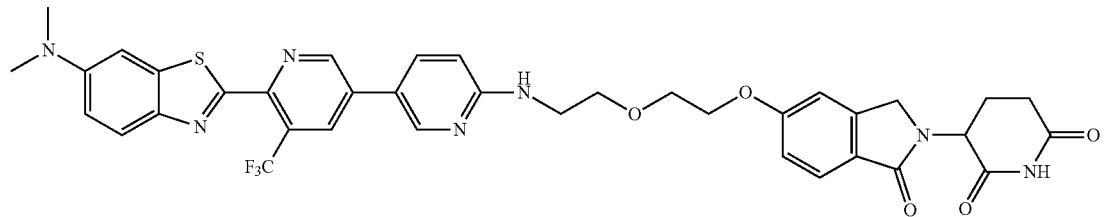
136179
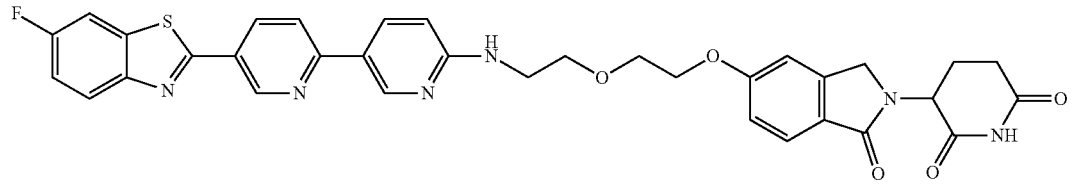

341 342
-continued
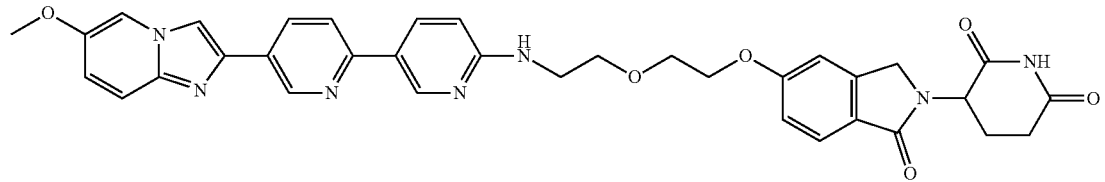
136571
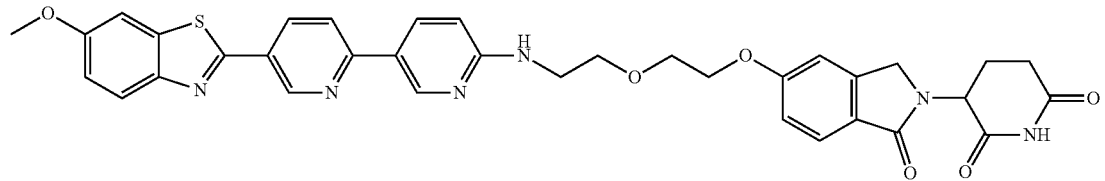
136572
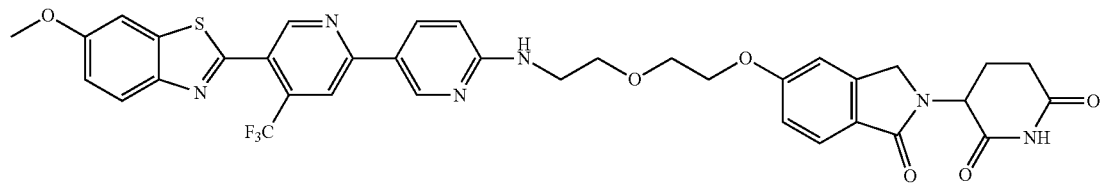
136573
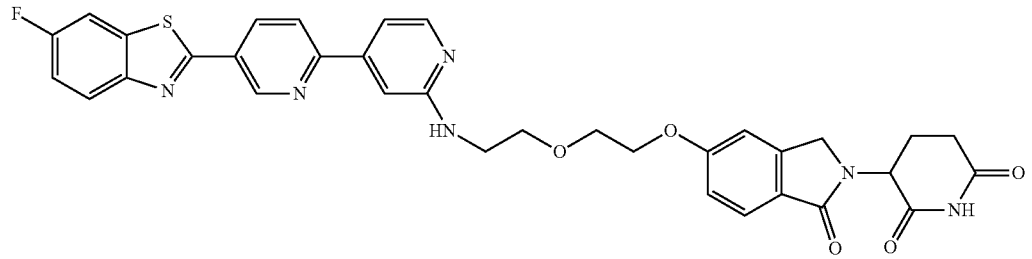
136574
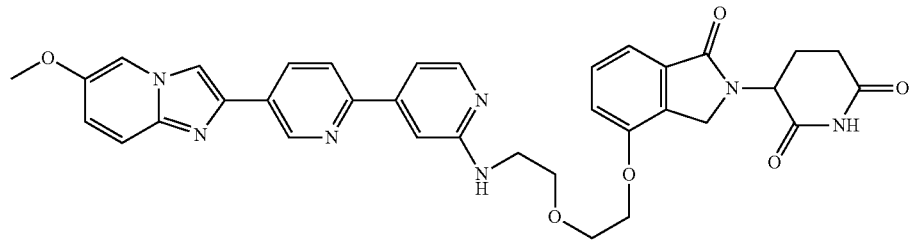
136575
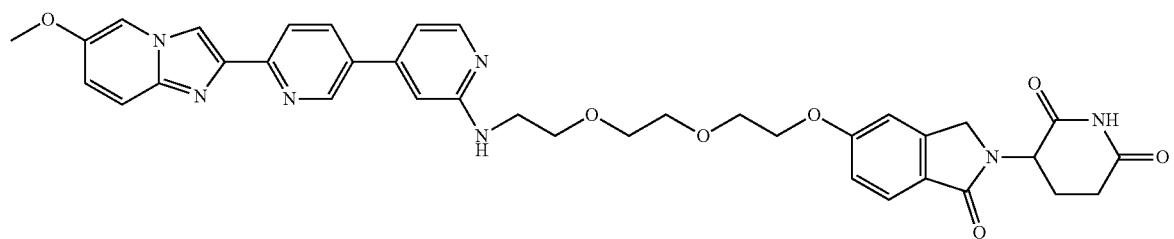
136576
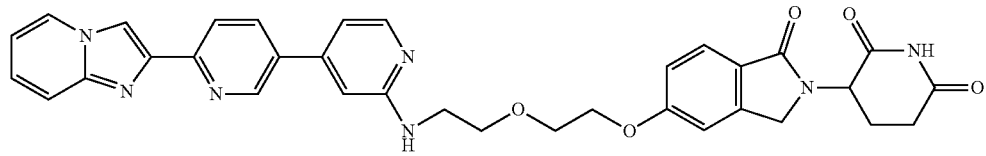
136577

-continued
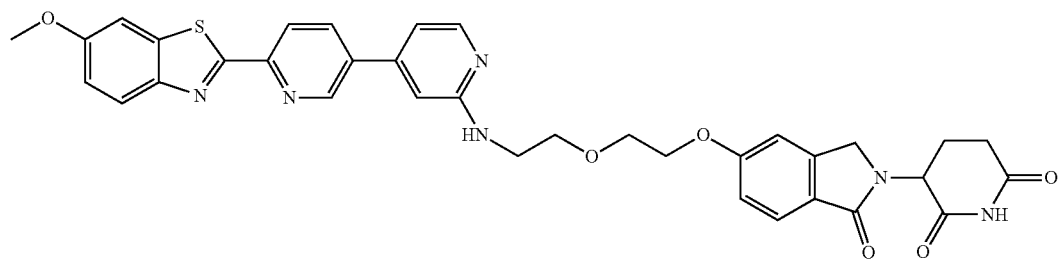
136578
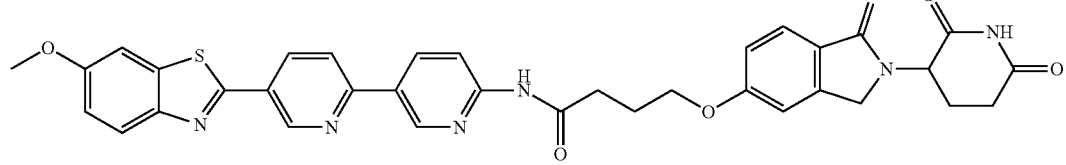
136579
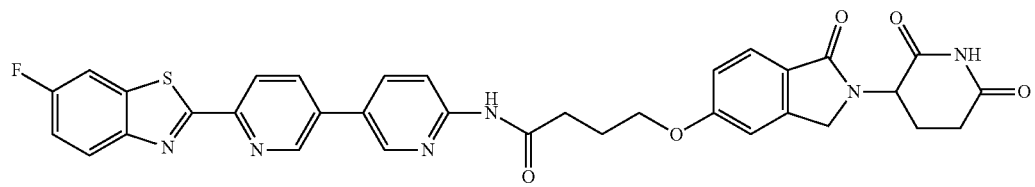
139571
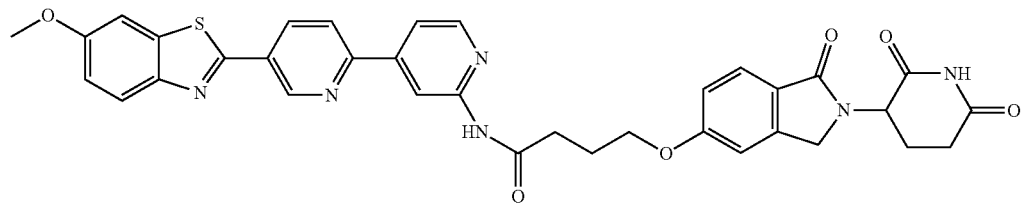
139573
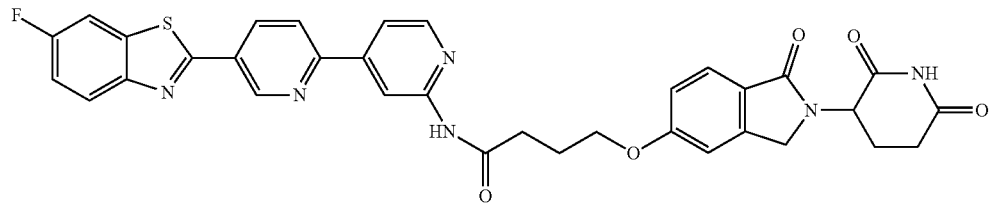
139575
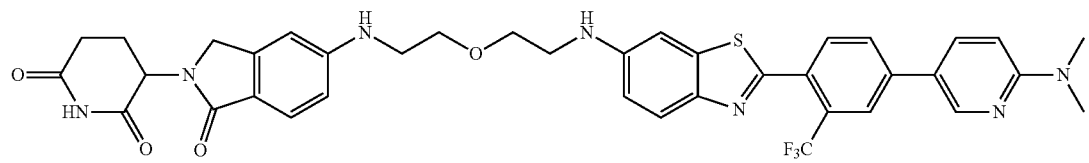
165514
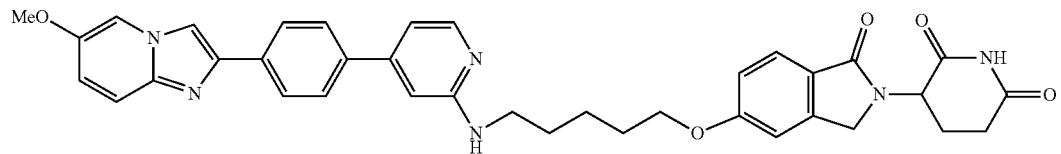
165802
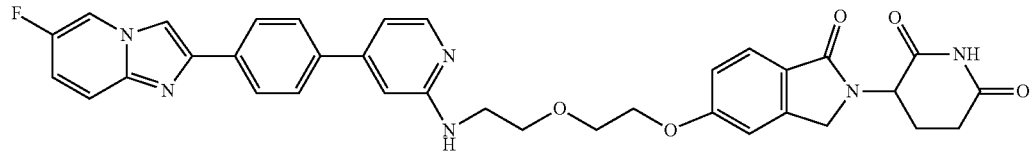
165824

-continued
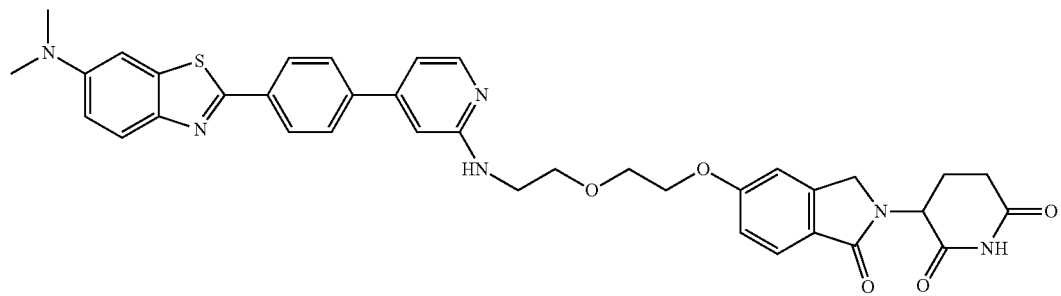
165950
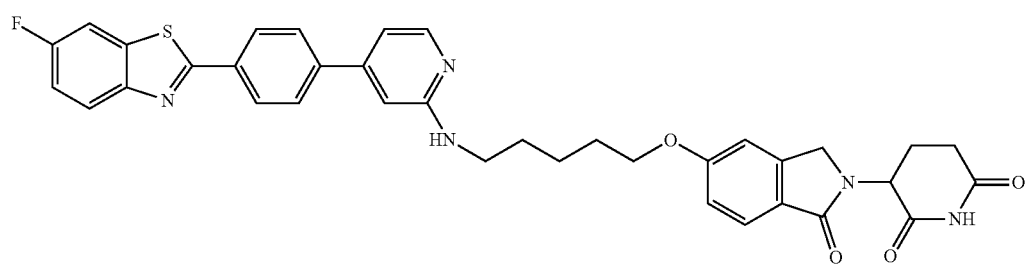
165825
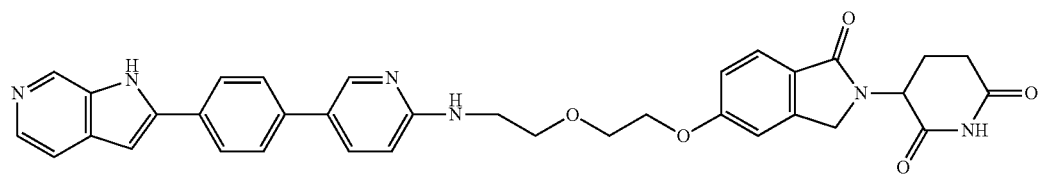
165954
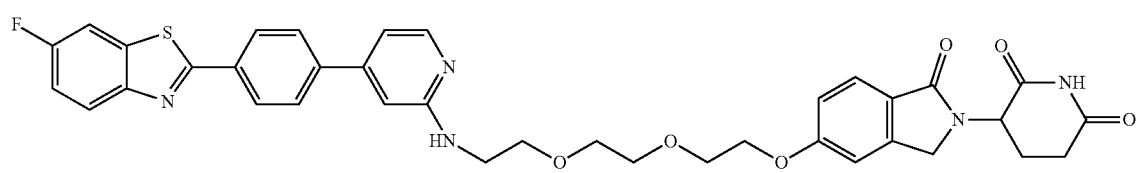
165923
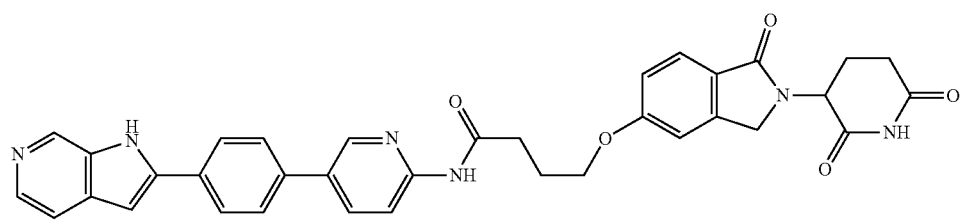
166099
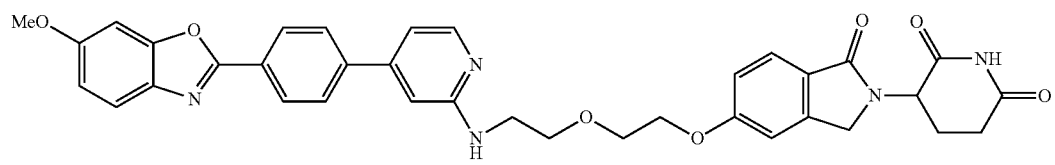
166123
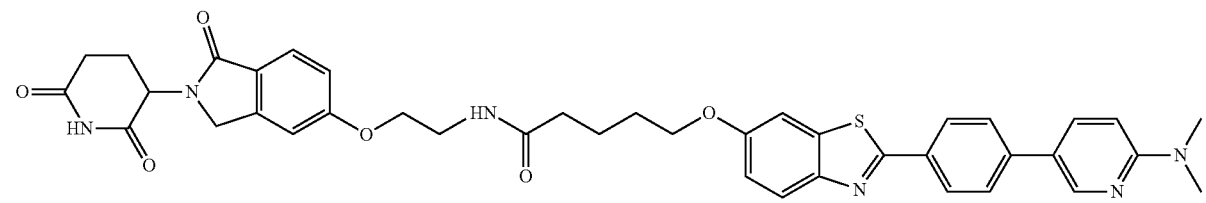
166097

-continued
166136
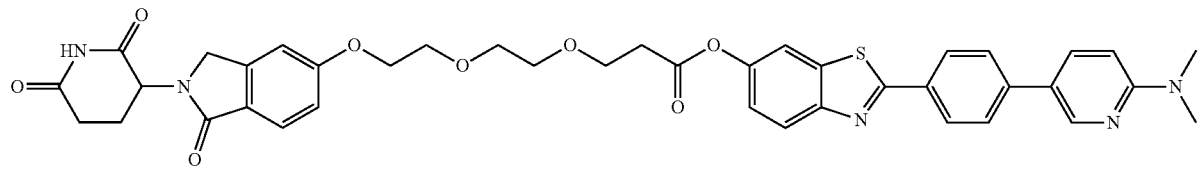
166124
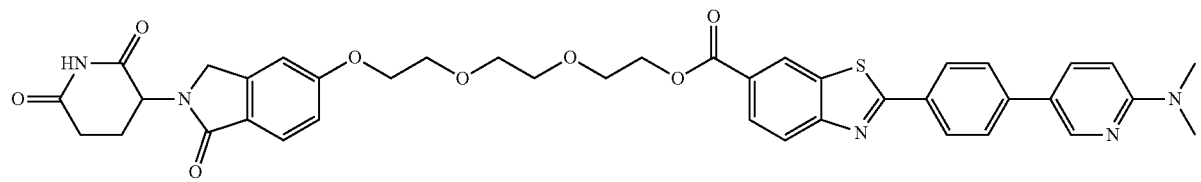
166330
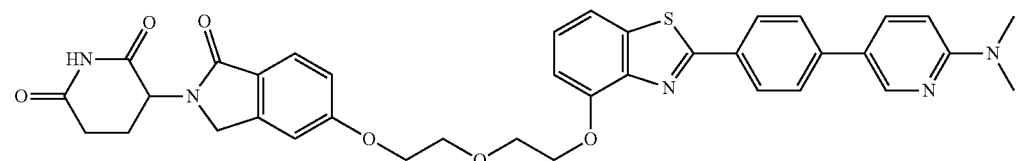
166344
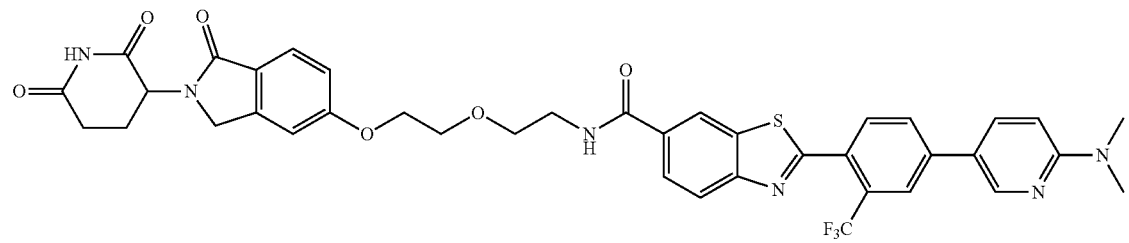
166362
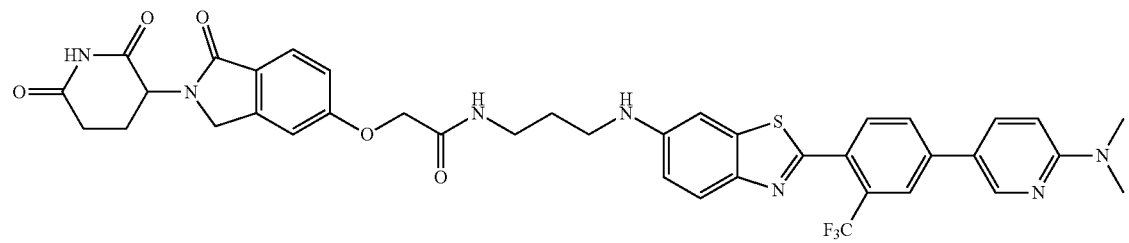
166522
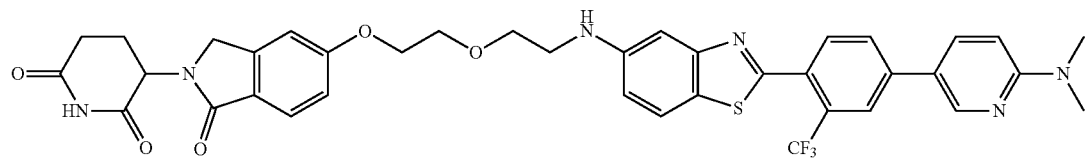
166531
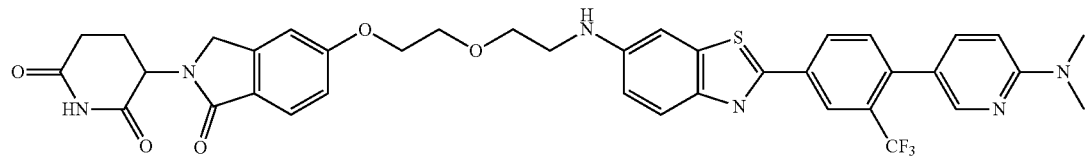
166807
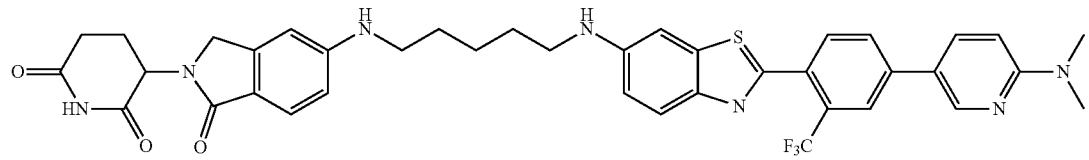

-continued

166879
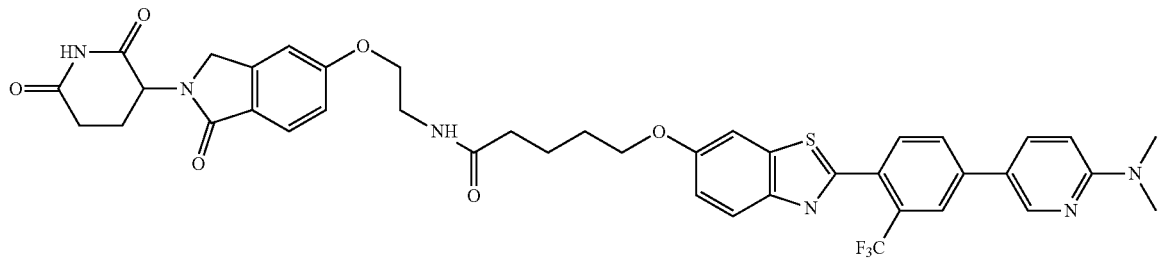

166935
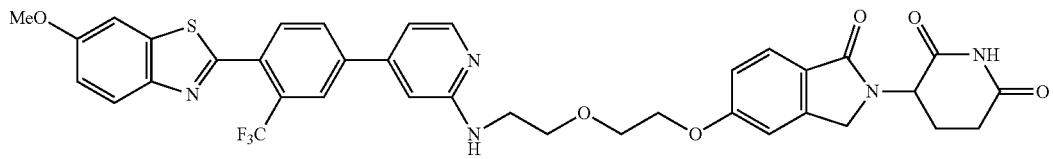

and

166965
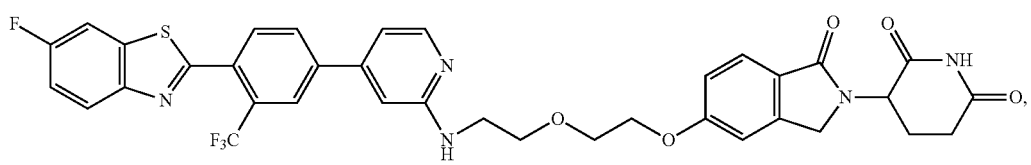

or the pharmaceutical acceptable salt, the enantiomer, the tautomer, the racemate, or the solvate thereof.

15. A method to reduce α-synuclein aggregation in a subject in need thereof, the method comprising administering to the subject an effective amount of a compound of Formula A, EBM-L-SBM     (Formula A)

wherein
EBM is an E3 ubiquitin ligase binding moiety having a chemical structure of:

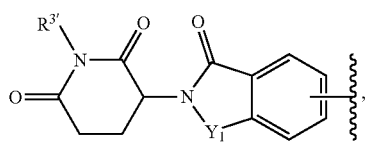

wherein $R^{3'}$ is H and $Y_1$ is $CH_2$;
L is a linker covalently attached to EBM and SBM; and
SBM is an α-synuclein protein binding moiety of Formula B or Formula C:

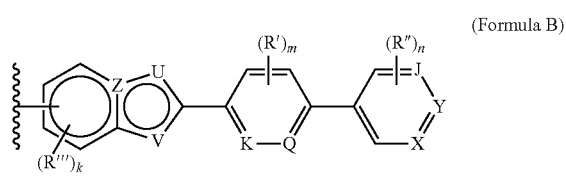     (Formula B)

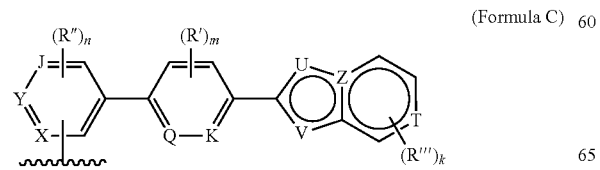     (Formula C)

or a pharmaceutical acceptable salt, an enantiomer, a tautomer, a racemate, or a solvate thereof, wherein
Z is C or N; U is O, S or CH; V is N; T is CH; Z and U are not heteroatoms at the same time;
K is CH or N; Q is CH or N; where K and Q are not N at the same time;
each occurrence of R''' is independently selected from the group consisting of H, OH, $NH_2$, $C_{1-6}$ alkyl, $C_{1-6}$ alkylamino, $C_{1-6}$ alkoxy and halogen: k is 0, 1, 2 or 3;
each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;
each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;
J is $CR^6$ or N; X is $CR^6$ or N; Y is $CR^6$ or N; where at least one of J, X and Y is N, but J and Y are not N at the same time, X and Y are not N at the same time; and
$R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo.

16. A method to reduce Lewy bodies in a subject in need thereof the method comprising administering to the subject an effective amount of a compound of Formula A, EBM-L-SBM     (Formula A)

wherein
EBM is an E3 ubiquitin ligase binding moiety having a chemical structure of:

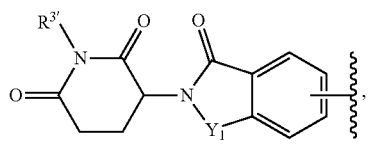

wherein R³' is H and Y₁ is CH₂;

L is a linker covalently attached to EBM and SBM; and

SBM is an α-synuclein protein binding moiety of Formula B or Formula C:

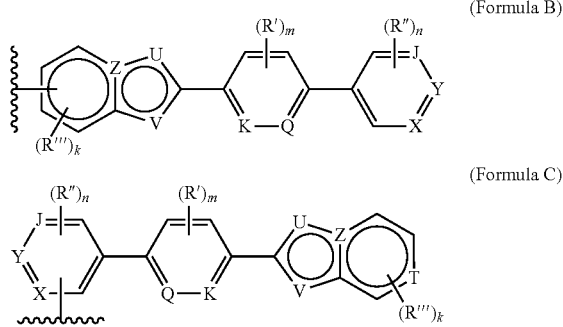

(Formula B)

(Formula C)

or a pharmaceutical acceptable salt, an enantiomer, a tautomer, a racemate, or a solvate thereof, wherein Z is C or N; U is O, S or CH; V is N; T is CH; Z and U are not heteroatoms at the same time;

K is CH or N; Q is CH or N; where K and Q are not N at the same time;

each occurrence of R'" is independently selected from the group consisting of H, OH, NH₂, $C_{1-6}$ alkyl, $C_{1-6}$ alkylamino, $C_{1-6}$ alkoxy and halogen; k is 0, 1, 2 or 3;

each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;

each occurrence of R" is independently selected from the group consisting of H, halo, OH, NH₂, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;

J is CR⁶ or N; X is CR⁶ or N; Y is CR⁶ or N; where at least one of J, X and Y is N, but J and Y are not N at the same time, X and Y are not N at the same time; and R⁶ is independently selected from the group consisting of H, NH₂, $C_{1-6}$ alkyl and $C_{1-6}$ alkoxy, wherein NH₂, $C_{1-6}$ alkyl or $C_{1-6}$ alkoxy is optionally substituted by 1 to 3 of $C_{1-3}$ alkyl, $C_{3-6}$ cycloalkyl and/or halo.

17. The method of claim 1, wherein SBM is the α-synuclein protein binding moiety of Formula B.

18. The method of claim 1, wherein SBM is the α-synuclein protein binding moiety of Formula C.

* * * * *

SEQUENCE LISTING

```
<160> NUMBER OF SEQ ID NOS: 3

<210> SEQ ID NO 1
<211> LENGTH: 140
<212> TYPE: PRT
<213> ORGANISM: Homo sapiens
```

<400> SEQUENCE: 1

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asn Glu Ala Tyr Glu Met Pro
            115                 120                 125

Ser Glu Glu Gly Tyr Gln Asp Tyr Glu Pro Glu Ala
    130                 135                 140
```

<210> SEQ ID NO 2
<211> LENGTH: 866
<212> TYPE: PRT
<213> ORGANISM: Homo sapiens

<400> SEQUENCE: 2

```
Met Glu Glu Gly Asn Asn Glu Glu Val Ile His Leu Asn Asn Phe
1               5                   10                  15

His Cys His Arg Gly Gln Glu Trp Ile Asn Leu Arg Asp Gly Pro Ile
            20                  25                  30

Thr Ile Ser Asp Ser Ser Asp Glu Glu Arg Ile Pro Met Leu Val Thr
        35                  40                  45

Pro Ala Pro Gln Gln His Glu Glu Glu Asp Leu Asp Asp Asp Val Ile
    50                  55                  60

Leu Thr Glu Asp Asp Ser Glu Asp Asp Tyr Gly Glu Phe Leu Asp Leu
65                  70                  75                  80

Gly Pro Pro Gly Ile Ser Glu Phe Thr Lys Pro Ser Gly Gln Thr Glu
                85                  90                  95

Arg Glu Pro Lys Pro Gly Pro Ser His Asn Gln Ala Ala Asn Asp Ile
            100                 105                 110

Val Asn Pro Arg Ser Glu Gln Lys Val Ile Ile Leu Glu Glu Gly Ser
            115                 120                 125

Leu Leu Tyr Thr Glu Ser Asp Pro Leu Glu Thr Gln Asn Gln Ser Ser
            130                 135                 140

Glu Asp Ser Glu Thr Glu Leu Leu Ser Asn Leu Gly Glu Ser Ala Ala
145                 150                 155                 160

Leu Ala Asp Asp Gln Ala Ile Glu Glu Asp Cys Trp Leu Asp His Pro
                165                 170                 175

Tyr Phe Gln Ser Leu Asn Gln Gln Pro Arg Glu Ile Thr Asn Gln Val
            180                 185                 190

Val Pro Gln Glu Arg Gln Pro Glu Ala Glu Leu Gly Arg Leu Leu Phe
        195                 200                 205

Gln His Glu Phe Pro Gly Pro Ala Phe Pro Arg Pro Glu Pro Gln Gln
    210                 215                 220
```

-continued

```
Gly Gly Ile Ser Gly Pro Ser Pro Gln Pro Ala His Pro Leu Gly
225                 230                 235                 240

Glu Phe Glu Asp Gln Gln Leu Ala Ser Asp Asp Glu Pro Gly Pro
            245                 250                 255

Ala Phe Pro Met Gln Glu Ser Gln Glu Pro Asn Leu Glu Asn Ile Trp
            260                 265                 270

Gly Gln Glu Ala Ala Glu Val Asp Gln Glu Leu Val Glu Leu Leu Val
            275                 280                 285

Lys Glu Thr Glu Ala Arg Phe Pro Asp Val Ala Asn Gly Phe Ile Glu
            290                 295                 300

Glu Ile Ile His Phe Lys Asn Tyr Tyr Asp Leu Asn Val Leu Cys Asn
305                 310                 315                 320

Phe Leu Leu Glu Asn Pro Asp Tyr Pro Lys Arg Glu Asp Arg Ile Ile
            325                 330                 335

Ile Asn Pro Ser Ser Ser Leu Leu Ala Ser Gln Asp Glu Thr Lys Leu
            340                 345                 350

Pro Lys Ile Asp Phe Phe Asp Tyr Ser Lys Leu Thr Pro Leu Asp Gln
            355                 360                 365

Arg Cys Phe Ile Gln Ala Ala Asp Leu Leu Met Ala Asp Phe Lys Val
370                 375                 380

Leu Ser Ser Gln Asp Ile Lys Trp Ala Leu His Glu Leu Lys Gly His
385                 390                 395                 400

Tyr Ala Ile Thr Arg Lys Ala Leu Ser Asp Ala Ile Lys Lys Trp Gln
            405                 410                 415

Glu Leu Ser Pro Glu Thr Ser Gly Lys Arg Lys Arg Lys Gln Met
            420                 425                 430

Asn Gln Tyr Ser Tyr Ile Asp Phe Lys Phe Glu Gln Gly Asp Ile Lys
            435                 440                 445

Ile Glu Lys Arg Met Phe Phe Leu Glu Asn Lys Arg Arg His Cys Arg
            450                 455                 460

Ser Tyr Asp Arg Arg Ala Leu Leu Pro Ala Val Gln Gln Glu Gln Glu
465                 470                 475                 480

Phe Tyr Glu Gln Lys Ile Lys Glu Met Ala Glu His Glu Asp Phe Leu
            485                 490                 495

Leu Ala Leu Gln Met Asn Glu Glu Gln Tyr Gln Lys Asp Gly Gln Leu
            500                 505                 510

Ile Glu Cys Arg Cys Tyr Gly Glu Phe Pro Phe Glu Glu Leu Thr
            515                 520                 525

Gln Cys Ala Asp Ala His Leu Phe Cys Lys Glu Cys Leu Ile Arg Tyr
            530                 535                 540

Ala Gln Glu Ala Val Phe Gly Ser Gly Lys Leu Glu Leu Ser Cys Met
545                 550                 555                 560

Glu Gly Ser Cys Thr Cys Ser Phe Pro Thr Ser Glu Leu Glu Lys Val
            565                 570                 575

Leu Pro Gln Thr Ile Leu Tyr Lys Tyr Glu Arg Lys Ala Glu Glu
            580                 585                 590

Glu Val Ala Ala Ala Tyr Ala Asp Glu Leu Val Arg Cys Pro Ser Cys
            595                 600                 605

Ser Phe Pro Ala Leu Leu Asp Ser Asp Val Lys Arg Phe Ser Cys Pro
            610                 615                 620

Asn Pro His Cys Arg Lys Glu Thr Cys Arg Lys Cys Gln Gly Leu Trp
625                 630                 635                 640
```

Lys Glu His Asn Gly Leu Thr Cys Glu Glu Leu Ala Glu Lys Asp Asp
                    645                 650                 655

Ile Lys Tyr Arg Thr Ser Ile Glu Glu Lys Met Thr Ala Ala Arg Ile
            660                 665                 670

Arg Lys Cys His Lys Cys Gly Thr Gly Leu Ile Lys Ser Glu Gly Cys
            675                 680                 685

Asn Arg Met Ser Cys Arg Cys Gly Ala Gln Met Cys Tyr Leu Cys Arg
        690                 695                 700

Val Ser Ile Asn Gly Tyr Asp His Phe Cys Gln His Pro Arg Ser Pro
705                 710                 715                 720

Gly Ala Pro Cys Gln Glu Cys Ser Arg Cys Ser Leu Trp Thr Asp Pro
                725                 730                 735

Thr Glu Asp Asp Glu Lys Leu Ile Glu Glu Ile Gln Lys Glu Ala Glu
                740                 745                 750

Glu Glu Gln Lys Arg Lys Asn Gly Glu Asn Thr Phe Lys Arg Ile Gly
            755                 760                 765

Pro Pro Leu Glu Lys Pro Val Glu Lys Val Gln Arg Val Glu Ala Leu
    770                 775                 780

Pro Arg Pro Val Pro Gln Asn Leu Pro Gln Pro Gln Met Pro Pro Tyr
785                 790                 795                 800

Ala Phe Ala His Pro Pro Phe Pro Leu Pro Pro Val Arg Pro Val Phe
                805                 810                 815

Asn Asn Phe Pro Leu Asn Met Gly Pro Ile Pro Ala Pro Tyr Val Pro
                820                 825                 830

Pro Leu Pro Asn Val Arg Val Asn Tyr Asp Phe Gly Pro Ile His Met
            835                 840                 845

Pro Leu Glu His Asn Leu Pro Met His Phe Gly Pro Gln Pro Arg His
    850                 855                 860

Arg Phe
865

<210> SEQ ID NO 3
<211> LENGTH: 923
<212> TYPE: PRT
<213> ORGANISM: Homo sapiens

<400> SEQUENCE: 3

Met Glu Glu Gly Asn Asn Glu Glu Val Ile His Leu Asn Asn Phe
1               5                   10                  15

His Cys His Arg Gly Gln Glu Trp Ile Asn Leu Arg Asp Gly Pro Ile
                20                  25                  30

Thr Ile Ser Asp Ser Ser Asp Glu Glu Arg Ile Pro Met Leu Val Thr
            35                  40                  45

Pro Ala Pro Gln Gln His Glu Glu Asp Leu Asp Asp Val Ile
    50                  55                  60

Leu Thr Glu Thr Asn Lys Pro Gln Arg Ser Arg Pro Asn Leu Ile Lys
65                  70                  75                  80

Pro Ala Ala Gln Trp Gln Asp Leu Lys Arg Leu Gly Glu Glu Arg Pro
                85                  90                  95

Lys Lys Ser Arg Ala Ala Phe Glu Ser Asp Lys Ser Ser Tyr Phe Ser
            100                 105                 110

Val Cys Asn Asn Pro Leu Phe Asp Ser Gly Ala Gln Asp Asp Ser Glu
        115                 120                 125

Asp Asp Tyr Gly Glu Phe Leu Asp Leu Gly Pro Pro Gly Ile Ser Glu
    130                 135                 140

-continued

```
Phe Thr Lys Pro Ser Gly Gln Thr Glu Arg Glu Pro Lys Pro Gly Pro
145                 150                 155                 160

Ser His Asn Gln Ala Ala Asn Asp Ile Val Asn Pro Arg Ser Glu Gln
                165                 170                 175

Lys Val Ile Ile Leu Glu Glu Gly Ser Leu Leu Tyr Thr Glu Ser Asp
            180                 185                 190

Pro Leu Glu Thr Gln Asn Gln Ser Ser Glu Asp Ser Glu Thr Glu Leu
        195                 200                 205

Leu Ser Asn Leu Gly Glu Ser Ala Ala Leu Ala Asp Asp Gln Ala Ile
    210                 215                 220

Glu Glu Asp Cys Trp Leu Asp His Pro Tyr Phe Gln Ser Leu Asn Gln
225                 230                 235                 240

Gln Pro Arg Glu Ile Thr Asn Gln Val Val Pro Gln Glu Arg Gln Pro
                245                 250                 255

Glu Ala Glu Leu Gly Arg Leu Leu Phe Gln His Glu Phe Pro Gly Pro
            260                 265                 270

Ala Phe Pro Arg Pro Glu Pro Gln Gln Gly Gly Ile Ser Gly Pro Ser
        275                 280                 285

Ser Pro Gln Pro Ala His Pro Leu Gly Glu Phe Glu Asp Gln Gln Leu
    290                 295                 300

Ala Ser Asp Asp Glu Glu Pro Gly Pro Ala Phe Pro Met Gln Glu Ser
305                 310                 315                 320

Gln Glu Pro Asn Leu Glu Asn Ile Trp Gly Gln Glu Ala Ala Glu Val
                325                 330                 335

Asp Gln Glu Leu Val Glu Leu Val Lys Glu Thr Glu Ala Arg Phe
            340                 345                 350

Pro Asp Val Ala Asn Gly Phe Ile Glu Glu Ile Ile His Phe Lys Asn
        355                 360                 365

Tyr Tyr Asp Leu Asn Val Leu Cys Asn Phe Leu Leu Glu Asn Pro Asp
    370                 375                 380

Tyr Pro Lys Arg Glu Asp Arg Ile Ile Ile Asn Pro Ser Ser Ser Leu
385                 390                 395                 400

Leu Ala Ser Gln Asp Glu Thr Lys Leu Pro Lys Ile Asp Phe Phe Asp
                405                 410                 415

Tyr Ser Lys Leu Thr Pro Leu Asp Gln Arg Cys Phe Ile Gln Ala Ala
            420                 425                 430

Asp Leu Leu Met Ala Asp Phe Lys Val Leu Ser Ser Gln Asp Ile Lys
        435                 440                 445

Trp Ala Leu His Glu Leu Lys Gly His Tyr Ala Ile Thr Arg Lys Ala
    450                 455                 460

Leu Ser Asp Ala Ile Lys Lys Trp Gln Glu Leu Ser Pro Glu Thr Ser
465                 470                 475                 480

Gly Lys Arg Lys Lys Arg Lys Gln Met Asn Gln Tyr Ser Tyr Ile Asp
                485                 490                 495

Phe Lys Phe Glu Gln Gly Asp Ile Lys Ile Glu Lys Arg Met Phe Phe
            500                 505                 510

Leu Glu Asn Lys Arg Arg His Cys Arg Ser Tyr Asp Arg Arg Ala Leu
        515                 520                 525

Leu Pro Ala Val Gln Gln Glu Gln Phe Tyr Glu Gln Lys Ile Lys
    530                 535                 540

Glu Met Ala Glu His Glu Asp Phe Leu Leu Ala Leu Gln Met Asn Glu
545                 550                 555                 560
```

Glu Gln Tyr Gln Lys Asp Gly Gln Leu Ile Glu Cys Arg Cys Cys Tyr
            565                 570                 575

Gly Glu Phe Pro Phe Glu Leu Thr Gln Cys Ala Asp Ala His Leu
            580                 585                 590

Phe Cys Lys Glu Cys Leu Ile Arg Tyr Ala Gln Glu Ala Val Phe Gly
            595                 600                 605

Ser Gly Lys Leu Glu Leu Ser Cys Met Glu Gly Ser Cys Thr Cys Ser
610                 615                 620

Phe Pro Thr Ser Glu Leu Glu Lys Val Leu Pro Gln Thr Ile Leu Tyr
625                 630                 635                 640

Lys Tyr Tyr Glu Arg Lys Ala Glu Glu Val Ala Ala Ala Tyr Ala
            645                 650                 655

Asp Glu Leu Val Arg Cys Pro Ser Cys Ser Phe Pro Ala Leu Leu Asp
            660                 665                 670

Ser Asp Val Lys Arg Phe Ser Cys Pro Asn Pro His Cys Arg Lys Glu
            675                 680                 685

Thr Cys Arg Lys Cys Gln Gly Leu Trp Lys Glu His Asn Gly Leu Thr
            690                 695                 700

Cys Glu Glu Leu Ala Glu Lys Asp Asp Ile Lys Tyr Arg Thr Ser Ile
705                 710                 715                 720

Glu Glu Lys Met Thr Ala Ala Arg Ile Arg Lys Cys His Lys Cys Gly
                725                 730                 735

Thr Gly Leu Ile Lys Ser Glu Gly Cys Asn Arg Met Ser Cys Arg Cys
            740                 745                 750

Gly Ala Gln Met Cys Tyr Leu Cys Arg Val Ser Ile Asn Gly Tyr Asp
            755                 760                 765

His Phe Cys Gln His Pro Arg Ser Pro Gly Ala Pro Cys Gln Glu Cys
            770                 775                 780

Ser Arg Cys Ser Leu Trp Thr Asp Pro Thr Glu Asp Asp Glu Lys Leu
785                 790                 795                 800

Ile Glu Glu Ile Gln Lys Glu Ala Glu Glu Gln Lys Arg Lys Asn
            805                 810                 815

Gly Glu Asn Thr Phe Lys Arg Ile Gly Pro Pro Leu Glu Lys Pro Val
            820                 825                 830

Glu Lys Val Gln Arg Val Glu Ala Leu Pro Arg Pro Val Pro Gln Asn
            835                 840                 845

Leu Pro Gln Pro Gln Met Pro Pro Tyr Ala Phe Ala His Pro Pro Phe
            850                 855                 860

Pro Leu Pro Pro Val Arg Pro Val Phe Asn Asn Phe Pro Leu Asn Met
865                 870                 875                 880

Gly Pro Ile Pro Ala Pro Tyr Val Pro Leu Pro Asn Val Arg Val
            885                 890                 895

Asn Tyr Asp Phe Gly Pro Ile His Met Pro Leu Glu His Asn Leu Pro
            900                 905                 910

Met His Phe Gly Pro Gln Pro Arg His Arg Phe
            915                 920